US011285014B1

(12) United States Patent
Josse et al.

(10) Patent No.: US 11,285,014 B1
(45) Date of Patent: Mar. 29, 2022

(54) EXPANDABLE INTER-BODY DEVICE, SYSTEM, AND METHOD

(71) Applicant: Warsaw Orthopedic, Inc., Warsaw, IN (US)

(72) Inventors: Loic Josse, Collierville, TN (US); Bertrand Peultier, Les Hopitaux Neufs (FR)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/307,706

(22) Filed: May 4, 2021

Related U.S. Application Data

(63) Continuation-in-part of application No. 17/123,897, filed on Dec. 16, 2020.

(30) Foreign Application Priority Data

Nov. 5, 2020 (WO) .................. PCT/IB2020/000932
Nov. 5, 2020 (WO) .................. PCT/IB2020/000942
Nov. 5, 2020 (WO) .................. PCT/IB2020/000953

(51) Int. Cl.
*A61F 2/44* (2006.01)
*A61F 2/30* (2006.01)

(52) U.S. Cl.
CPC ............ *A61F 2/4425* (2013.01); *A61F 2/447* (2013.01); *A61F 2002/30398* (2013.01); *A61F 2002/30433* (2013.01); *A61F 2002/443* (2013.01)

(58) Field of Classification Search
CPC ........................................... A61F 2/4455–447
See application file for complete search history.

(56) References Cited

U.S. PATENT DOCUMENTS

| 4,401,112 A | 8/1983 | Rezaian |
| 4,553,273 A | 11/1985 | Wu |

(Continued)

FOREIGN PATENT DOCUMENTS

| DE | 44 16 605 C1 | 6/1995 |
| EP | 0 767 636 A1 | 4/1997 |

(Continued)

OTHER PUBLICATIONS

International Search Report, and Written Opinion for Application. No. PCT/US201 9/019067, dated Jun. 3, 2019.

(Continued)

*Primary Examiner* — Ellen C Hammond
(74) *Attorney, Agent, or Firm* — Fox Rothschild LLP

(57) ABSTRACT

Expandable spinal implants, systems and methods are disclosed. An expandable spinal implant may include a proximal end plate, a superior endplate, an inferior endplate, and a moving mechanism that is operably coupled to the superior and inferior endplates. The proximal end plate may include at least one bone screw aperture configured to orient a bone screw across a bone screw relief of the superior endplate and/or inferior endplate. The moving mechanism may include a wedge, a first sliding frame, a second sliding frame, a screw guide housing a rotatable first set screw and a rotatable second set screw. A spacing between the superior and inferior endplates may be adjusted upon simultaneous rotation of the first and second set screws and an angle of inclination between the superior and inferior endplates may be adjusted upon translating either of the first set screw and second set screw.

20 Claims, 82 Drawing Sheets

(56) References Cited

U.S. PATENT DOCUMENTS

| | | |
|---|---|---|
| 4,636,217 A | 1/1987 | Ogilvie et al. |
| 4,759,769 A | 7/1988 | Hedman et al. |
| 5,059,193 A | 10/1991 | Kuslich |
| 5,171,278 A | 12/1992 | Pisharodi |
| 5,336,223 A | 8/1994 | Rogers |
| 5,390,683 A | 2/1995 | Pisharodi |
| 5,522,899 A | 6/1996 | Michelson |
| 5,554,191 A | 9/1996 | Lahille et al. |
| 5,575,790 A | 11/1996 | Chen et al. |
| 5,609,635 A | 3/1997 | Michelson |
| 5,653,762 A | 8/1997 | Pisharodi |
| 5,658,336 A | 8/1997 | Pisharodi |
| 5,665,122 A | 9/1997 | Kambin |
| 5,693,100 A | 12/1997 | Pisharodi |
| 5,697,977 A | 12/1997 | Pisharodi |
| 5,702,391 A | 12/1997 | Lin |
| 5,702,453 A | 12/1997 | Rabbe et al. |
| 5,702,455 A | 12/1997 | Saggar |
| 5,797,918 A | 8/1998 | McGuire et al. |
| 5,800,550 A | 9/1998 | Sertich |
| 5,865,848 A | 2/1999 | Baker |
| 5,893,890 A | 4/1999 | Pisharodi |
| 5,931,777 A | 8/1999 | Sava |
| 5,980,522 A | 11/1999 | Koros et al. |
| 6,045,579 A | 4/2000 | Hochshuler et al. |
| 6,074,343 A | 6/2000 | Nathanson et al. |
| 6,080,193 A | 6/2000 | Hochshuler et al. |
| 6,099,531 A | 8/2000 | Bonutti |
| 6,102,949 A | 8/2000 | Biedermann et al. |
| 6,102,950 A | 8/2000 | Vaccaro |
| 6,106,557 A | 8/2000 | Robioneck et al. |
| 6,113,638 A | 9/2000 | Williams et al. |
| 6,117,174 A | 9/2000 | Nolan |
| 6,132,465 A | 10/2000 | Ray et al. |
| 6,159,211 A | 12/2000 | Boriani et al. |
| 6,159,244 A | 12/2000 | Suddaby |
| 6,176,882 B1 | 1/2001 | Biedermann et al. |
| 6,179,873 B1 | 1/2001 | Zientek |
| 6,190,414 B1 | 2/2001 | Young et al. |
| 6,193,757 B1 | 2/2001 | Foley et al. |
| 6,217,579 B1 | 4/2001 | Koros |
| 6,245,108 B1 | 6/2001 | Biscup |
| 6,309,421 B1 | 10/2001 | Pisharodi |
| 6,342,074 B1 | 1/2002 | Simpson |
| 6,371,989 B1 | 4/2002 | Chauvin et al. |
| 6,395,031 B1 | 5/2002 | Foley et al. |
| 6,423,063 B1 | 7/2002 | Bonutti |
| 6,432,106 B1 | 8/2002 | Fraser |
| 6,436,140 B1 | 8/2002 | Liu et al. |
| 6,443,989 B1 | 9/2002 | Jackson |
| 6,443,990 B1 | 9/2002 | Aebi et al. |
| 6,454,806 B1 | 9/2002 | Cohen et al. |
| 6,454,807 B1 | 9/2002 | Jackson |
| 6,461,359 B1 | 10/2002 | Tribus et al. |
| 6,491,724 B1 | 12/2002 | Ferree |
| 6,520,991 B2 | 2/2003 | Huene |
| 6,520,993 B2 | 2/2003 | James et al. |
| 6,527,803 B1 | 3/2003 | Crozet et al. |
| 6,562,074 B2 | 5/2003 | Gerbec et al. |
| 6,576,016 B1 | 6/2003 | Hochshuler et al. |
| 6,623,525 B2 | 9/2003 | Ralph et al. |
| 6,629,998 B1 | 10/2003 | Lin |
| 6,635,086 B2 | 10/2003 | Lin |
| 6,648,917 B2 | 11/2003 | Gerbec et al. |
| 6,676,703 B2 | 1/2004 | Biscup |
| 6,685,742 B1 | 2/2004 | Jackson |
| 6,723,126 B1 | 4/2004 | Berry |
| 6,770,096 B2 | 8/2004 | Bolger et al. |
| 6,773,460 B2 | 8/2004 | Jackson |
| 6,821,298 B1 | 11/2004 | Jackson |
| 6,835,206 B2 | 12/2004 | Jackson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,923,814 B1 | 8/2005 | Hildebrand et al. |
| 6,926,737 B2 | 8/2005 | Jackson |
| 6,953,477 B2 | 10/2005 | Berry |
| 6,964,687 B1 | 11/2005 | Bernard et al. |
| 6,974,480 B2 | 12/2005 | Messerli et al. |
| 6,984,234 B2 | 1/2006 | Bray |
| 7,112,222 B2 | 9/2006 | Fraser et al. |
| 7,135,043 B2 | 11/2006 | Nakahara et al. |
| 7,137,997 B2 | 11/2006 | Paul |
| 7,172,627 B2 | 2/2007 | Fiere et al. |
| 7,204,853 B2 | 4/2007 | Gordon et al. |
| 7,232,464 B2 | 6/2007 | Mathieu et al. |
| 7,238,203 B2 | 7/2007 | Bagga et al. |
| 7,316,714 B2 | 1/2008 | Gordon et al. |
| 7,407,483 B2 | 8/2008 | Perez-Cruet et al. |
| 7,481,766 B2 | 1/2009 | Lee et al. |
| 7,491,168 B2 | 2/2009 | Raymond et al. |
| 7,537,565 B2 | 5/2009 | Bass |
| 7,618,456 B2 | 11/2009 | Mathieu et al. |
| 7,625,394 B2 | 12/2009 | Molz, IV et al. |
| 7,655,046 B2 | 2/2010 | Dryer et al. |
| 7,678,148 B2 | 3/2010 | Peterman |
| 7,703,727 B2 | 4/2010 | Selness |
| 7,708,778 B2 | 5/2010 | Gordon et al. |
| 7,708,779 B2 | 5/2010 | Edie et al. |
| 7,727,280 B2 | 6/2010 | McLuen |
| 7,753,958 B2 | 7/2010 | Gordon et al. |
| 7,780,594 B2 | 8/2010 | Hutton |
| 7,806,932 B2 | 10/2010 | Webb et al. |
| 7,815,682 B1 | 10/2010 | Peterson et al. |
| 7,819,801 B2 | 10/2010 | Miles et al. |
| 7,828,849 B2 | 11/2010 | Lim |
| 7,846,167 B2 | 12/2010 | Garcia et al. |
| 7,846,207 B2 | 12/2010 | Lechmann et al. |
| 7,850,731 B2 | 12/2010 | Brittan et al. |
| 7,850,733 B2 | 12/2010 | Baynham et al. |
| 7,862,616 B2 | 1/2011 | Lechmann et al. |
| 7,875,076 B2 | 1/2011 | Mathieu et al. |
| 7,892,173 B2 | 2/2011 | Miles et al. |
| 7,909,869 B2 | 3/2011 | Gordon et al. |
| 7,914,559 B2 | 3/2011 | Carls et al. |
| 7,967,821 B2 | 6/2011 | Sicvol et al. |
| 7,981,031 B2 | 7/2011 | Frasier et al. |
| 8,016,836 B2 | 9/2011 | Corrao et al. |
| 8,062,375 B2 | 11/2011 | Glerum et al. |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,182,539 B2 | 5/2012 | Tyber et al. |
| 8,257,442 B2 | 9/2012 | Edie et al. |
| 8,262,570 B2 | 9/2012 | White et al. |
| 8,262,662 B2 | 9/2012 | Beardsley et al. |
| 8,287,597 B1 | 10/2012 | Pimenta et al. |
| 8,303,498 B2 | 11/2012 | Miles et al. |
| 8,303,658 B2 | 11/2012 | Peterman |
| 8,303,663 B2 | 11/2012 | Jimenez et al. |
| 8,317,866 B2 | 11/2012 | Palmatier et al. |
| 8,323,185 B2 | 12/2012 | Perez-Cruet et al. |
| 8,328,872 B2 | 12/2012 | Duffield et al. |
| 8,343,048 B2 | 1/2013 | Warren, Jr. |
| 8,353,826 B2 | 1/2013 | Weiman |
| 8,355,780 B2 | 1/2013 | Miles et al. |
| 8,382,842 B2 | 2/2013 | Greenhalgh et al. |
| 8,388,527 B2 | 3/2013 | Miles et al. |
| 8,398,713 B2 | 3/2013 | Weiman |
| 8,403,990 B2 | 3/2013 | Dryer et al. |
| 8,419,797 B2 | 4/2013 | Biedermann et al. |
| 8,425,528 B2 | 4/2013 | Berry et al. |
| 8,435,298 B2 | 5/2013 | Weiman |
| 8,480,576 B2 | 7/2013 | Sandhu |
| 8,496,706 B2 | 7/2013 | Ragab et al. |
| 8,500,634 B2 | 8/2013 | Miles et al. |
| 8,506,635 B2 | 8/2013 | Palmatier et al. |
| 8,517,935 B2 | 8/2013 | Marchek et al. |
| 8,518,120 B2 | 8/2013 | Glerum et al. |
| 8,535,380 B2 | 9/2013 | Greenhalgh et al. |
| 8,550,994 B2 | 10/2013 | Miles et al. |

(56) References Cited

U.S. PATENT DOCUMENTS

| | | |
|---|---|---|
| 8,556,808 B2 | 10/2013 | Miles et al. |
| 8,556,979 B2 | 10/2013 | Glerum et al. |
| 8,579,809 B2 | 11/2013 | Parker |
| 8,579,979 B2 | 11/2013 | Edie et al. |
| 8,579,981 B2 | 11/2013 | Lim et al. |
| 8,602,984 B2 | 12/2013 | Raymond et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,663,329 B2 | 3/2014 | Ernst |
| 8,668,715 B2 | 3/2014 | Sandhu |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,559 B2 | 4/2014 | Miles et al. |
| 8,709,083 B2 | 4/2014 | Duffield et al. |
| 8,709,085 B2 | 4/2014 | Lechmann et al. |
| 8,709,086 B2 | 4/2014 | Glerum |
| 8,715,353 B2 | 5/2014 | Bagga et al. |
| 8,740,983 B1 | 6/2014 | Arnold et al. |
| 8,753,271 B1 | 6/2014 | Miles et al. |
| 8,753,396 B1 | 6/2014 | Hockett et al. |
| 8,764,649 B2 | 7/2014 | Miles et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,305 B2 | 8/2014 | Kleiner |
| 8,827,902 B2 | 9/2014 | Dietze, Jr. et al. |
| 8,828,085 B1 | 9/2014 | Jensen |
| 8,840,668 B1 | 9/2014 | Donahoe et al. |
| 8,845,731 B2 | 9/2014 | Weiman |
| 8,845,732 B2 | 9/2014 | Weiman |
| 8,845,734 B2 | 9/2014 | Weiman |
| 8,852,282 B2 | 10/2014 | Farley et al. |
| 8,864,833 B2 | 10/2014 | Glerum et al. |
| 8,888,853 B2 | 11/2014 | Glerum et al. |
| 8,894,708 B2 | 11/2014 | Thalgott et al. |
| 8,894,711 B2 | 11/2014 | Varela |
| 8,894,712 B2 | 11/2014 | Varela |
| 8,906,095 B2 | 12/2014 | Christensen et al. |
| 8,920,500 B1 | 12/2014 | Pimenta et al. |
| 8,926,704 B2 | 1/2015 | Glerum et al. |
| 8,936,641 B2 | 1/2015 | Cain |
| 8,940,049 B1 | 1/2015 | Jimenez et al. |
| 8,968,363 B2 | 3/2015 | Weiman et al. |
| 8,986,344 B2 | 3/2015 | Sandhu |
| 8,992,425 B2 | 3/2015 | Karpowicz et al. |
| 8,992,544 B2 | 3/2015 | Sasing |
| 9,005,292 B2 | 4/2015 | Melamed |
| 9,005,293 B2 | 4/2015 | Moskowitz et al. |
| 9,005,295 B2 | 4/2015 | Kueenzi et al. |
| 9,017,412 B2 | 4/2015 | Wolters et al. |
| 9,034,045 B2 | 5/2015 | Davenport et al. |
| 9,050,146 B2 | 6/2015 | Woolley et al. |
| 9,050,194 B2 | 6/2015 | Thibodeau |
| 9,060,877 B2 | 6/2015 | Kleiner |
| 9,072,563 B2 | 7/2015 | Garcia et al. |
| 9,084,591 B2 | 7/2015 | Reglos et al. |
| 9,113,854 B2 | 8/2015 | Ellman |
| 9,119,730 B2 | 9/2015 | Glerum et al. |
| 9,125,757 B2 | 9/2015 | Weiman |
| 9,132,021 B2 | 9/2015 | Mermuys et al. |
| 9,138,217 B2 | 9/2015 | Smith et al. |
| 9,138,330 B2 | 9/2015 | Hansell et al. |
| 9,138,331 B2 | 9/2015 | Aferzon |
| 9,149,367 B2 | 10/2015 | Davenport et al. |
| 9,155,628 B2 | 10/2015 | Glerum et al. |
| 9,155,631 B2 | 10/2015 | Seifert et al. |
| 9,179,903 B2 | 11/2015 | Cianfrani et al. |
| 9,179,952 B2 | 11/2015 | Biedermann et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,192,483 B1 | 11/2015 | Radcliffe et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,271,846 B2 | 3/2016 | Lim et al. |
| 9,308,099 B2 | 4/2016 | Triplett et al. |
| 9,320,610 B2 | 4/2016 | Alheidt et al. |
| 9,351,845 B1 | 5/2016 | Pimenta et al. |
| 9,351,848 B2 | 5/2016 | Glerum et al. |
| 9,357,909 B2 | 6/2016 | Perez-Cruet et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |
| 9,364,343 B2 | 6/2016 | Duffield et al. |
| 9,370,434 B2 | 6/2016 | Weiman |
| 9,370,435 B2 | 6/2016 | Walkenhorst et al. |
| 9,381,008 B2 | 7/2016 | Thornburg |
| 9,386,916 B2 | 7/2016 | Predick et al. |
| 9,387,092 B2 | 7/2016 | Mermuys et al. |
| 9,402,673 B2 | 8/2016 | Cormier et al. |
| 9,402,739 B2 | 8/2016 | Weiman et al. |
| 9,408,596 B2 | 8/2016 | Blain |
| 9,408,708 B2 | 8/2016 | Greenhalgh |
| 9,414,828 B2 | 8/2016 | Abidin et al. |
| 9,414,934 B2 | 8/2016 | Cain |
| 9,414,937 B2 | 8/2016 | Carlson et al. |
| 9,421,110 B2 | 8/2016 | Masson et al. |
| 9,427,331 B2 | 8/2016 | Amin |
| 9,445,919 B2 * | 9/2016 | Palmatier ............... A61F 2/4425 |
| 9,452,063 B2 | 9/2016 | Glerum et al. |
| 9,456,903 B2 | 10/2016 | Glerum et al. |
| 9,456,906 B2 | 10/2016 | Gray et al. |
| 9,468,405 B2 | 10/2016 | Miles et al. |
| 9,474,622 B2 | 10/2016 | McLaughlin et al. |
| 9,474,625 B2 | 10/2016 | Weiman |
| 9,480,573 B2 | 11/2016 | Perloff et al. |
| 9,480,576 B2 | 11/2016 | Pepper et al. |
| 9,480,579 B2 | 11/2016 | Davenport et al. |
| 9,486,133 B2 | 11/2016 | Lee et al. |
| 9,486,325 B2 | 11/2016 | Davenport et al. |
| 9,486,327 B2 | 11/2016 | Martynova et al. |
| 9,486,328 B2 | 11/2016 | Jimenez et al. |
| 9,492,287 B2 | 11/2016 | Glerum et al. |
| 9,492,288 B2 | 11/2016 | Wagner et al. |
| 9,492,289 B2 | 11/2016 | Davenport et al. |
| 9,498,349 B2 | 11/2016 | Patterson et al. |
| 9,510,954 B2 | 12/2016 | Glerum et al. |
| 9,522,070 B2 | 12/2016 | Flower et al. |
| 9,526,620 B2 | 12/2016 | Slivka et al. |
| 9,526,625 B2 | 12/2016 | Cain |
| 9,532,821 B2 | 1/2017 | Moskowitz et al. |
| 9,539,103 B2 | 1/2017 | McLaughlin et al. |
| 9,539,108 B2 | 1/2017 | Glerum et al. |
| 9,545,320 B2 | 1/2017 | Padovani et al. |
| 9,549,723 B2 | 1/2017 | Hynes et al. |
| 9,549,824 B2 | 1/2017 | McAfee |
| 9,561,116 B2 | 2/2017 | Weiman et al. |
| 9,566,163 B2 | 2/2017 | Suddaby et al. |
| 9,566,166 B2 | 2/2017 | Parry et al. |
| 9,566,168 B2 | 2/2017 | Glerum et al. |
| 9,572,560 B2 | 2/2017 | Mast et al. |
| 9,572,677 B2 | 2/2017 | Davenport et al. |
| 9,572,681 B2 | 2/2017 | Mathieu et al. |
| 9,579,124 B2 | 2/2017 | Gordon et al. |
| 9,579,139 B2 | 2/2017 | Cormier et al. |
| 9,579,213 B2 | 2/2017 | Bal et al. |
| 9,585,649 B2 | 3/2017 | Blain et al. |
| 9,585,762 B2 | 3/2017 | Suddaby et al. |
| 9,585,766 B2 | 3/2017 | Robinson |

(56) References Cited

U.S. PATENT DOCUMENTS

| | | |
|---|---|---|
| 9,585,767 B2 | 3/2017 | Robinson |
| 9,592,129 B2 | 3/2017 | Slivka et al. |
| 9,597,195 B2 | 3/2017 | Cain |
| 9,603,713 B2 | 3/2017 | Moskowitz et al. |
| 9,603,717 B2 | 3/2017 | Ibarra et al. |
| 9,615,818 B2 | 4/2017 | Baudouin et al. |
| 9,615,936 B2 | 4/2017 | Duffield et al. |
| 9,622,732 B2 | 4/2017 | Martinelli et al. |
| 9,622,875 B2 | 4/2017 | Moskowitz et al. |
| 9,622,876 B1 | 4/2017 | Greenhalgh et al. |
| 9,629,729 B2 | 4/2017 | Grimberg, Jr. et al. |
| 9,636,097 B2 | 5/2017 | Bass |
| 9,642,720 B2 | 5/2017 | Radcliffe et al. |
| 9,649,198 B2 | 5/2017 | Wolters et al. |
| 9,655,746 B2 | 5/2017 | Seifert |
| 9,655,747 B2 | 5/2017 | Glerum et al. |
| 9,662,224 B2 | 5/2017 | Weiman et al. |
| 9,668,784 B2 | 6/2017 | Brumfield et al. |
| 9,668,876 B2 | 6/2017 | Blain et al. |
| 9,668,879 B2 | 6/2017 | Jimenez et al. |
| 9,675,465 B2 | 6/2017 | Padovani et al. |
| 9,675,467 B2 | 6/2017 | Duffield et al. |
| 9,675,468 B1 | 6/2017 | Jensen |
| 9,693,871 B2 | 7/2017 | Richerme et al. |
| 9,700,428 B2 | 7/2017 | Niemiec et al. |
| 9,707,092 B2 | 7/2017 | Davenport et al. |
| 9,713,536 B2 | 7/2017 | Foley et al. |
| 9,717,601 B2 | 8/2017 | Miller |
| 9,730,684 B2 | 8/2017 | Beale et al. |
| 9,730,806 B2 | 8/2017 | Capote |
| 9,737,288 B2 | 8/2017 | Karpowicz et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,770,343 B2 | 9/2017 | Weiman |
| 9,782,265 B2 | 10/2017 | Weiman et al. |
| 9,788,971 B1 | 10/2017 | Stein |
| 9,795,370 B2 | 10/2017 | O'Connell et al. |
| 9,795,371 B2 | 10/2017 | Miles et al. |
| 9,801,733 B2 | 10/2017 | Wolters et al. |
| 9,801,734 B1 | 10/2017 | Stein et al. |
| 9,808,352 B2 | 11/2017 | Suddaby et al. |
| 9,826,966 B2 | 11/2017 | Mast et al. |
| 9,827,024 B2 | 11/2017 | Cormier et al. |
| 9,827,107 B1 | 11/2017 | Arnin |
| 9,833,333 B2 | 12/2017 | Duffield et al. |
| 9,833,336 B2 | 12/2017 | Davenport et al. |
| 9,839,527 B2 | 12/2017 | Robinson |
| 9,839,528 B2 | 12/2017 | Weiman et al. |
| 9,848,993 B2 | 12/2017 | Moskowitz et al. |
| 9,848,996 B2 | 12/2017 | Faulhaber |
| 9,855,151 B2 | 1/2018 | Weiman |
| 9,867,715 B2 | 1/2018 | McLaughlin et al. |
| 9,872,779 B2 | 1/2018 | Miller et al. |
| 9,889,019 B2 | 2/2018 | Rogers et al. |
| 9,907,671 B2 | 3/2018 | Fessler |
| 9,907,673 B2 | 3/2018 | Weiman et al. |
| 9,918,709 B2 | 3/2018 | Sandhu |
| 9,924,859 B2 | 3/2018 | Lee et al. |
| 9,924,940 B2 | 3/2018 | Moskowitz et al. |
| 9,925,062 B2 | 3/2018 | Glerum et al. |
| 9,925,064 B2 | 3/2018 | Duffield et al. |
| 9,931,223 B2 | 4/2018 | Cain |
| 9,937,053 B2 | 4/2018 | Melkent et al. |
| 9,943,342 B2 | 4/2018 | Tanaka et al. |
| 9,943,418 B2 | 4/2018 | Davenport et al. |
| 9,949,841 B2 | 4/2018 | Glerum et al. |
| 9,956,087 B2 | 5/2018 | Seifert et al. |
| 9,962,270 B2 | 5/2018 | Alheidt et al. |
| 9,962,271 B2 | 5/2018 | Glerum |
| 9,962,272 B1 | 5/2018 | Daffinson et al. |
| 9,968,461 B2 | 5/2018 | Zappacosta et al. |
| 9,968,462 B2 | 5/2018 | Weiman |
| 9,974,531 B2 | 5/2018 | Miles et al. |
| 9,974,662 B2 | 5/2018 | Hessler et al. |
| 9,974,664 B2 | 5/2018 | Emerick et al. |
| 9,980,825 B2 | 5/2018 | Nichols et al. |
| 9,980,826 B2 | 5/2018 | Martynova et al. |
| 9,987,141 B2 | 6/2018 | Duffield et al. |
| 9,987,143 B2 | 6/2018 | Robinson et al. |
| 9,987,144 B2 | 6/2018 | Seifert et al. |
| 9,987,146 B1 | 6/2018 | Lentner et al. |
| 9,993,239 B2 | 6/2018 | Karpowicz et al. |
| 9,993,350 B2 | 6/2018 | Cain |
| 10,004,607 B2 | 6/2018 | Weiman et al. |
| 10,016,282 B2 | 7/2018 | Seifert et al. |
| 10,016,284 B2 | 7/2018 | Moskowitz et al. |
| 10,022,239 B1 | 7/2018 | Lentner et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,772 B2 | 7/2018 | Glerum et al. |
| 10,034,773 B2 | 7/2018 | McLaughlin et al. |
| 10,039,539 B2 | 8/2018 | Friedrich et al. |
| 10,039,650 B2 | 8/2018 | Lamborne et al. |
| 10,052,214 B2 | 8/2018 | Jimenez et al. |
| 10,060,469 B2 | 8/2018 | Jimenez et al. |
| 10,070,852 B2 | 9/2018 | Mast et al. |
| 10,076,320 B2 | 9/2018 | Mast et al. |
| 10,076,423 B2 | 9/2018 | Miller et al. |
| 10,080,666 B2 | 9/2018 | Suddaby et al. |
| 10,080,669 B2 | 9/2018 | Davenport et al. |
| 10,085,846 B2 | 10/2018 | Grotz |
| 10,085,849 B2 | 10/2018 | Weiman et al. |
| 10,092,417 B2 | 10/2018 | Weiman et al. |
| 10,098,758 B2 | 10/2018 | Matthews et al. |
| 10,098,759 B2 | 10/2018 | Weiman |
| 10,111,755 B2 | 10/2018 | Foley et al. |
| 10,111,758 B2 | 10/2018 | Robinson |
| 10,117,754 B2 | 11/2018 | Davenport et al. |
| 10,117,755 B2 | 11/2018 | Emerick et al. |
| 10,137,002 B2 | 11/2018 | Padovani et al. |
| 10,137,006 B2 | 11/2018 | Dewey et al. |
| 10,137,007 B2 | 11/2018 | Dewey et al. |
| 10,137,009 B2 | 11/2018 | Weiman et al. |
| 10,149,671 B2 | 12/2018 | Predick et al. |
| 10,149,710 B2 | 12/2018 | Tanaka et al. |
| 10,154,781 B2 | 12/2018 | Weiman |
| 10,154,912 B2 | 12/2018 | Glerum |
| 10,154,914 B2 | 12/2018 | Robinson |
| 10,159,584 B2 | 12/2018 | Carnes et al. |
| 10,166,117 B1 | 1/2019 | Daffinson et al. |
| 10,172,515 B2 | 1/2019 | Lee et al. |
| 10,172,652 B2 | 1/2019 | Woolley et al. |
| 10,178,987 B2 | 1/2019 | Predick et al. |
| 10,179,053 B2 | 1/2019 | Zappacosta et al. |
| 10,182,922 B2 | 1/2019 | Nichols et al. |
| 10,188,527 B2 | 1/2019 | Rogers et al. |
| 10,195,050 B2 | 2/2019 | Palmatier et al. |
| 10,201,431 B2 | 2/2019 | Slater et al. |
| 10,213,192 B2 | 2/2019 | Capote |
| 10,213,193 B2 | 2/2019 | Karpowicz et al. |
| 10,219,798 B2 | 3/2019 | Capote |
| 10,219,913 B2 | 3/2019 | Matthews et al. |
| 10,219,914 B2 | 3/2019 | Faulhaber |
| 10,219,915 B1 | 3/2019 | Stein |
| 10,226,356 B2 | 3/2019 | Grotz |
| 10,226,359 B2 | 3/2019 | Glerum et al. |
| 10,238,375 B2 | 3/2019 | O'Connell et al. |
| 10,238,383 B2 | 3/2019 | Moskowitz et al. |
| 10,238,503 B2 | 3/2019 | Branch et al. |
| 10,245,015 B2 | 4/2019 | Predick et al. |
| 10,251,643 B2 | 4/2019 | Moskowitz et al. |
| 10,265,191 B2 | 4/2019 | Lim et al. |
| 10,278,686 B2 | 5/2019 | Baudouin et al. |
| 10,278,786 B2 | 5/2019 | Friedrich et al. |
| 10,278,830 B1 | 5/2019 | Walker et al. |
| 10,278,831 B2 | 5/2019 | Sandul |
| 10,278,832 B2 | 5/2019 | Nichols et al. |
| 10,285,680 B2 | 5/2019 | Friedrich et al. |
| 10,285,819 B2 | 5/2019 | Greenhalgh |
| 10,285,824 B2 | 5/2019 | Robinson |
| 10,292,828 B2 | 5/2019 | Greenhalgh |
| 10,299,777 B2 | 5/2019 | Mast et al. |

(56) References Cited

U.S. PATENT DOCUMENTS

| | | |
|---|---|---|
| 10,299,934 B2 | 5/2019 | Seifert et al. |
| 10,299,937 B2 | 5/2019 | McAfee |
| 10,307,268 B2 | 6/2019 | Moskowitz et al. |
| 10,314,719 B2 | 6/2019 | Hessler et al. |
| 10,322,007 B2 | 6/2019 | Masson et al. |
| 10,322,009 B2 | 6/2019 | Aghayev et al. |
| 10,327,909 B2 | 6/2019 | Baynham |
| 10,327,912 B1 | 6/2019 | Suddaby |
| 10,327,917 B2 | 6/2019 | Glerum et al. |
| 10,342,675 B2 | 7/2019 | Alheidt |
| 10,350,085 B2 | 7/2019 | Glerum et al. |
| 10,357,233 B2 | 7/2019 | Miles et al. |
| 10,363,142 B2 | 7/2019 | McClintock et al. |
| 10,363,144 B2 | 7/2019 | Overes et al. |
| 10,369,004 B2 | 8/2019 | Faulhaber |
| 10,369,008 B2 | 8/2019 | Jimenez et al. |
| 10,369,010 B2 | 8/2019 | Robinson et al. |
| 10,369,012 B2 | 8/2019 | Fessler |
| 10,376,377 B2 | 8/2019 | Seifert et al. |
| 10,390,962 B2 | 8/2019 | Weiman |
| 10,390,964 B2 | 8/2019 | Faulhaber |
| 10,398,563 B2 | 9/2019 | Engstrom |
| 10,398,566 B2 | 9/2019 | Olmos et al. |
| 10,413,419 B2 | 9/2019 | Thibodeau |
| 10,413,422 B2 | 9/2019 | Flower et al. |
| 10,413,423 B2 | 9/2019 | Overes et al. |
| 10,426,450 B2 | 10/2019 | Vogel et al. |
| 10,426,633 B2 | 10/2019 | Moskowitz et al. |
| 10,426,634 B1 | 10/2019 | Al-Jazaeri et al. |
| 10,441,430 B2 | 10/2019 | Ludwig et al. |
| 10,449,056 B2 | 10/2019 | Cain |
| 10,456,122 B2 | 10/2019 | Koltz et al. |
| 10,470,894 B2 | 11/2019 | Foley et al. |
| 10,478,319 B2 | 11/2019 | Moskowitz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,500,064 B2 | 12/2019 | Robinson |
| 10,512,550 B2 | 12/2019 | Bechtel et al. |
| 10,517,645 B2 | 12/2019 | van der Pol |
| 10,524,924 B2 | 1/2020 | Davenport et al. |
| 10,531,903 B2 | 1/2020 | Daly et al. |
| 10,537,436 B2 | 1/2020 | Maguire et al. |
| 10,537,438 B2 | 1/2020 | Martynova et al. |
| 10,555,729 B1 | 2/2020 | Cole et al. |
| 10,561,411 B1 | 2/2020 | Cole et al. |
| 10,575,960 B2 | 3/2020 | Duffield et al. |
| 10,583,015 B2 | 3/2020 | Olmos et al. |
| 10,603,078 B2 | 3/2020 | Simpson et al. |
| 10,610,376 B2 | 4/2020 | Kuyler et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,166 B2 | 5/2020 | Weiman et al. |
| 10,667,925 B2 | 6/2020 | Emerick et al. |
| 10,667,927 B2 | 6/2020 | Lamborne et al. |
| 10,675,157 B2 | 6/2020 | Zakelj et al. |
| 10,682,241 B2 | 6/2020 | Glerum et al. |
| 10,687,963 B2 | 6/2020 | Jimenez et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,572 B2 | 7/2020 | Daffinson et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,729,561 B2 | 8/2020 | Glerum |
| 10,743,858 B1 | 8/2020 | Cole et al. |
| 10,744,002 B2 | 8/2020 | Glerum et al. |
| 10,758,366 B2 | 9/2020 | Daffinson et al. |
| 10,758,367 B2 | 9/2020 | Weiman et al. |
| 10,758,369 B2 | 9/2020 | Rogers et al. |
| 10,765,528 B2 | 9/2020 | Weiman et al. |
| 10,772,737 B2 | 9/2020 | Gray et al. |
| 10,779,955 B2 | 9/2020 | Kuyler et al. |
| 10,779,957 B2 | 9/2020 | Weiman et al. |
| 10,786,364 B2 | 9/2020 | Davenport et al. |
| 10,786,369 B2 | 9/2020 | Carnes et al. |
| 10,799,368 B2 | 10/2020 | Glerum et al. |
| 10,835,387 B2 | 11/2020 | Weiman et al. |
| 10,842,640 B2 | 11/2020 | Weiman et al. |
| 10,842,644 B2 | 11/2020 | Weiman et al. |
| 10,856,997 B2 | 12/2020 | Cowan et al. |
| 10,869,769 B2 | 12/2020 | Eisen et al. |
| 10,874,523 B2 | 12/2020 | Weiman et al. |
| 10,874,524 B2 | 12/2020 | Bjork |
| 2002/0045943 A1 | 4/2002 | Uk |
| 2002/0045945 A1 | 4/2002 | Liu et al. |
| 2002/0116066 A1 | 8/2002 | Chauvin et al. |
| 2002/0128713 A1 | 9/2002 | Ferree |
| 2002/0151976 A1 | 10/2002 | Foley et al. |
| 2003/0050701 A1 | 3/2003 | Michelson |
| 2003/0130739 A1 | 7/2003 | Gerbec et al. |
| 2004/0172134 A1 | 9/2004 | Berry |
| 2004/0186570 A1 | 9/2004 | Rapp |
| 2004/0193158 A1 | 9/2004 | Lim et al. |
| 2004/0249461 A1 | 12/2004 | Ferree |
| 2004/0254643 A1 | 12/2004 | Jackson |
| 2004/0254644 A1 | 12/2004 | Taylor |
| 2005/0015149 A1 | 1/2005 | Michelson |
| 2005/0033429 A1 | 2/2005 | Kuo |
| 2005/0033439 A1 | 2/2005 | Gordon et al. |
| 2006/0122701 A1 | 6/2006 | Kiester |
| 2006/0129244 A1 | 6/2006 | Ensign |
| 2009/0024158 A1 | 1/2009 | Viker |
| 2009/0292361 A1 | 11/2009 | Lopez |
| 2010/0082109 A1 | 4/2010 | Greenhalgh et al. |
| 2010/0191336 A1 | 7/2010 | Greenhalgh |
| 2010/0211176 A1 | 8/2010 | Greenhalgh |
| 2011/0118843 A1 | 5/2011 | Mathieu et al. |
| 2011/0130838 A1 | 6/2011 | Morgenstern Lopez |
| 2011/0218572 A1 | 9/2011 | Lechmann et al. |
| 2012/0101581 A1 | 4/2012 | Mathieu et al. |
| 2012/0109142 A1 | 5/2012 | Dayan |
| 2012/0109309 A1 | 5/2012 | Mathieu et al. |
| 2012/0109310 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0197401 A1 | 8/2012 | Duncan et al. |
| 2012/0209385 A1 | 8/2012 | Aferzon |
| 2012/0215316 A1 | 8/2012 | Mohr et al. |
| 2013/0190876 A1 | 7/2013 | Drochner et al. |
| 2013/0226191 A1 | 8/2013 | Thoren et al. |
| 2013/0231747 A1 | 9/2013 | Olmos et al. |
| 2013/0317312 A1 | 11/2013 | Eastlack et al. |
| 2014/0107790 A1 | 4/2014 | Combrowski |
| 2014/0114420 A1 | 4/2014 | Robinson |
| 2014/0163682 A1 | 6/2014 | Iott et al. |
| 2014/0180419 A1 | 6/2014 | Dmuschewsky |
| 2014/0194992 A1 | 7/2014 | Medina |
| 2014/0277500 A1 | 9/2014 | Logan et al. |
| 2015/0223945 A1 | 8/2015 | Weiman et al. |
| 2015/0230931 A1 | 8/2015 | Greenhalgh |
| 2016/0008924 A1 | 1/2016 | Canourgues et al. |
| 2016/0022434 A1 | 1/2016 | Robinson |
| 2016/0081681 A1 | 3/2016 | Waugh et al. |
| 2016/0089247 A1 | 3/2016 | Nichols et al. |
| 2016/0095710 A1 | 4/2016 | Juszczyk et al. |
| 2016/0242930 A1 | 8/2016 | Duffield et al. |
| 2016/0256291 A1 | 9/2016 | Miller |
| 2016/0296340 A1 | 10/2016 | Gordon et al. |
| 2016/0310291 A1 | 10/2016 | Greenhalgh |
| 2016/0345952 A1 | 12/2016 | Kucharzyk et al. |
| 2016/0367377 A1 | 12/2016 | Faulhaber |
| 2017/0010025 A1 | 1/2017 | Mayershofer |
| 2017/0029635 A1 | 2/2017 | Doll et al. |
| 2017/0035406 A1 | 2/2017 | Abidin et al. |
| 2017/0049651 A1 | 2/2017 | Lim et al. |
| 2017/0049653 A1 | 2/2017 | Lim et al. |
| 2017/0095345 A1 | 4/2017 | Davenport et al. |
| 2017/0100255 A1 | 4/2017 | Hleihil et al. |
| 2017/0100257 A1 | 4/2017 | Weiman et al. |
| 2017/0105844 A1 | 4/2017 | Kuyler et al. |

(56) References Cited

U.S. PATENT DOCUMENTS

| | | |
|---|---|---|
| 2017/0151065 A1 | 6/2017 | Warren et al. |
| 2017/0156882 A1 | 6/2017 | Rathbun et al. |
| 2017/0156884 A1 | 6/2017 | Rathbun et al. |
| 2017/0189204 A1 | 7/2017 | Riemhofer et al. |
| 2017/0202678 A1 | 7/2017 | Duffield et al. |
| 2017/0215856 A1 | 8/2017 | Martinelli et al. |
| 2017/0224502 A1 | 8/2017 | Wolters et al. |
| 2017/0246006 A1 | 8/2017 | Carnes et al. |
| 2017/0290677 A1 | 10/2017 | Olmos et al. |
| 2017/0296352 A1 | 10/2017 | Richerme et al. |
| 2017/0367842 A1 | 12/2017 | Predick et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0030362 A1 | 2/2018 | Kosler et al. |
| 2018/0031810 A1 | 2/2018 | Hsu et al. |
| 2018/0036136 A1 | 2/2018 | Duffield et al. |
| 2018/0036138 A1 | 2/2018 | Robinson |
| 2018/0116891 A1 | 5/2018 | Beale et al. |
| 2018/0193164 A1 | 7/2018 | Shoshtaev |
| 2018/0206999 A1 | 7/2018 | Suddaby |
| 2018/0256356 A1 | 9/2018 | Robinson et al. |
| 2018/0256359 A1 | 9/2018 | Greenhalgh |
| 2018/0256360 A1 | 9/2018 | Cain |
| 2018/0256362 A1 | 9/2018 | Slivka et al. |
| 2018/0263784 A1 | 9/2018 | Bechtel et al. |
| 2018/0280142 A1 | 10/2018 | Schultz et al. |
| 2018/0303473 A1 | 10/2018 | Spann et al. |
| 2018/0303621 A1 | 10/2018 | Brotman et al. |
| 2018/0303625 A1 | 10/2018 | Alheidt et al. |
| 2018/0311048 A1 | 11/2018 | Glerum et al. |
| 2018/0318101 A1 | 11/2018 | Engstrom |
| 2018/0318102 A1 | 11/2018 | Seifert et al. |
| 2018/0338838 A1 | 11/2018 | Cryder et al. |
| 2018/0338841 A1 | 11/2018 | Miller et al. |
| 2018/0344307 A1 | 12/2018 | Hynes et al. |
| 2018/0360616 A1 | 12/2018 | Luu |
| 2019/0000640 A1 | 1/2019 | Weiman |
| 2019/0000702 A1 | 1/2019 | Lim et al. |
| 2019/0000707 A1 | 1/2019 | Lim et al. |
| 2019/0020121 A1 | 1/2019 | Paulotto et al. |
| 2019/0021716 A1 | 1/2019 | Waugh et al. |
| 2019/0021873 A1 | 1/2019 | Dmuschewsky |
| 2019/0046329 A1 | 2/2019 | Padovani et al. |
| 2019/0046381 A1 | 2/2019 | Lim et al. |
| 2019/0046383 A1 | 2/2019 | Lim et al. |
| 2019/0060083 A1 | 2/2019 | Weiman et al. |
| 2019/0082949 A1 | 3/2019 | Weiman |
| 2019/0083081 A1 | 3/2019 | Ortiz et al. |
| 2019/0091033 A1 | 3/2019 | Dewey et al. |
| 2019/0105175 A1 | 4/2019 | Zappacosta et al. |
| 2019/0125328 A1 | 5/2019 | Blain |
| 2019/0133434 A1 | 5/2019 | Lee et al. |
| 2019/0133645 A1 | 5/2019 | Gordon et al. |
| 2019/0133780 A1 | 5/2019 | Matthews et al. |
| 2019/0133784 A1 | 5/2019 | Gunn et al. |
| 2019/0133788 A1 | 5/2019 | Weiman et al. |
| 2019/0142480 A1 | 5/2019 | Woolley et al. |
| 2019/0151115 A1 | 5/2019 | Nichols et al. |
| 2019/0183656 A1 | 6/2019 | Stein |
| 2019/0201209 A1 | 7/2019 | Branch et al. |
| 2019/0201210 A1 | 7/2019 | Besaw et al. |
| 2019/0209155 A1 | 7/2019 | Mast et al. |
| 2019/0216453 A1 | 7/2019 | Predick et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0254650 A1 | 8/2019 | Martinelli et al. |
| 2019/0254838 A1 | 8/2019 | Miller et al. |
| 2019/0254839 A1 | 8/2019 | Nichols et al. |
| 2019/0262139 A1 | 8/2019 | Wolters |
| 2019/0269521 A1 | 9/2019 | Shoshtaev |
| 2019/0274670 A1 | 9/2019 | O'Connell et al. |
| 2019/0274671 A1 | 9/2019 | Lauf et al. |
| 2019/0274836 A1 | 9/2019 | Eisen et al. |
| 2019/0282373 A1 | 9/2019 | Alheidt |
| 2019/0290446 A1 | 9/2019 | Masson et al. |
| 2019/0290447 A1 | 9/2019 | Stein |
| 2019/0298416 A1 | 10/2019 | Rezach |
| 2019/0298524 A1 | 10/2019 | Lauf et al. |
| 2019/0298540 A1 | 10/2019 | Aghayev et al. |
| 2019/0321022 A1 | 10/2019 | Karpowicz et al. |
| 2019/0321190 A1 | 10/2019 | Wagner et al. |
| 2019/0328540 A1 | 10/2019 | Seifert et al. |
| 2019/0336301 A1 | 11/2019 | Engstrom |
| 2019/0336304 A1 | 11/2019 | Burkhardt et al. |
| 2019/0350573 A1 | 11/2019 | Vogel et al. |
| 2019/0358049 A1 | 11/2019 | Faulhaber |
| 2019/0358050 A1 | 11/2019 | Fessler |
| 2019/0358051 A1 | 11/2019 | Flower et al. |
| 2019/0380840 A1 | 12/2019 | Tyber et al. |
| 2019/0388232 A1 | 12/2019 | Purcell et al. |
| 2020/0008951 A1 | 1/2020 | McClintock et al. |
| 2020/0030114 A1 | 1/2020 | Cain |
| 2020/0030116 A1 | 1/2020 | Jimenez et al. |
| 2020/0038200 A1 | 2/2020 | Foley et al. |
| 2020/0054461 A1 | 2/2020 | Marrocco et al. |
| 2020/0060844 A1 | 2/2020 | Mathieu et al. |
| 2020/0078190 A1 | 3/2020 | Rogers et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0129306 A1 | 4/2020 | Miller et al. |
| 2020/0129307 A1 | 4/2020 | Hunziker et al. |
| 2020/0138591 A1 | 5/2020 | Moskowitz et al. |
| 2020/0138593 A1 | 5/2020 | Martynova et al. |
| 2020/0146840 A1 | 5/2020 | Black et al. |
| 2020/0205993 A1 | 7/2020 | Davenport et al. |
| 2020/0222202 A1 | 7/2020 | Kuyler et al. |
| 2020/0229944 A1 | 7/2020 | Suh et al. |
| 2020/0246159 A1 | 8/2020 | Suh et al. |
| 2020/0246162 A1 | 8/2020 | Schultz et al. |
| 2020/0261242 A1 | 8/2020 | Bost et al. |
| 2020/0268524 A1 | 8/2020 | Glerum et al. |
| 2020/0276028 A1 | 9/2020 | Blain et al. |
| 2020/0289287 A1 | 9/2020 | Emerick et al. |
| 2020/0297507 A1 | 9/2020 | Iott et al. |
| 2020/0330239 A1 | 10/2020 | Davenport et al. |
| 2020/0330245 A1 | 10/2020 | Glerum |
| 2020/0345511 A1 | 11/2020 | Daffinson et al. |
| 2020/0352731 A1 | 11/2020 | Berry |
| 2020/0352738 A1 | 11/2020 | Berry |
| 2020/0360153 A1 | 11/2020 | Weiman et al. |
| 2020/0375753 A1 | 12/2020 | McLaughlin et al. |
| 2020/0375755 A1 | 12/2020 | Cain |
| 2020/0383797 A1 | 12/2020 | Predick et al. |
| 2020/0383799 A1 | 12/2020 | Cain |
| 2020/0390565 A1 | 12/2020 | Jimenez et al. |
| 2020/0397593 A1 | 12/2020 | Davenport et al. |
| 2020/0405498 A1 | 12/2020 | Gray et al. |
| 2020/0405499 A1 | 12/2020 | Gerbec et al. |
| 2020/0405500 A1 | 12/2020 | Cain |

FOREIGN PATENT DOCUMENTS

| | | |
|---|---|---|
| EP | 0 880 950 A1 | 12/1998 |
| EP | 0 857 042 B1 | 11/2001 |
| EP | 1 442 732 A1 | 8/2004 |
| EP | 1 124 512 B1 | 9/2004 |
| EP | 1 107 711 B1 | 10/2004 |
| EP | 1 506 753 A1 | 2/2005 |
| EP | 1 459 711 B1 | 7/2007 |
| FR | 3082115 A1 | 12/2019 |
| GB | 2 377 387 A | 1/2003 |
| WO | 92/14423 A1 | 9/1992 |
| WO | 97/ 00054 A1 | 1/1997 |
| WO | 99/ 26562 A1 | 6/1999 |
| WO | 99/66867 A1 | 12/1999 |
| WO | 00/12033 A1 | 3/2000 |
| WO | 00/25706 A1 | 5/2000 |
| WO | 00/ 49977 A1 | 8/2000 |
| WO | 02/19952 A1 | 3/2002 |
| WO | 03/105673 A2 | 12/2003 |

(56) References Cited

FOREIGN PATENT DOCUMENTS

| WO | 2014/133755 A1 | 9/2014 |
| WO | 2017/168208 A1 | 10/2017 |
| WO | 2018049227 A1 | 3/2018 |

OTHER PUBLICATIONS

International Search Report and Written Opinion for Application No. PCT/US2019/019060, dated Jun. 5, 2019.
International Search Report and Written Opinion, PCT/IB2020/000942, dated Aug. 10, 2021.
International Search Report and Written Opinion, PCT/IB2020/000932, dated Jul. 29, 2021.

* cited by examiner

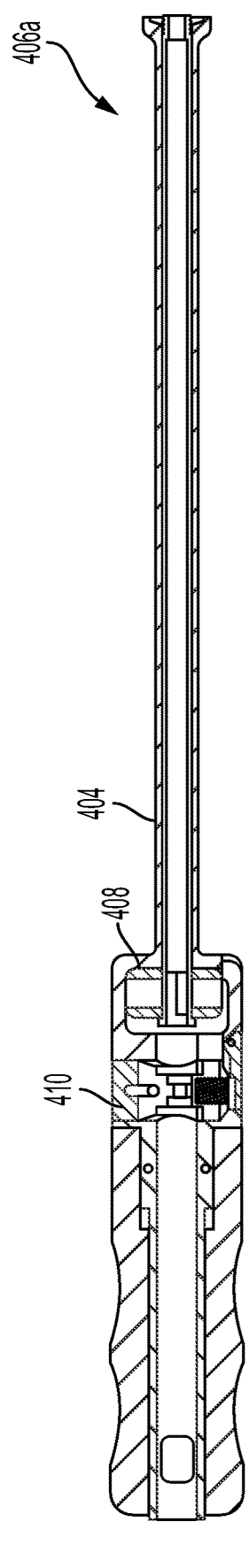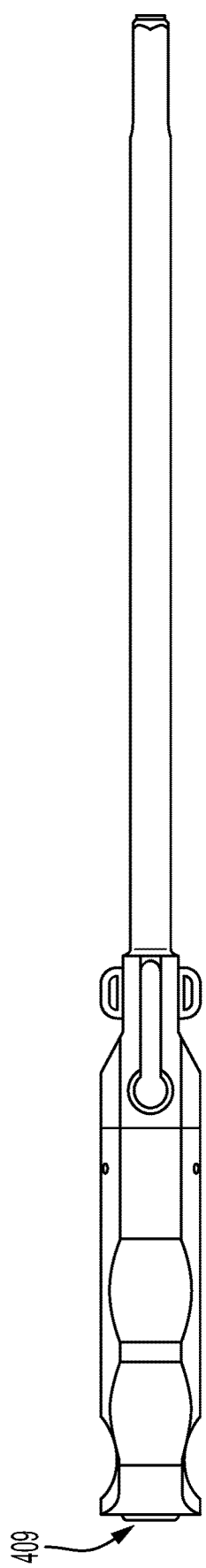
FIG. 19A
FIG. 19B

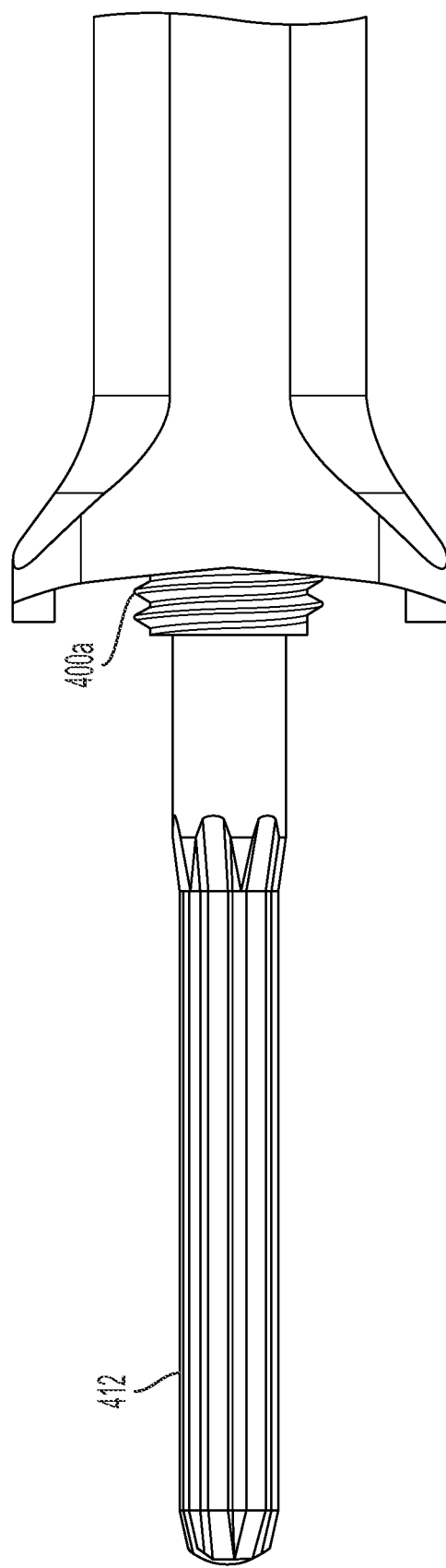

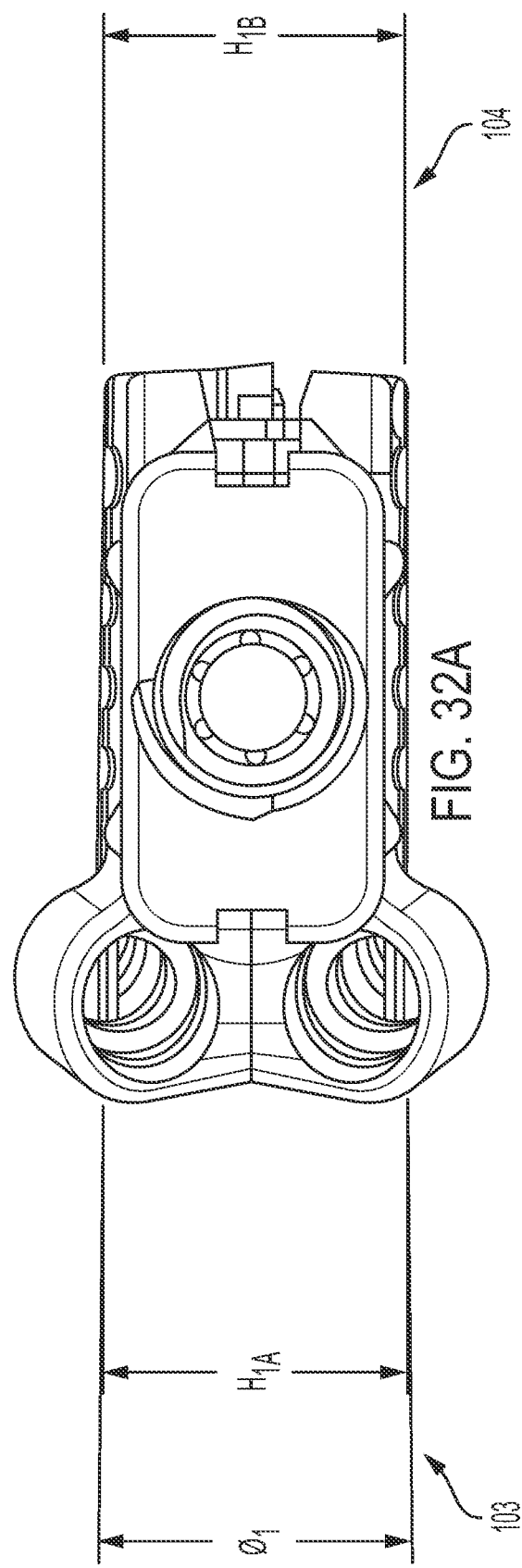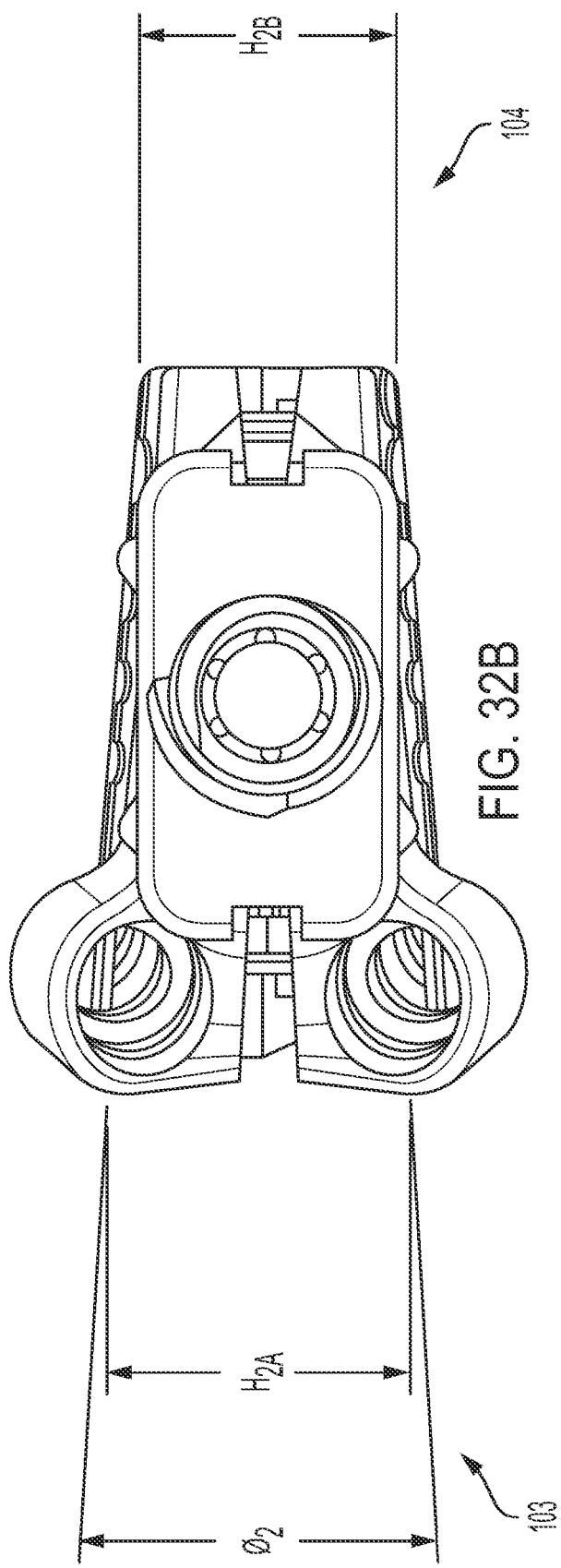

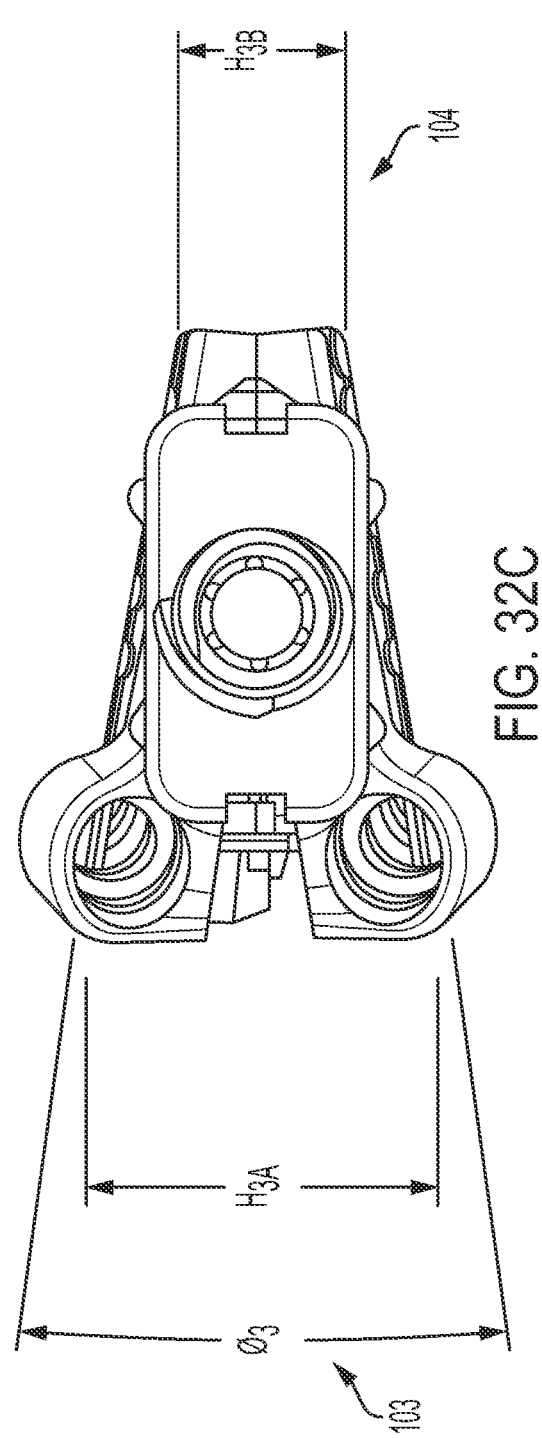
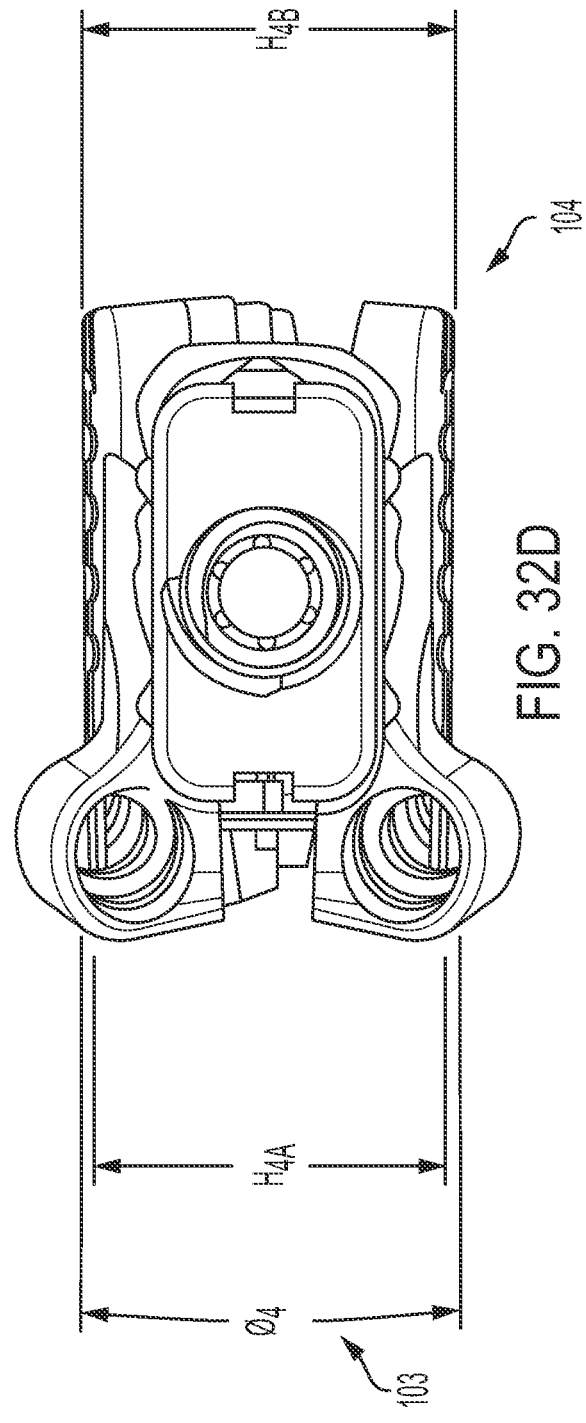

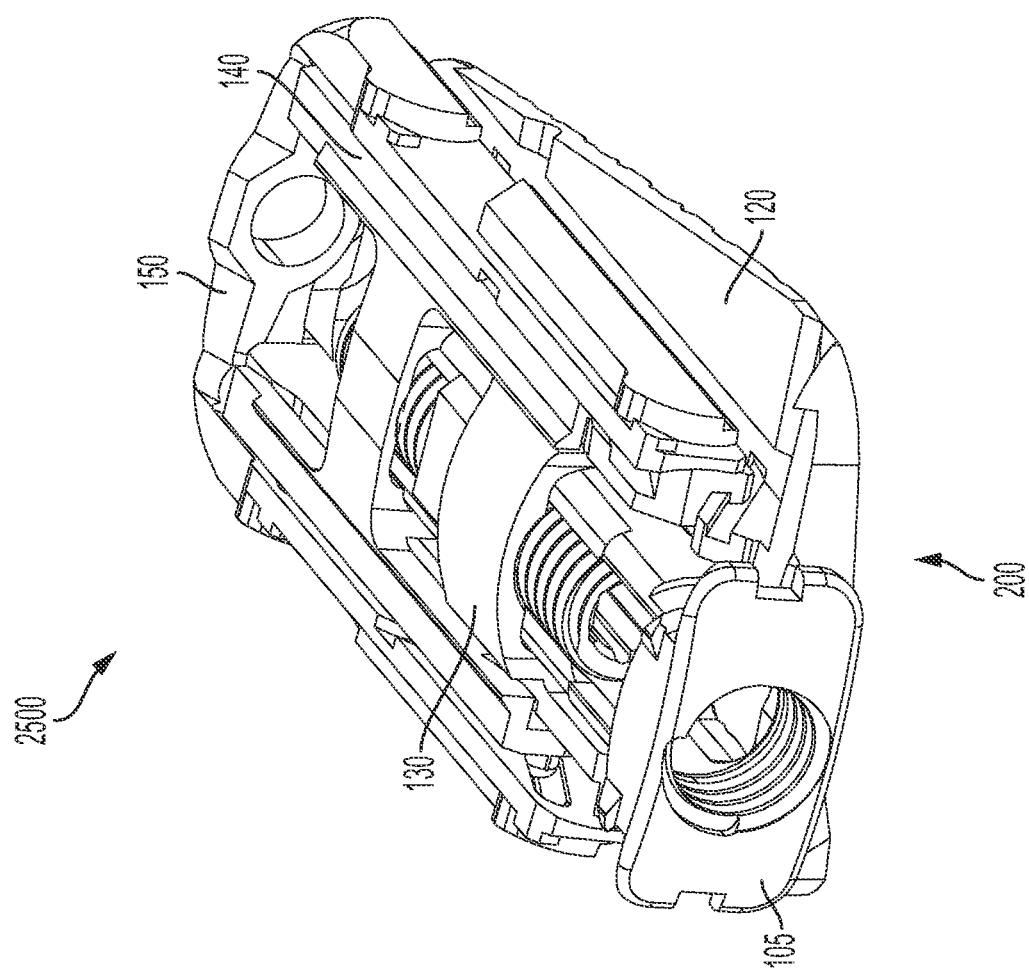

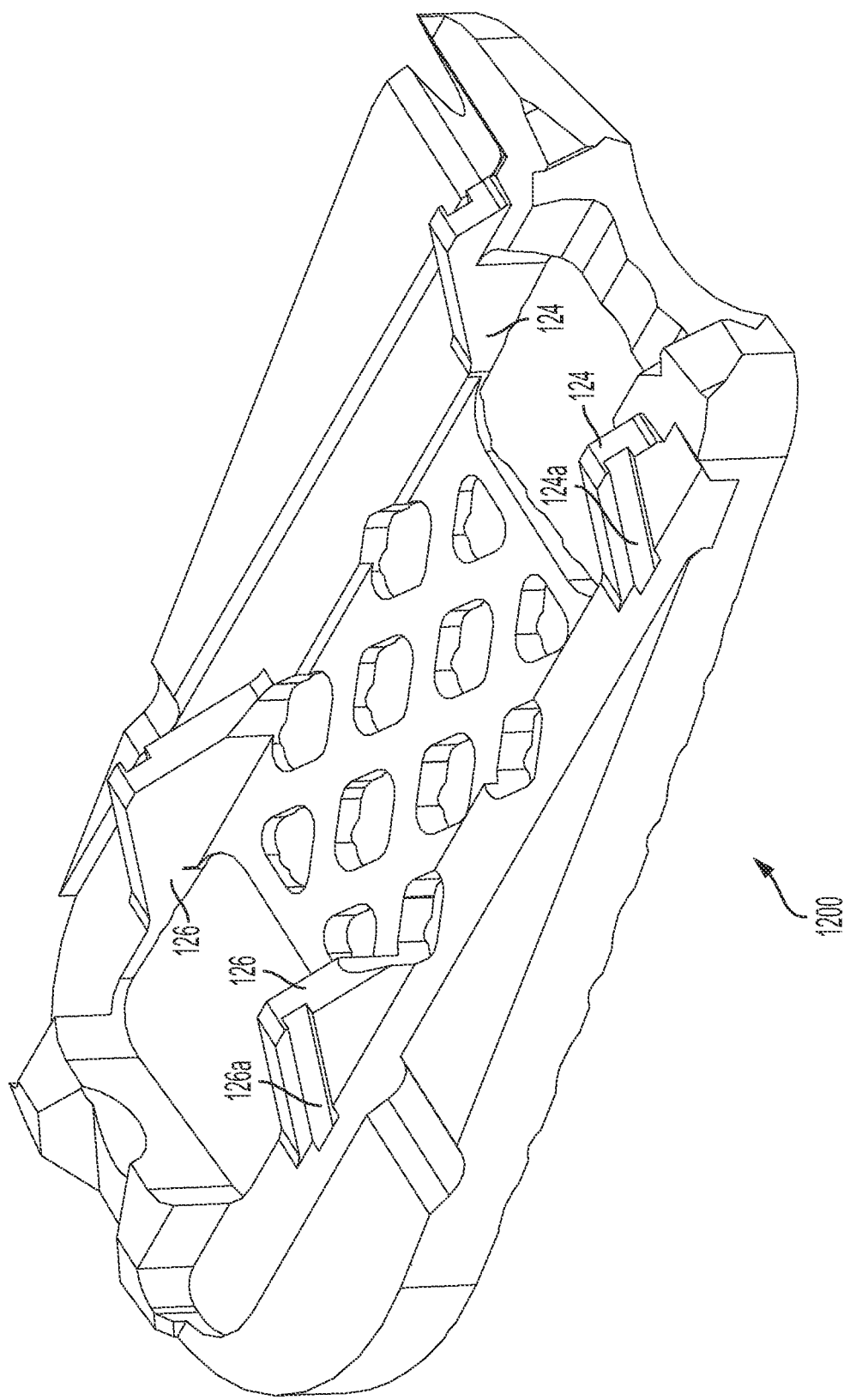

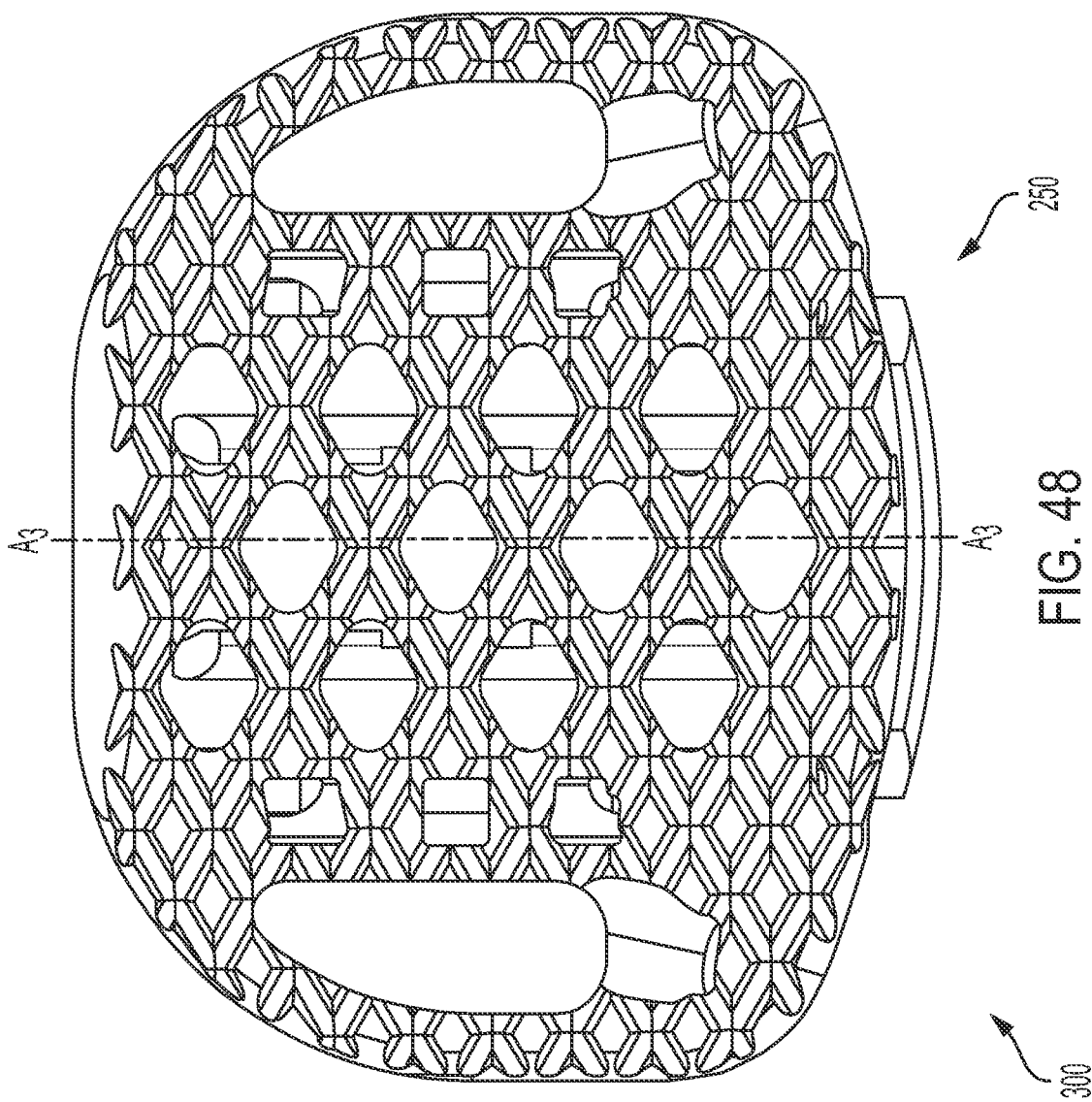

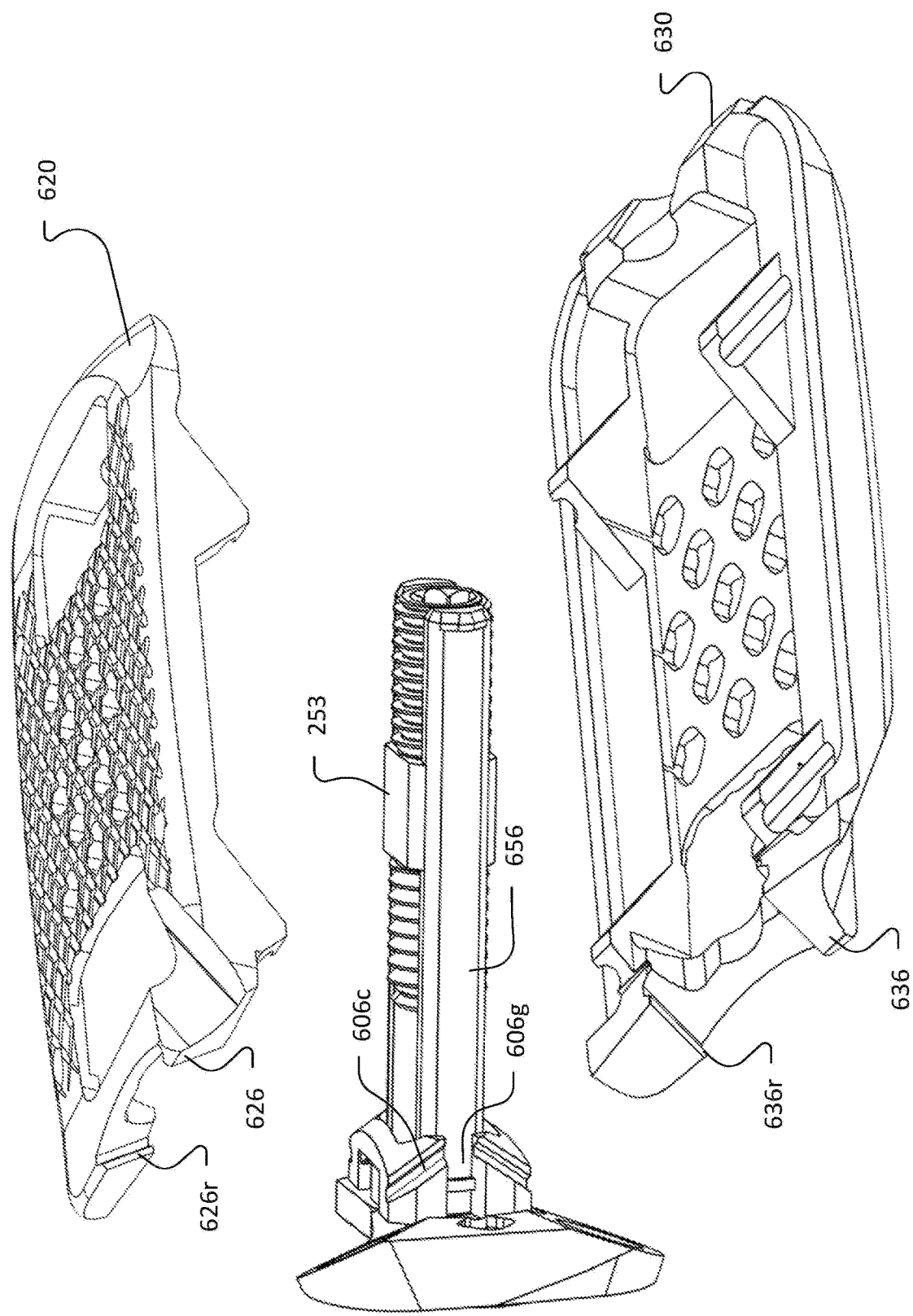

EXPANDABLE INTER-BODY DEVICE, SYSTEM, AND METHOD

CROSS-REFERENCE TO RELATED APPLICATIONS

This application is a continuation in part of U.S. patent application Ser. No. 17/123,897, titled Expandable Inter-Body Device, System, and Method, filed Dec. 16, 2020 which claims priority to and incorporates by reference co-related patent applications, PCT/FR2020/000257, titled Expandable Inter-Body Device, System, and Method, filed Nov. 5, 2020; PCT/FR2020/000259, titled Screwdriver and Complimentary Screws, filed Nov. 5, 2020; and PCT/FR2020/000258, titled Expandable Inter-Body Device, System, and Method, filed Nov. 5, 2020. The contents of each are hereby incorporated in their entireties.

FIELD

The present disclosure generally relates to medical devices for the treatment of musculoskeletal disorders, and more particularly to a surgical device that includes an expandable spinal implant, systems for implanting and manipulating the expandable spinal implant, and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, they may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, inter-body devices may be introduced to a space between adjacent vertebral bodies (the interbody space) to properly space the vertebral bodies and provide a receptacle for bone growth promoting materials, e.g., grafting.

More recently, interbody devices have been introduced that provide additional capability beyond static spacing of the vertebral bodies. For example, some devices have expansion capability such that the implant may be introduced to the interbody space in a collapsed state and then expanded to produce additional spacing and, in some cases, introduce or restore curvature to the spine by expanding selectively. However, many existing expandable interbody designs have limited ranges of expansion.

An additional problem exists related to subsidence of spinal surfaces due to existing interbody devices having inadequately-sized load-bearing surfaces. In the case of expandable devices, the loads on the load-bearing surfaces, including loads generated during expansion of the implant, are often significant. An expandable implant with relatively large surface areas is needed to bear the loads, including the loads generated during implant expansion, in an attempt to avoid a need for follow-on surgery due to subsidence of spinal surfaces.

A further problem is instability of existing expandable interbody devices as they are expanded. Often, the load-bearing surfaces move relative to one another, as well as relative to an inserter, as the interbody device is expanded such that there is a risk of undesired shifts in the positioning of the interbody device within the interverterbral space. Additionally, and depending at least partly on the particular insertion technique employed, anatomical features such as the iliac crest and rib cage pose challenges to the adjustment of inter-body designs in situ.

The present disclosure seeks to address these and other shortcomings in the existing relevant arts.

SUMMARY

The techniques of this disclosure generally relate to highly adjustable interbody devices that are expandable to selectively increase/decrease a spacing distance between endplates of the interbody device. Additionally, the disclosed interbody devices are selectively adjustable to increase/decrease an angle of inclination between endplates of the interbody device.

In one aspect, the present disclosure provides an expandable spinal implant deployable between a contracted position and an expanded position. The spinal implant may include a superior endplate having a first outside surface and a first inside surface opposite the first outside surface, a first proximal end and a first distal end opposite the first proximal end, and a first lateral surface and a second lateral surface opposite the first lateral surface, the first and second lateral surfaces extending between the first proximal end and the first distal end. The spinal implant may include a inferior endplate having a second outside surface and a second inside surface opposite the second outside surface, a second proximal end and a second distal end opposite the second proximal end, and a third lateral surface and a fourth lateral surface opposite the third lateral surface, the third and fourth lateral surfaces extending between the second proximal end and the second distal end. The spinal implant may include a proximal end plate having at least one bone screw aperture. The spinal implant may include a moving mechanism operably coupled to the superior endplate and the inferior endplate and positioned therebetween, the moving mechanism may have a wedge, a first sliding frame and a second sliding frame disposed on opposite sides of the wedge, a screw guide housing a rotatable first set screw and a rotatable second set screw opposite the first set screw, the first set screw being operably coupled to the second sliding frame and the second set screw being operably coupled to the wedge. In some embodiments, the first set screw and second set screw are configured to rotate in a first rotation direction and a second rotation direction about a rotation axis projecting in a longitudinal direction of the moving mechanism. In some embodiments, the moving mechanism is configured to operably adjust a spacing between the superior and inferior endplates upon simultaneous rotation of the first and second set screws along the rotation axis, and the moving mechanism is configured to operably adjust an angle of inclination between the superior and inferior endplates upon translating the first set screw or second set screw along the rotation axis.

In another aspect, the present disclosure provides that the second sliding frame is operably coupled to the first set screw and inferior endplate and movable in the longitudinal direction of the moving mechanism by rotation of the first set screw along the rotation axis.

In another aspect, the present disclosure provides that in some embodiments the second sliding frame includes a pair of first protrusions that are operably coupled to corresponding first channels of the first sliding frame, and upon movement of the second sliding frame in the longitudinal direction the first sliding frame also moves in the longitudinal direction.

In another aspect, the present disclosure provides that in some embodiments, the superior endplate further includes a first plurality of inclined ramps and the inferior endplate further includes a second plurality of inclined ramps.

In another aspect, the present disclosure provides that in some embodiments, the first plurality of inclined ramps further include a first plurality of grooves and the second plurality of inclined ramps includes a second plurality of grooves.

In another aspect, the present disclosure provides that in some embodiments, the first sliding frame further includes first distal contact surfaces and first proximate contact surfaces configured to act against the first plurality of inclined ramps of the superior endplate.

In another aspect, the present disclosure provides that in some embodiments, the first sliding frame further includes a first plurality of guide walls operably coupled to the first plurality of grooves of the superior endplate.

In another aspect, the present disclosure provides that in some embodiments the second sliding frame further includes a second plurality of guide walls operably coupled to the second plurality of grooves of the inferior endplate.

In another aspect, the present disclosure provides that in some embodiments, the second sliding frame further includes a third plurality of ramps.

In another aspect, the present disclosure provides that in some embodiments, the wedge further includes a plurality of engagement surfaces configured to operably engage the third plurality of ramps of the second sliding frame.

In another aspect, the present disclosure provides that in some embodiments, the wedge further includes a plurality of lateral protrusions.

In another aspect, the present disclosure provides that in some embodiments, the first sliding frame further includes a first plurality of channels and the wedge further includes a second plurality of protrusions operably coupled to the first plurality of channels of the first sliding frame.

In another aspect, the present disclosure provides that in some embodiments, the proximal end plate includes a plurality of attachment points radially disposed around a central aperture, for example.

In another aspect, the present disclosure provides that in some embodiments, at least one of the first outside surface and second outside surface includes a bone screw relief and the at least one bone screw aperture is configured to orient a bone screw such that it extends over the bone screw relief without coming into contact with it, for example.

In another aspect, the present disclosure provides that in some embodiments, the proximal end plate includes a contoured block having superior channels and inferior channels, the superior endplate includes medial proximal rails seated within the superior channels, respectively, and the inferior endplate includes medial proximal rails seated within the inferior channels, respectively, for example.

In another aspect, the present disclosure provides that in some embodiments, the at least one bone screw aperture comprises a superior bone screw aperture and an inferior bone screw aperture, the superior endplate comprises a superior bone screw relief, and the inferior endplate comprises an inferior bone screw relief, for example. In various embodiments, the superior bone screw aperture may be configured to orient a corresponding superior bone screw such that it extends across the superior bone screw relief without coming into contact with it, for example. In various embodiments, the inferior bone screw aperture may be configured to orient a corresponding inferior bone screw such that it extends across the inferior bone screw relief without coming into contact with it, for example.

In another aspect, the present disclosure provides that in some embodiments, the superior bone screw aperture may be configured to orient the corresponding superior bone screw such that it extends diagonally across the superior endplate at a first angle with respect to the first lateral surface, for example Additionally, the inferior bone screw aperture may be configured to orient the corresponding inferior bone screw such that it extends diagonally across the inferior endplate at a second angle with respect to the third lateral surface, and the first angle and second angle may be different, for example.

In another aspect, the present disclosure provides that in some embodiments, the proximal end plate includes at least one bone screw lock, and the at least one bone screw lock is rotatable between an unlocked position and a locked position, for example. Additionally, in various embodiments, when the at least one bone screw lock is in the locked position, the at least one bone screw lock prevents the corresponding superior bone screw and the corresponding inferior bone screw from backing out, for example.

In another aspect, the present disclosure provides a spinal implant system adjustable in situ between vertebral bodies of a patient. The system may include an expandable spinal implant deployable between a contracted position and an expanded position. The spinal implant may include a superior endplate having a first outside surface and a first inside surface opposite the first outside surface, a first proximal end and a first distal end opposite the first proximal end, and a first lateral surface and a second lateral surface opposite the first lateral surface, the first and second lateral surfaces extending between the first proximal end and the first distal end. The spinal implant may include a inferior endplate having a second outside surface and a second inside surface opposite the second outside surface, a second proximal end and a second distal end opposite the second proximal end, and a third lateral surface and a fourth lateral surface opposite the third lateral surface, the third and fourth lateral surfaces extending between the second proximal end and the second distal end. The spinal implant may include a proximal end plate having at least one bone screw aperture. The spinal implant may include a moving mechanism operably coupled to the superior endplate, inferior endplate, and proximal end plate, for example. The moving mechanism may have a wedge, a first sliding frame and a second sliding frame disposed on opposite sides of the wedge, a screw guide housing a rotatable first set screw and a rotatable second set screw opposite the first set screw, the first set screw being operably coupled to the second sliding frame and the second set screw being operably coupled to the wedge. In some embodiments, the first set screw and second set screw are configured to rotate in a first rotation direction and a second rotation direction about a rotation axis projecting in a longitudinal direction of the moving mechanism. In some embodiments, the moving mechanism is configured to operably adjust a spacing between the superior and inferior endplates upon simultaneous rotation of the first and second set screws along the rotation axis, and the moving mechanism is configured to operably adjust an angle of inclination between the superior and inferior endplates upon translating the first set screw or second set screw along the rotation axis. Additionally, the system may include a first surgical tool configured to adjust the expandable spinal implant and a second surgical tool configured to install at least one anchoring screw.

In another aspect, the present disclosure provides an expandable spinal implant, including a superior endplate and an inferior endplate extending in a longitudinal direction. In various embodiments, at least one of the superior endplate and inferior endplate have at least one bone screw relief. The spinal implant may include a proximal end plate having at least one bone screw aperture configured to orient a bone screw such that the bone screw extends across the at least one bone screw relief and the proximal end plate may be operably coupled to the superior endplate and the inferior endplate, for example. The spinal implant may further include a wedge and a sliding frame operably coupled to the wedge, at least one of the wedge and sliding frame being operably coupled to one endplate of the superior and inferior endplates, and a moving mechanism operably coupled to the wedge and sliding frame, the moving mechanism defining a rotation axis extending in the longitudinal direction. In some embodiments, the moving mechanism is configured to selectively move at least one of the wedge and sliding frame forward/backward in the longitudinal direction. In some embodiments, upon moving both the wedge and sliding frame simultaneously forward/backward the superior and inferior endplates expand/contract with respect to one another, and the wedge and sliding frame are further configured to selectively rotate, at least partially, about the rotation axis upon movement of the wedge in the longitudinal direction to thereby adjust an inclination of the superior endplate with respect to the inferior endplate in a lateral direction perpendicular to the longitudinal direction.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 19A-19B are side views of a first surgical tool for use with disclosed expandable spinal implants in accordance with the principles of the present disclosure;

FIG. 22 is an enlarged side view of a tip portion of the first surgical tool of FIG. 21 in accordance with the principles of the present disclosure;

FIGS. 32A-32F are various side views illustrating some exemplary expansion ranges of an expandable spinal implant in accordance with the principles of the present disclosure;

FIG. 45 is perspective view of a top endplate for use with the embodiment of FIG. 43 in accordance with the principles of the present disclosure;

FIG. 46B is perspective view of an endplate for use with the embodiment of FIG. 43 in accordance with the principles of the present disclosure;

FIG. 48 is a top down view of the embodiment of FIG. 47 in accordance with the principles of the present disclosure;

FIG. 53B is an exploded parts view of an example proximal end plate, top endplate, and bottom endplate in accordance with the principles of the present disclosure;

DETAILED DESCRIPTION

Figure 1:
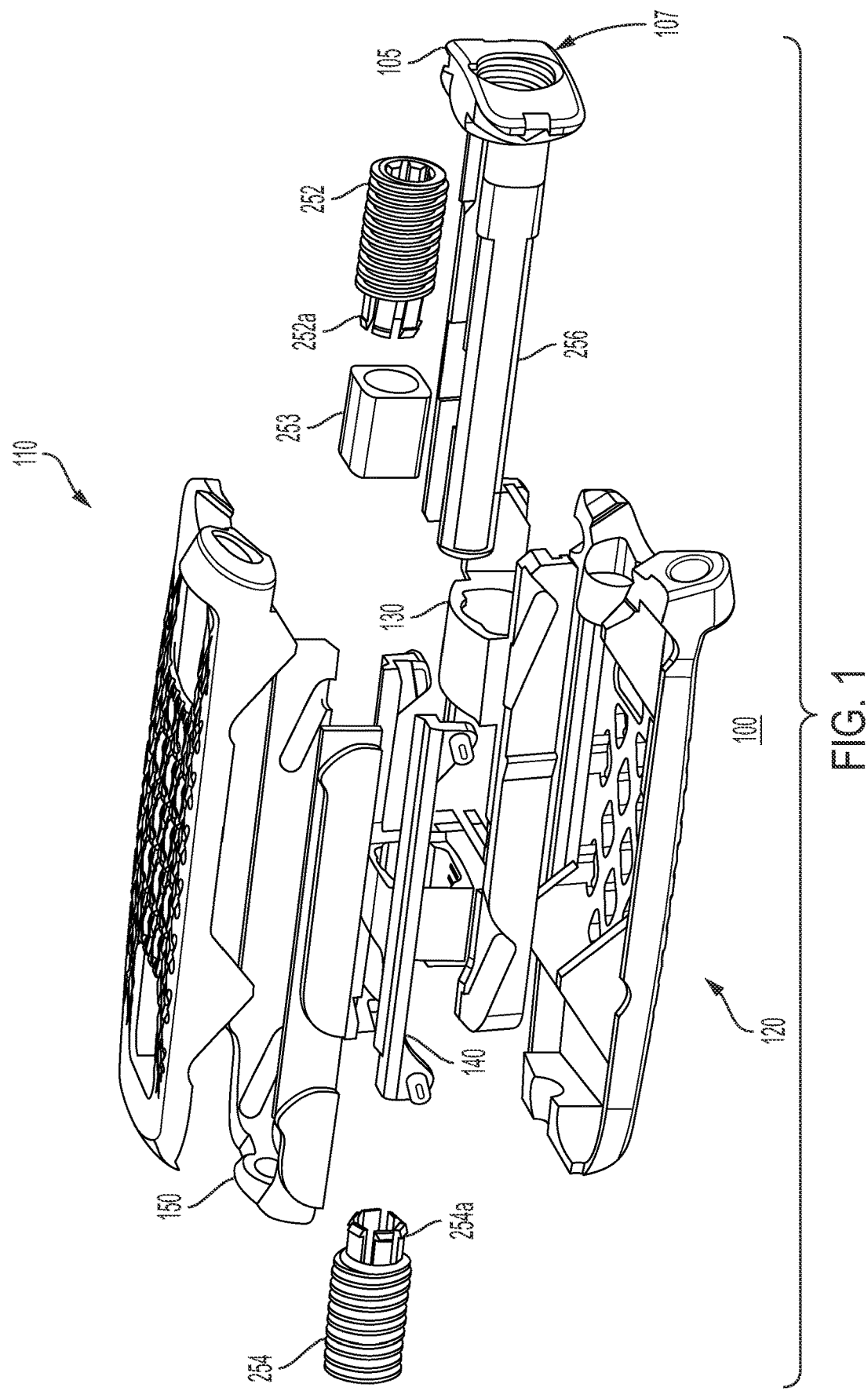
FIG. 1 is an exploded parts view of an expandable spinal implant in accordance with the principles of the present disclosure.

The exemplary embodiments of, for example, an anterior expandable inter-body device, lateral expandable inter-body device, inter-body device systems, and inter-body device methods of use are discussed in terms of medical devices for the treatment of musculoskeletal disorders and more particularly, in terms of various inter-body devices suitable as spinal implants for anterior surgical techniques, oblique surgical techniques, and lateral surgical techniques. Exemplary embodiments are also discussed with related emphasis on specialized adjustment instruments such as, for example, an instrument capable of adjusting a spacing of the aforementioned various interbody devices between adjacent vertebrates of a spine by expansion and contraction as well as adjusting an angle of inclination with respect to the coronal plane and/or sagittal plane of a patient. Disclosed devices and systems may be capable of adjusting the curvature of a patient's spine for lordosis correction and a kyphosis correction. Likewise, an instrument capable of installing various anchoring screws is described in conjunction with disclosed inter-body devices. Apertures for receiving anchoring screws may optionally be provided on one of the top or bottom portions of the implant, both, or neither, to the extent desired to further secure the implant to the vertebra after insertion in the disc space. Although disclosed, for example, as one aperture on each of the top and bottom, multiple apertures can be provided on either the top or bottom portion or both. Additionally, such apertures may be formed along the proximal end of the implant in various positions, including adjacent to the corner or corners of the proximal face of the implant or near the center of the proximal face of the implant.

As used herein, standard anatomical terms of location have their ordinary meaning as they would be understood by a person of ordinary skill in the art unless clearly defined or explained otherwise. It should be understood that various aspects disclosed herein may be combined in different combinations than the combinations specifically presented in the description and accompanying drawings. For example, characteristics of one embodiment may be combined or substituted with characteristics of another different embodiment unless those characteristics are clearly explained as being mutually exclusive. It should also be understood that, depending on the example, certain acts or events of any of the processes or methods described herein may be performed in a different sequence, may be added, merged, or left out altogether (e.g., all described acts or events may not be necessary to carry out the disclosed techniques and methods). In addition, while certain aspects of this disclosure are described as being performed by a single module or unit for purposes of clarity, it should be understood that the techniques of this disclosure may be performed by a combination of units or modules associated with, for example, a medical device.

In some embodiments, the present system includes an expandable spinal implant suitable for insertion for oblique techniques, postero-lateral procedures and/or transforaminal lumbar interbody fusions (sometimes referred to as TLIF procedures), direct posterior (sometimes referred to as PLIF procedures), direct lateral (sometimes referred to as DLIF procedures), anterior lumbar interbody fusions (sometimes referred to as ALIF procedures), or variations of these procedures, in which the present implant is inserted into an interverterbral space and then expanded in order to impart and/or augment a lordotic and/or kyphotic curve of the spine.

In some embodiments, the spinal implant system may also be employed to restore and/or impart sagittal balance to a patient by increasing and/or restoring an appropriate lordotic and/or kyphotic angle between vertebral bodies at a selected level where the spinal implant is implanted and expanded. Additionally, some embodiments may also be employed to restore and/or impart coronal balance for correction of, for example, scoliosis. In the various embodiments described, the spinal implant system may be useful in a variety of complex spinal procedures for treating spinal conditions beyond one-level fusions. Furthermore, the spinal implant system described in the enclosed embodiments may also be used as a fusion device with an expandable height for tailoring the implant to a particular interbody disc space to restore the spacing between adjacent vertebral bodies and facilitate spinal fusion between the adjacent vertebral bodies.

In some embodiments, and as mentioned above, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral oblique, and/or antero lateral oblique approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Generally, similar spatial references of different aspects or components, e.g., a "proximal end" of an end plate and a "proximal end" of a wedge, indicate similar spatial orientation and/or positioning, i.e., that each "proximal end" is situated on or directed towards the same end of the device. Further, the use of various spatial terminology herein should not be interpreted to limit the various insertion techniques or orientations of the implant relative to the positions in the spine.

As used in the specification and including the appended claims, "treating" or "treatment" of a disease or condition refers to performing a procedure that may include administering one or more drugs, biologics, bone grafts (including allograft, autograft, xenograft, for example) or bone-growth promoting materials to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise. The term "bone growth promoting material" as used herein may include, but is not limited to: bone graft (autograft, allograft, xenograft) in a variety of forms and compositions (including but not limited to morselized bone graft); osteoinductive material such as bone morphogenetic proteins (BMP) (including but not limited to INFUSE® available from Medtronic) and alternative small molecule osteoinductive substances; osteoconductive materials such as demineralized bone matrix (DBM) in a variety of forms and compositions (putty, chips, bagged (including but not limited to the GRAFTON® family of products available from Medtronic)); collagen sponge; bone putty; ceramic-based void fillers; ceramic powders; and/or other substances suitable for inducing, conducting or facilitating bone growth and/or bony fusion of existing bony structures. Such bone growth promoting materials may be provided in a variety of solids, putties, liquids, colloids, solutions, or other preparations suitable for being packed or placed into or around the various implants 100, 200, 300 and embodiments described herein.

The components of the expandable spinal implant systems described herein can be fabricated from biologically acceptable materials suitable for medical applications, including metals, synthetic polymers, ceramics and bone material and/or their composites. For example, the components of expandable spinal implant system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaprolactone and their combinations.

Various components of spinal implant system may be formed or constructed of material composites, including but not limited to the above-described materials, to achieve various desired characteristics such as strength, rigidity, elasticity, compliance, biomechanical performance, durability and radiolucency or imaging preference. The components of expandable spinal implant system, individually or collectively, may also be fabricated from a heterogeneous material such as a combination of two or more of the above-described materials. The components of the expandable spinal implant systems may be monolithically formed, integrally connected or include fastening elements and/or instruments, as described herein. For example, in some embodiments the expandable spinal implant systems may comprise expandable spinal implants 100, 200, 300 comprising PEEK and/or titanium structures (or combinations thereof) with radiolucent markers (such as tantalum pins and/or spikes) selectively placed in the implant to provide a medical practitioner with placement and/or sizing information when the expandable spinal implant 100, 200, 300 may be placed in the spine. The components of the expandable spinal implant system may be formed using a variety of subtractive and additive manufacturing techniques, including, but not limited to machining, milling, extruding, molding, 3D-printing, sintering, coating, vapor deposition, and laser/beam melting. These components and/or implants may further be customized or custom made for a specific patient or patient population. Furthermore, various components of the expandable spinal implant system may be coated or treated with a variety of additives or coatings to improve biocompatibility, bone growth promotion or other features. For example, endplates 110, 120, may be selectively coated with bone growth promoting or bone ongrowth promoting surface treatments that may include, but are not limited to: titanium coatings (solid, porous or textured), hydroxyapatite coatings, or titanium plates (solid, porous or textured), and/or may have various nano-coated or nano-sized features for enhanced bone ingrowth surfaces.

The expandable spinal implant system may be employed, for example, with a minimally invasive procedure, including percutaneous techniques, mini-open and open surgical techniques to deliver and introduce instrumentation and/or one or more spinal implants at a surgical site within a body of a patient, for example, a section of a spine. In some embodiments, the expandable spinal implant system may be employed with surgical procedures, as described herein, and/or, for example, corpectomy, discectomy, fusion and/or fixation treatments that employ spinal implants to restore the mechanical support function of vertebrae. In some embodiments, the expandable spinal implant system may be employed with surgical approaches, including but not limited to: anterior lumbar interbody fusions (ALIF), posterior lumbar interbody fusion (PLIF), oblique lumbar interbody fusion, transforaminal lumbar interbody fusion (TLIF), various types of anterior fusion procedures, and any fusion procedure in any portion of the spinal column (sacral, lumbar, thoracic, and cervical, for example).

Figure 63:
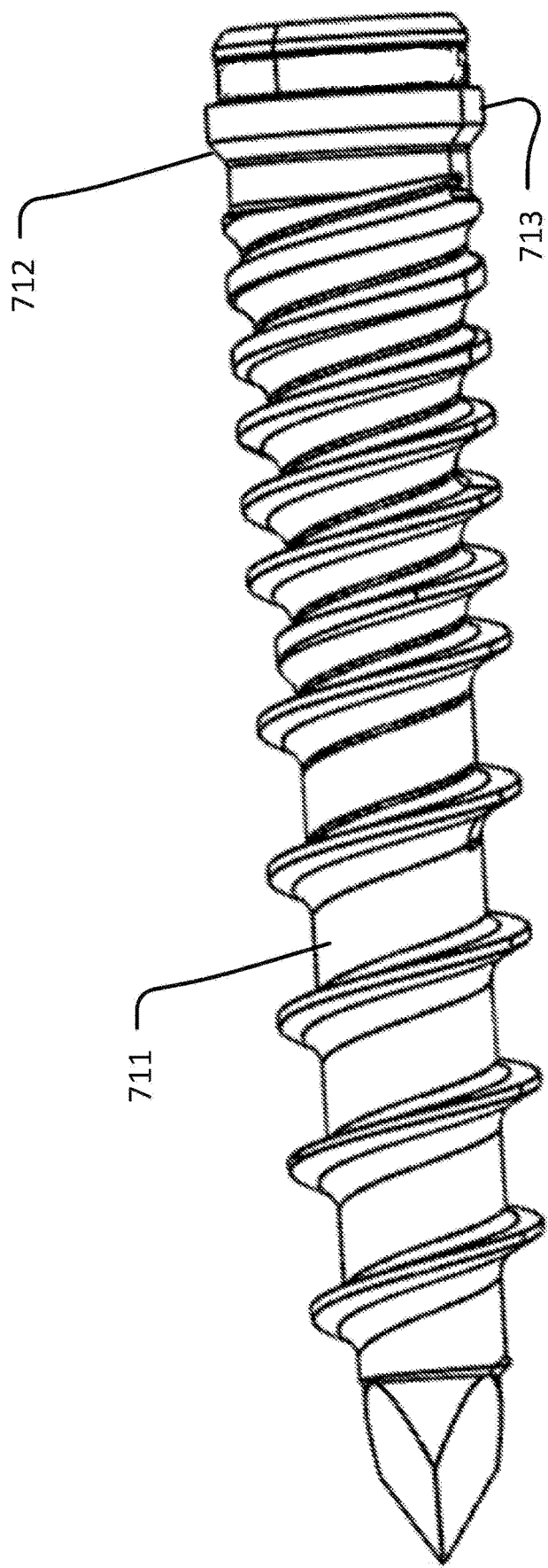
FIG. 63 is a side view of an example bone screw in accordance with the principles of the present disclosure.
Figure 64:
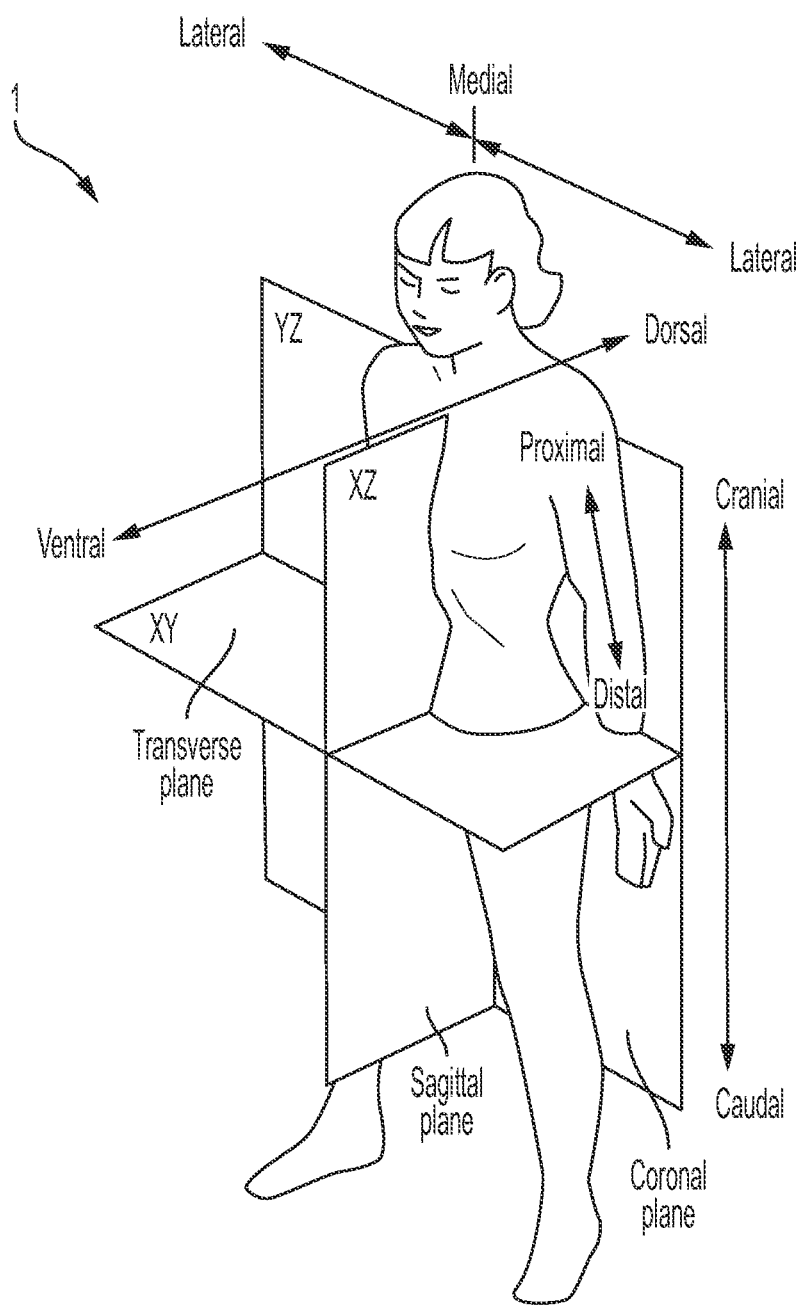
FIG. 64 is a reference diagram illustrating various cardinal directions and planes with respect to a patient that the various exemplary embodiments disclosed herein may operate, adjust, and/or move along in accordance with the principles of the present disclosure.

Generally in FIGS. 1-50, exemplary embodiments of expandable spinal implants 100, 200, and 300 are shown. Exemplary embodiments of surgical tools 400, 450, and 500 are highlighted in exemplary FIGS. 18A-24B and 38A-39C and are disclosed in conjunction with expandable spinal implant 100 as an inter-body spinal implant system. For example, surgical tools 400, 450, and 500 are discussed concurrently with exemplary spinal implant 100. It shall be understood that the same or similar surgical tools highlighted in exemplary FIGS. 18A-24B and 38A-39C may be employed with expandable spinal implants 100, 200, and 300. Similar and/or identical numbering of corresponding elements may be used interchangeably between the two exemplary embodiments of an expandable spinal implants 100, 200, and 300 for ease of understanding and convenience in explanation. For example, moving mechanism 250 is predominately discussed concurrently with exemplary spinal implant 100 although the same or similar moving mechanism 250 may be employed with expandable spinal implant 200. FIG. 63 is provided solely as a reference illustration showing a patient 1 and various standard medical terms and orientations with respect to cardinal directions and planes of the body of patient 1 in which expandable spinal implants 100 and 200 may act.

Referring generally to FIGS. 1-42 exemplary expandable spinal implant 100, moving mechanism 250, first surgical tool 400, and second surgical tool 500 are illustrated. Spinal implant 100 may be configured to be inserted in an intervertebral disc space between adjacent vertebral bodies accordingly to a variety of surgical techniques, e.g., anterior techniques, oblique techniques, and lateral techniques. Referring generally to FIGS. 43-46 a second exemplary expandable spinal implant 200 is illustrated. Spinal implant 200 may be configured to be inserted in an intervertebral disc space between adjacent vertebral bodies accordingly to a variety of surgical techniques, e.g., anterior techniques, and oblique techniques.

Figure 2:
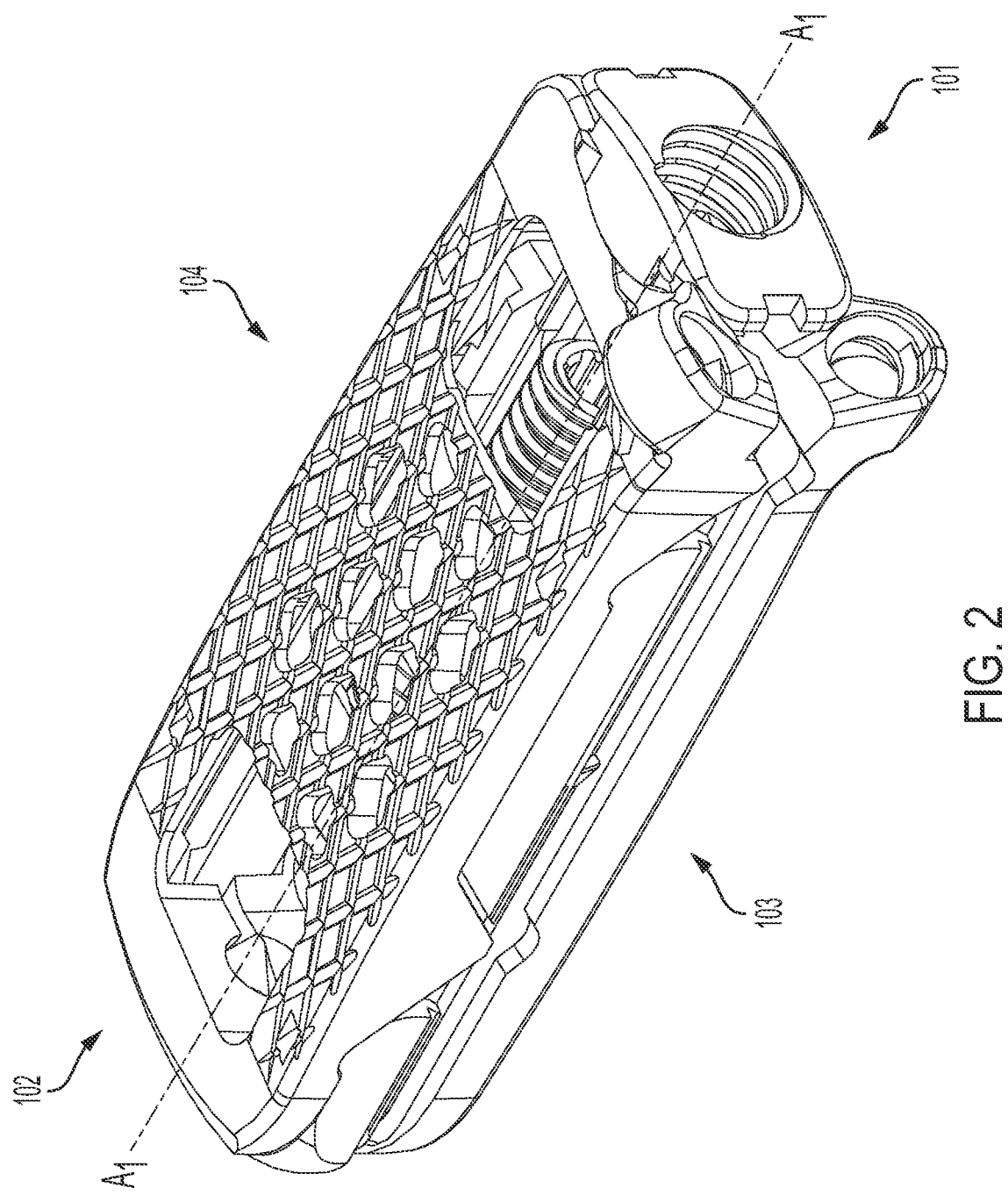
FIG. 2 is a perspective view of an expandable spinal implant in accordance with the principles of the present disclosure.

FIG. 1 is an exploded parts view of an expandable spinal implant 100 and FIG. 2 is a perspective view of the expandable spinal implant 100 in accordance with the principles of the present disclosure. Exemplary spinal implant 100 includes a top endplate 110 (first endplate) and a bottom endplate 120 (inferior endplate) and a moving mechanism 250. Spinal implant 100 includes a proximal end 101 and a distal end 102 opposite the proximal end 101, and a first lateral end 103 and a second lateral end 104 opposite the first lateral end 103. The first and second lateral ends 103, 104 extend between the proximal end 101 and the distal end 102. The proximal end 101 may, for example, include one or more exposed screw guide endplates 105 defining a corresponding screw guide aperture 107, or multiple apertures, if any, which are disposed between endplates 110 and 120. The screw guide endplate 105 and screw guide aperture 107 will be described in greater detail below. Additionally, it shall be understood that reference to other parts of spinal implant 100 may be in terms of the above orientation with reference to spinal implant 100 generally, e.g., endplate 110 may also include a proximal end 101 and a distal end 102 opposite the proximal end 101, and a first lateral end 103 and a second lateral end 104 opposite the first lateral end 103.

Exemplary spinal implant 100 includes a moving mechanism 250 that may be operably coupled to top endplate 110 and bottom endplate 120 as will be explained in greater detail below. Moving mechanism 250 may include, for example, a first set screw 252 and an axially aligned second set screw 254. First and second set screws 252, 254 each may feature a retaining portion 252a, 254a that may be operably coupled to an interior retaining portion of sliding block 253. Sliding block 253 may be retained within a central guide cavity of screw guide body 256 and configured to slide back and forth within central guide cavity along rail portion 256a (see FIG. 13) while coupled to first and second set screws 252, 254. First and second set screws 252, 254 may be configured to rotate about first reference axis $A_1$ and slide forward/backward via sliding block 253 along rotation axis $A_1$. In the disclosed embodiment, rotation axis $A_1$ extends longitudinally along the center of expandable spinal implant and may be defined, at least partly, by first and second set screws 252, 254. First reference axis $A_1$ may be understood as a projection passing through a central portion of screw guide aperture 107 in a direction parallel to an extension direction of screw guide body 256. First reference axis $A_1$ may also be understood as a rotation axis that first and second set screws 252, 254 may rotate about. Additionally, first and second set screws 252, 254 may move forward and backward along first reference axis $A_1$.

Exemplary spinal implant 100 may further include a bottom sliding frame 130, an angled wedge 140, and a top sliding frame 150 that are operably coupled to each other. Additionally, bottom sliding frame 130 may be operably coupled to first set screw 252 and angled wedge 140 may be operably coupled to second set screw 254. Bottom sliding frame 130, angled wedge 140, and top sliding frame 150 may be configured to move forward and backwards by rotation of first and second screws 252, 254. As will be explained in further detail below, the various geometries of the acting surfaces between bottom sliding frame 130, angled wedge 140, and top sliding frame 150 may facilitate the expansion/contraction and angular adjustment of endplates 110, 120 of expandable spinal implant 100.

A first functional feature of moving mechanism 250 is that it may be further configured to increase and decrease a spacing between the top and bottom endplates 110, 120 upon simultaneous rotation of the first and second set screws 252, 254 in a clockwise and counterclockwise direction, respectively. A second functional feature of moving mechanism 250 is that it may be further configured to increase and decrease an angle of inclination between the top and bottom endplates 110, 120 upon rotation of the first set screw 252 in a clockwise and counterclockwise direction, respectively. Additional functions and attributes of moving mechanism 250 will be described in greater detail below.

Figure 3:
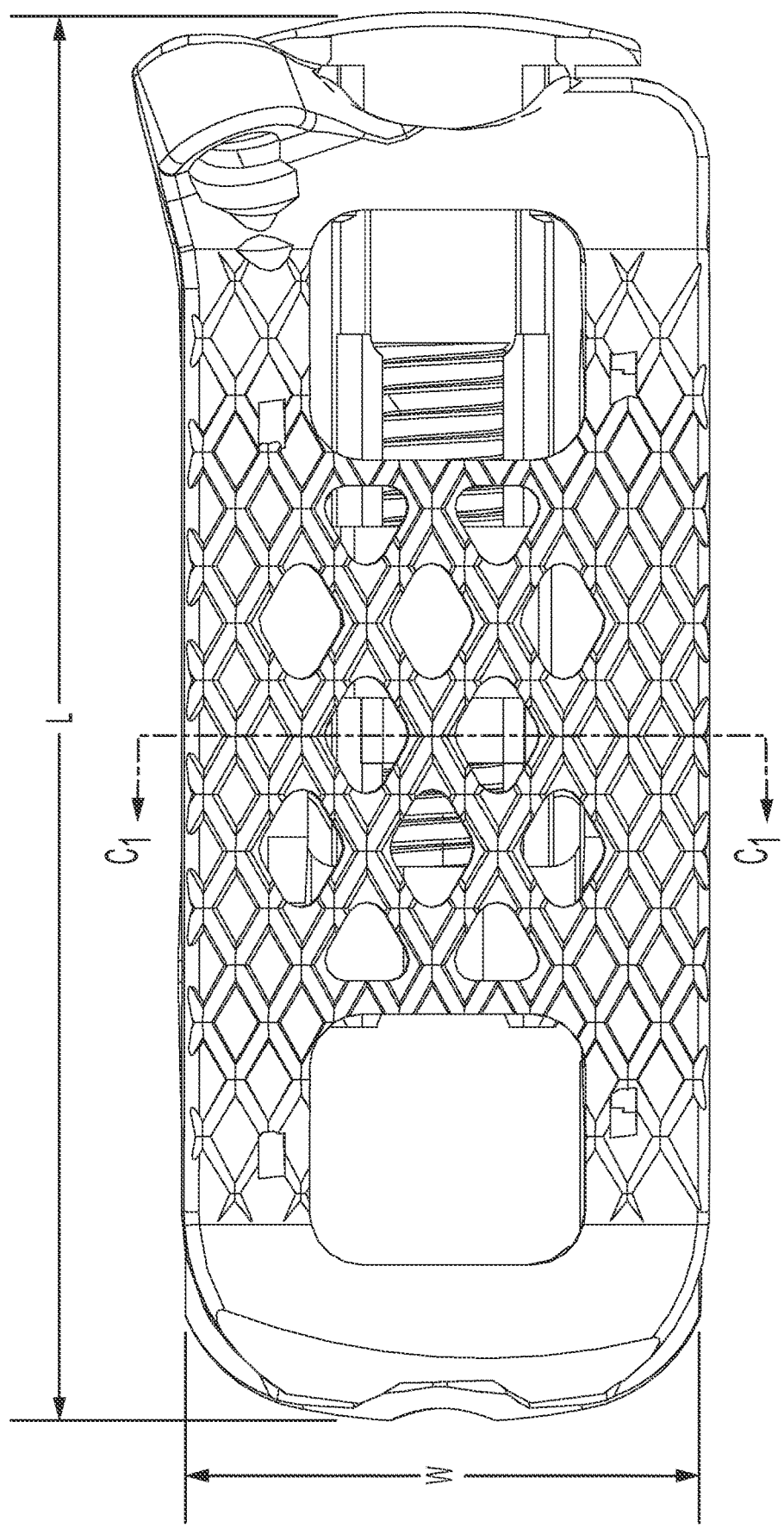
FIG. 3 is a top down view of an expandable spinal implant in accordance with the principles of the present disclosure.

FIG. 3 is a top down view of expandable spinal implant 100 showing a first cross section $C_1$ extending through a mid-section plane of expandable spinal implant 100 in the width wise direction. As illustrated, spinal implant 100 may include a plurality of openings in each of top endplate 110 and bottom endplate 120. In the disclosed embodiment, top and bottom endplates 110, 120 may, for example, feature a textured outside surface having a diamond tread pattern. In other embodiments, the plurality of openings may have alternate shapes and/or be disposed in alternate locations in other embodiments. For example, top and bottom endplates 110, 120 may comprise various anti-migration, anti-expulsion, and/or osseointegration features including, but not limited to: ridges, teeth, pores, and coatings (including but not limited to porous titanium coatings such as those provided on Capstone PTC™ implants available from Medtronic). The endplates 110, 120 may each further comprise at least one opening 110$x$, 120$x$ (see FIGS. 8-9) defined therein, and configured to allow bone growth materials to be packed, placed, or loaded into spinal implant 100. In the exemplary embodiment 110$x$, 120$x$ are shown having a rectangular shape, although other embodiments may have alternating shapes.

Figure 4A:
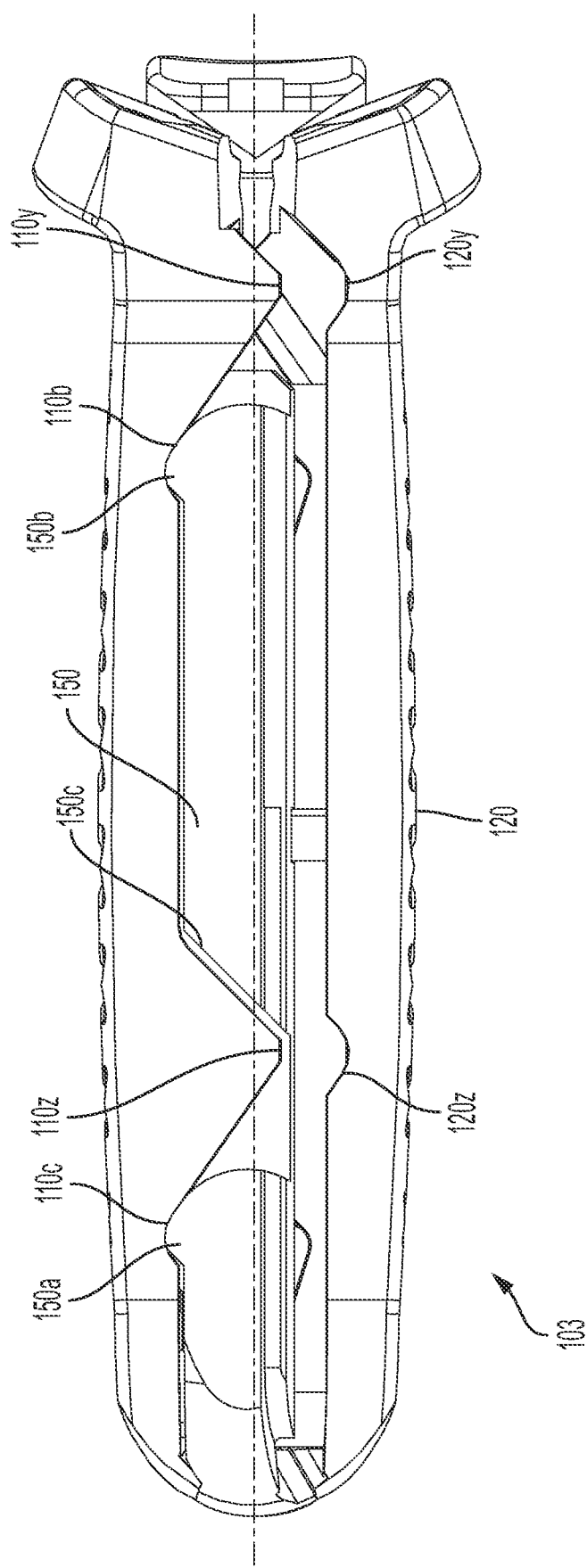
FIGS. 4A and 4B are lateral side views of an expandable spinal implant in accordance with the principles of the present disclosure.
Figure 4B:
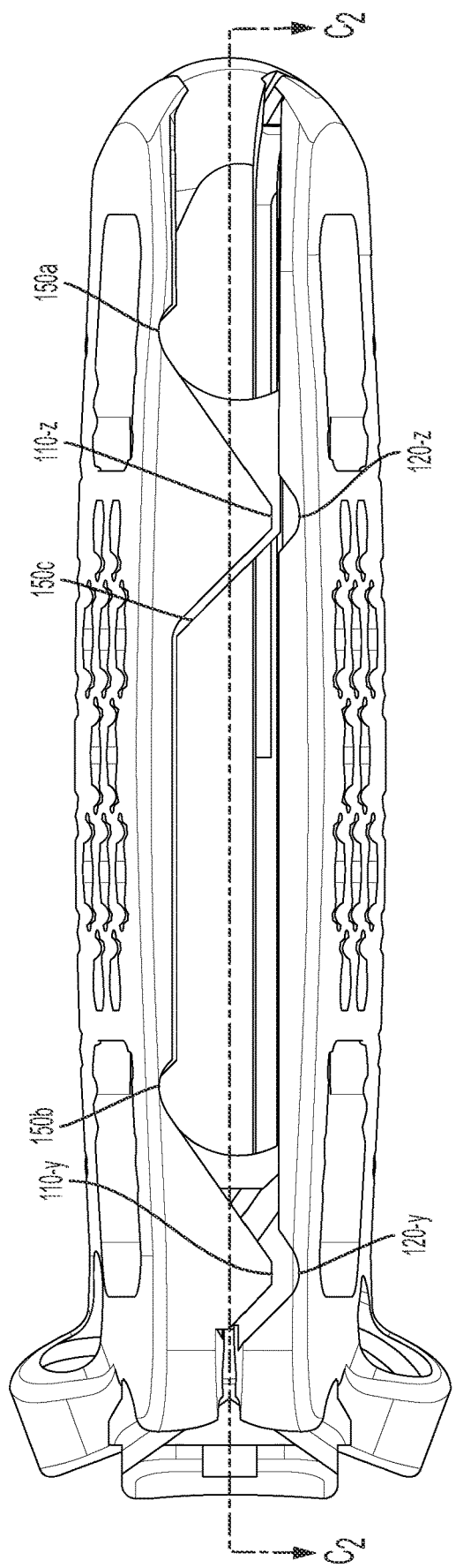
Figure 5:
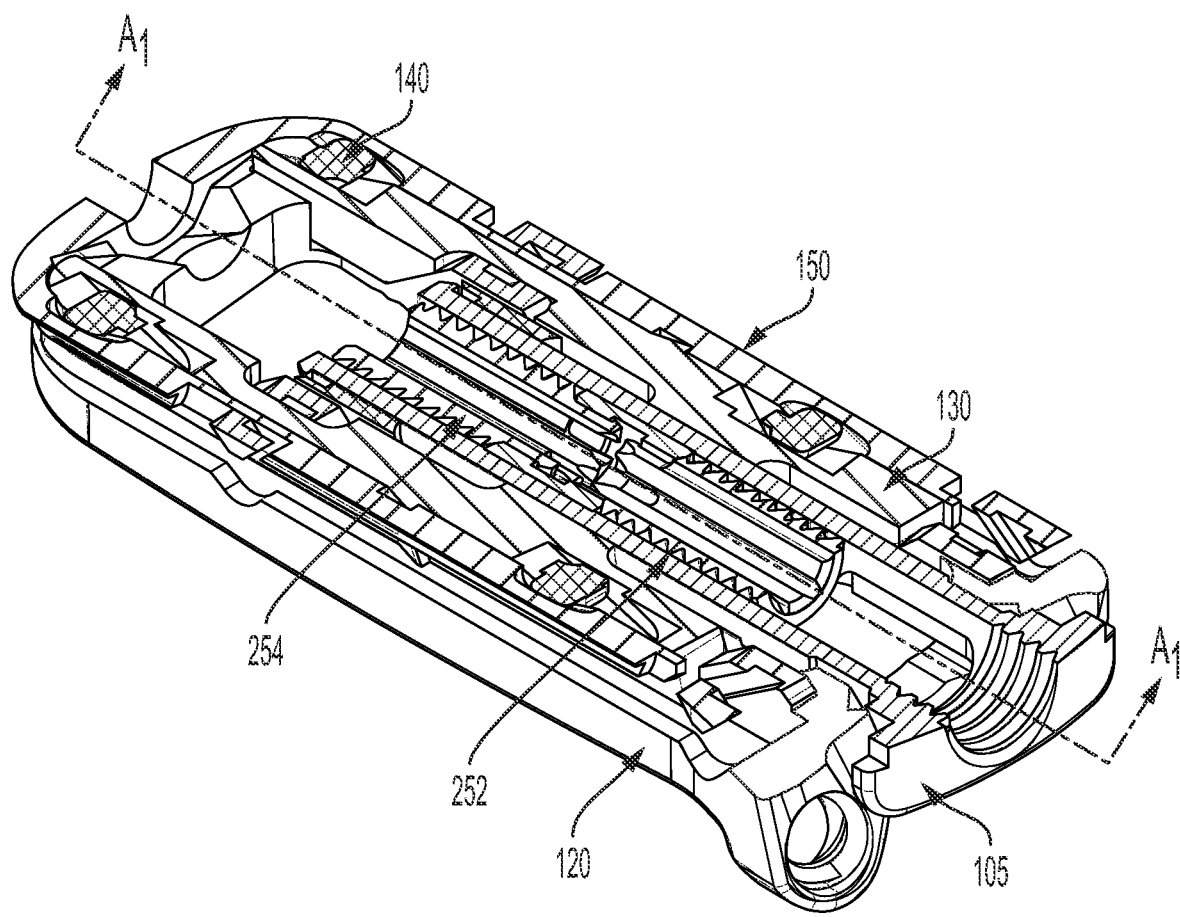
FIG. 5 is a perspective view of a cross section of the expandable spinal implant of line $C_2$ from FIGS. 4A and 4B in accordance with the principles of the present disclosure.

FIG. 4A is a lateral side view of first lateral end 103 and FIG. 4B is a lateral side view of second lateral end 104 in accordance with the principles of the present disclosure. As shown in FIGS. 4A and 4B, a second cross section $C_2$ extending through a mid-section plane of expandable spinal implant 100 in the length wise (longitudinal) direction is shown. In the exemplary embodiment, expandable spinal implant 100 may be in a contracted position where a lateral height between endplates 110, 120 of first lateral end 103 may be greater than a lateral height between endplates 110, 120 of second lateral end 104. FIG. 5 is a perspective view illustrating the second cross section $C_2$ of expandable spinal implant 100 and FIG. 6 is a perspective view illustrating the first cross section $C_1$ of expandable spinal implant 100.

FIGS. 4A and 4B illustrate top sliding frame 150 contacting top endplate 110 on an underside thereof. For example, first distal contact surfaces 150$a$ may be curved surfaces of top sliding frame 150 that are configured to contact an underside of top endplate 110 at distal indented surfaces 110$c$ and corresponding inclined surfaces of first distal ramps 116. Similarly, first proximate contact surfaces 150$b$ may be curved surfaces configured to contact an underside of top endplate 110 at proximate indented surfaces 110$b$ and corresponding proximate sides of first proximal ramps 114. Additionally, top sliding frame 150 includes inclined contact surfaces 150$c$ configured to contact a proximate side of first distal ramps 116. Furthermore, in a collapsed position, a first distal tip portion 110$z$ of first distal ramps 116 may extend into a corresponding first distal extension recess 120$z$ of bottom endplate 120. Similarly, in a collapsed position a first proximate tip portion 110$y$ of first proximal ramps 114 may extend into a corresponding first proximate extension recess 120$y$ of bottom endplate 120. At least one advantage of this arrangement is that the spinal implant 100 may feature a relatively large expansion\contraction range and a relatively large inclination range while maintaining a relatively small footprint.

Figure 6:
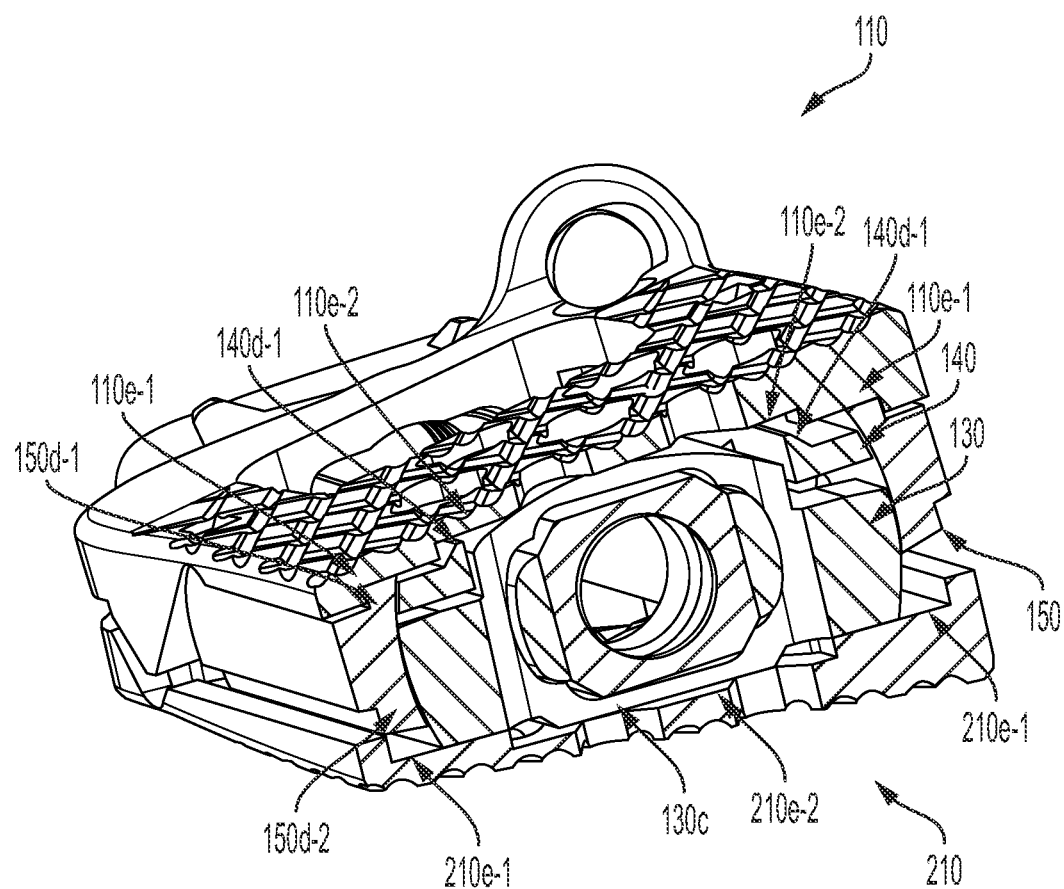
FIG. 6 is a perspective view of a cross section of the expandable spinal implant of line $C_1$ from FIG. 3 in accordance with the principles of the present disclosure.

Referring generally to FIGS. 5 and 6, top sliding frame 150 is operably coupled to top endplate 110 on an underside thereof. FIG. 5 is a perspective view of a cross section of the expandable spinal implant of line $C_2$ from FIGS. 4A and 4B and FIG. 6 is a perspective view of a cross section of the expandable spinal implant of line $C_1$ from FIG. 3. In the disclosed embodiment, top sliding frame 150 may feature curved interior surfaces facing first and second set screws 252, 254. Additionally, top sliding frame 130 may include first top rail portions 150$d$-1 and first bottom rail portions 150$d$-2 extending lengthwise along an interior side of top sliding frame 150. First top rail portions 150$d$-1 and first bottom rail portions 150$d$-2 may extend lengthwise through first top channel portions 110$e$-1 and first bottom channel portions 120$e$-1 in a direction parallel with first reference axis $A_1$, respectively. In this way, top sliding frame 150 may operably move forward and backwards between first and inferior endplates 110, 120 in a direction parallel with first reference axis $A_1$.

Referring to FIG. 6, angled wedge 140 may feature curved exterior surfaces facing the curved interior surfaces of top sliding frame 150. Additionally, angled wedge 140 may include second top rail portions 140$d$-1 extending lengthwise along an interior side of angled wedge 140. Second top rail portions 140$d$-1 may extend lengthwise through second top channel portions 110$e$-2 in a direction parallel with first reference axis $A_1$. In the exemplary embodiment, second top rail portions 140$d$-1 are inclined such that a gap exists between second top rail portions 140$d$-1 and second top channel portions 110$e$-2. In this way, angled wedge 140 may operably move forward and backwards within second top channel portions 110$e$-2 in a direction parallel with first reference axis $A_1$ and first endplate 110 may pivot laterally side to side in a direction perpendicular with first reference axis $A_1$.

Bottom sliding frame 130 may feature curved exterior surfaces facing the curved interior surfaces of top sliding frame 150. Additionally, bottom sliding frame 130 may also include a central aperture 130$b$ (see FIG. 11) such that the central aperture 130$b$ surrounds sliding block 253 and screw guide body 256, at least partly. Furthermore, bottom sliding frame 130 may feature a curved upper surface 130$a$ (see FIG. 11) that is concave with respect to first set screw 252 and a flat lower surface 130$c$. In this way, bottom sliding frame 130 may operably move forward and backwards within second bottom channel portion 120$e$-2 in a direction parallel with first reference axis $A_1$ and first endplate 110 may pivot laterally side to side in a direction perpendicular with first reference axis $A_1$.

Figure 7:
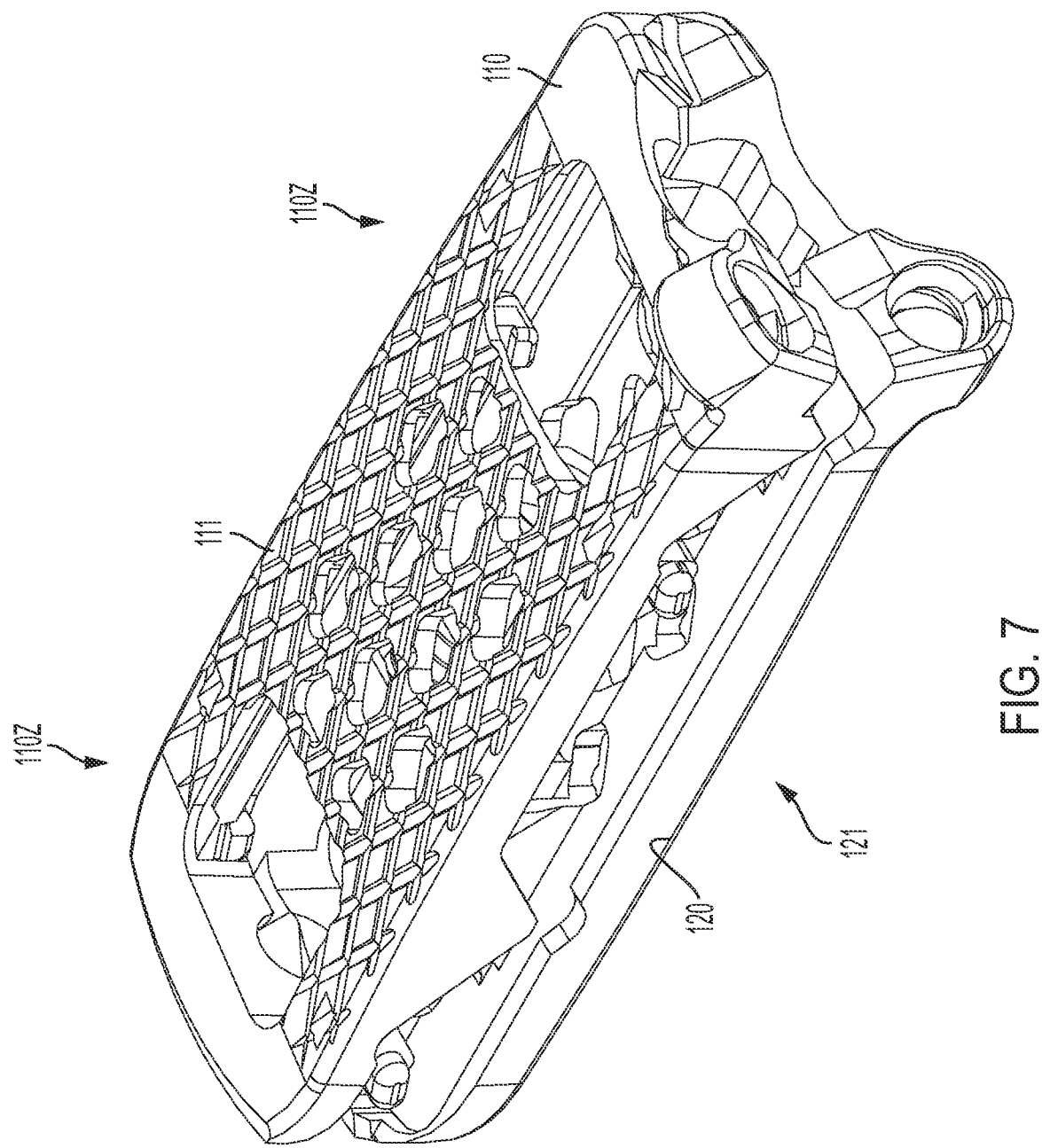
FIG. 7 is a perspective view of a top endplate and bottom endplate of an expandable spinal implant in accordance with the principles of the present disclosure.
Figure 8:
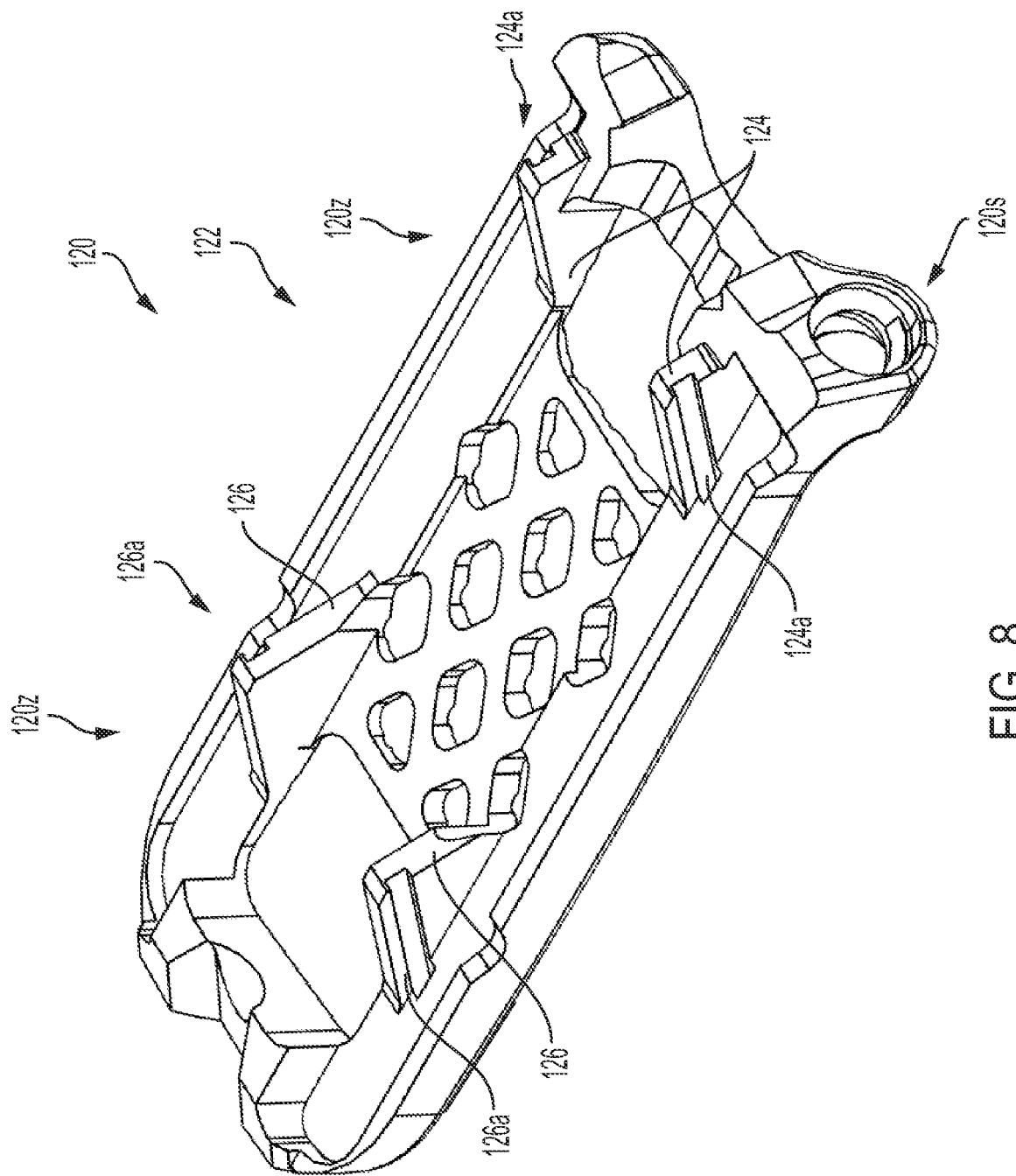
FIG. 8 is a perspective view of a bottom endplate in accordance with the principles of the present disclosure.
Figure 9:
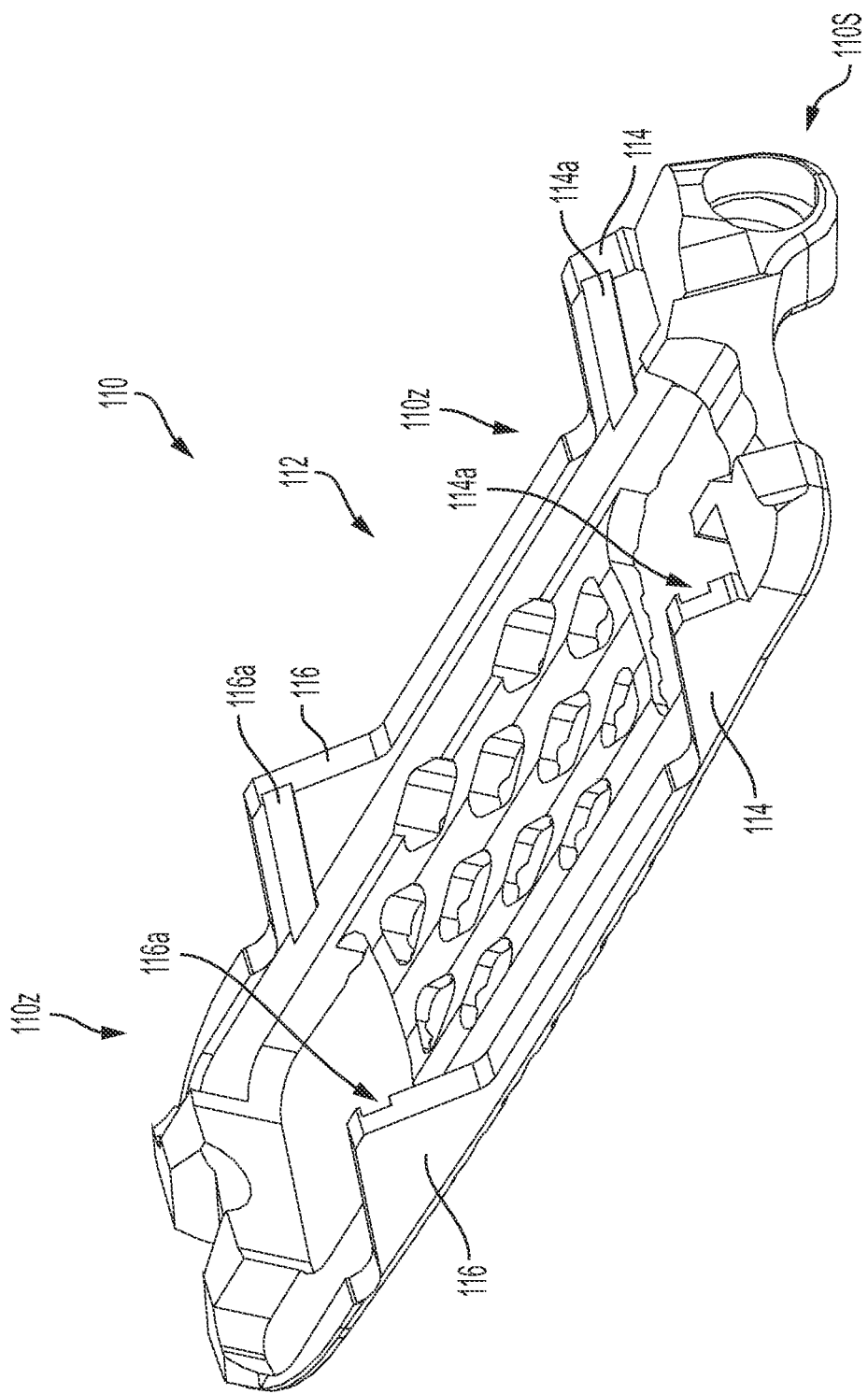
FIG. 9 is a perspective view of a top endplate in accordance with the principles of the present disclosure.

Referring generally to FIGS. 7-9 various perspective views of a top endplate 110 and bottom endplate 120 of an expandable spinal implant 100 in accordance with the principles of the present disclosure are illustrated. One of the top endplate 110 and/or bottom endplate 120 may include an anchoring aperture 110$s$, 120$s$ on a proximal end 101 thereof for receiving an anchoring screw, if such is optionally desired, as will be explained in further detail below. Top endplate 110 may include a first outside surface 111 and a first inside surface 112 opposite the first outside surface 111. Similarly, bottom endplate 120 may include a second outside surface 121 and a second inside surface 122. The outside surfaces 111, 121 may be configured to be positioned between and/or contact vertebral bodies in a patients spine and have various surface characteristics. For example, in some embodiments, outside surfaces 111 and 122 may have substantially linear surface profiles extending across faces of textured surfaces thereof. In other embodiments, outside surfaces 111 and 122 may have curved surface profiles extending across faces of textured surfaces thereof. Inside surfaces 112, 122, may surround moving mechanism 250 and have various contours, guides, cavities, ramps, and other operable characteristics that facilitate movement and/or provide mechanical advantage to other operable and movable corresponding parts to facilitate expansion, contraction, angular adjustment, lateral pivoting, absorption of compression forces, shear forces, etc. as will be explained in greater detail below.

In the exemplary embodiment, top endplate 110 includes a pair of first proximal ramps 114 and a pair of first distal ramps 116 opposite the first proximal ramps 114. Each ramp of the first proximal ramps 114 includes an inclined surface extending away from inside surface 112. Additionally, each ramp of first proximal ramps 114 includes a first proximal groove 114a on an inside surface thereof. Similarly, each ramp of first distal ramps 116 includes inclined surfaces extending away from inside surface 112. Additionally, each ramp of first distal ramps 116 includes a first distal groove 116a on an inside surface thereof. Each of first distal ramps 116 and first proximal ramps 114 may include an outside lateral surface that partly defines a respective lateral end 103, 104 of expandable spinal implant 100. Bottom endplate 120 includes a pair of second proximal ramps 124 and a pair of second distal ramps 126 opposite the second proximal ramps 124. Each ramp of the second proximal ramps 124 includes an inclined surface extending away from inside surface 122. Additionally, each ramp of second proximal ramps 124 includes a second proximal groove 124a on an outside lateral surface thereof. Similarly, each ramp of second distal ramps 126 includes inclined surfaces extending away from inside surface 112 and moving mechanism 250. Additionally, each ramp of second distal ramps 126 includes a second distal groove 126a on an outside lateral surface thereof. Each of second distal ramps 126 and second proximate ramps 124 may include an outside lateral surface that is inset (spaced inside) from first distal ramps 116 and first proximal ramps 114 towards moving mechanism 250. Furthermore, each groove 114a, 116a, 124a, and 126a may extend in a parallel direction with a corresponding inclined surface of a corresponding ramp 114, 116, 124, and 126.

Figure 10A:
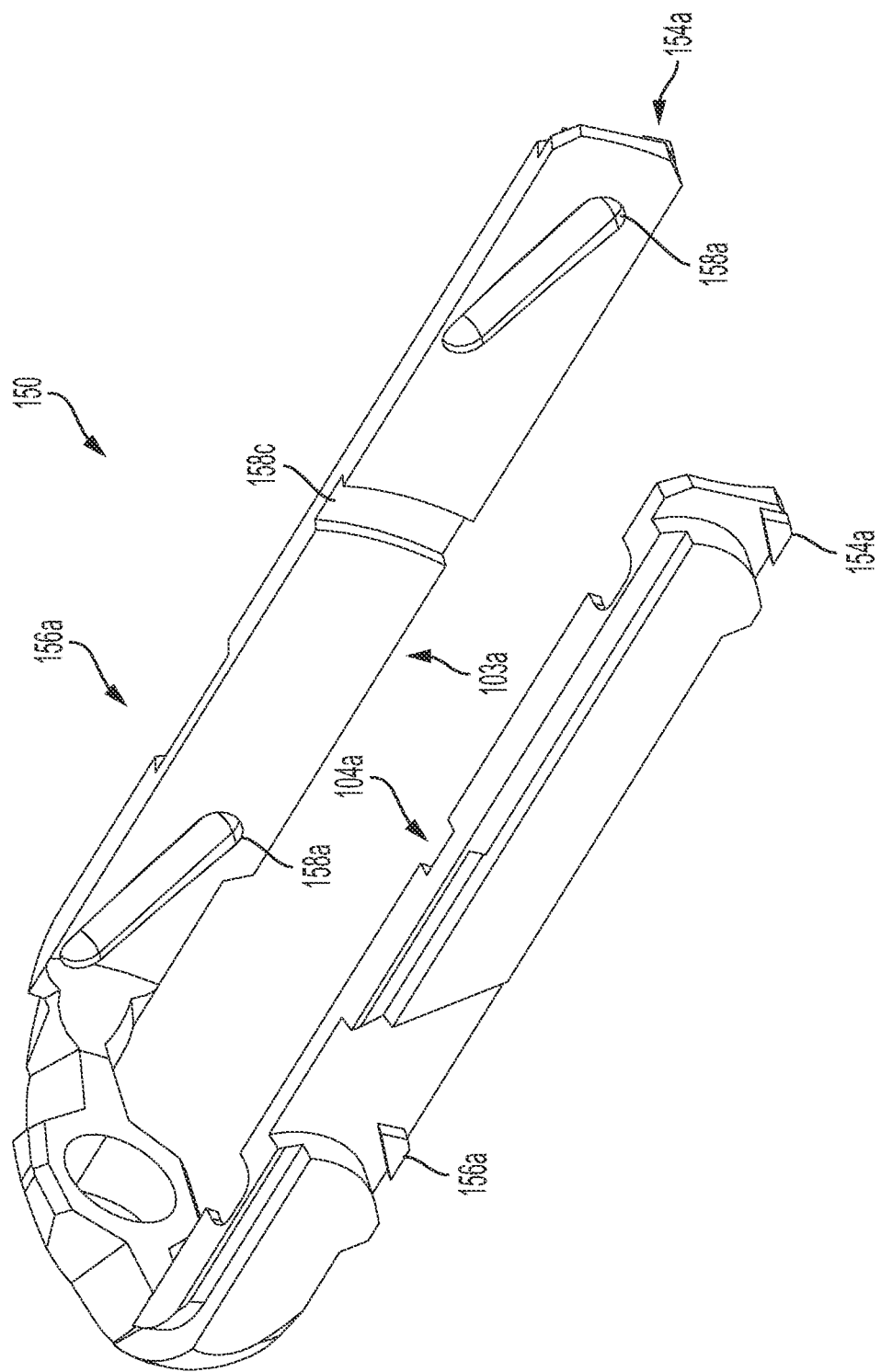
FIGS. 10A-10D are various perspective views of an exemplary top sliding frame in accordance with the principles of the present disclosure.
Figure 10B:
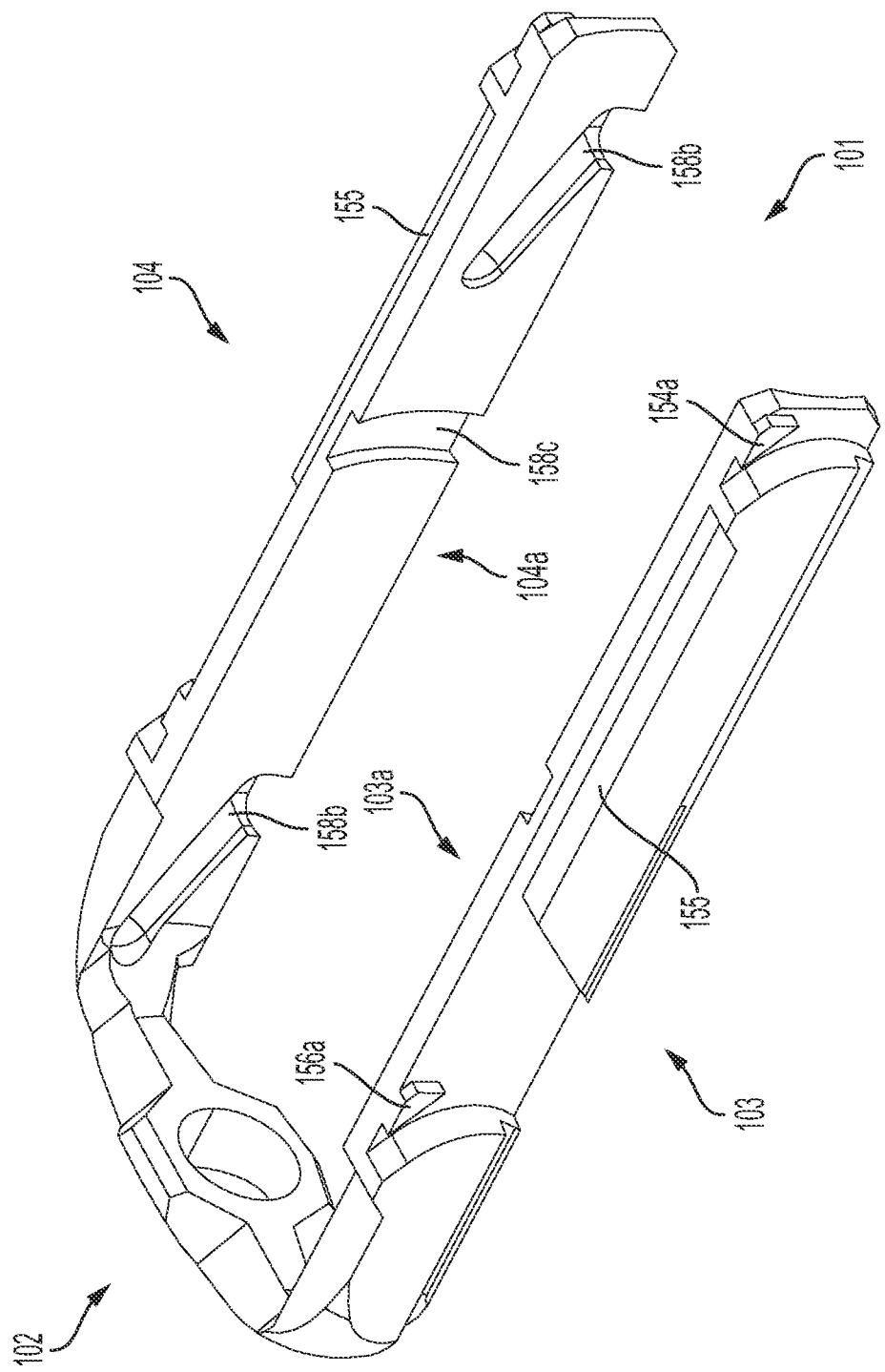
Figure 10C:
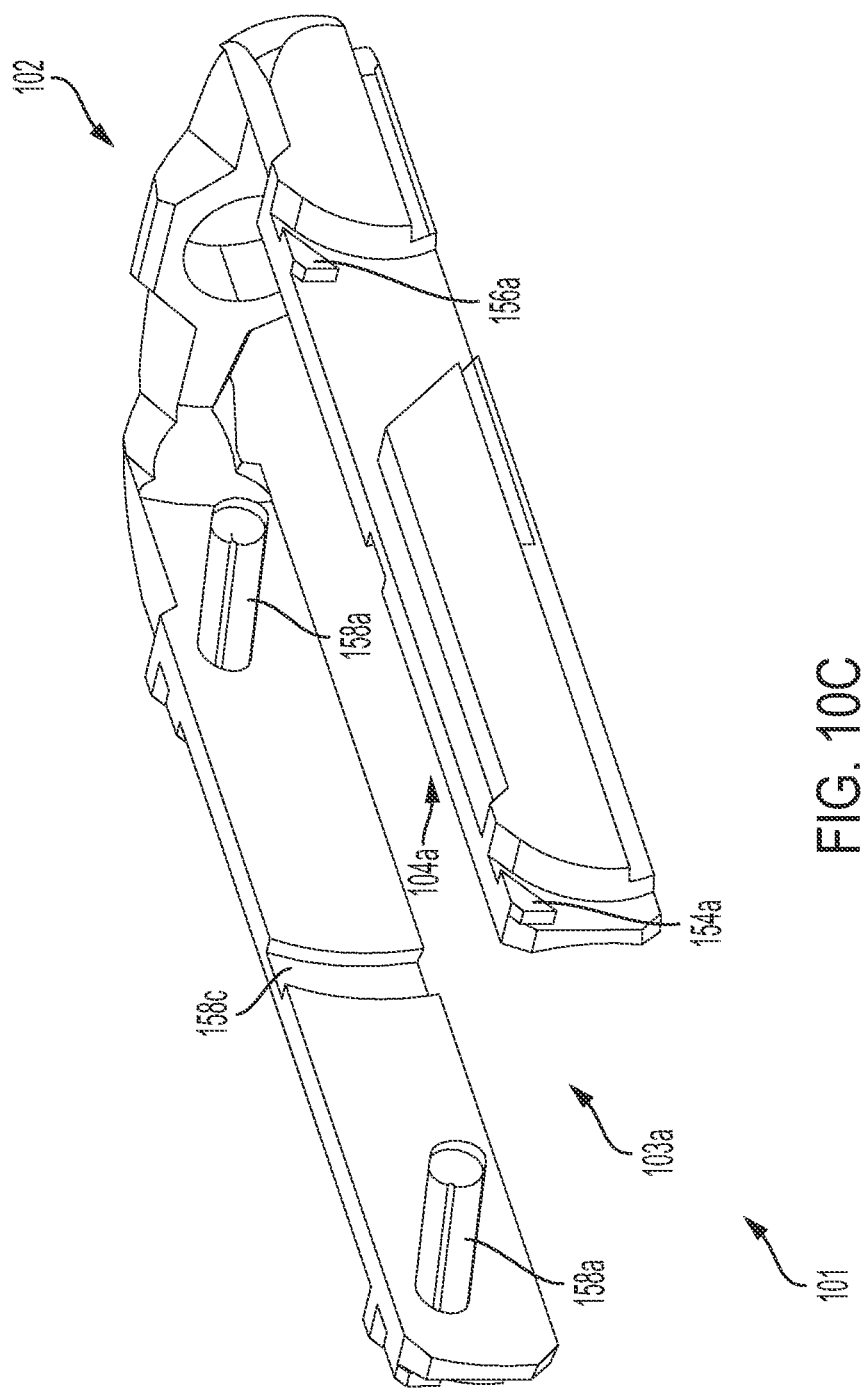
Figure 10D:
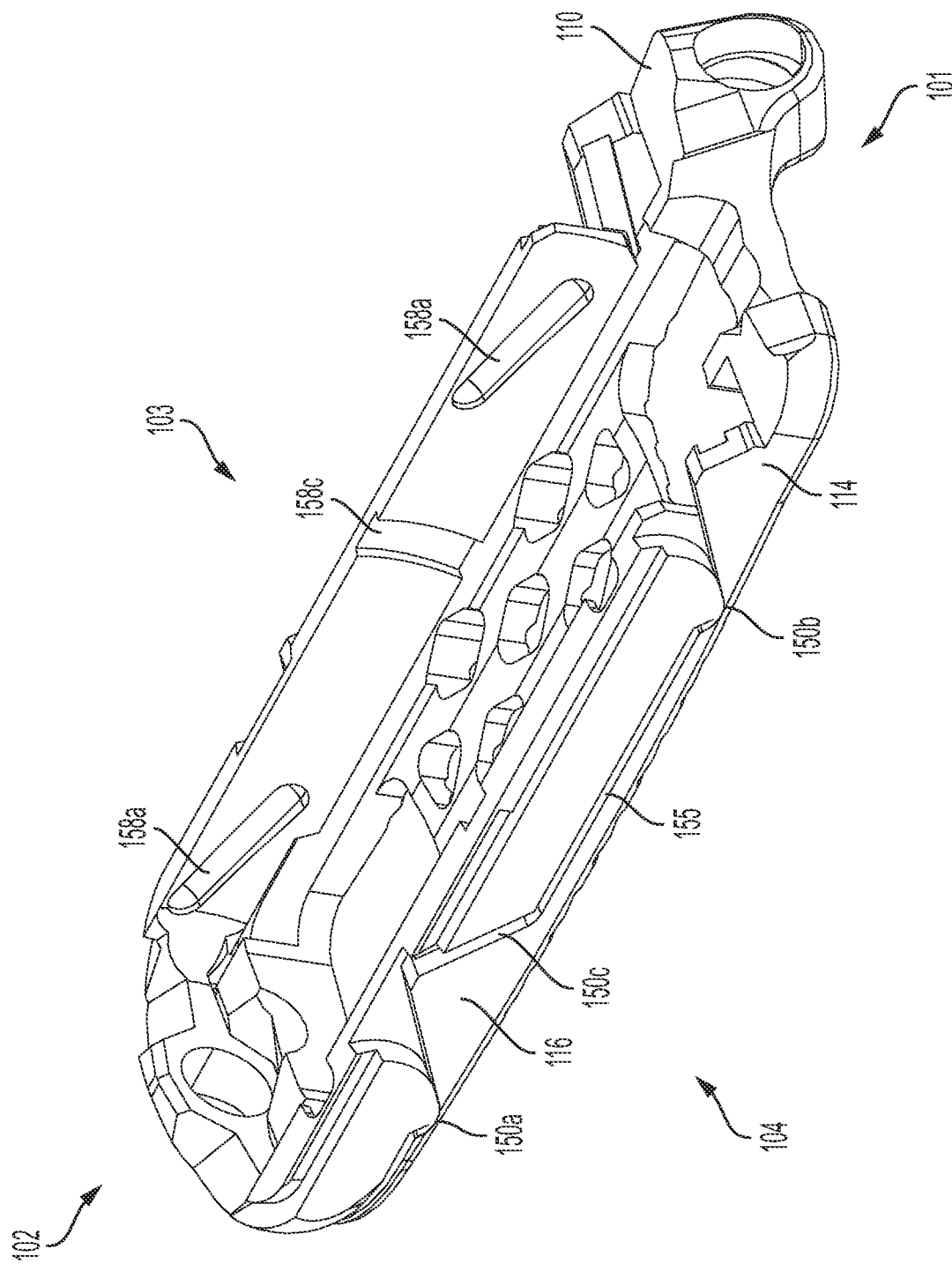
Figure 11:
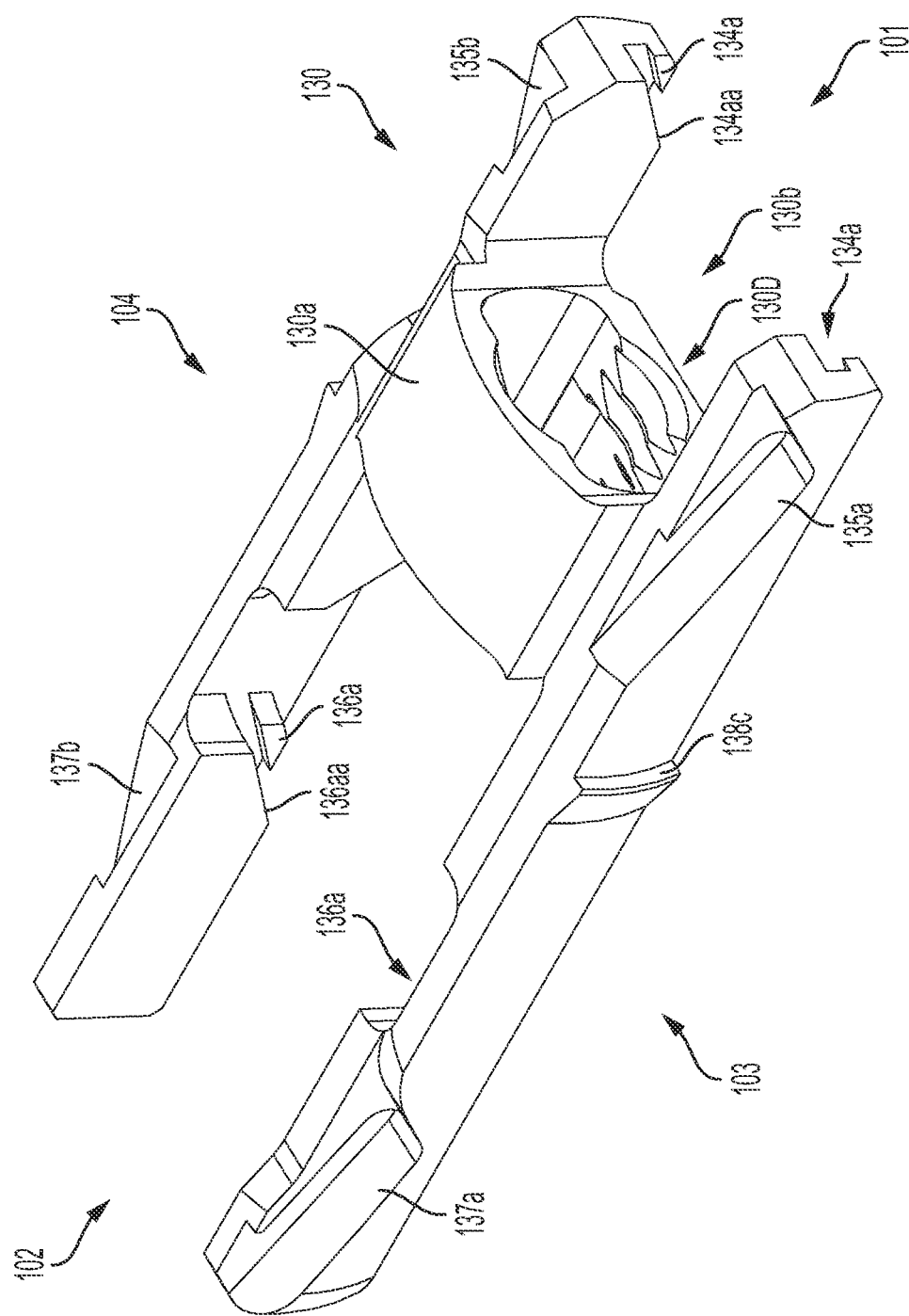
FIG. 11 is a perspective view of an exemplary bottom sliding frame in accordance with the principles of the present disclosure.
Figure 12A:
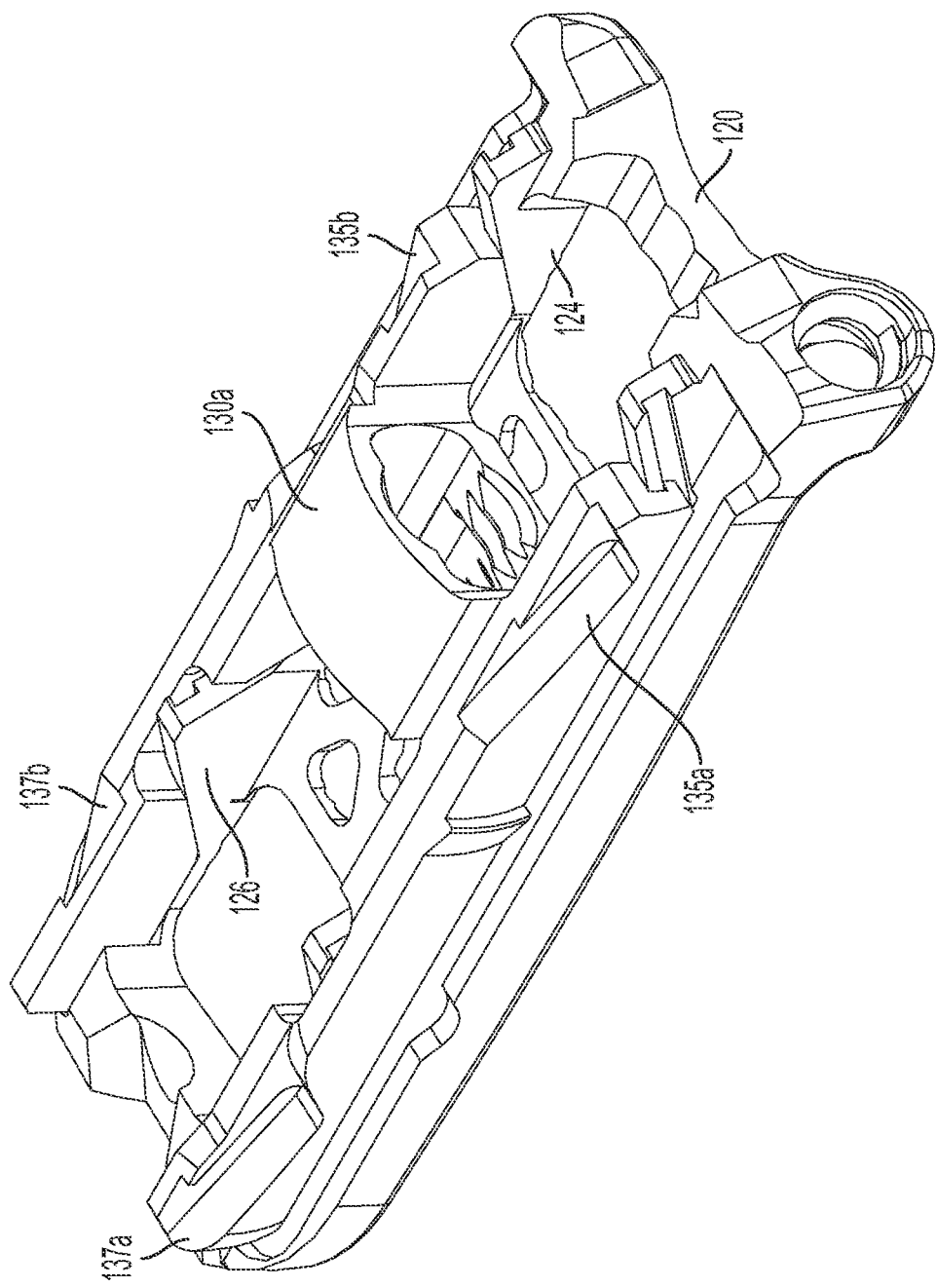
FIGS. 12A-12E are partial parts perspective views of various components for use with expandable spinal implant in accordance with the principles of the present disclosure.
Figure 12B:
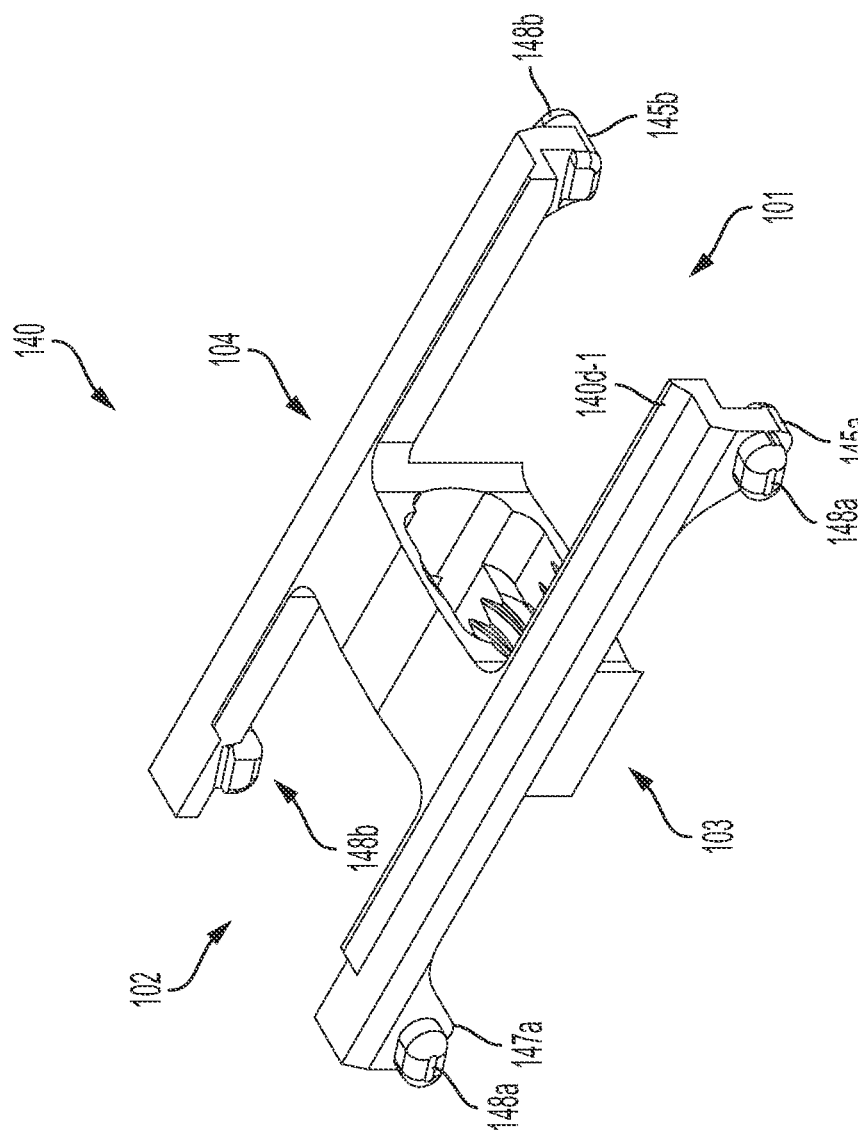
Figure 12C:
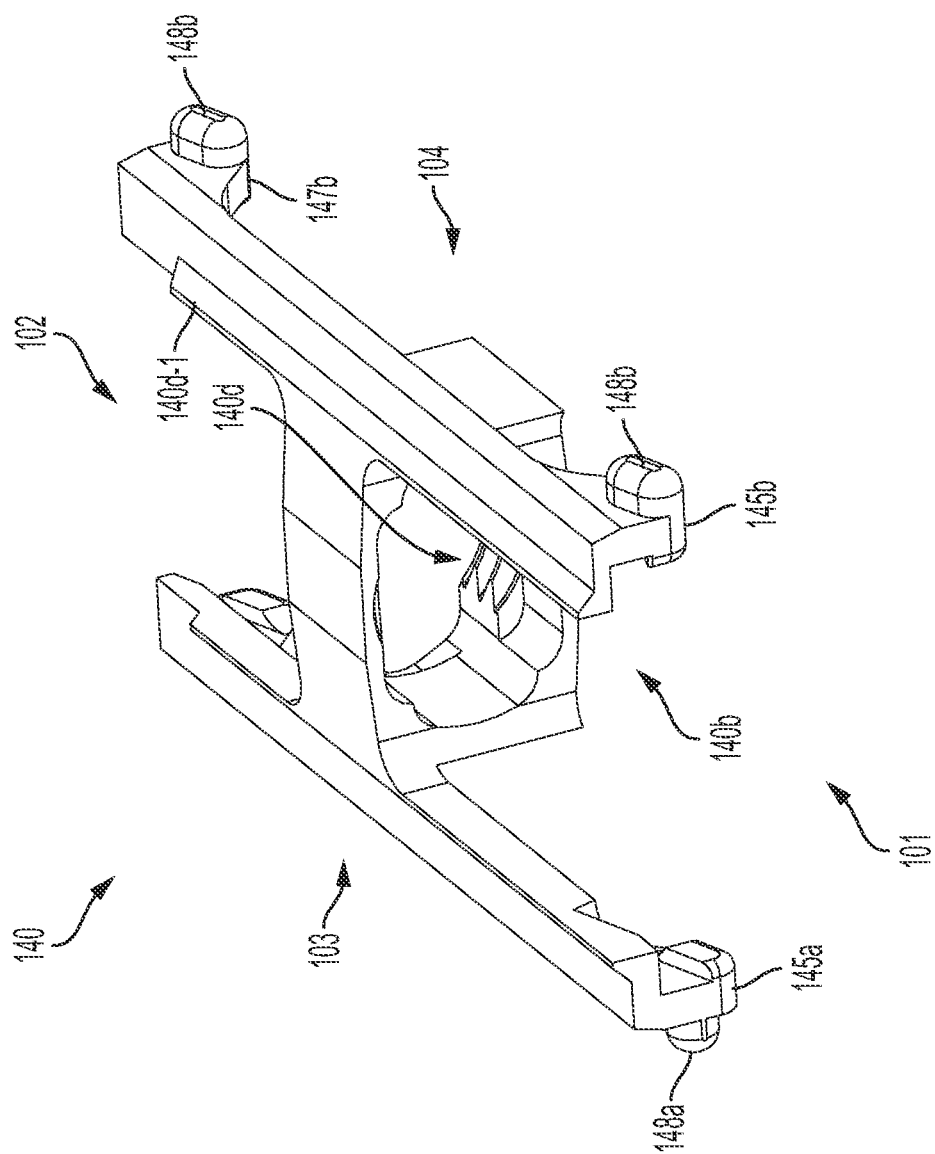
Figure 12D:
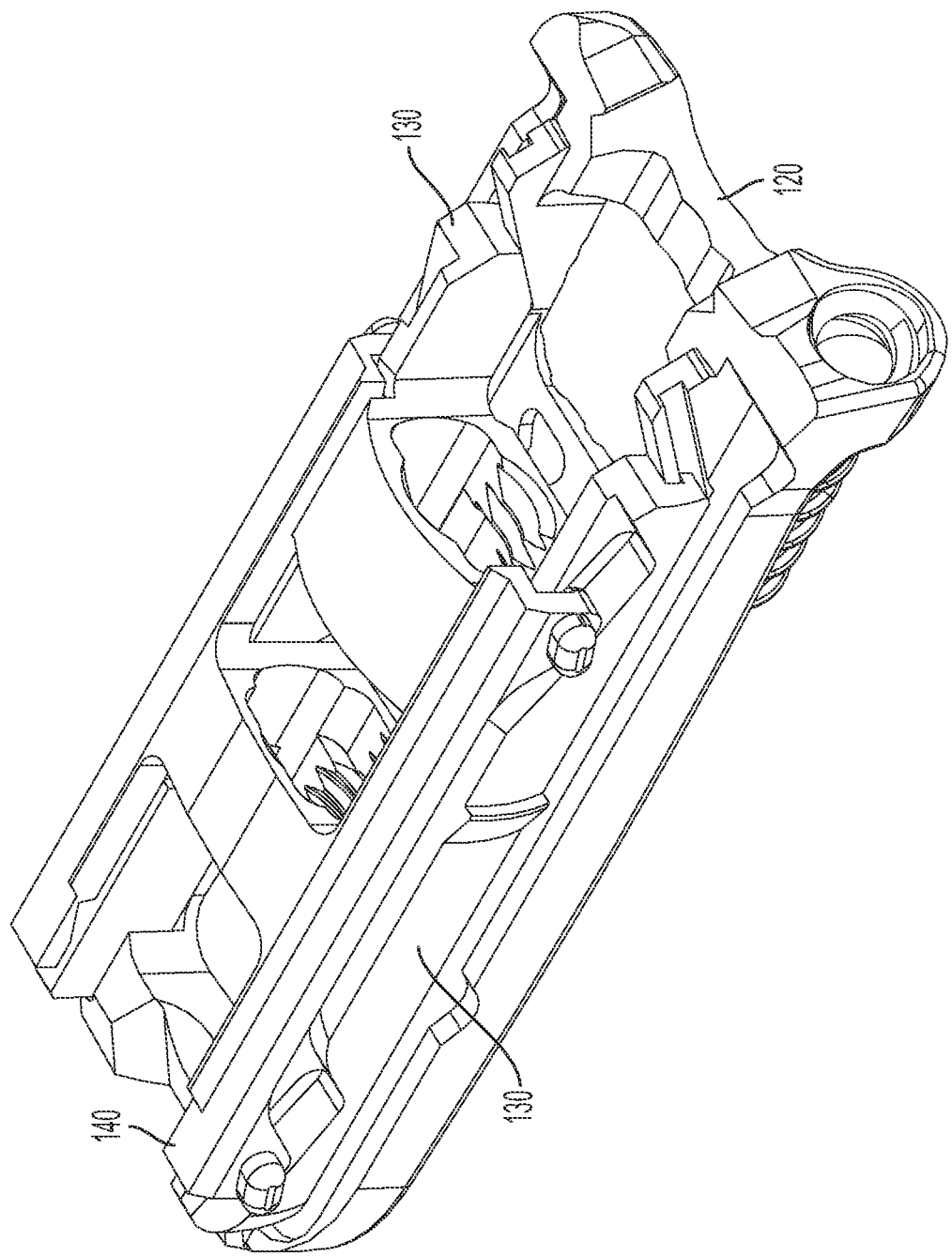
Figure 12E:
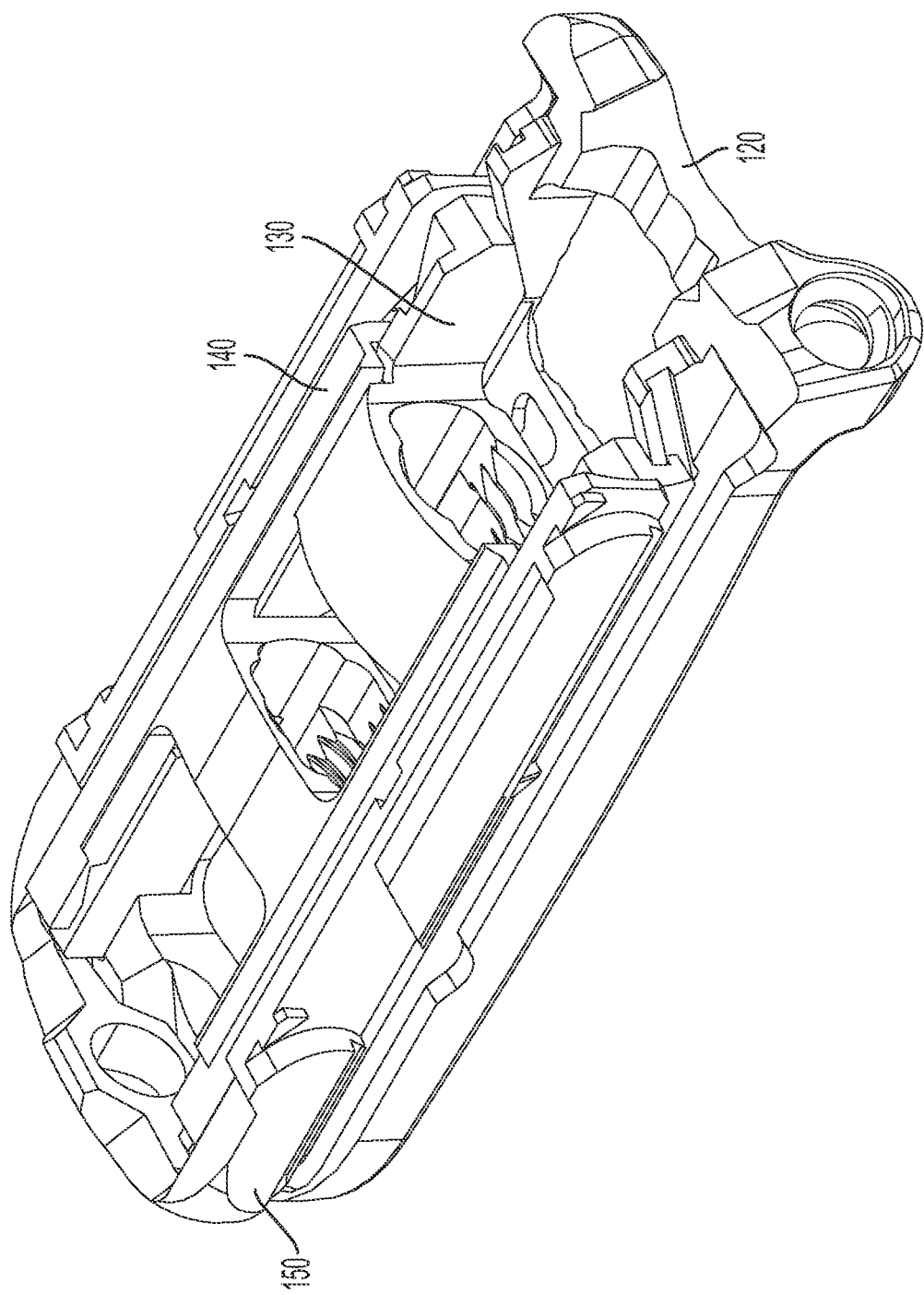
Figure 13:
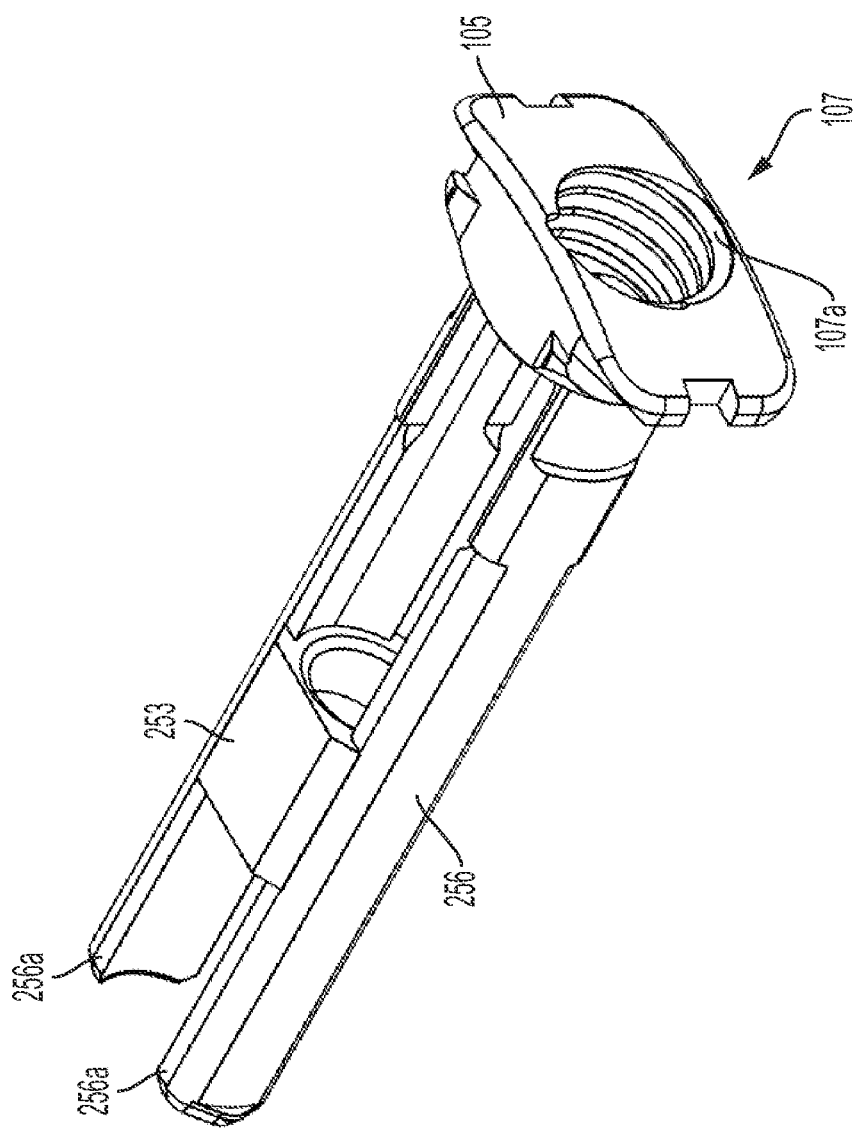
FIG. 13 is a perspective view of a screw guide body for use with an expandable spinal implant in accordance with the principles of the present disclosure.
Figure 14:
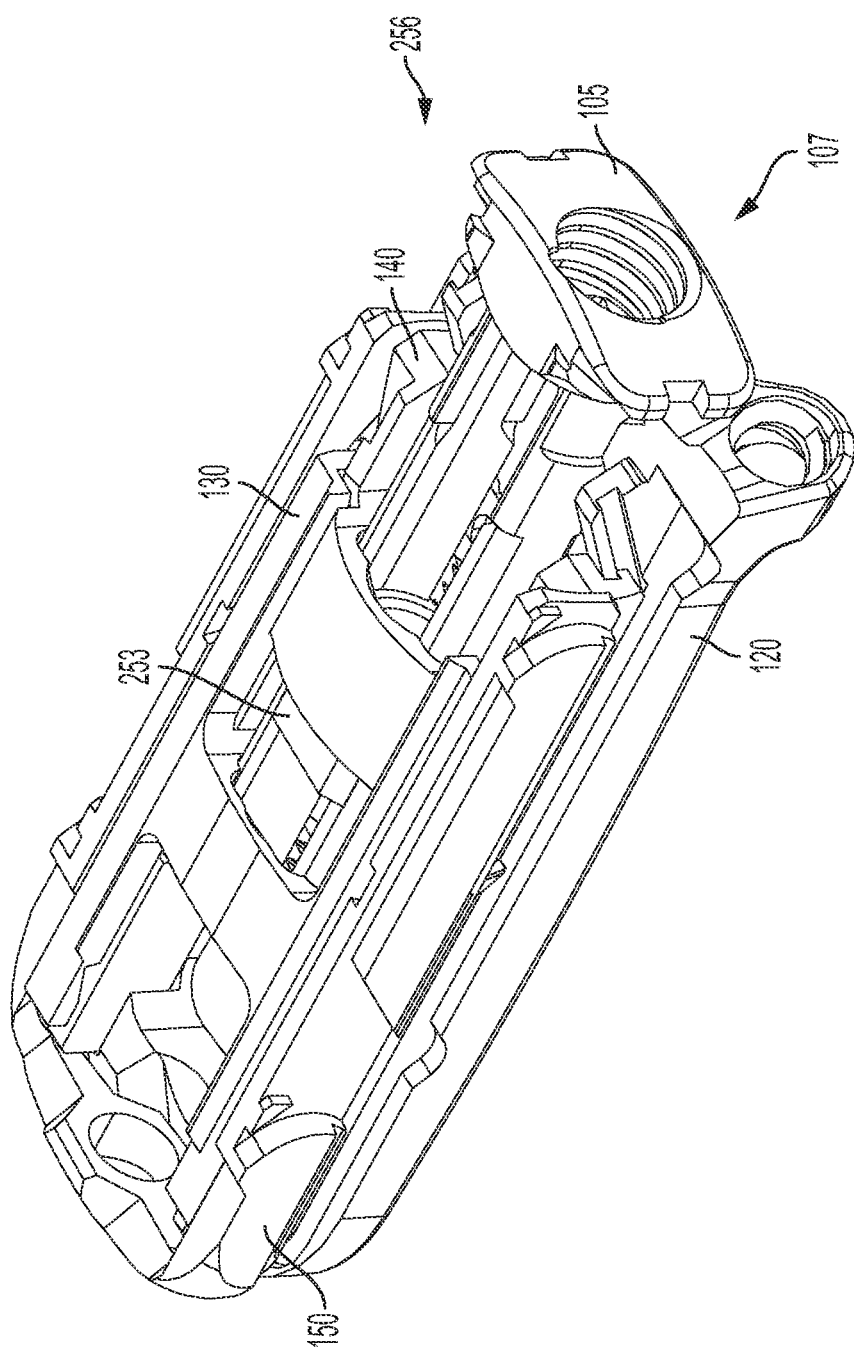
FIG. 14 is a perspective view of an expandable spinal implant with the top endplate removed in accordance with the principles of the present disclosure.

Referring generally to FIGS. 10-14 various perspective views of top sliding frame 150, angled wedge 140, and bottom sliding frame 130 for use with expandable spinal implant 100 in accordance with the principles of the present disclosure are illustrated. FIGS. 10A-10D are various perspective views of an exemplary top sliding frame 150 in accordance with the principles of the present disclosure. FIG. 11 is a perspective view of an exemplary bottom sliding frame 130 in accordance with the principles of the present disclosure. FIGS. 12A-12E are partial parts perspective views of various components for use with expandable spinal implant 100 in accordance with the principles of the present disclosure. FIG. 13 is a perspective view of a screw guide body for use with an expandable spinal implant 100 and FIG. 14 is a perspective view of an expandable spinal implant 100 with the top endplate 110 removed in accordance with the principles of the present disclosure.

FIG. 10A illustrates top sliding frame 150 turned upside down from its normal upright position as compared to when top sliding frame 150 is installed in expandable spinal implant 100. FIGS. 10B and 10C illustrate top sliding frame 150 right side up in different perspective views for ease of explanation. Top sliding frame 150 may include a pair of first proximate guide walls 154a and a pair of first distal guide walls 156a. In the disclosed embodiment, guide walls 154a and 156a are wedge shaped and have a corresponding size relative to the width of first proximate grooves 114a and first distal grooves 116a, respectively. However, in other embodiments they make take any shape provided they enable top sliding frame 150 to be slidably connected to top endplate 110. In the disclosed embodiment, top sliding frame 150 may be slidably coupled to first proximate grooves 114a by first proximate guide walls 154a. Similarly, top sliding frame 150 may be slidably coupled to first distal grooves 116a by first distal guide walls 156a.

Additionally, top sliding frame 150 may include a plurality of channels 158a, 158b, 158c on the inside lateral surfaces thereof. For example, the first inside lateral surface 103a of top sliding frame 150 includes a first pair of channels 158a and the second inside lateral surface 104a of top sliding frame 150 includes a second pair of channels 158b. In the disclosed embodiment, the first and second pair of channels 158a, 158b may be inclined with respect to the longitudinal direction of top sliding frame 150 and may be hemispherical shaped, although in other embodiments different cross sectional shapes, e.g., conical, dovetail, tongue and groove, etc. may be used. Additionally, the first and second pair of channels 158a, 158b may be inclined oppositely from one another, e.g., first pair of channels 158a may extend from a bottom portion of distal end 102 of top sliding frame 150 towards a top portion of the proximal end 101 of top sliding frame 150 (see FIG. 10C) and second pair of channels 158b may extend from a bottom portion of the proximal end 101 of top sliding frame 150 towards a top portion the distal end 102 (see FIG. 10B). Furthermore, second pair of channels 158b may have an opening on an underside thereof extending through a bottom portion of top sliding frame 150 (see FIG. 10b). Top sliding frame 150 may also include a pair of third channels 158c. Third channels 158c may extend vertically along first inside lateral surface 103a and second inside lateral surface 104a. Top sliding frame 150 may further include a pair of guide rails 155 disposed on outside surfaces of first lateral end 103 and second lateral end 104, respectively. Guide rails 155 may extend substantially parallel to the longitudinal direction of top sliding frame 150.

FIG. 10D illustrates top sliding frame 150 operably coupled to top endplate 110 in an upside down orientation for ease of explanation. As illustrated, first proximate guide walls 154a and first distal guide walls 156a are operably coupled to first proximate grooves 114a and first distal grooves 116a, respectively. First distal contact surfaces 150a, first proximate contact surfaces 150b, and inclined contact surfaces 150c may each act against a correspond ramp 114, 116 of top endplate 110 to facilitate expansion and angular adjustment of expandable spinal implant 100, as will be explained in more detail below.

FIG. 11 illustrates bottom sliding frame 130 and FIG. 12A illustrates bottom sliding frame 130 operably coupled to bottom endplate 120. Bottom sliding frame 130 may include a pair of proximal contact surfaces 134aa and a pair of distal contact surfaces 136aa configured to act against a corresponding surface of ramps 124, 126, of bottom endplate 120. Bottom sliding frame 130 may further include a pair of second proximate guide walls 134a and a pair of second distal guide walls 136a. In the disclosed embodiment, guide walls 134a and 136a are wedge shaped, although in other embodiments they make take any shape provided they enable bottom sliding frame 130 to be slidably connected to bottom endplate 120. In the disclosed embodiment, bottom sliding frame 130 may be slidably coupled to second proximate grooves 124a by second proximate guide walls 134a. Similarly, bottom sliding frame 130 may be slidably coupled to second distal grooves 126a by second distal guide walls 136a. Additionally, bottom sliding frame 130 includes a pair of protrusions 138c disposed on opposite outside lateral surfaces of bottom sliding frame 130. For example, each protrusion 138c has a curved wedge shaped profile and may be disposed at a longitudinal mid-section area on an outside surface of lateral ends 103 and 104, respectively. Protrusions 138c may be configured to engage with third channels 158c of top sliding frame 150 and are designed to facilitate expansion/contraction and angular adjustment of expandable spinal implant 100. For example, the curved wedge shape of protrusions 138c enables a freedom of movement within third channels 158c. Bottom sliding frame may further include a pair of third proximate ramps 135a, 135b and a pair of third distal ramps 137a, 137b. Each ramp of third proximate ramps 135a, 135b may be inclined oppositely with respect to a longitudinal direction of bottom sliding frame 130 and each ramp of third distal ramps 137a, 137b may be inclined oppositely with respect to a longitudinal direction of bottom sliding frame 130. Additionally, ramps 135a and 137a may be inclined in the same direction and ramps 135b and 137b may also be inclined in the same direction. Bottom sliding frame 130 may further include a first threaded portion 130d that may be configured to engage first set screw 252. In this way, first set screw 252 may be configured to move bottom sliding frame 130 forward upon rotation of first set screw 252 in a first direction and move bottom sliding frame 130 backwards upon rotation of first set screw 252 in a second direction.

FIG. 12B illustrates angled wedge 140 in a first perspective view and FIG. 12C illustrates angled wedge 140 in a second perspective view. As illustrated, angled wedge 140 can include a pair of proximate engagement surfaces 145a and 145b and a pair of distal engagement surfaces 147a and 147b. Proximate engagement surfaces 145a and 145b may be configured to engage third proximate ramps 135a and 135b of bottom sliding frame 130 and distal engagement surfaces 147a and 147b may be configured to engage third distal ramps 137a and 137b. For example, engagement surfaces 145a, 145b, 147a, and 147b may be configured to slide along the corresponding surface of ramps 135a, 135b, 137a, and 137b of bottom sliding frame 130.

Additionally, angled wedge 140 may include a plurality of protrusions 148a, 148b on the outside lateral surfaces thereof. For example, the first outside lateral surface 103 of angled wedge 140 includes a first pair of protrusions 148a and the second outside lateral surface 104 of top sliding frame 150 includes a second pair of protrusions 148b. In the disclosed embodiment, the first and second pair of protrusions 148a and 148b may be inclined and protrude laterally from a corresponding lateral surface and have an elongated hemispherical shape, although in other embodiments different cross sectional shapes, e.g., conical, dovetail, tongue and groove, etc. may be used. Additionally, the first and second pair of protrusions 148a, 148b may be inclined oppositely from one another, e.g., first pair of protrusions 148a may extend from a bottom portion of distal end 102 of angled wedge 140 towards a top portion of proximal end 101 of top sliding frame 150 (see FIG. 12B) and second pair of protrusions 148b may extend from a bottom portion of proximal end 101 of angled wedge 140 to a top portion of the distal end 102 (see FIG. 12C). Protrusions 148a, 148b may be configured to operably couple to channels 158a, 158b and slide forward and backwards along an interior surface of channels 158a, 158b. For example, protrusions 148a, 148b may correspond in cross sectional shape and angular orientation to that of channels 158a, 158b.

FIG. 12D illustrates angled wedge 140 operably coupled with bottom sliding frame 130 such that engagement surfaces 145a, 145b, 147a, and 147b are engaged with a corresponding one of ramps 135a, 135b, 137a, and 137b. In turn, bottom sliding frame 130 may be operably coupled to bottom endplate 120. FIG. 12E illustrates top sliding frame 150 operably coupled to angled wedge 140 such that protrusions 148a, 148b may be configured to slide forward and backwards along an interior surface of channels 158a, 158b (not visible).

FIG. 13 illustrates screw guide body 256 operably coupled to sliding block 253. As illustrated screw guide body 256 may include a rail portion 256a extending longitudinally along top and bottom portions of screw guide body 256 in the lengthwise direction. Sliding block 253 may be operably coupled to screw guide body 256 such that sliding block 253 may be configured to slide forward and backwards along rail portion 256a. As explained above, sliding block 253 may also be coupled to first and second set screws 252, 254. Accordingly, sliding block 253 and first and second set screws 252, 254 may be operably coupled to screw guide body 256 such that sliding block 253 may be configured to slide forward and backwards along rail portion 256a while remaining coupled to first and second set screws 252, 254. Additionally, screw guide body 256 may include threaded portion 107a, which will be explained in further detail below.

Figure 15:
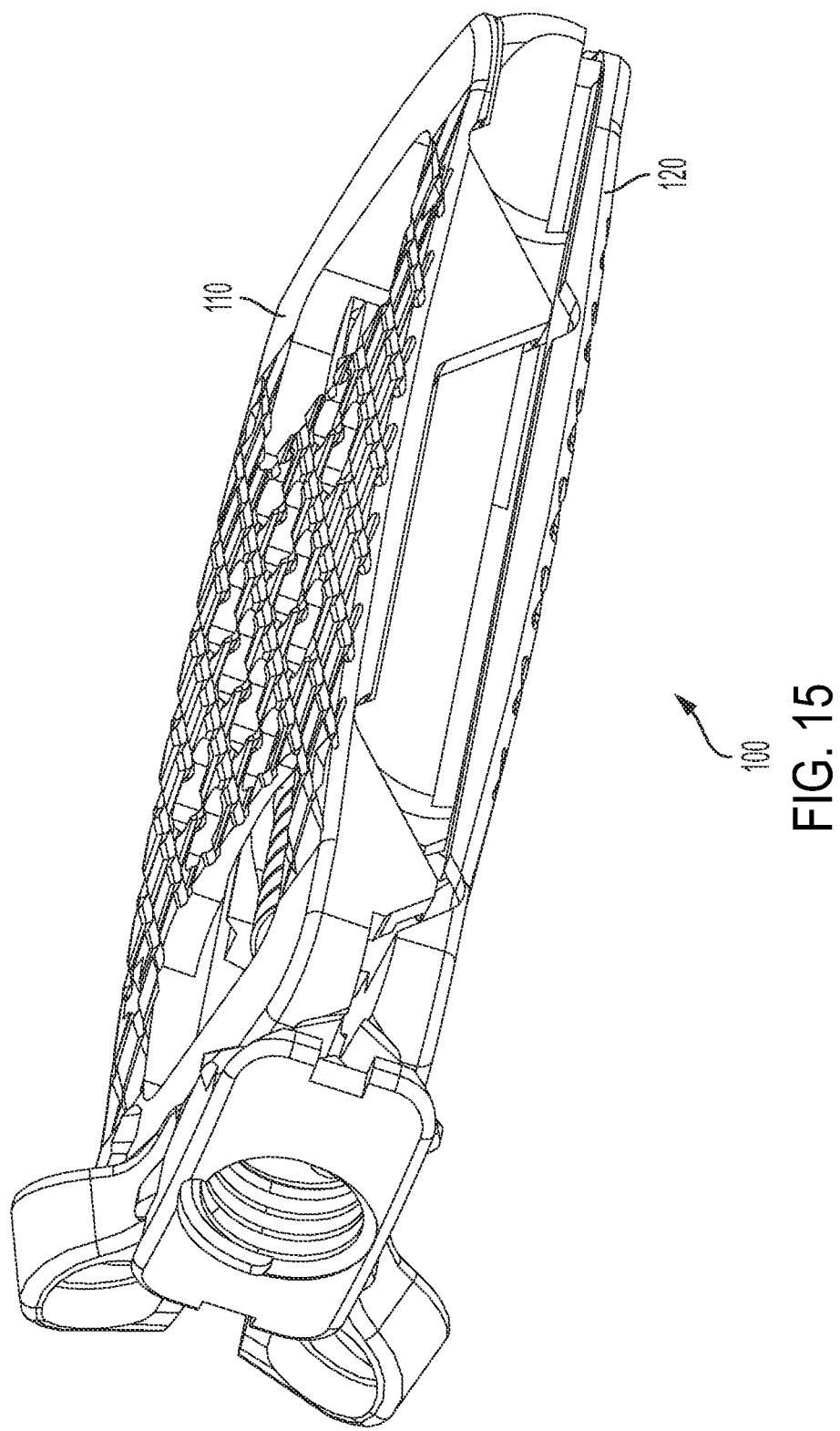
FIG. 15 is an alternate perspective view of an expandable spinal implant in accordance with the principles of the present disclosure.
Figure 16:
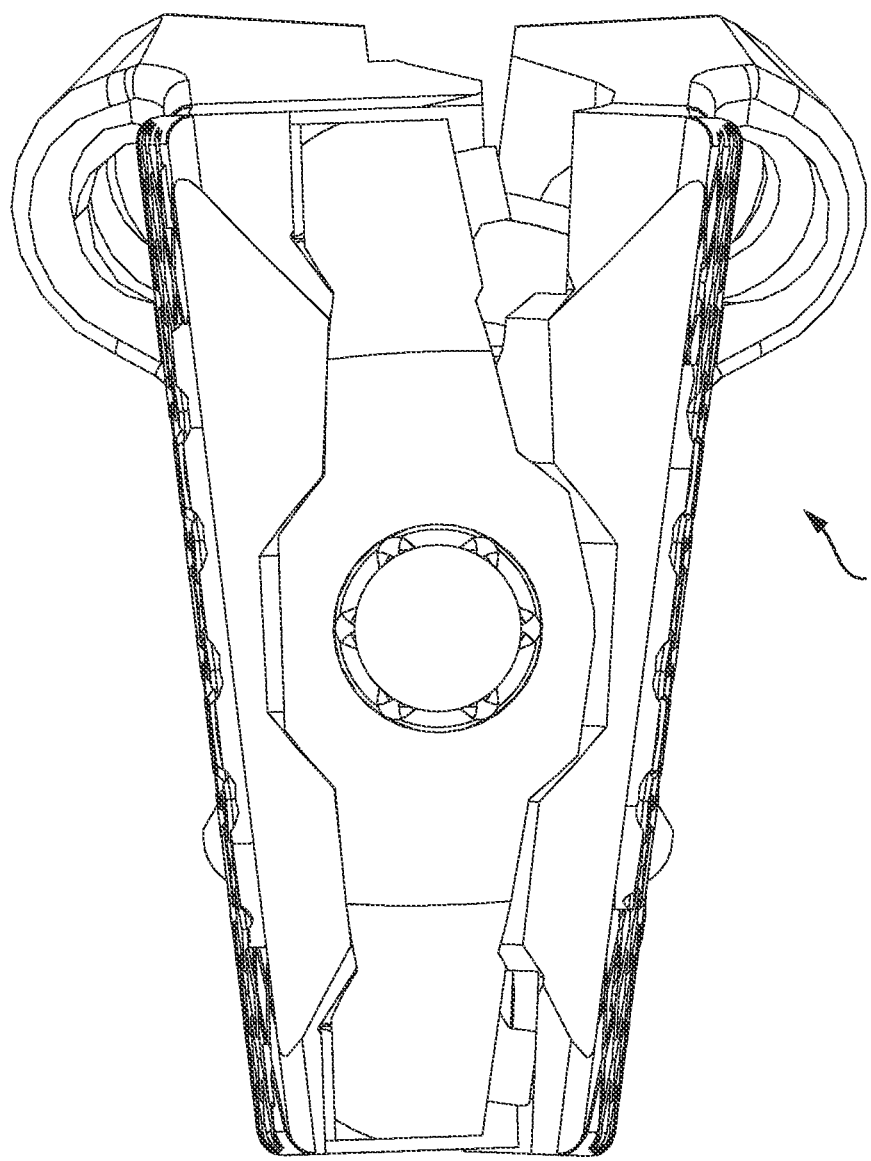
FIG. 16 is rear side profile view of an expandable spinal implant in accordance with the principles of the present disclosure.
Figure 17:
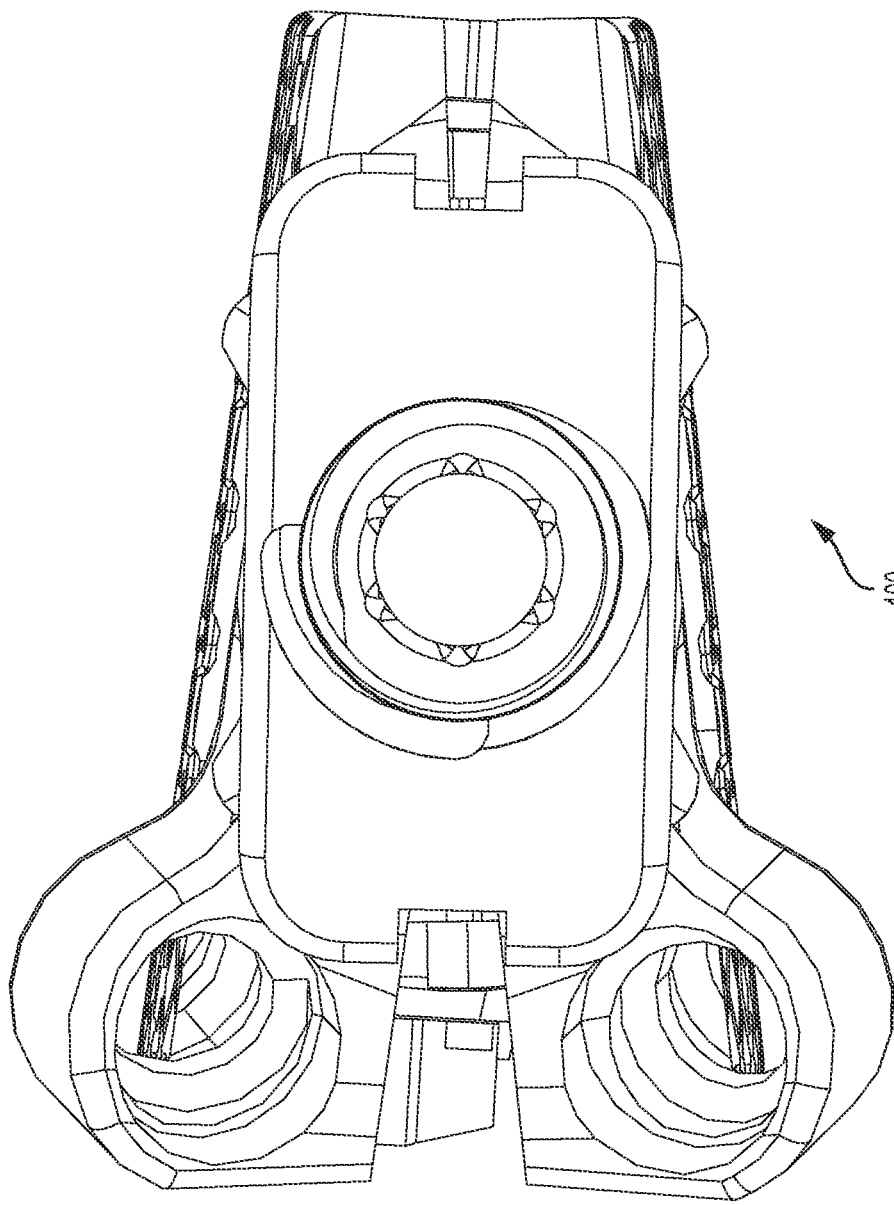
FIG. 17 is front side profile view of an expandable spinal implant in accordance with the principles of the present disclosure.

FIG. 14 illustrates bottom sliding frame 130 being operably coupled to bottom endplate 120. In turn, angled wedge 140 may be operably coupled to top sliding frame 150 and bottom sliding frame 130. Additionally, screw guide body 256 may be operably coupled to sliding block 253. FIG. 15 is an alternate perspective view of an assembled expandable spinal implant 100. FIG. 16 is rear side profile view of an assembled expandable spinal implant 100 in accordance with the principles of the present disclosure. FIG. 17 is front side profile view of an assembled expandable spinal implant 100 in accordance with the principles of the present disclosure.

Figure 18A:
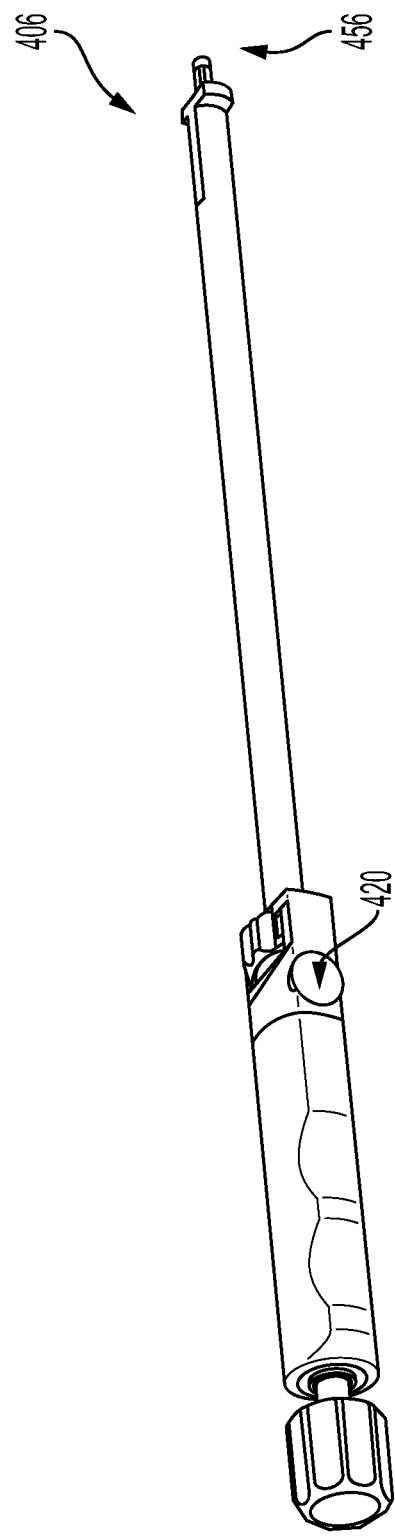
FIG. 18A is a perspective view of one embodiment of a first surgical tool for use with disclosed expandable spinal implants in accordance with the principles of the present disclosure.
Figure 18B:
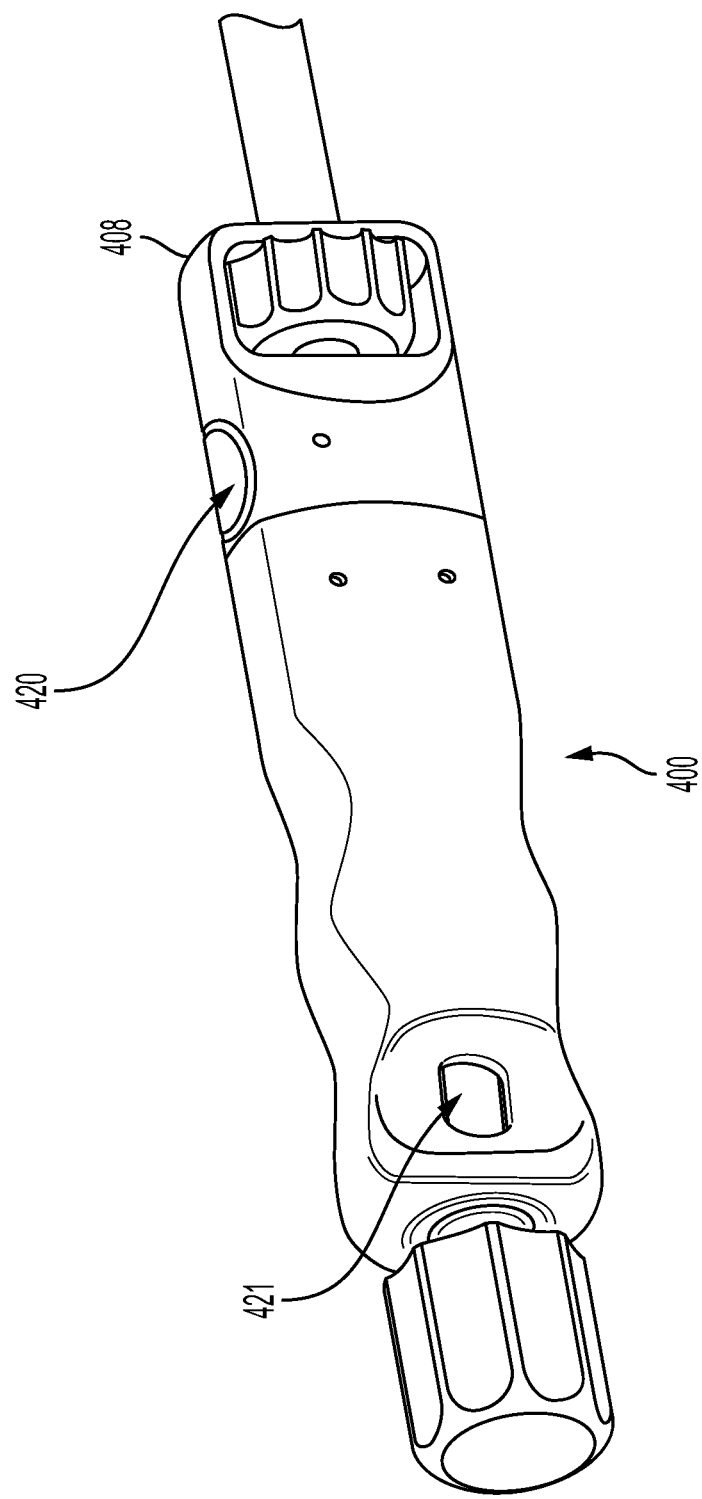
FIG. 18B is an enlarged side view of a handle portion of the first surgical tool of FIG. 18 in accordance with the principles of the present disclosure.
Figure 20:
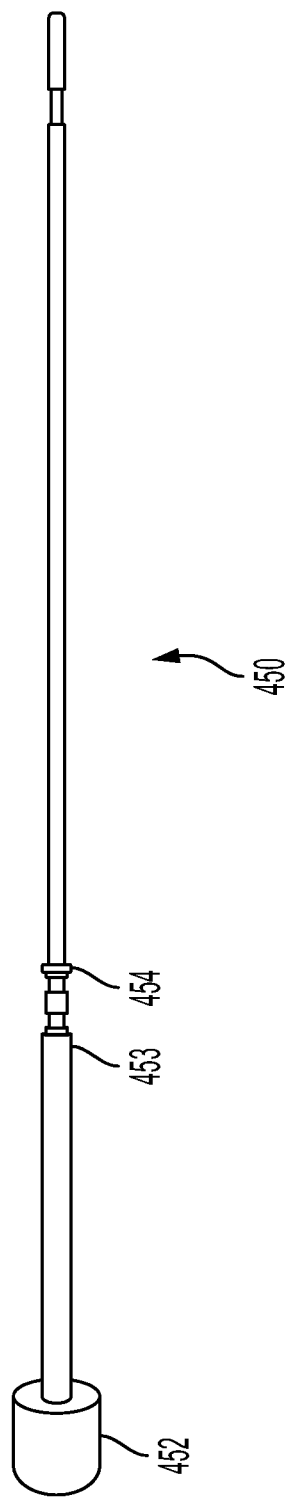
FIG. 20 is a side view of an adjustment rod for use with disclosed first surgical tool in accordance with the principles of the present disclosure.

Referring generally to FIGS. 18A-24B various surgical tools for use with expandable spinal implant 100 are illustrated. FIGS. 18A-18B are perspective views of a first surgical tool 400 of an adjustable spinal implant system in accordance with the principles of the present disclosure. FIGS. 19A-19B are side views of the first surgical tool 400 and FIG. 20 illustrates a corresponding adjustment rod 450 configured for insertion inside of first surgical tool 400. Tip 406 may be configured to connect to spinal implant 100 such that spinal implant 100 may be securely attached to first surgical tool 400 by engaging locking mechanism 408. Similarly, tip 406 may be configured to disconnect from spinal implant 100 such that spinal implant 100 is no longer securely attached to first surgical tool 400 by disengaging locking mechanism 408. For example, FIG. 19A shows tip 406 in a first locking position with tip grips 406a being expanded for gripping onto spinal implant 100 and FIG. 19B shows tip 406 in a second locking position with tip grips 406a being retracted. Locking mechanism 408 may be configured to toggle between the first locking position and second locking position. In some embodiments, when locking mechanism 408 is engaged in the first locking position, spinal implant 100 may be fixedly coupled to first surgical tool 400. This may be advantageous for initial positioning of spinal implant 100 between vertebral bodies during surgery. Additionally, first surgical tool 400 includes a positioning mechanism 410 configured to position adjustment rod 450 in a first position and a second position. First surgical tool 400 may also include a push button 420 to toggle between positioning adjustment rod 450 in a first position to engage both first and second set screws 252, 254 and a second position to engage only the first set screw 252 (see FIG. 18B). Furthermore, in some embodiments first surgical tool 400 may include a window 421 to identify whether both first and second set screws 252 254 are engaged for parallel expansion/contraction of spinal implant 100 or whether only the first set screw 252 is engaged for adjusting an angle of inclination of spinal implant 100.

In the exemplary embodiment, first surgical tool 400 includes a central shaft aperture 409 extending through handle 402, shaft 404, and tip 406. Central shaft aperture 409 may be configured to receive adjustment rod 450 therein such that adjustment knob 452 is rotatable therein and protrudes, at least partly, from both ends. Adjustment rod 450 includes an adjustment knob 452, first and second positioning surfaces 453, 454 and keyed circumferential surface 456. When adjustment rod 450 is positioned within central shaft aperture 409, adjustment knob 452 protrudes from one end and keyed circumferential surface 456 protrudes from the other end. With adjustment rod 450 inserted within central shaft aperture 409 positioning mechanism 410 can extend and retract adjustment rod 450 in the longitudinal direction of shaft 404. When first surgical tool 400 is in a first position, keyed circumferential surface 456 may engage with both first and second set screws 252, 254 along the axis $A_1$ and when first surgical tool 400 is in the second position, keyed circumferential surface 456 may engage only the first set screw 252 along axis $A_1$. Positioning mechanism 410 may be configured to be toggled between a first position and a second position where it can act against positioning surfaces 453, 454 to extend and retract adjustment rod 450 in the longitudinal direction of shaft 404. For example, in the first position positioning mechanism 410 may extend adjustment rod 450 from tip 406 to an extended position where circumferential surface 456 may engage with internal circumferential surfaces of the first and second set screws 252, 254. In the second position, positioning mechanism 410 may retract adjustment rod 450 through tip 406 to a partially retracted position where circumferential surface 456 may only engage with internal circumferential surface of the first set screw 252. An internal gearing of positioning mechanism 410 may include internal locking pins and surfaces that act against positioning surfaces 453, 454 such that when an exposed turn dial knob of positioning mechanism 410 is turned to a particular position, the internal locking pins and surfaces act against the inclined and recessed surfaces of positioning surfaces 453, 454.

Additionally, in some embodiments, first surgical tool 400 may be configured to receive adjustment rods 450 of varying lengths having varying outside circumferential surfaces 456 and positioning surfaces 453, 454. For example, first surgical tool 400 may be configured to receive a first relatively shorter adjustment rod 450 optimized for use for a spinal implant 100 using corresponding relatively smaller endplates 110, 120 and a corresponding smaller moving mechanism 250 having a relatively shorter longitudinal axis and/or length optimized for such relatively shorter endplates. For example still, first surgical tool 400 may be configured to receive a second relatively longer adjustment rod 450 optimized for use for a spinal implant 100 using corresponding relatively larger endplates and a corresponding larger moving mechanism 250 having a relatively longer longitudinal axis optimized for such relatively longer endplates.

Furthermore, in some embodiments, first surgical tool 400 may be configured to operate in three modes. In the first mode, tip grips 406a are securely connected to spinal implant 100. In the second mode, adjustment rod 450 may be positioned in a first position such that upon selective rotation of adjustment knob 452 a spacing between endplates 110, 120 may selectively increase/decrease in minute increments. For example, by translating each of first set screw 252 and second set screw 254. In the third mode, adjustment rod 450 may be positioned in a second position such that upon selective rotation of adjustment knob 452 an angle of inclination between endplates 110, 120 may selectively increase/decrease in minute increments. For example, by only translating first set screw 252 an angle of inclination between endplates 110, 120 may increase/decrease by moving one lateral side of the endplates 110,120 towards/away from each other and moving the opposite lateral side of the endplates 110,120 in an opposite direction. In some embodiments, this may also happen by only translating second set screw 254 e.g., by a surgical tool 400 having a circumferential engagement surface 456 that will only engage a single set screw 252, 254 at a time.

Additionally, in some embodiments, first surgical tool 400 may be configured to receive multiple types of adjustment rods 450. In at least one embodiment, first surgical tool 400 may receive a first adjustment rod 450 with an outside circumferential surface 456 that is configured to engage (1) both the first and second set screws 252, 254 at the same time and (2) the first set screw 252. For example, the first adjustment rod 450 may be toggled between (1) a first position where outside circumferential surface 456 is fully extended and configured to engage both the first and second set screws 252, 254, and (2) a second position where outside circumferential surface 456 is partially extended (and/or partially retracted) to engage only the first set screw 252. In an alternate embodiment, first surgical tool 400 may receive a second adjustment rod 450 with an outside circumferential surface 456 that is configured to engage only one set screw 252, 254 at a time. For example, the outside circumferential surface 456 may have an engagement surface with a longitudinal length that corresponds to a single set screw 252, 254 such that it only engages with a single set screw 252, 254 at a time. For example, the second adjustment rod 450 may be toggled between (1) a first position where outside circumferential surface 456 is fully extended and configured to engage the second set screw 254 independently of the first set screw 252 and (2) a second position where outside circumferential surface 456 is partially extended (and/or partially retracted) to engage only the first set screw 252. At least one advantage of having first surgical tool 400 being configured to receive multiple types of adjustment rods 450 of varying lengths and having outside circumferential surfaces of different lengths is that a surgeon can quickly and easily select the appropriate adjustment rod 450. For example, a surgeon may select first adjustment rod 450 to expand/contract a spacing between endplates 110, 120 by the same or substantially the same amount while maintaining the angle of inclination between endplates 110, 120, i.e., by engaging both first and second set screws 252, 254. Additionally, a surgeon may select second adjustment rod 450 to selectively increase/decrease an angle of inclination between endplates of spinal implant 100 at the first lateral side 103 and second lateral side 104, i.e., by only engaging one of first and second set screws 252, 254 at a time.

In some embodiments, spinal implant 100 may comprise a three position inner drive shaft (not illustrated) complimentary to or in place of components of moving mechanism 250. The three position inner drive shaft may enable the first and second set screws 252, 254 to be adjusted independently from one another as well as enabling the first and second set screws 252, 254 to be adjusted concurrently or simultaneously. In other embodiments, spinal implant 100 may include a screw guide aperture 107 on both sides of the spinal implant 100 thereby providing access to the first set screw 252 independently from second set screw 254.

Figure 21:
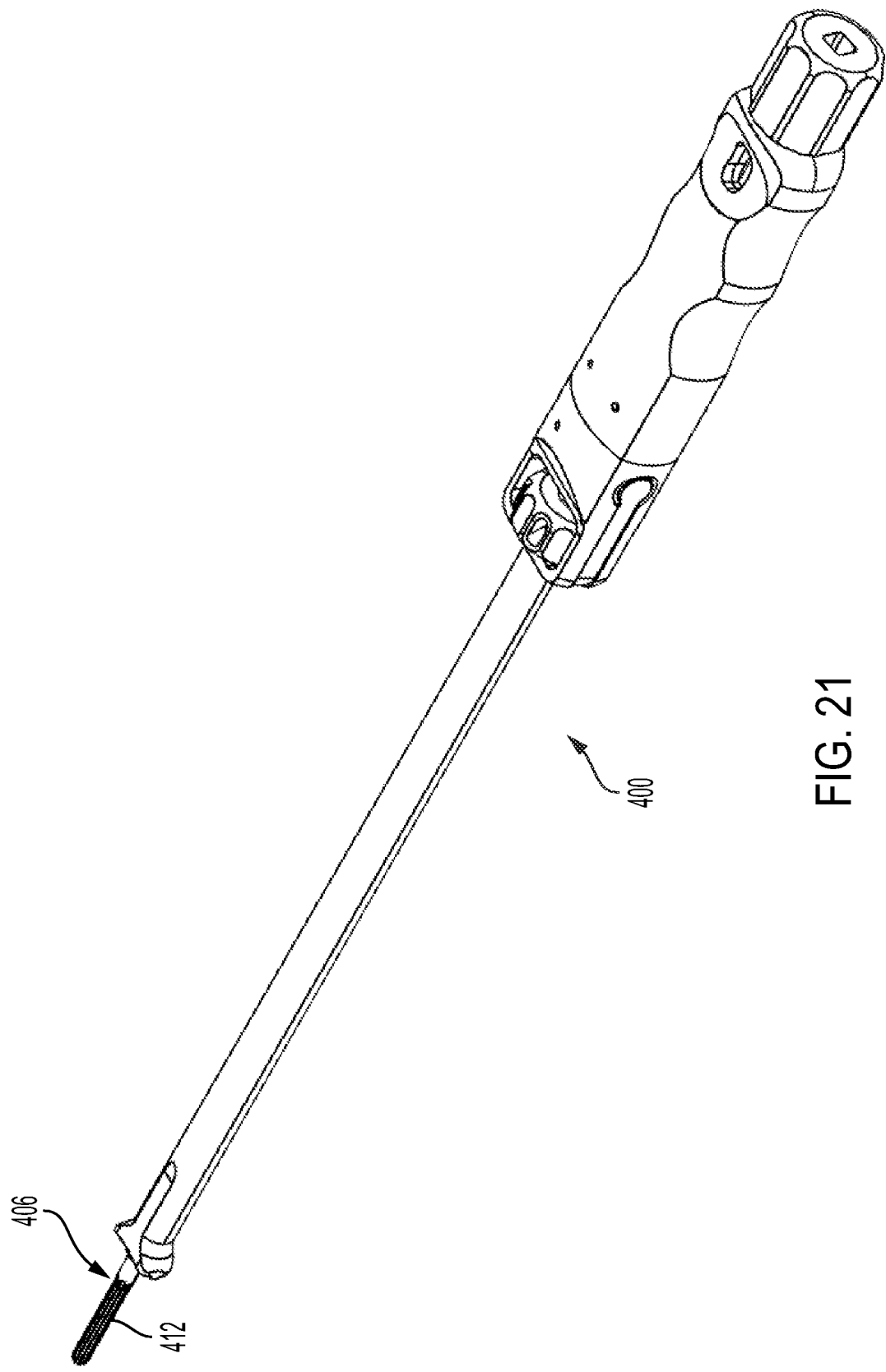
FIG. 21 is a perspective view of a different embodiment of a first surgical tool for use with disclosed expandable spinal implants in accordance with the principles of the present disclosure.

FIG. 21 is a perspective view of a different embodiment of a first surgical tool 400 for use with disclosed expandable spinal implants 100 and FIG. 22 is an enlarged side view of a tip portion 406 of the first surgical tool 400 of FIG. 21 in accordance with the principles of the present disclosure. In the disclosed embodiment, first surgical tool 400 may further include a threaded portion 400*a* operably configured to engage with a corresponding threaded portion 107*a* (see FIG. 13) of an expandable spinal implant 100. An advantage of this arrangement may be that the spinal implant 100 may be rigidly secured to first surgical tool 400 for insertion, removal, and/or adjustment.

Figure 23A:
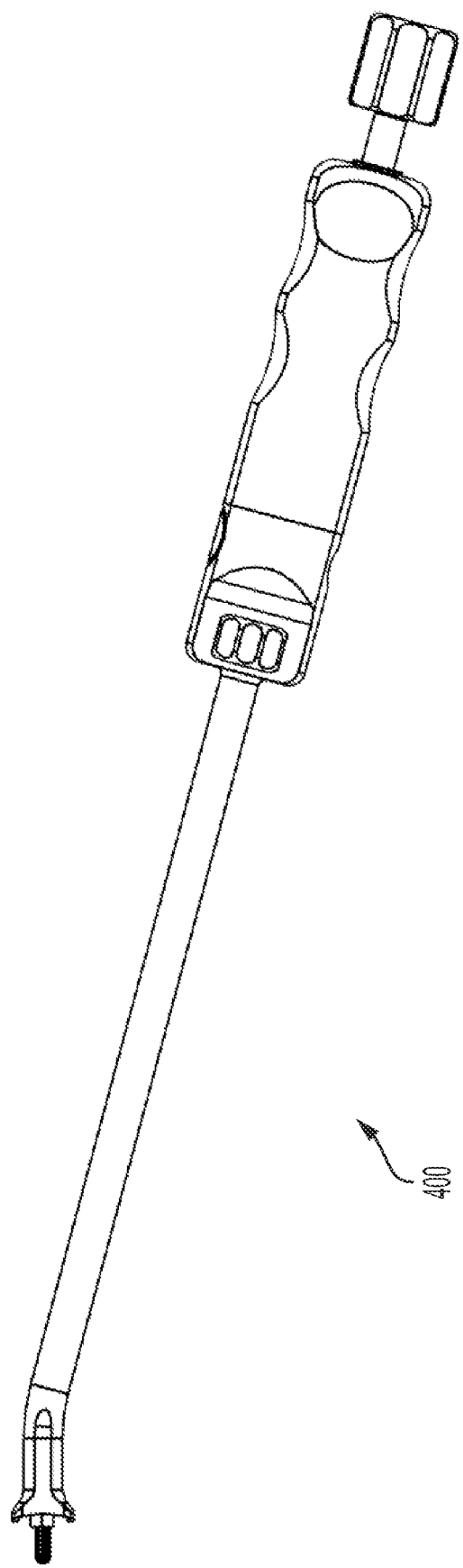
FIG. 23A is a perspective view of a different embodiment of a first surgical tool for use with disclosed expandable spinal implants in accordance with the principles of the present disclosure.
Figure 23B:
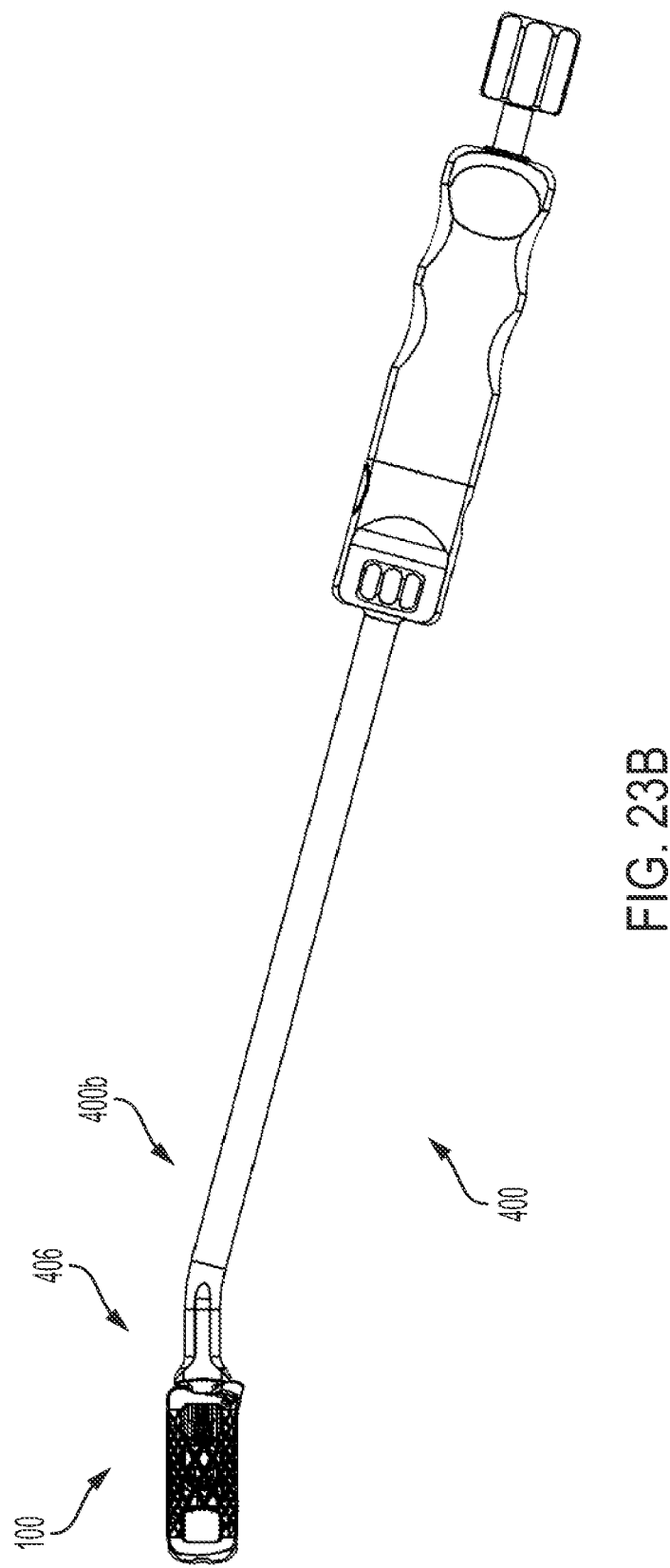
FIG. 23B is a perspective view of a different embodiment of a first surgical tool being inserted into an expandable spinal implant in accordance with the principles of the present disclosure.
Figure 24A:
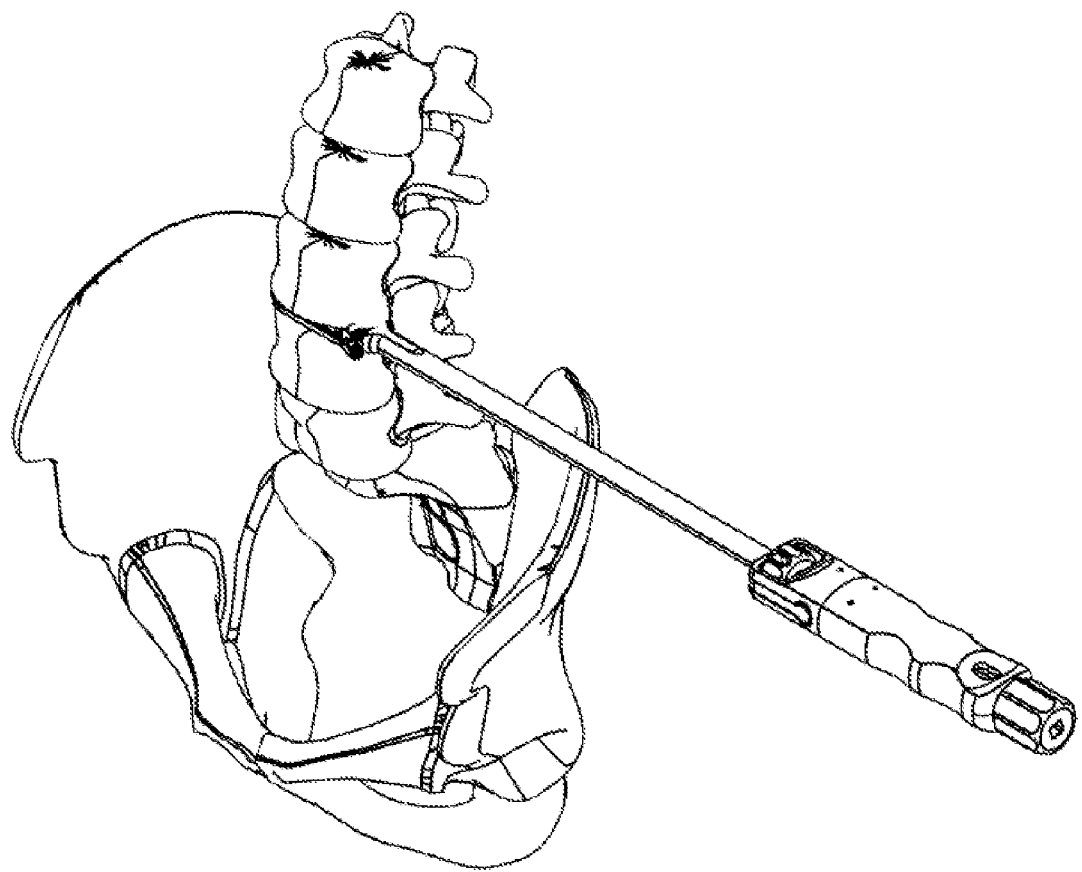
FIG. 24A is a perspective view of an expandable spinal implant between adjacent vertebrae and a first surgical tool in an adjustment position.
Figure 24B:
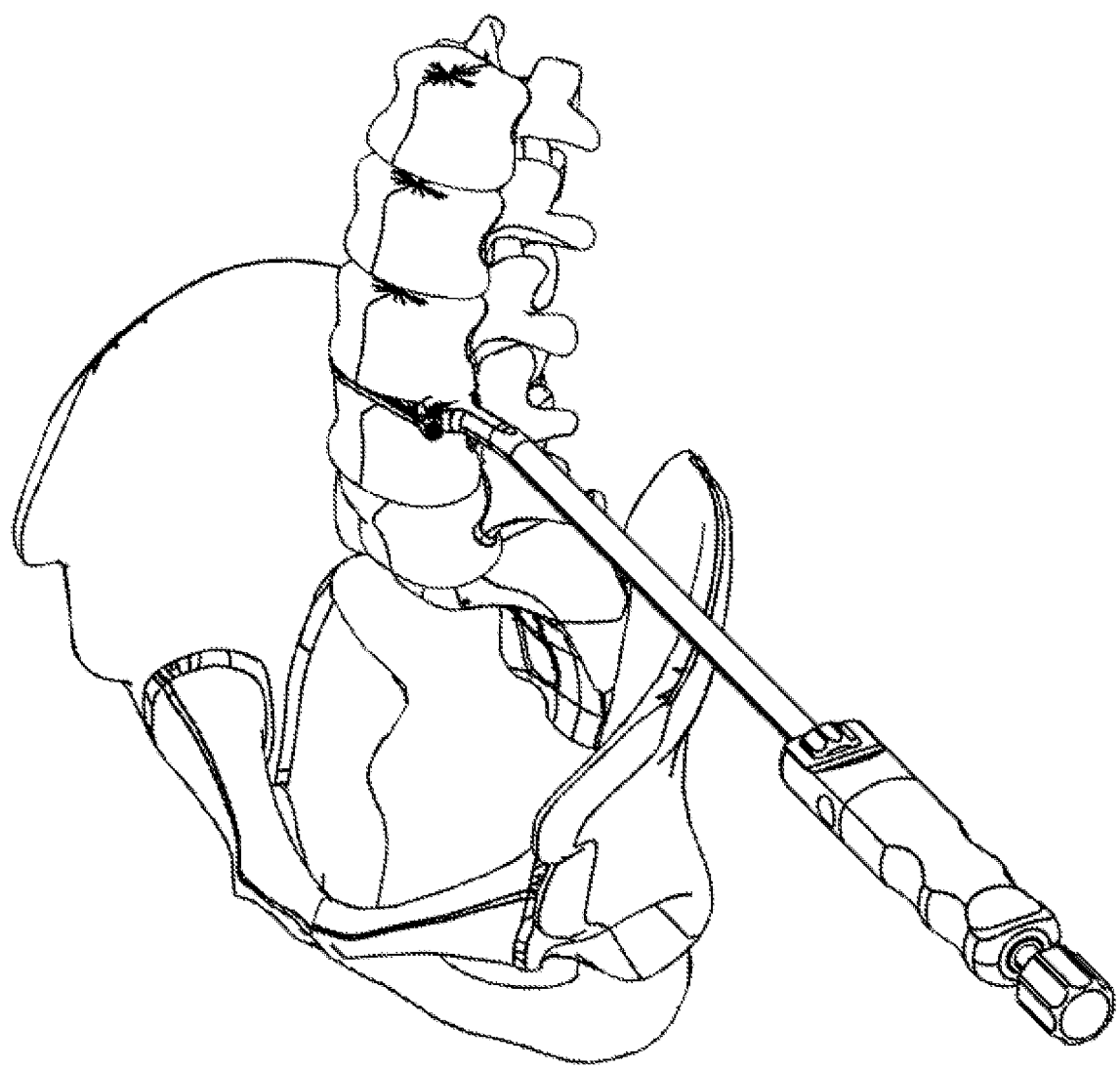
FIG. 24B is a perspective view of an expandable spinal implant between adjacent vertebrae and a curved first surgical tool in an adjustment position.

FIG. 23A is a perspective view of a different embodiment of a first surgical tool and FIG. 23B is a perspective view of the embodiment of FIG. 23A fixedly and operably engaged with expandable spinal implant 100 in accordance with the principles of the present disclosure. As illustrated, first surgical tool 400 includes a bent portion 400*b* adjacent the tip end 406. In some embodiments, bent portion 400*b* may be bent by about 5-25 degrees with respect to shaft 404. In other embodiments, bent portion 400*b* may be bent by about 10-15 degrees with respect to shaft 404. In at least one embodiment, bent portion 400*b* may be bent by about 15 degrees with respect to shaft 404. FIG. 24A is a perspective view of an expandable spinal implant 100 between adjacent vertebrae and a straight first surgical tool 400 in an adjustment position and FIG. 24B is a perspective view of an expandable spinal implant 100 between adjacent vertebrae and a curved first surgical tool 400 in an adjustment position.

Spinal implant systems of the present disclosure can be employed with a surgical arthrodesis procedure, such as, for example, an interbody fusion for treatment of an applicable condition or injury of an affected section of a spinal column and adjacent areas within a body, such as, for example, intervertebral disc space between adjacent vertebrae, and with additional surgical procedures and methods. In some embodiments, spinal implant systems can include an intervertebral implant that can be inserted between adjacent vertebral bodies to space apart articular joint surfaces, provide support for and maximize stabilization of vertebrae. In some embodiments, spinal implant systems may be employed with one or a plurality of vertebra.

Consistent with the disclosed embodiments herein, a medical practitioner may obtain access to a surgical site including vertebrae such as through incision and retraction of tissues. Spinal implant systems of the present disclosure can be used in any existing surgical method or technique including open surgery, mini-open surgery, minimally invasive surgery and percutaneous surgical implantation, whereby vertebrae are accessed through a mini-incision, retractor, tube or sleeve that provides a protected passageway to the area, including, for example, an expandable retractor wherein the sleeve may be formed from multiple portions that may be moved apart or together and may be inserted with the portions closed or together and then expanded to allow for insertion of implants of larger size than the closed cross section of the unexpanded retractor portions. In one embodiment, the components of the spinal implant system are delivered through a surgical pathway to the surgical site along a surgical approach into intervertebral disc space between vertebrae. Various surgical approaches and pathways may be used.

As will be appreciated by one of skill in the art, a preparation instrument (not shown) may be employed to remove disc tissue, fluids, adjacent tissues and/or bone, and scrape and/or remove tissue from endplate surfaces of a first vertebra and/or endplate surface of a second vertebra in preparation for or as part of the procedures utilizing a system of the present disclosure. In some embodiments, the footprint of spinal implant 100 may be selected after trialing using trialing instruments (not shown) that may approximate the size and configuration of spinal implant 100. In some embodiments, such trials may be fixed in size and/or be fitted with moving mechanisms 250 similar to embodiments described herein. In some embodiments, spinal implant 100 may be visualized by fluoroscopy and oriented before introduction into intervertebral disc space. Furthermore, first and second surgical tools 400, 500 (see FIG. 38A) and spinal implant 100 may be fitted with fiducial markers to enable image guided surgical navigation to be used prior to and/or during a procedure.

Components of a spinal implant systems of the present disclosure can be delivered or implanted as a pre-assembled device or can be assembled in situ. In one embodiment, spinal implant 100 may be made of a single piece construction that may not be disassembled without destroying the device. In other embodiments, spinal implant 100 may comprise removable parts. Components of spinal implant systems may be expanded, contracted, completely or partially revised, removed or replaced in situ. In some embodiments, spinal implant 100 can be delivered to the surgical site via mechanical manipulation and/or a free hand technique.

Additionally, components of spinal implant 100 can include radiolucent materials, e.g., polymers. Radiopaque markers may be included for identification under x-ray, fluoroscopy, CT or other imaging techniques. Furthermore, first and second surgical tools 400, 500 (see FIGS. 18A, 38A) may be radiolucent and may optionally include markers added at a tip portion thereof to permit them to be seen on fluoroscopy/x-ray while advancing into the patient. At least one advantage to having spinal implant 100 may be that a medical practitioner can verify the positioning of spinal implant 100 relative to adjacent vertebral bodies and make further adjustments to the spacing between endplates 110, 120, angle of inclination between endplates 110, 120, and the overall positioning of the device within a patient's body. In this way, spinal implant 100 may correct alignment of a patient's spine in a coronal plane.

Figure 25:
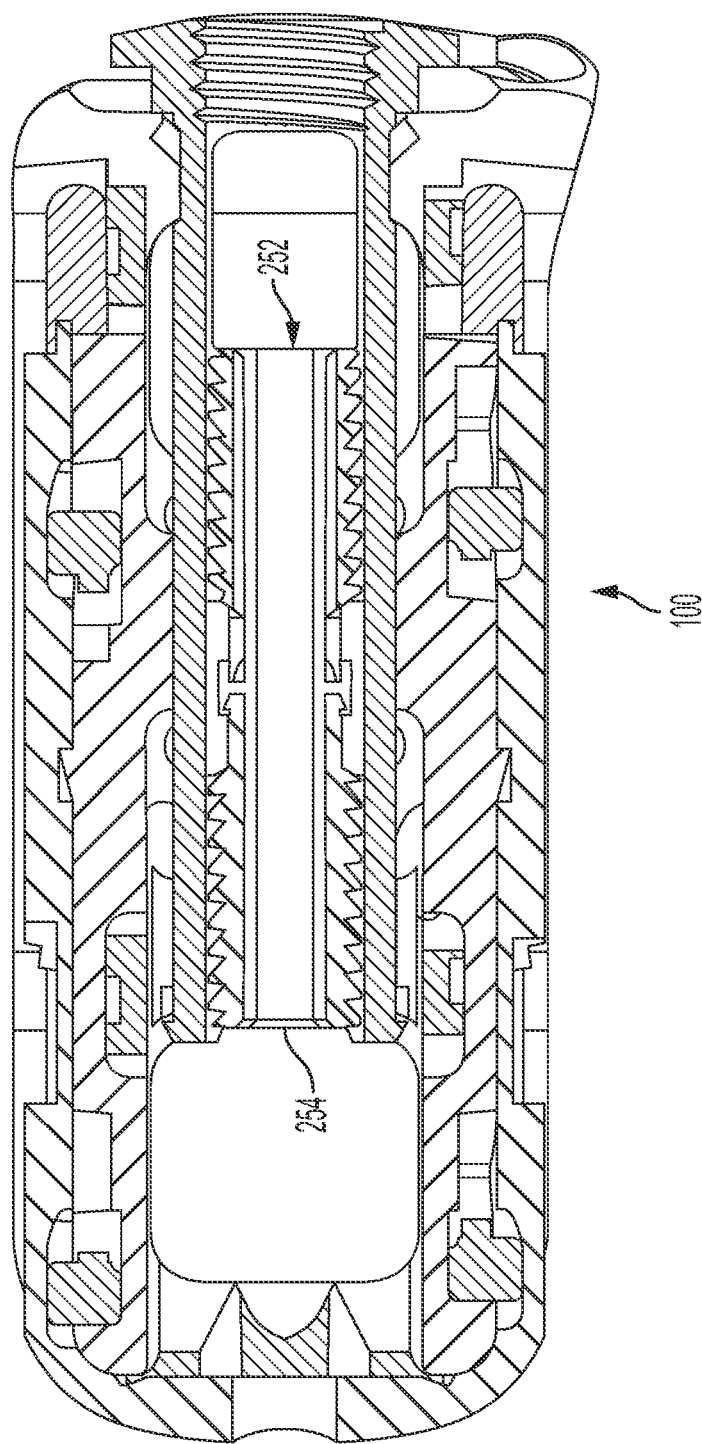
FIG. 25 is a top down cut out view of an expandable spinal implant in accordance with the principles of the present disclosure.
Figure 26:
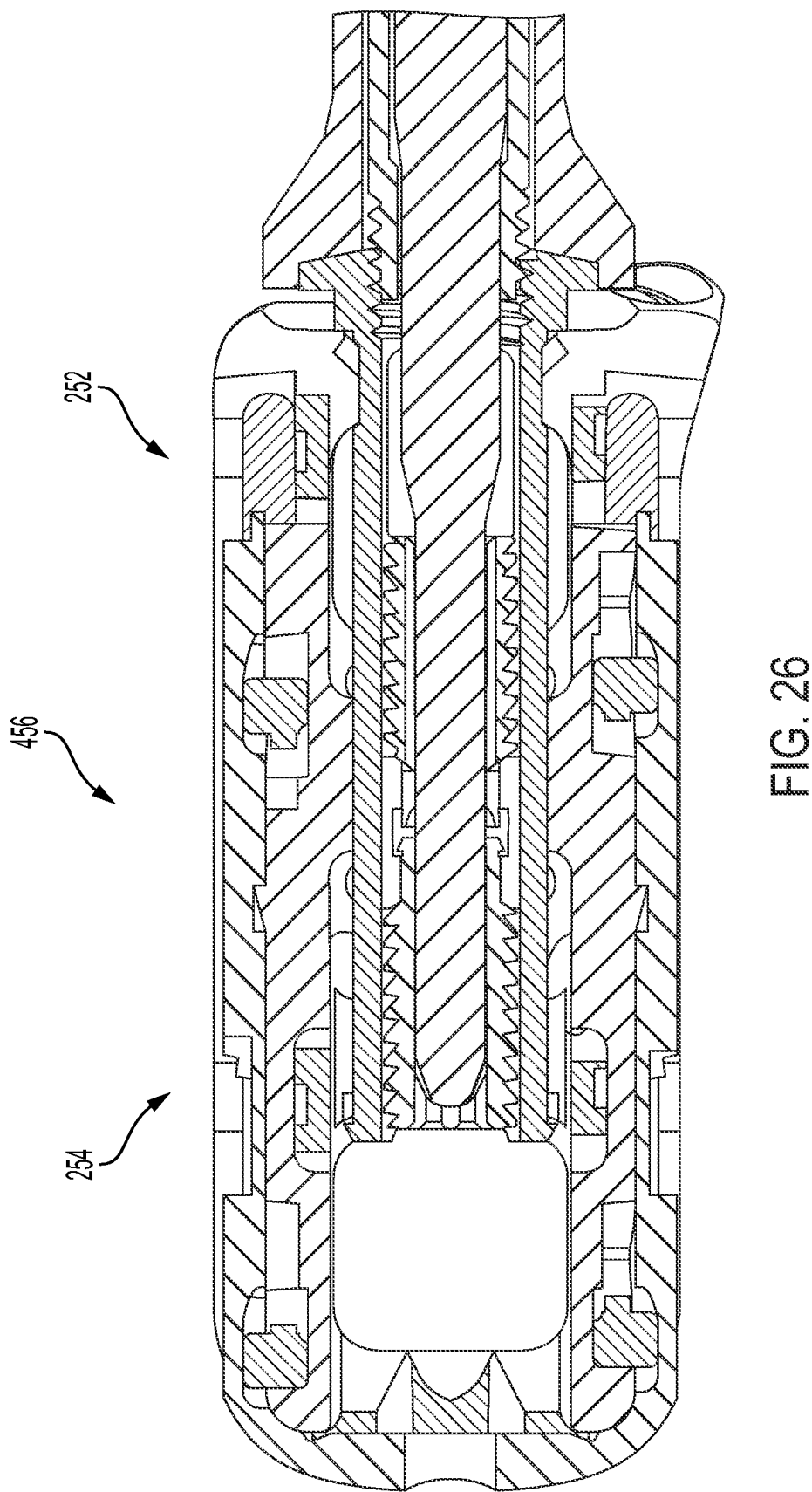
FIG. 26 is a top down cut out view of the expandable spinal implant of FIG. 25 and a first surgical tool in a first adjustment position in accordance with the principles of the present disclosure.

Referring generally to FIGS. 25-34B, operable functional characteristics of moving mechanism 250 and expandable spinal implant 100 will be disclosed. FIG. 25 is a top down cut out view of an expandable spinal implant 100 and FIG. 26 is a top down cut out view of the expandable spinal implant of FIG. 25 and a first surgical tool 400 in a first adjustment position in accordance with the principles of the present disclosure. As illustrated in FIG. 26, tip 406 may be inserted through screw guide aperture 107 and into moving mechanism 250. Moving mechanism 250 includes a first set screw 252 and a second set screw 254 having respective internal cavities configured to operably receive tip 406. As explained above, the first and second set screws 252, 254 may be operably coupled to angled wedge 140 and bottom sliding frame 130, respectively. In the exemplary embodiment, the second set screw 254 has a reverse thread pitch relative to the first set screw 252. In some embodiments, the thread pitch may be an M6 thread pitch, however other embodiments may have other thread pitches.

Each internal cavity of set screws 252, 254 comprises an internal circumferential surface that may be keyed to the outside circumferential surface 412 of tip 406 of first surgical tool 400. For example, the outside circumferential surface 412 may resemble the geometry of the tip of a torx driver, hex driver, or the like and the internal circumferential surfaces of the first and second set screws 252, 254 may resemble the geometry of the cavity of the head of a torx screw, hex screw, or the like. In some embodiments, the internal circumferential surfaces of the first and second set screws 252, 254 may be configured for a Torx T20 driver or the like, however other embodiments may be differently sized. In other embodiments, the connection between the outside circumferential surface 412 and the inner circumferential surfaces of first and second set screws 252, 254 may comprise a variety of drive interfaces including but not limited to: multi-lobular drives; hexalobular drives; cross or Phillips head drives; straight or "flat head" drives; square or other polygonal drives; and/or combinations thereof. It shall be understood that any suitable geometrical shape or surface profile may be used by the exemplary embodiments disclosed herein provided the outside circumferential surface 412 is operably keyed to engage with the internal circumferential surfaces of the first and second set screws 252, 254.

Figure 27:
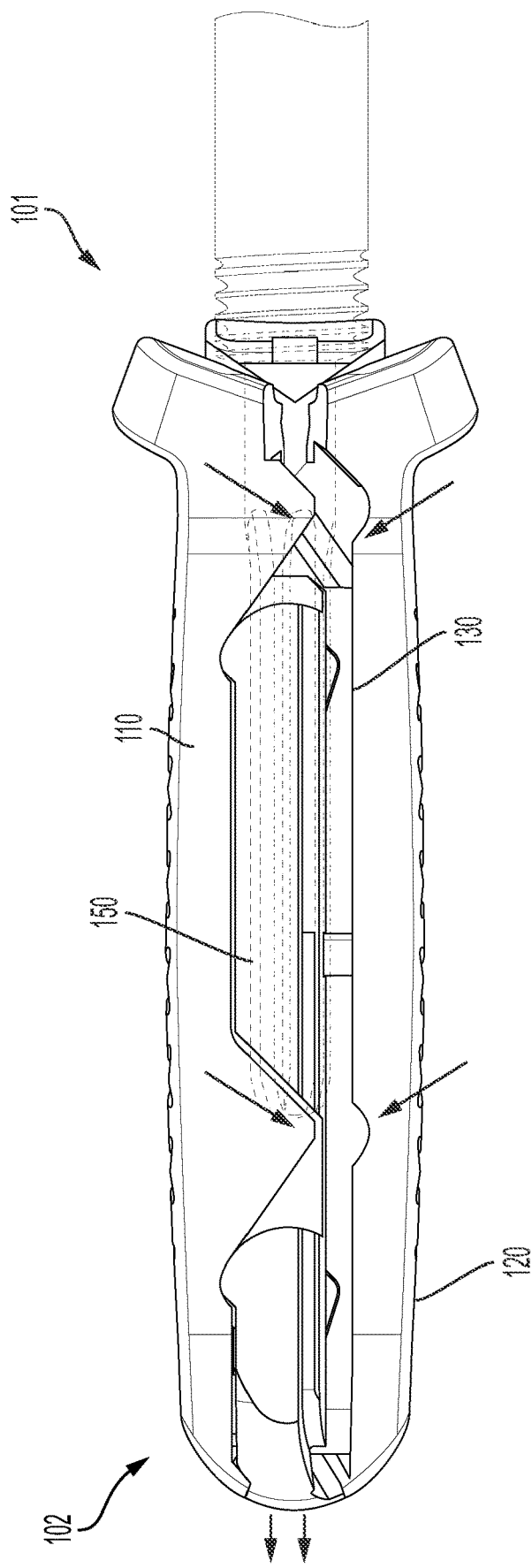
FIG. 27 is a lateral side profile view of an expandable spinal implant showing movement of relevant parts upon rotation of the first surgical tool in a first direction when the first surgical tool is in the first adjustment position of FIG. 26 in accordance with the principles of the present disclosure.

In the exemplary embodiment of FIG. 26, outside circumferential surface 412 may be engaged with both the first and second set screws 252, 254 and when first surgical tool 400 is rotated in a first direction (clockwise direction) the outside circumferential surface 412 rotates both set screws 252, 254 thereby causing angled wedge 140 and bottom sliding frame 130 to move forward towards distal end 102 and away from proximal end 101 (because angled wedge 140 and bottom sliding frame 130 are directly coupled to first and second set screws 252, 254, respectively). Additionally, because protrusions 138c of bottom sliding frame 130 (see FIG. 11) are operably coupled to third channels 158c of top sliding frame 150 (see FIGS. 10C-10D), movement of bottom sliding frame 130 towards distal end 102 and away from proximal end 101 also causes the same longitudinal movement of top sliding frame 150, i.e., movement of bottom sliding frame forward and backward also causes movement of top sliding frame forwards and backwards in a direction parallel to first reference axis $A_1$. For example, as shown in FIG. 27, top sliding frame 150 and bottom sliding frame 130 are represented as moving from proximal end 101 to distal end 102 by arrows to thereby move endplates 110, 120 to a collapsed position, i.e., spinal implant 100 may be in a vertically collapsed position in FIG. 27.

Figure 28:
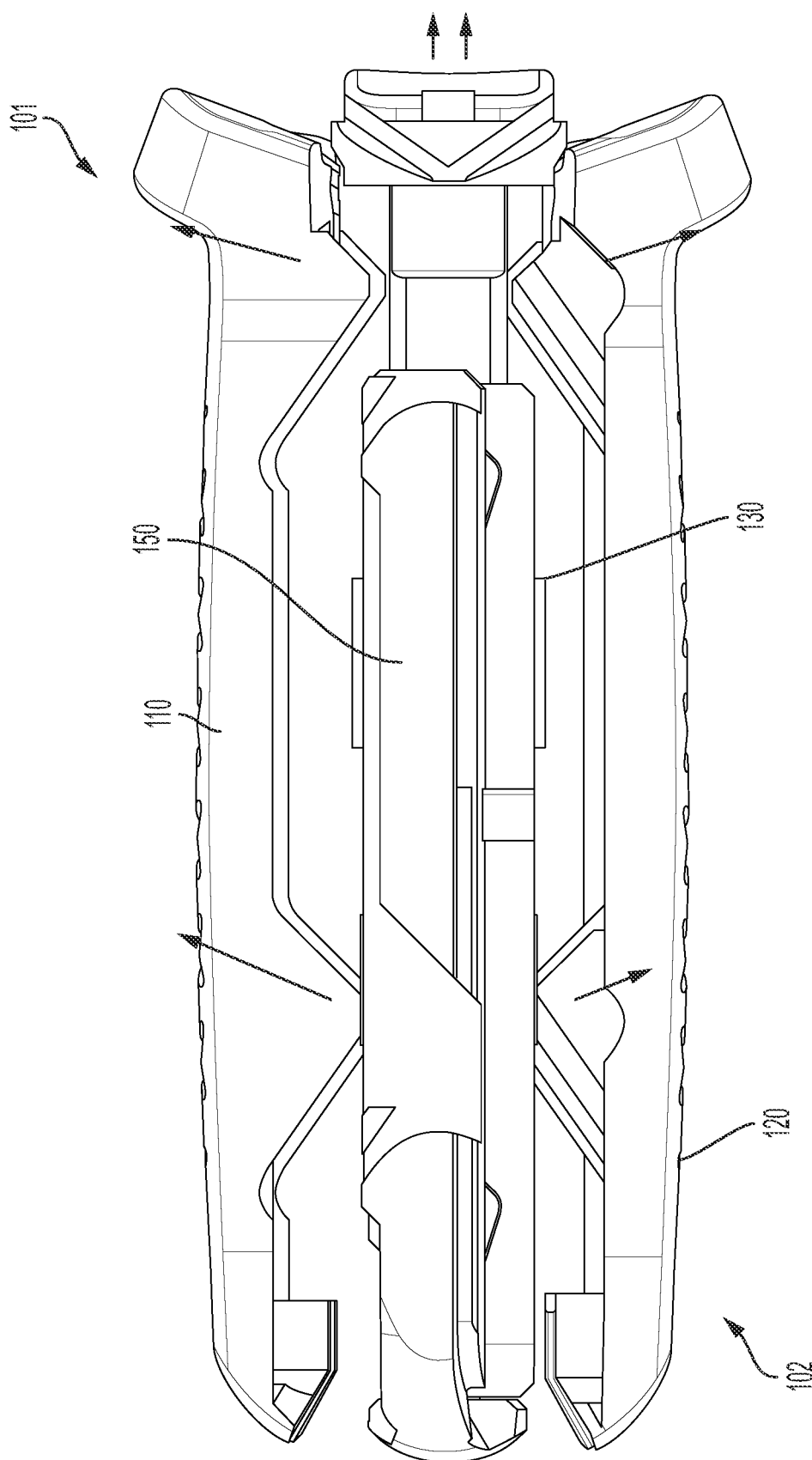
FIG. 28 is a lateral side profile view of an expandable spinal implant showing movement of relevant parts upon rotation of the first surgical tool in a second direction when the first surgical tool is in the first adjustment position of FIG. 26 in accordance with the principles of the present disclosure.

Similarly, when outside circumferential surface 412 is engaged with both the first and second set screws 252, 254 and when first surgical tool 400 is rotated in a second direction (counter-clockwise direction) the outside circumferential surface 412 rotates both set screws 252, 254 thereby causing angled wedge 140 and bottom sliding frame 130 to move backwards towards proximal end 101 and away from distal end 102 (because angled wedge 140 and bottom sliding frame 130 are directly coupled to first and second set screws 252, 254, respectively). Additionally, bottom sliding frame 130 may be operably coupled to top sliding frame 150 as explained above, top sliding frame 150 also moves towards proximal end 101 and away from distal end 102. For example, as shown in FIG. 28, top sliding frame 150 and bottom sliding frame 130 are represented as moving from distal end 102 to proximal end 101 to thereby move endplates 110, 120 to an expanded position, i.e., spinal implant 100 may be in a vertically expanded position in FIG. 28.

Top sliding frame 150 effectuates the above explained expansion/contraction motion because first distal contact surfaces 150a and first proximate contact surfaces 150b (see FIG. 10D) act against inclined surfaces of corresponding ramps 114, 116 of top endplate 110 (represented by arrows) and first proximate guide walls 154a and first distal guide walls 156a (see FIG. 10B) are retained by first proximal grooves 114a and first distal grooves 116a, respectively. Similarly, bottom sliding frame 130 effectuates this expansion motion because inclined contact surfaces 136aa and 134aa (see FIG. 11) act against corresponding inclined surfaces of ramps 124, 126 of bottom endplate 120 (represented by arrows) and second proximate guide walls 134a and second distal guide walls 136a (see FIG. 11) are retained by second proximal grooves 124a and second distal grooves 126a. In summary, when positioning the first surgical tool 400 in the first position and translating the first surgical tool 400 in either the first or second direction the moving mechanism 250 operably adjusts a spacing between the top and bottom endplates by simultaneous rotation of the first and second set screws 252, 254.

Figure 29:
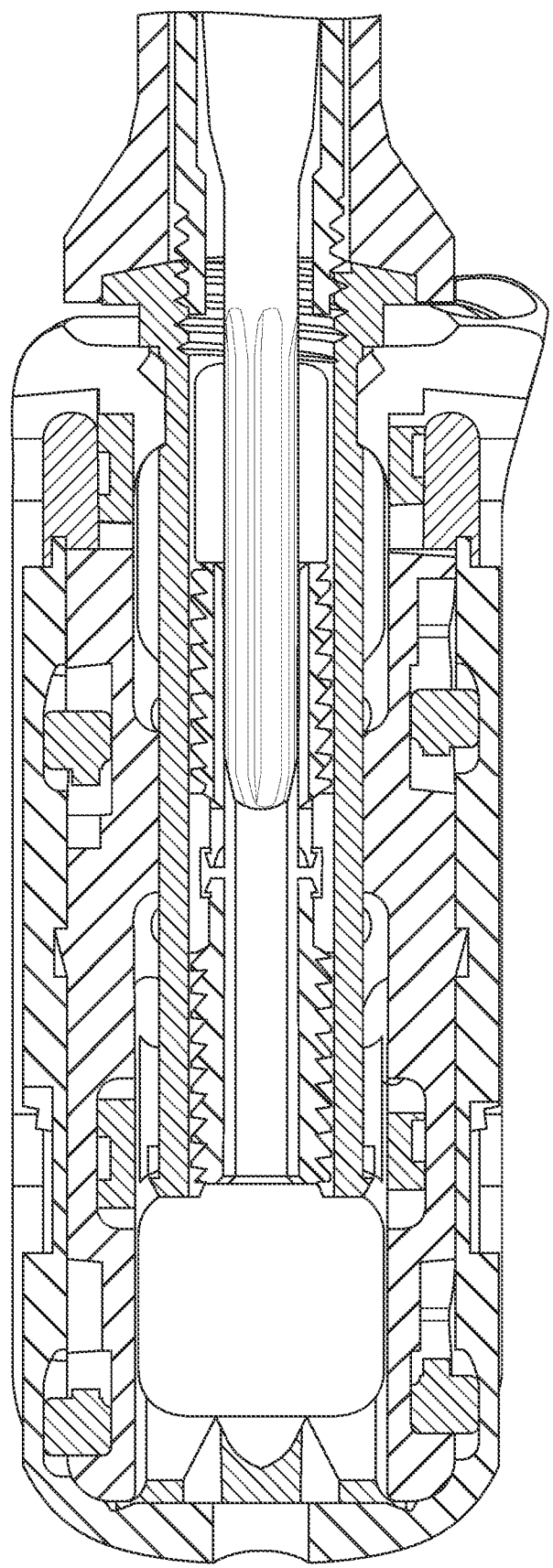
FIG. 29 is a top down cut out view of the expandable spinal implant of FIG. 25 and a first surgical tool in a second adjustment position in accordance with the principles of the present disclosure.
Figure 30A:
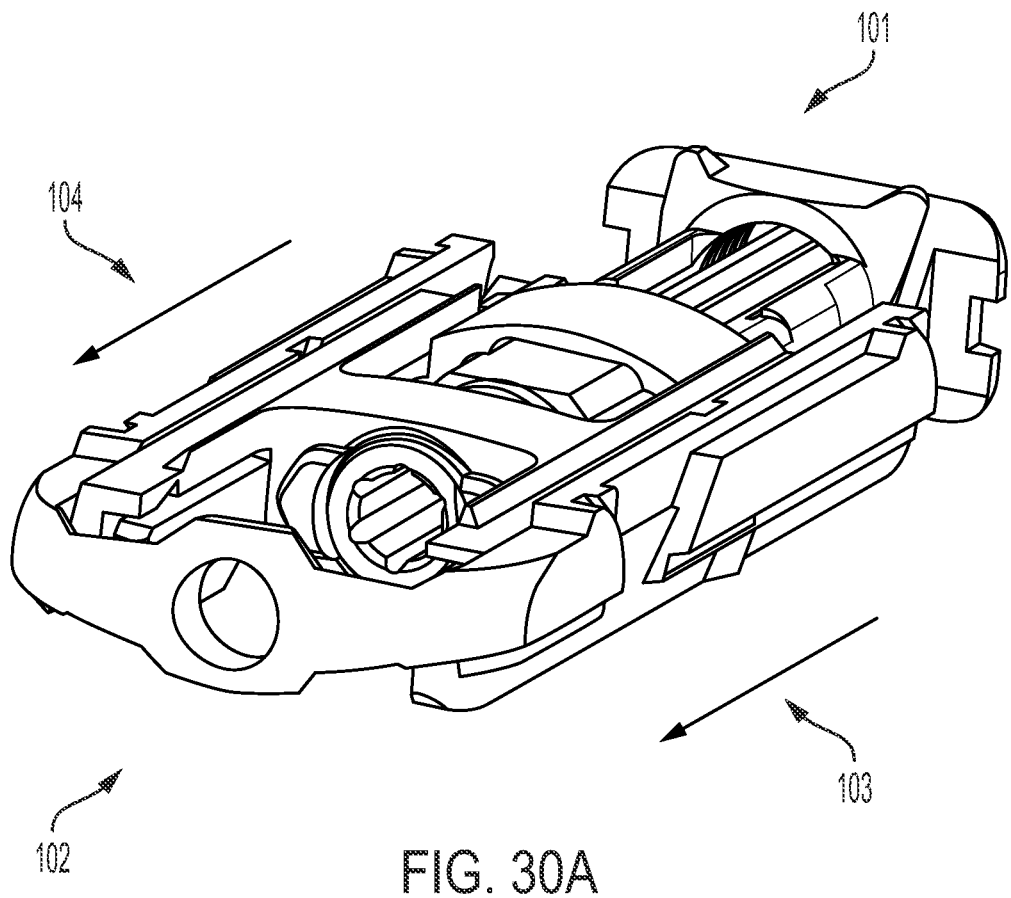
FIG. 30A is a perspective view of an expandable spinal implant showing movement of relevant parts upon rotation of the first surgical tool in a first direction when the first surgical tool is in the second adjustment position of FIG. 29 in accordance with the principles of the present disclosure.
Figure 30B:
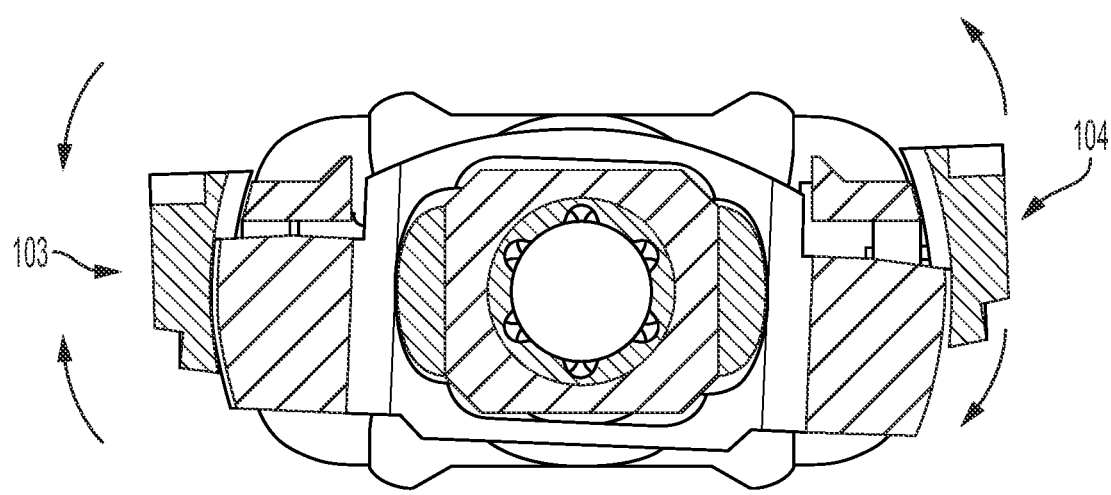
FIG. 30B is a front side view of an expandable spinal implant showing movement of relevant parts upon rotation of the first surgical tool in a first direction when the first surgical tool is in the second adjustment position of FIG. 29 in accordance with the principles of the present disclosure.

In the exemplary embodiment of FIG. 29, outside circumferential surface 412 may be engaged with only the first set screw 252 and when first surgical tool 400 is rotated in a first direction (clockwise direction) the outside circumferential surface 412 rotates set screw 252 thereby causing angled wedge 140 to move forward towards distal end 102 and away from proximate end 101. This occurs because angled wedge 140 may be coupled to first set screw 252. For example, as shown in FIG. 30A, angled wedge 140 is represented as moving from proximal end 101 to distal end 102 by arrows. As illustrated by arrows in FIG. 30B, when angled wedge 140 moves forward towards distal end 102 it causes top sliding frame 150 and bottom sliding frame 130 to move away from one another at second lateral end 104 and move towards one another at first lateral end 104. For example, when angled wedge 140 moves forward towards distal end 102 it causes a distance between endplates 110, 120 at corresponding first lateral ends thereof to increase and also causes a distance between endplates 110, 120 at corresponding second lateral ends thereof to decrease. Therefore, rotation of only the first set screw 252 adjusts an angle of inclination between endplates 110, 120.

Figure 31A:
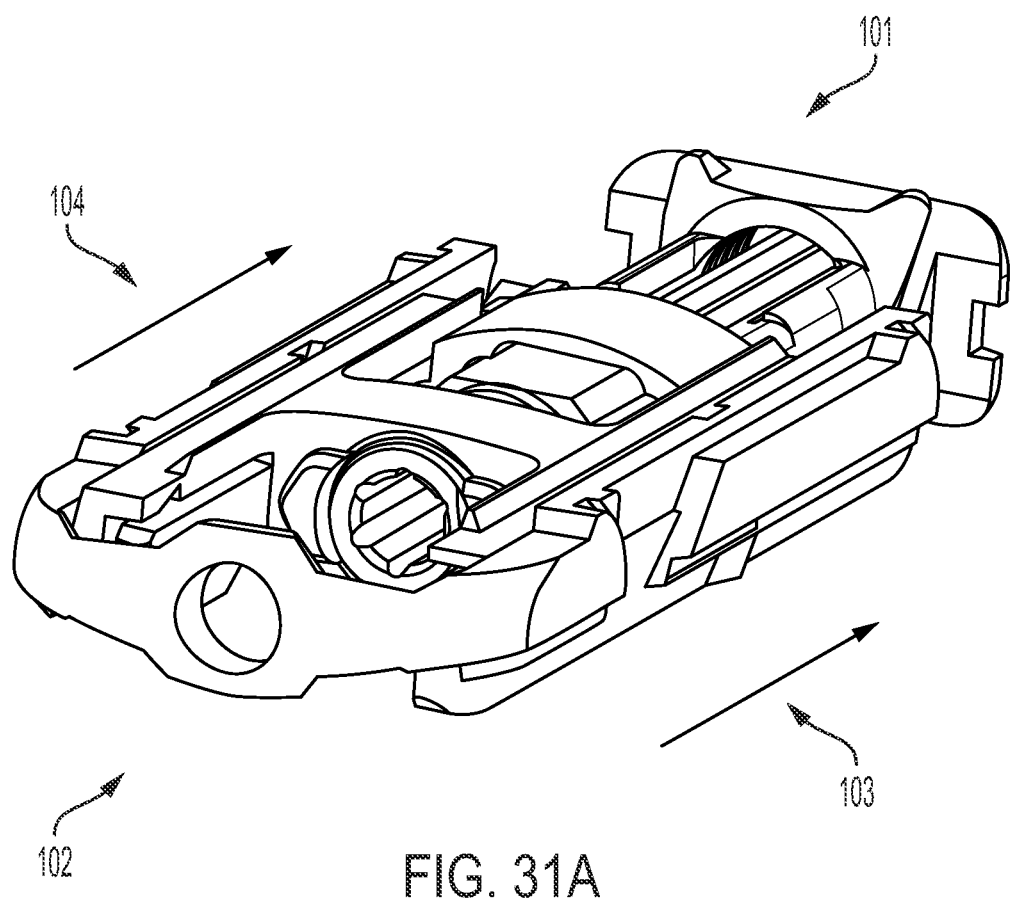
FIG. 31A is a perspective view of an expandable spinal implant showing movement of relevant parts upon rotation of the first surgical tool in a second direction when the first surgical tool is in the second adjustment position of FIG. 29 in accordance with the principles of the present disclosure.
Figure 31B:
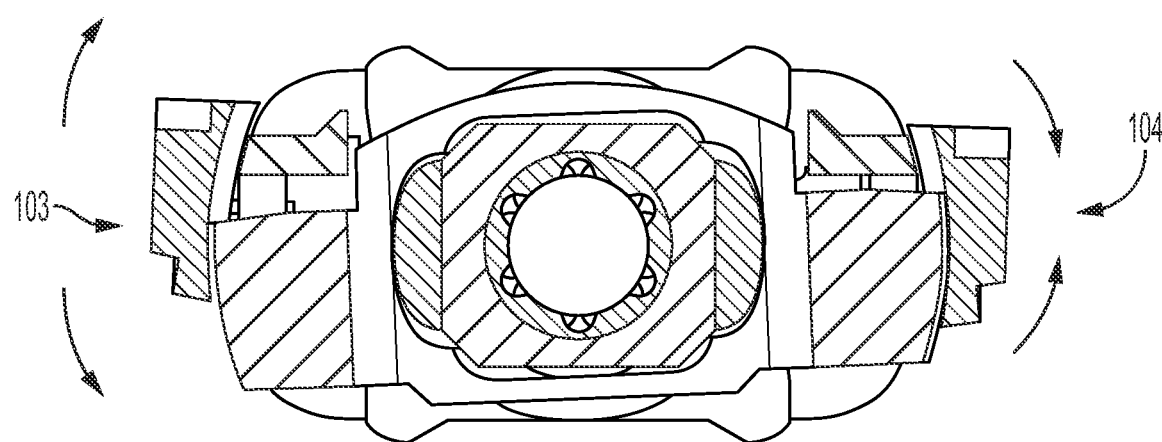
FIG. 31B is a front side view of an expandable spinal implant showing movement of relevant parts upon rotation of the first surgical tool in a second direction when the first surgical tool is in the second adjustment position of FIG. 29 in accordance with the principles of the present disclosure.

Similarly, when outside circumferential surface 412 is engaged with only the first set screw 252 and when first surgical tool 400 is rotated in a second direction (counter-clockwise direction) the outside circumferential surface 412 rotates first set screw 252 thereby causing angled wedge 140 to move backwards towards proximal end 101 and away from distal end 102. For example, as shown in FIG. 31A, angled wedge 140 is represented as moving from distal end 102 towards proximal end 101 by arrows. As illustrated by arrows in FIG. 31B, when angled wedge 140 moves backwards towards proximal end 101 it causes top sliding frame 150 and bottom sliding frame 130 to move away from one another at first lateral end 103 and move towards one another at second lateral end 104. For example, when angled wedge 140 moves backward towards proximal end 101 it causes a distance between endplates 110, 120 at corresponding second lateral ends thereof to increase and also causes a distance between endplates 110, 120 at corresponding first lateral ends thereof to decrease. Therefore, rotation of only the first set screw 252 adjusts an angle of inclination between endplates 110, 120.

Angled wedge 140 effectuates this inclination type motion because it acts against both top sliding frame 150 and bottom sliding frame 130. For example, angled wedge 140 effectuates inclination of top sliding frame 150 because protrusions 148a are oppositely inclined from protrusions 148b are operably retained within corresponding oppositely inclined channels 158a, 158b of top sliding frame 150. In this way forward and backward movement of angled wedge 140 causes top sliding frame 150 to rotate. Similarly, angled wedge 140 effectuates inclination of bottom sliding frame 130 because engagement surfaces 145a, 145b, 147a, and 147b (see FIGS. 12B-12C) slide along and act against ramps 135a, 135b, 137a, and 137b (where ramps 135a, 137a are inclined oppositely from ramps 135b and 137b) of bottom sliding frame 130 (see FIG. 11). In summary, when positioning the first surgical tool 400 in the second position and translating the first surgical tool 400 in either the first or second direction the moving mechanism 250 operably adjusts an inclination between the top and bottom endplates 110, 120 by rotation of the first set screw 252. Furthermore, in some embodiments, such inclination type motion may occur by rotation of only the second set screw 254.

Figure 32E:
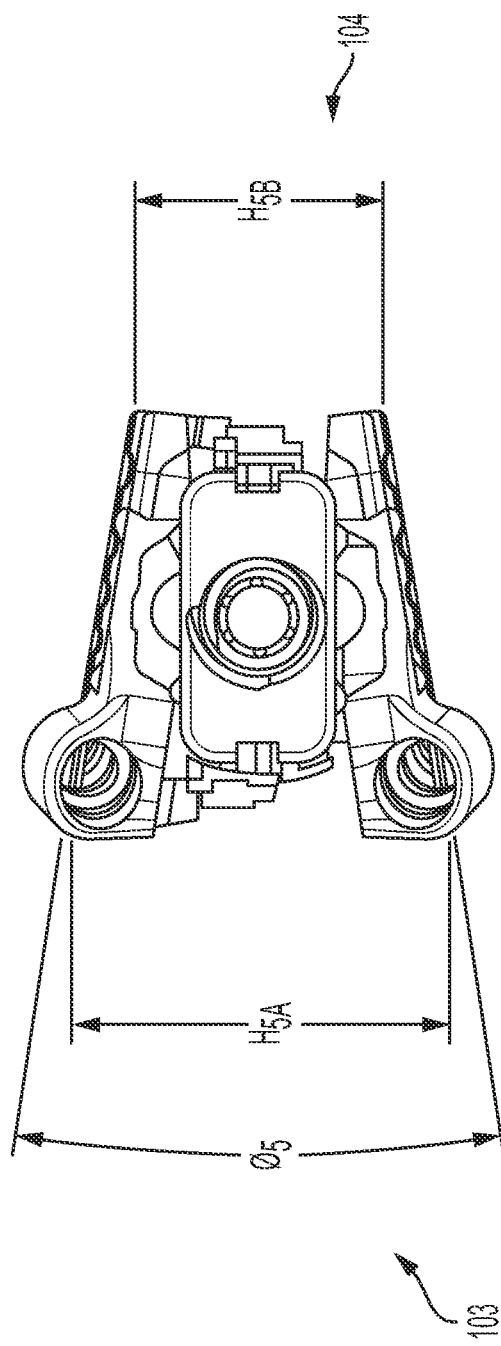

FIGS. 32A-32F are various side views illustrating some exemplary expansion ranges of an expandable spinal implant 100 in six alternate configurations accordance with the principles of the present disclosure. FIG. 32A illustrates spinal implant 100 in a first position and FIG. 32B illustrates spinal implant 100 in a second position. In the first position, a first height $H_{1A}$ between endplates 110, 120 of first lateral end 103 may be about 9.4 mm, a first height $H_{1B}$ between endplates 110, 120 of second lateral end 104 may be about 9.1 mm, and a first angle of inclination Oi between endplates 110, 120 may be about 0.8°. In the second position, a second height $H_{2A}$ between endplates 110, 120 of first lateral end 103 may be about 10.9 mm, a second height $H_{2B}$ between endplates 110, 120 of second lateral end 104 may be about 7.6 mm, and a second angle of inclination $\theta_2$ between endplates 110, 120 may be about 9.7°.

FIG. 32C illustrates spinal implant 100 in a third position and FIG. 32D illustrates spinal implant 100 in a fourth position. In the third position, a third height $H_{3A}$ between endplates 110, 120 of first lateral end 103 may be about 12.6 mm, a third height $H_{3B}$ between endplates 110, 120 of second lateral end 104 may be about 5.9 mm, and a third angle of inclination $\theta_3$ between endplates 110, 120 may be about 19.2°. In the fourth position, a fourth height $H_{4A}$ between endplates 110, 120 of first lateral end 103 may be about 12.7 mm, a fourth height $H_{2B}$ between endplates 110, 120 of second lateral end 104 may be about 12.4 mm, and a fourth angle of inclination $\theta_4$ between endplates 110, 120 may be about 0.8°.

Figure 32F:
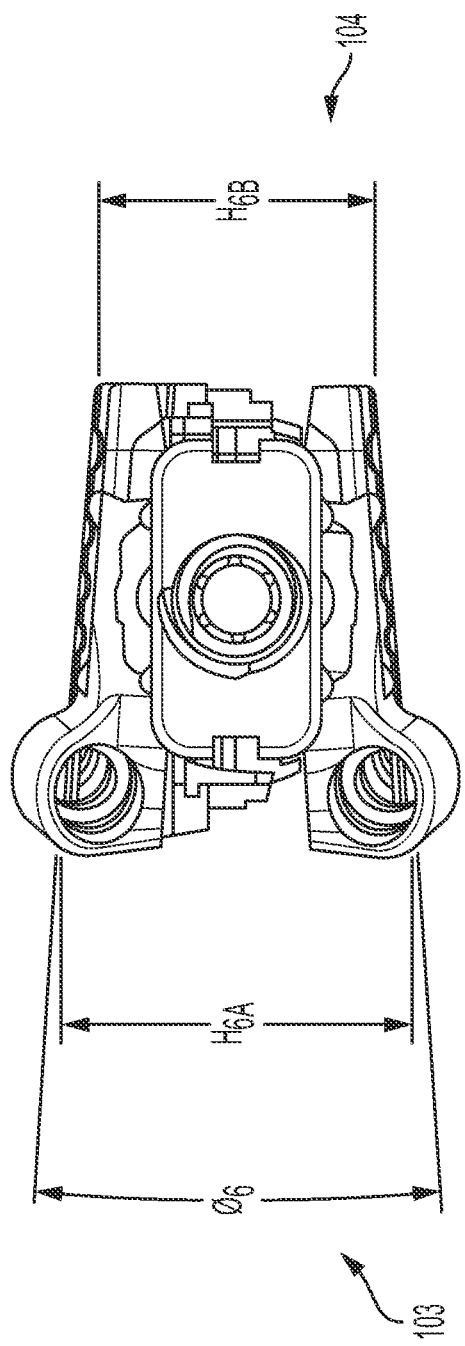

FIG. 32E illustrates spinal implant 100 in a fifth position and FIG. 32F illustrates spinal implant 100 in a sixth position. In the fifth position, a fifth height HSA between endplates 110, 120 of first lateral end 103 may be about 19.5 mm, a fifth height HSB between endplates 110, 120 of second lateral end 104 may be about 12.5 mm, and a third angle of inclination $\theta_5$ between endplates 110, 120 may be about 10.2°. In the sixth position, a sixth height $H_{6A}$ between endplates 110, 120 of first lateral end 103 may be about 16 mm, a sixth height $H_{6B}$ between endplates 110, 120 of second lateral end 104 may be about 12.7 mm, and a fourth angle of inclination $\theta_4$ between endplates 110, 120 may be about 9.7°. It shall be appreciated that the foregoing disclosure is exemplary in nature and the ranges disclosed herein are non-limiting examples intended merely to showcase six viable positions of expandable spinal implant 100. Additionally, although specific ranges are provided herein with reference to exemplary spinal implant 100, other embodiments may have alternate corresponding dimensions, i.e., height, from those provided above.

Figure 34:
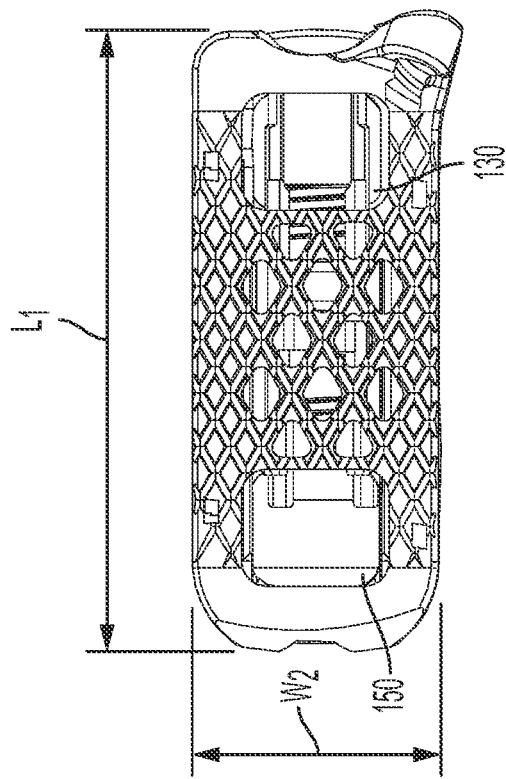
FIG. 33 and FIG. 34 are top down views illustrating some exemplary expansion ranges of an expandable spinal implant in accordance with the principles of the present disclosure.
Figure 33:
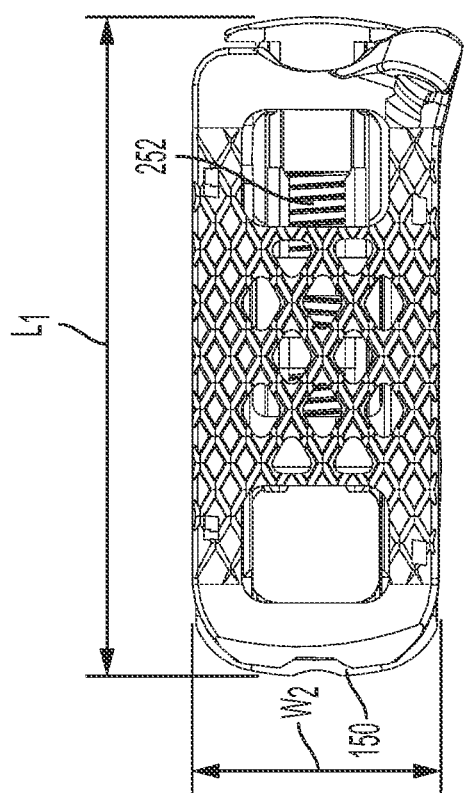

FIGS. 33 and 34 are top down views illustrating some exemplary dimensions and expansion range differences of an expandable spinal implant 100 in accordance with the principles of the present disclosure. In FIG. 33, expandable spinal implant 100 has a first length $L_1$ and a first width $W_1$ in a first position. For example, spinal implant 100 is illustrated with top sliding frame 150 relatively far forward towards distal end 102 and moving mechanism 250 near proximal end 101. In the illustrated position, a total length of expandable spinal implant 100 may be about 53 mm, in part because a tip portion of top sliding frame 150 partially extends from a tip portion of endplates 110, 120. In FIG. 34, expandable spinal implant 100 has a second length $L_2$ and a second width $W_2$ in a second position. For example, spinal implant 100 is illustrated with top sliding frame 150 relatively far rearward towards proximal end 101 and moving mechanism 250 relatively near distal side 102. In the illustrated position, a total length of expandable spinal implant 100 may be about 50.3 mm, in part because only endplates 110, 120 define the length of expandable spinal implant 100. Additionally, in each of first and second positions a width of spinal implant 100 remains constant, although in other embodiments having relatively narrower endplates a width may ostensibly be defined, at least partly, by other internal components of spinal implant 100. FIGS. 33 and 34 also illustrate a functional aspect of moving mechanism 250 in that sliding block 253, and set screws 252, 254 may slide back and forth along screw guide body 256.

Figure 35:
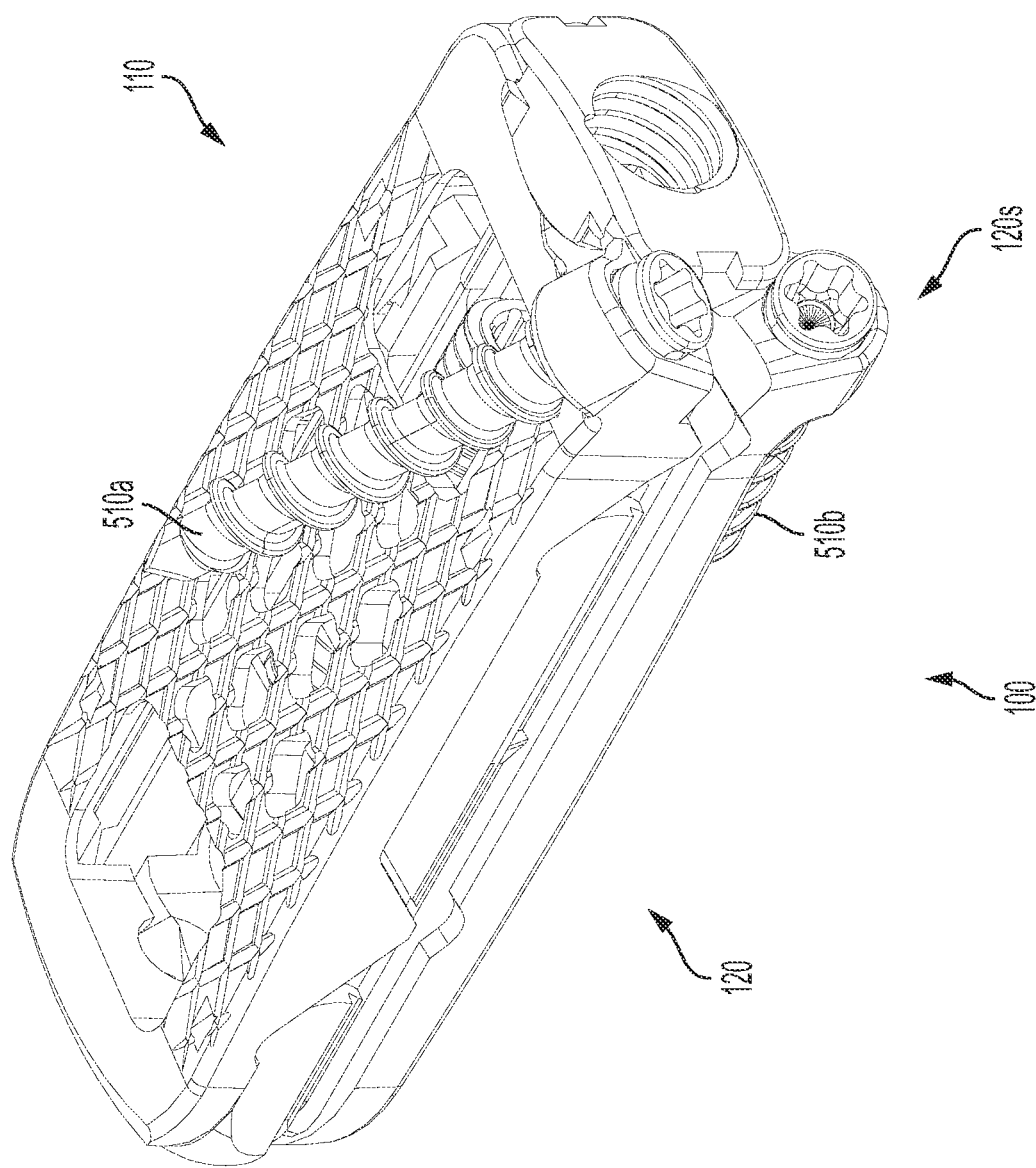
FIG. 35 is a perspective view of an expandable spinal implant including a pair of anchoring screws in accordance with the principles of the present disclosure.
Figure 36:
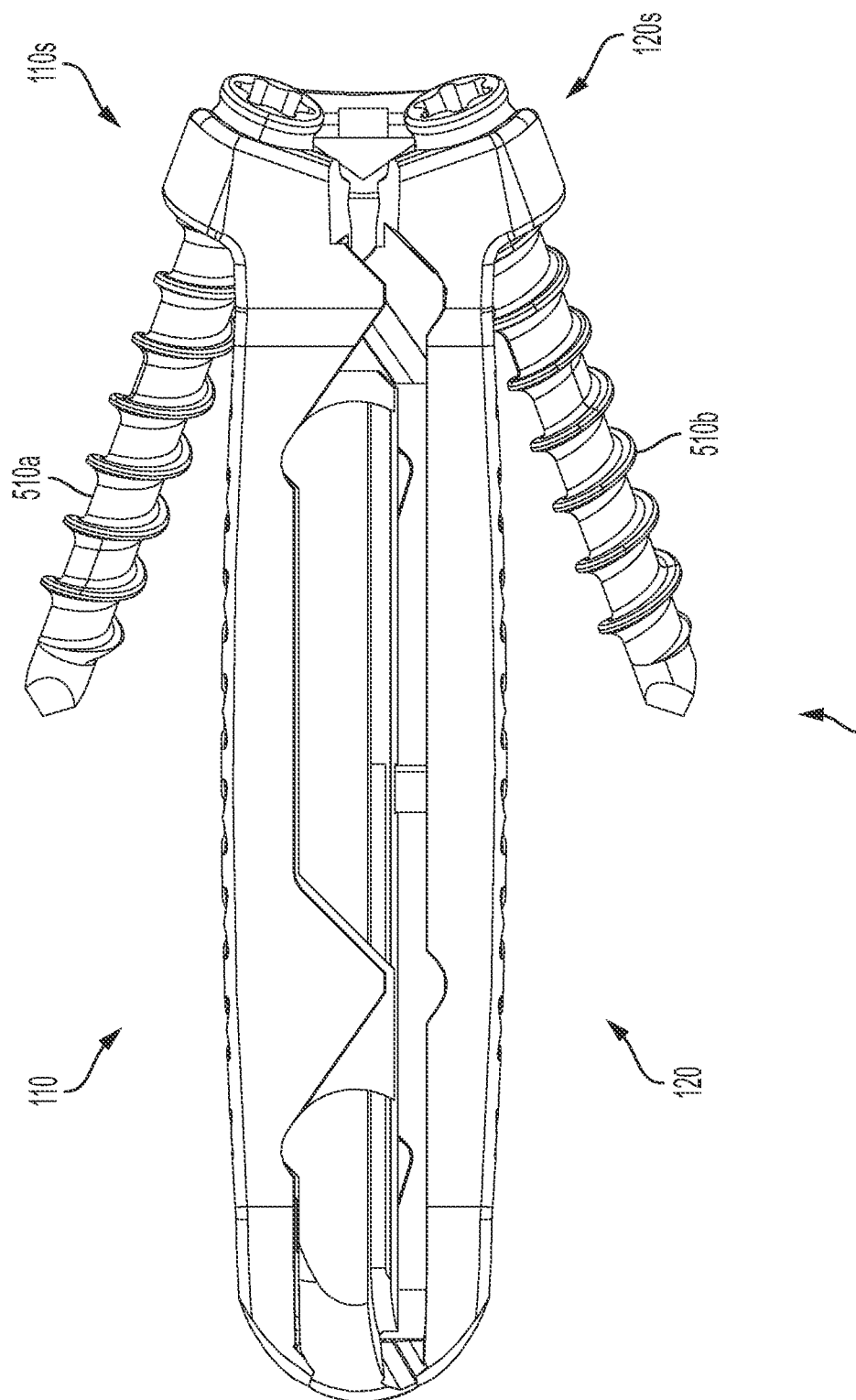
FIG. 36 is a lateral side view of the expandable spinal implant including a pair of anchoring screws of FIG. 35 in accordance with the principles of the present disclosure.
Figure 37:
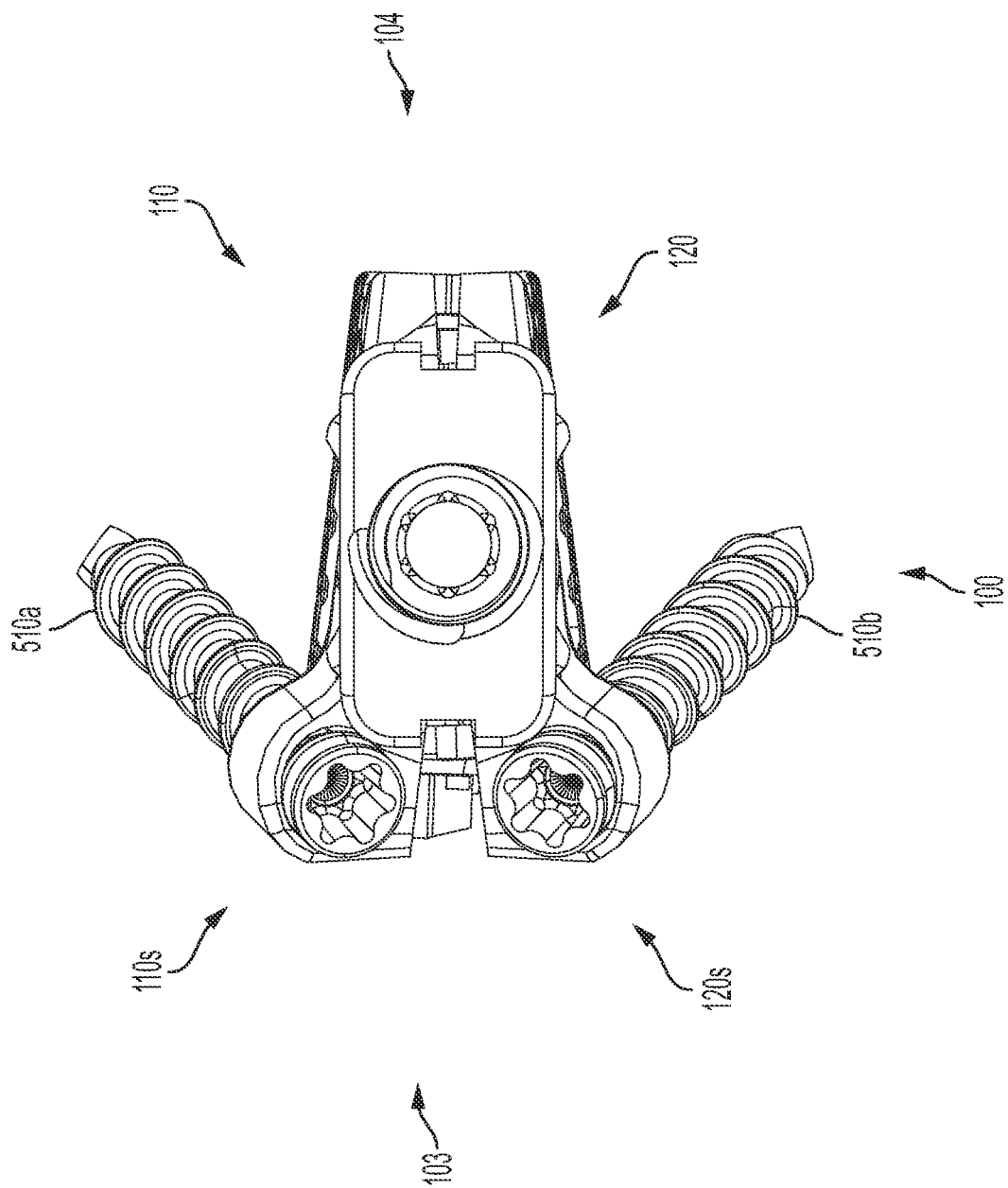
FIG. 37 is a front side view of the expandable spinal implant including a pair of anchoring screws of FIG. 35 in accordance with the principles of the present disclosure.

Referring generally to FIGS. 35-42, exemplary spinal implant 100 is discussed in view of second surgical tool 500. FIGS. 35-37 illustrate various perspective views, lateral side views and front side views of spinal implant 100 with first and second anchoring screws 510a, 510b. Anchoring screws 510a, 510b may penetrate through anchoring apertures 110s, 120s of top and bottom endplates 110, 120, respectively. As best illustrated in FIGS. 36, 37 one or more anchoring apertures 110s, 120s may be disposed adjacent a proximal end 101 of expandable spinal implant 100 and be shaped such that one or more anchoring screws 510a, 510b are inclined away from endplates 110, 120 from a corner region where first lateral end 103 and proximal end 101 adjoin one another towards a region where second lateral end 104 and distal end 102 adjoin each other. For example, anchoring apertures 110s, 120s may be inclined with respect to endplates 110, 120 and may be shaped and/or oriented such that anchoring screws extend diagonally from proximal end 101 to distal end 102. These apertures may further include features, thread forms, and/or protrusions for enhanced screw retention and/or separate screw retention features and/or internal or external locking features and or partial or full covers.

Figure 38A:
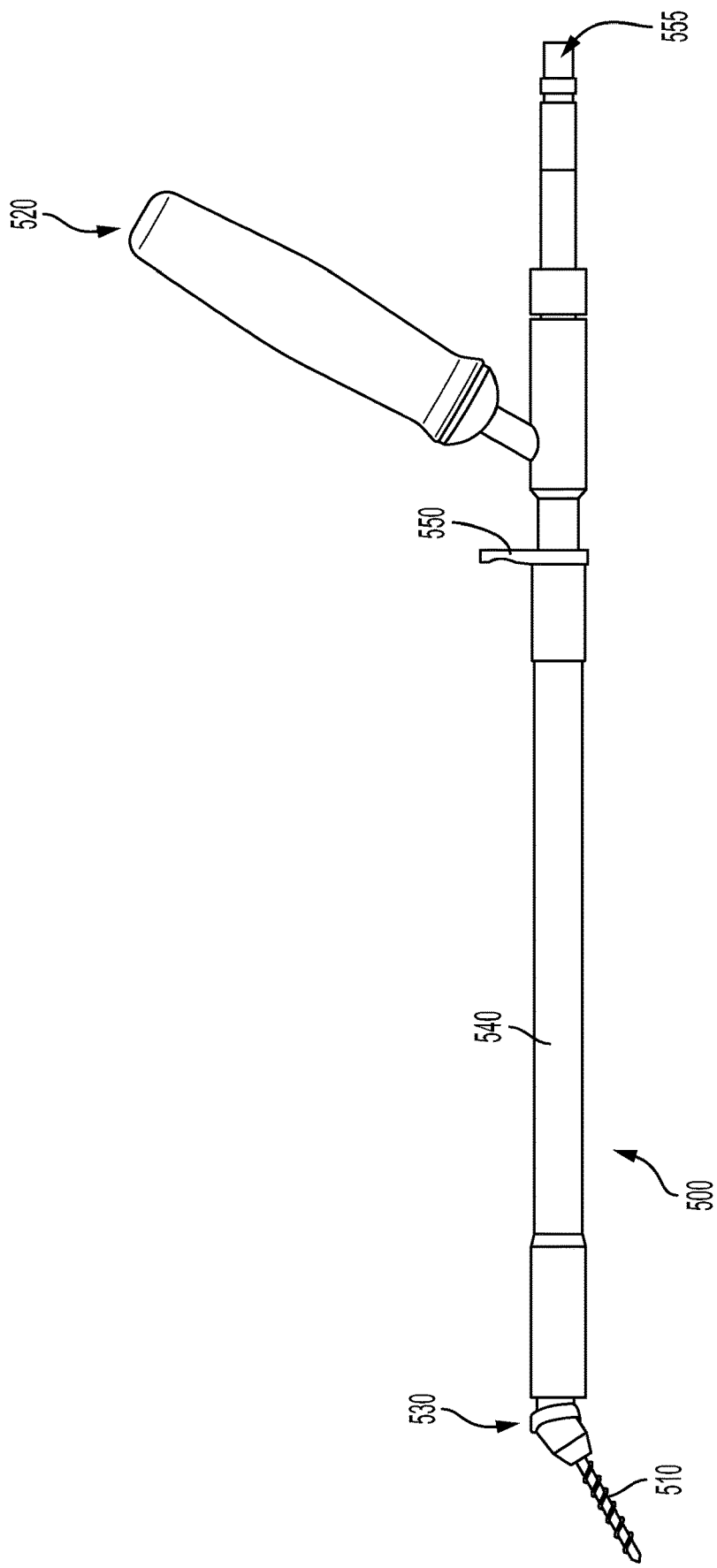
FIG. 38A is a side view of a second surgical device suitable for use with disclosed expandable spinal implants in accordance with the principles of the present disclosure.
Figure 38B:
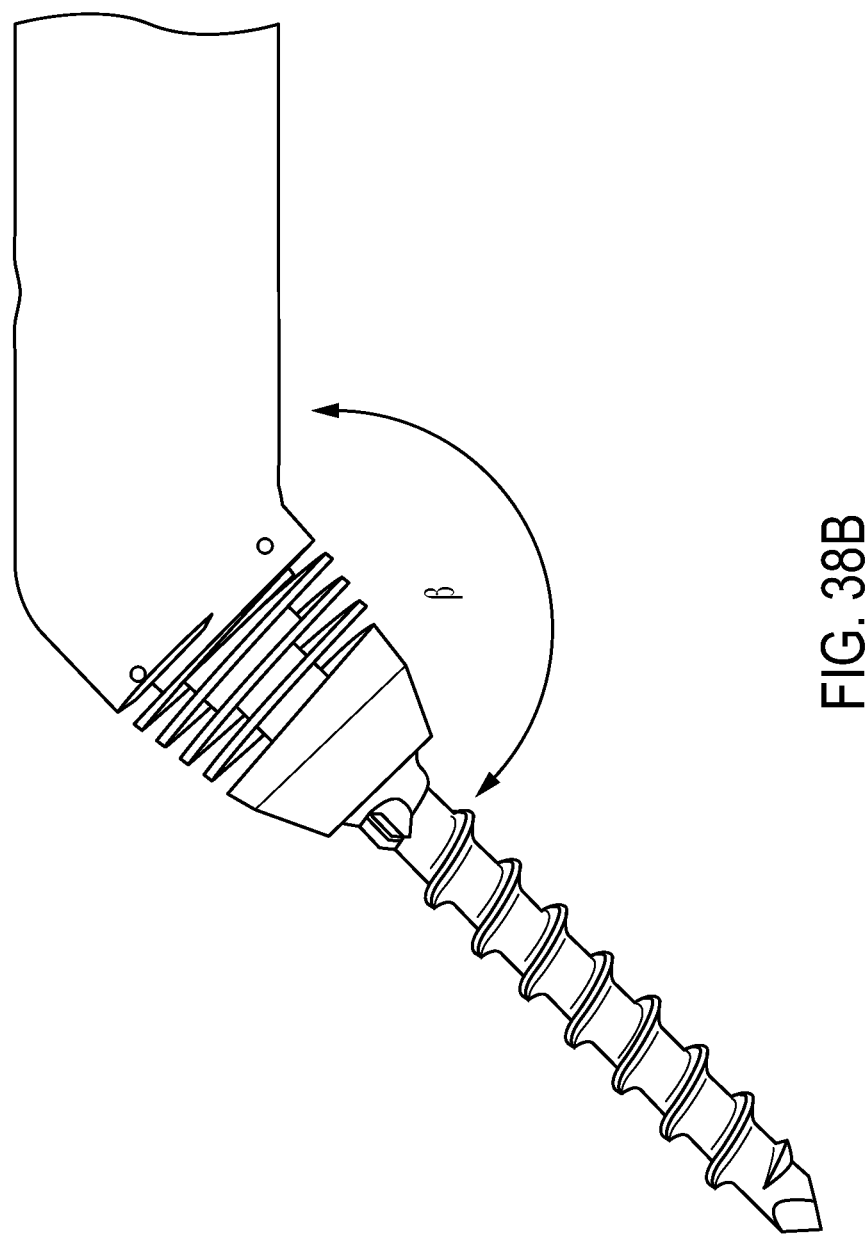
FIG. 38B is a side view of an enlarged region of FIG. 38 in accordance with the principles of the present disclosure.

FIG. 38A is a side view of a second surgical tool 500 suitable for use with disclosed embodiments and systems herein, e.g., to drive one or more anchoring screws, for example, 510a-510b. FIG. 39 is a side view of an enlarged region of FIG. 38. Exemplary, second surgical tool 500 includes a ratcheting drive shaft 555, a positioning handle 520, a tip portion 530, a drive shaft housing 540, and a trigger 550. Ratcheting drive shaft 555 may be configured to connect and disconnect with a ratcheting handle (not shown)

and rotate within ratcheting drive shaft housing 540. For example, the drivable connection may comprise a variety of drive interfaces including but not limited to: multi-lobular drives; hexalobular drives; cross or Phillips head drives; straight or "flat head" drives; square or other polygonal drives; and/or combinations thereof. Positioning handle 520 may be configured to assist with maintaining and controlling the second surgical tool 500, e.g., in view of torque transmitted through ratcheting drive shaft 555. Tip portion 530 may be angled at a degree β with respect to a longitudinal direction of drive shaft housing 540. In some embodiments, tip portion 530 may be angled such that the degree β corresponds to the inclination of anchoring screws 510a, 510b and the inclination of anchoring aperture 110s, 120s. For example, anchoring apertures 110s, 120s may be inclined about 30°-50°, and more particularly about 40°, with respect to an outside surface 111, 121 of endplates 110, 120. This arrangement may be advantageous for driving anchoring screws 510a-510b while spinal implant 100 is positioned between adjacent vertebral bodies. Tip portion 530 may secure an anchoring screw 510a, 510b in an internal cavity therein such that the anchoring screw 510a, 510b may not disconnect during initial positioning of the anchoring screw 510a, 510b. For example, tip portion 530 may have a flexible elastic member configured to securely retain a head portion of the anchoring screw 510a, 510b. Tip portion 530 may, however, release the anchoring screw 510a, 510b when it is sufficiently anchored into an anatomical feature, such as a vertebrae for example. This feature may be particularly advantageous during surgery for maintaining the anchoring screw 510a, 510b in tip portion 530 such that the anchoring screw 510a, 510b does not uncouple from tip portion 530 when initially positioning the anchoring screw 510a, 510b in an anchoring aperture, for example anchoring apertures 110s, 120s. Additionally, in some embodiments tip portion 530 may be operably coupled with trigger 550 such that trigger 550 may disconnect the anchoring screw 510a, 510b when the anchoring screw 510a, 510b is installed. In some embodiments, trigger 550 may not be necessary because tip portion 530 may self-release the anchoring screw 510a, 510b after installation.

Figure 39A:
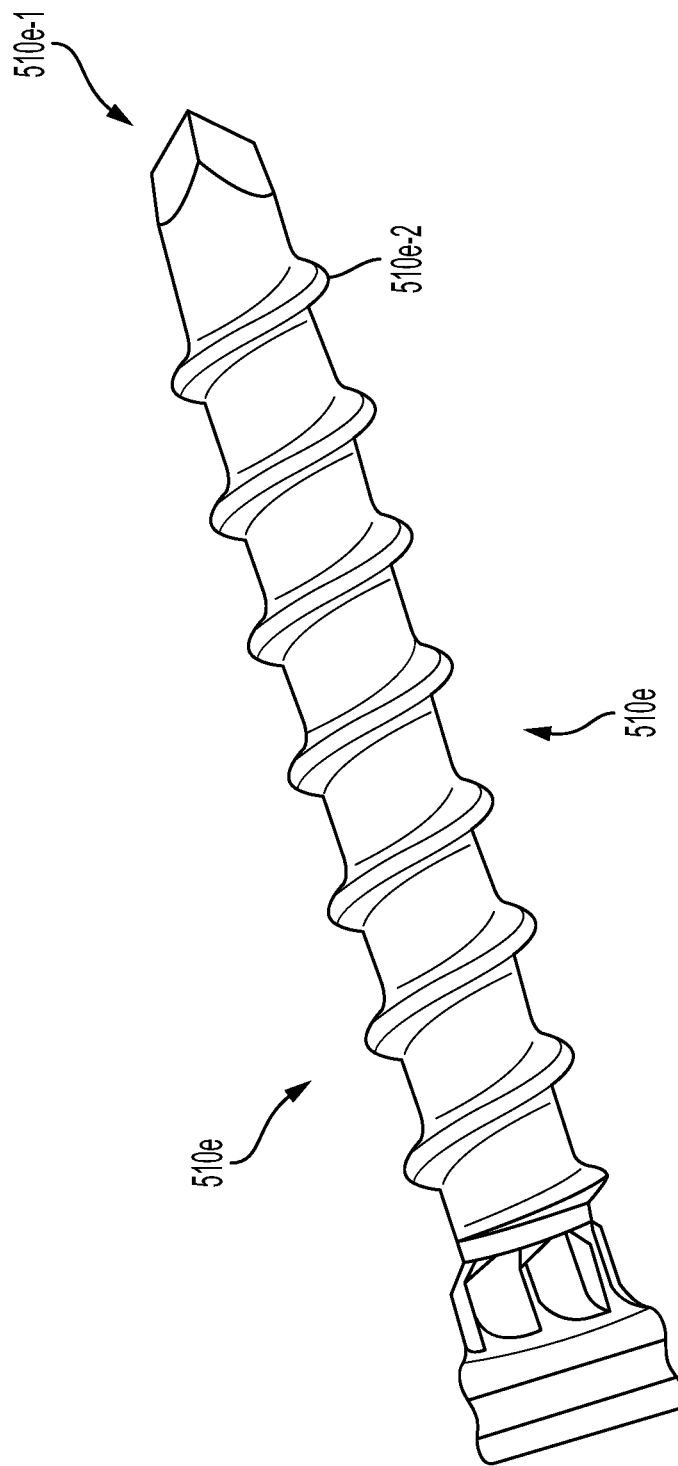
FIGS. 39A-39C are various perspective views of exemplary anchoring screws suitable for use in conjunction with the second surgical tool FIGS. 38A-38B in accordance with the principles of the present disclosure.
Figure 39B:
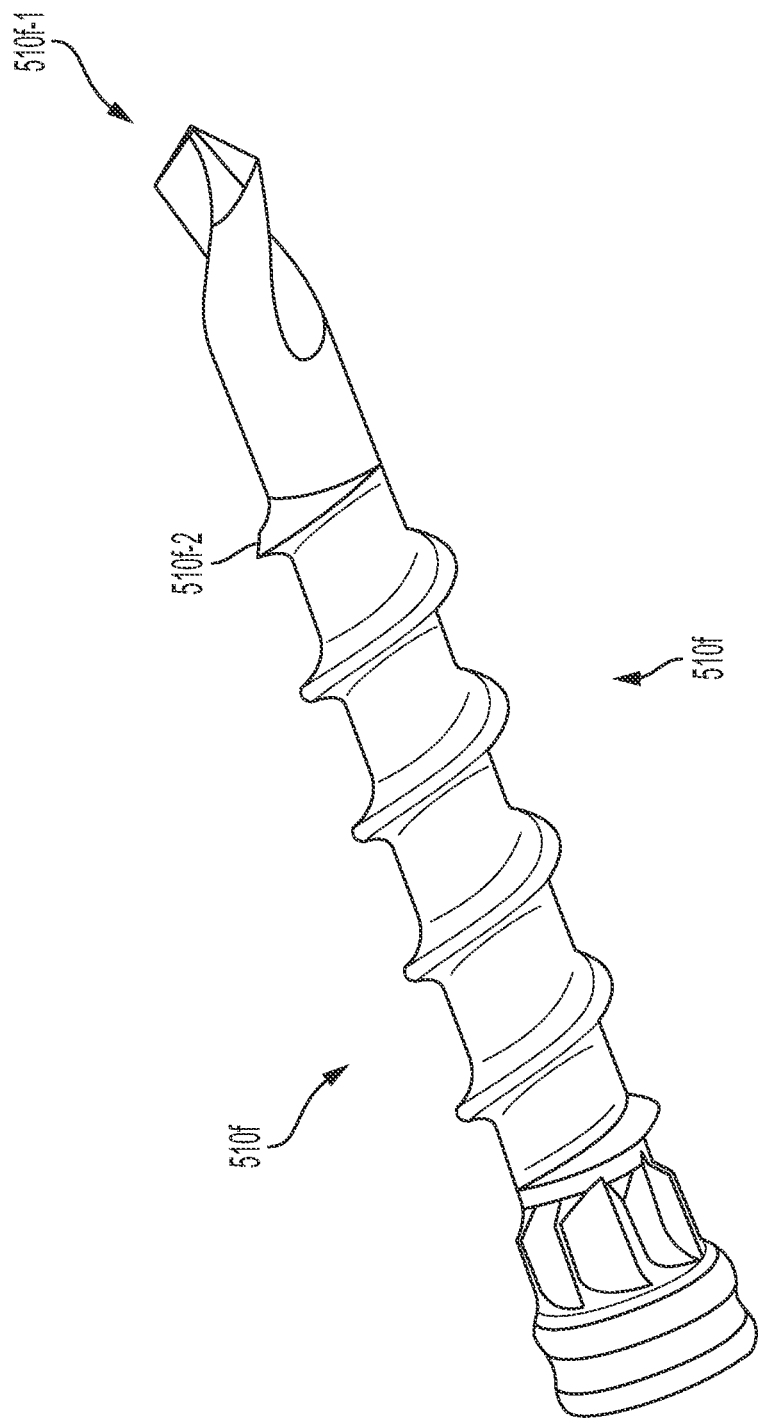
Figure 39C:
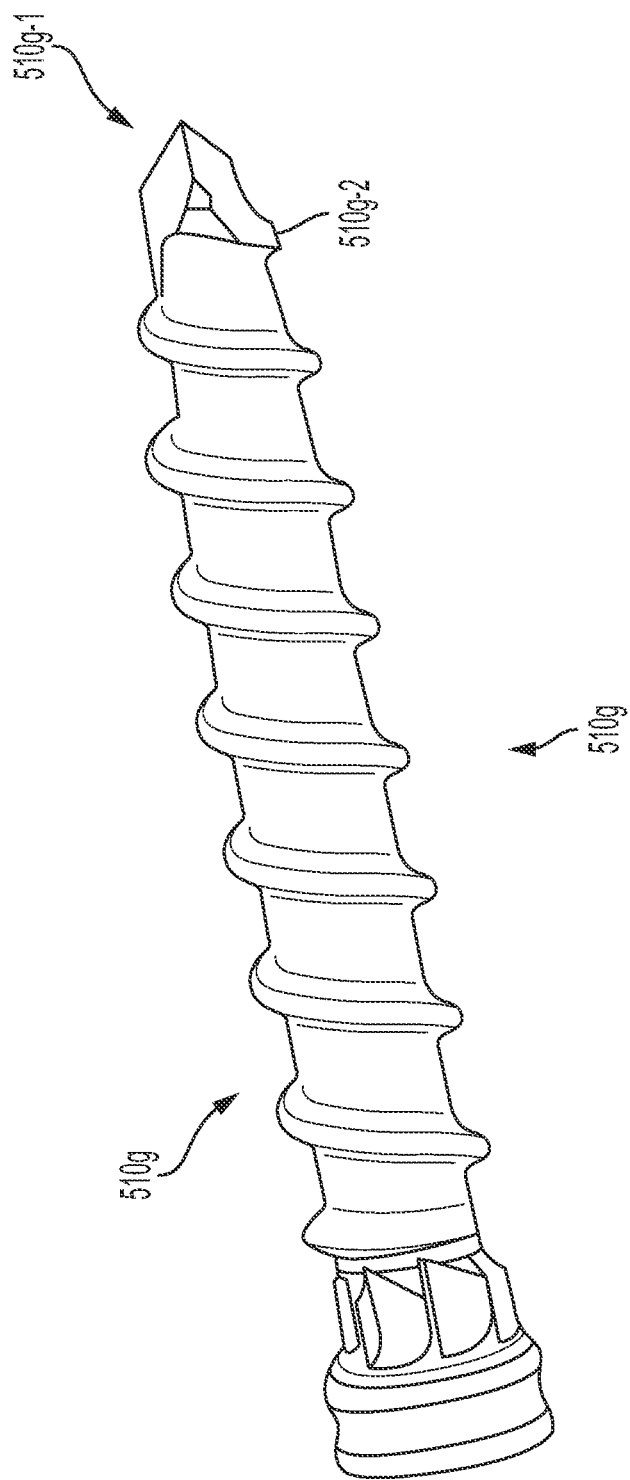

FIGS. 39A-39C are various perspective views of exemplary anchoring screws suitable for use with disclosed embodiments herein in conjunction with the second surgical tool 500. FIG. 39A shows a trocar tip bone screw 510e, FIG. 39B shows a flutes or fluted tip bone screw 510f, and FIG. 39C shows a speed bone screw 510g. Each bone screw 510e-510g may have a thread pitch and sizing that corresponds to a size of anchoring apertures 110s, 120s. Trocar tip bone screw 510e includes an angled tip portion 510e-1 and a thread pattern including threads 510e-2. Threads 510e-2 may be spaced back from angled tip portion 510e-1 which may facilitate with aligning bone screw 510e with anchoring apertures 110s, 120s. For example, in some embodiments, threads 510e-2 are spaced back about 3 mm from angled tip portion 510e-1. Fluted tip bone screw 510f includes a cutting tip 510f-1 and a thread pattern included threads 510f-2. Cutting tip 510f-1 may extend a relatively long distance from the beginning of threads 510f-2 such that the cutting tip 510f-1 may pre-drill into an adjacent vertebral body before the threads 510f-2 engage with anchoring apertures 110s, 120s. For example, in some embodiments, threads 510f-2 are spaced back about 8 mm from cutting tip 510f-1. Speed bone screw 510g includes a conical tip 510g-1 and a thread pattern including threads 510g-2. Different from trocar tip bone screw 510e and fluted tip bone screw 510f, threads 510g-2 of speed bone screw 510g may begin immediately adjacent conical tip 510g-1.

Figure 41:
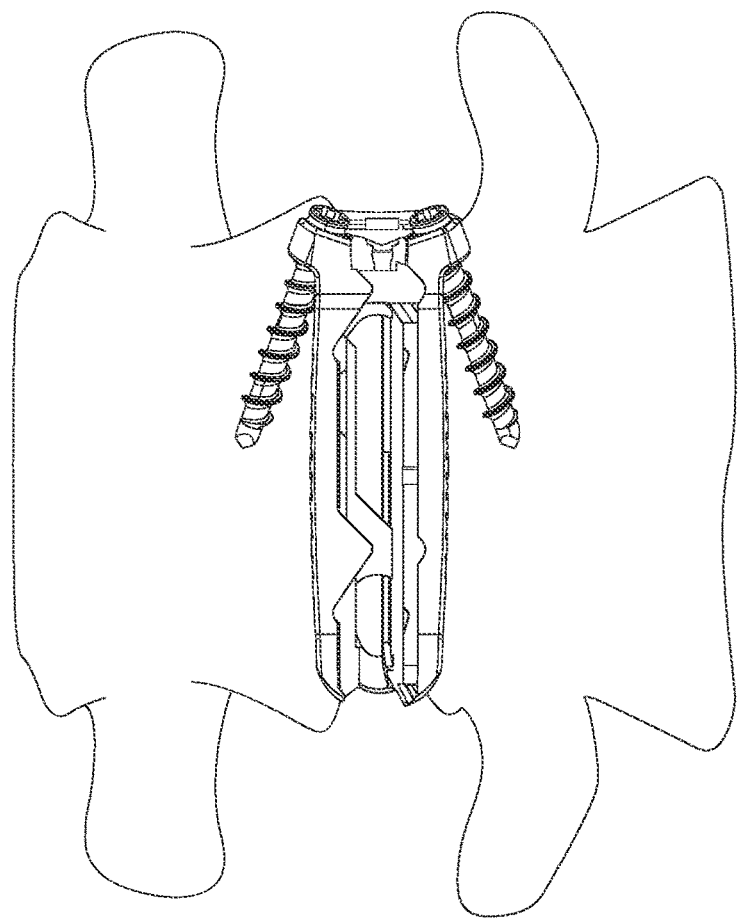
FIG. 41 is a lateral side view of the expandable spinal implant of FIG. 40 in accordance with the principles of the present disclosure.
Figure 40:
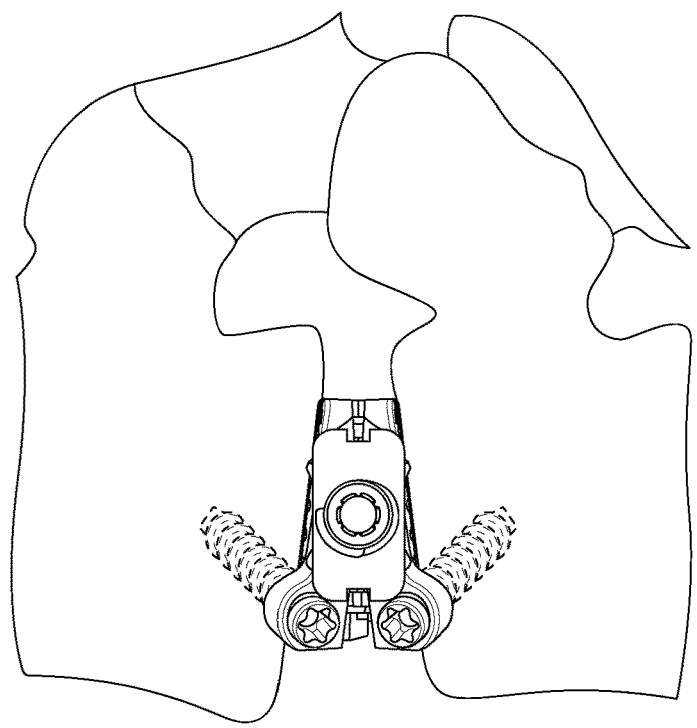
FIG. 40 is a front side view of an expandable spinal implant including a pair of anchoring screws installed into adjacent vertebrae of a patient in accordance with the principles of the present disclosure.
Figure 42:
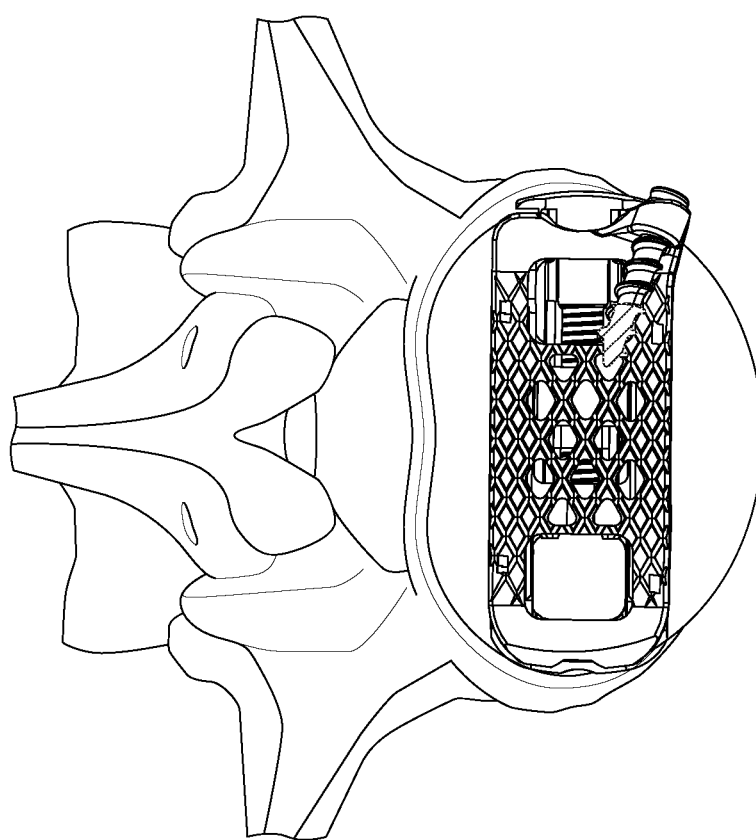
FIG. 42 is a top down view of the expandable spinal implant of FIG. 40 in accordance with the principles of the present disclosure.

FIG. 40 is a front side view of an expandable spinal implant 100 that may include none, one or a pair of anchoring screws installed into adjacent vertebrae of a patient, FIG. 41 is a lateral side view of the expandable spinal implant of FIG. 40, and FIG. 42 is a top down view of the expandable spinal implant of FIG. 40 in accordance with the principles of the present disclosure. As illustrated best in FIGS. 41, and 42, interior surfaces of anchoring apertures 110s, 120s, abut (directly contact an edge portion) a corresponding end portion of an adjacent vertebrae. At least one advantage of this geometry may be that anchoring apertures 110s, 120s can provide further lateral stability and facilitate with positioning of expandable spinal implant 100 in a correct position. An additional advantage is that this arrangement may assist a surgeon in being able to install and/or access bone screws.

Figure 43:
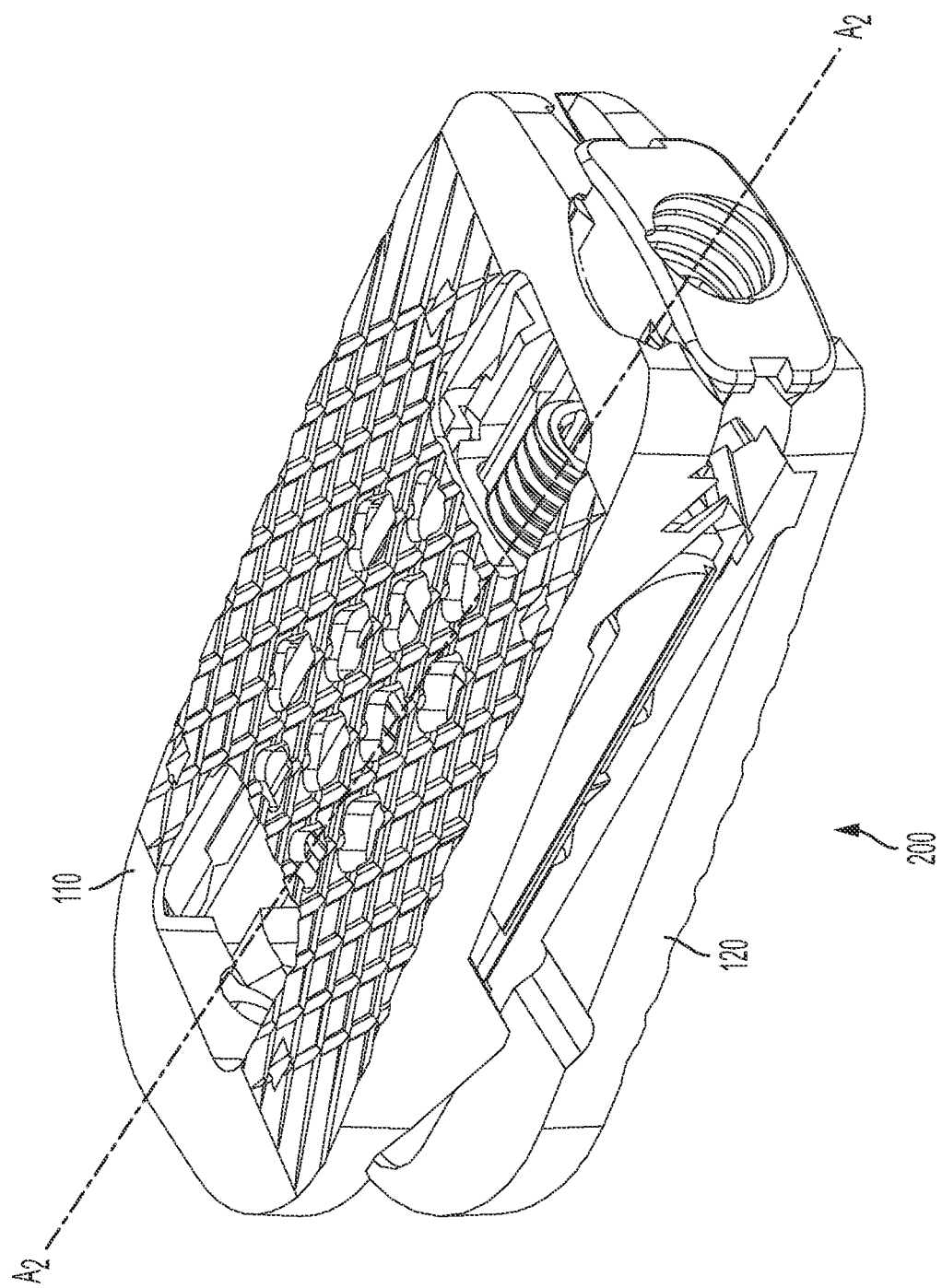
FIG. 43 is a perspective view of a different expandable spinal implant including an offset moving mechanism in accordance with the principles of the present disclosure.
Figure 44:
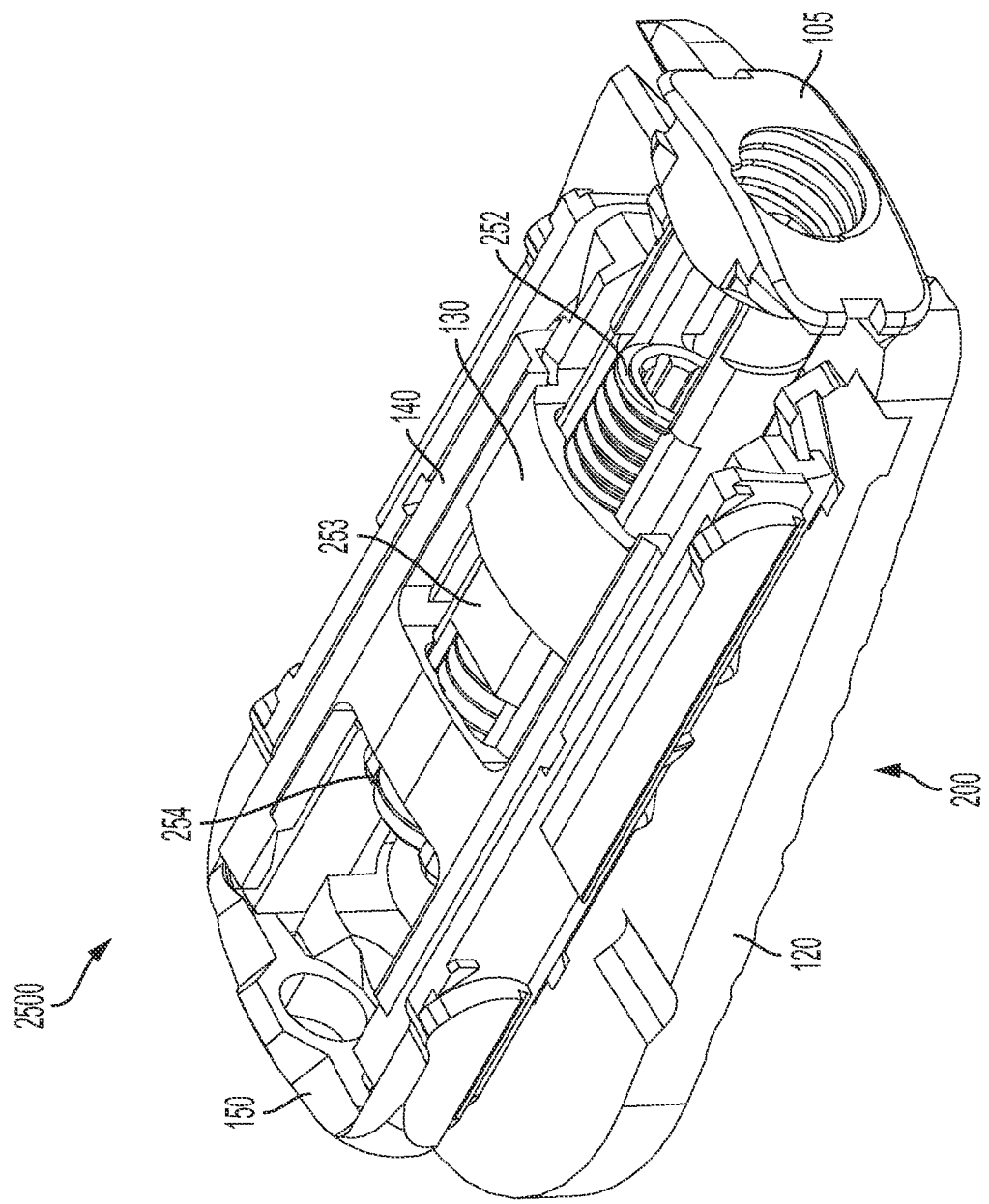
FIG. 44 is a perspective view of the embodiment of FIG. 43 with the top endplate removed in accordance with the principles of the present disclosure.
Figure 46A:
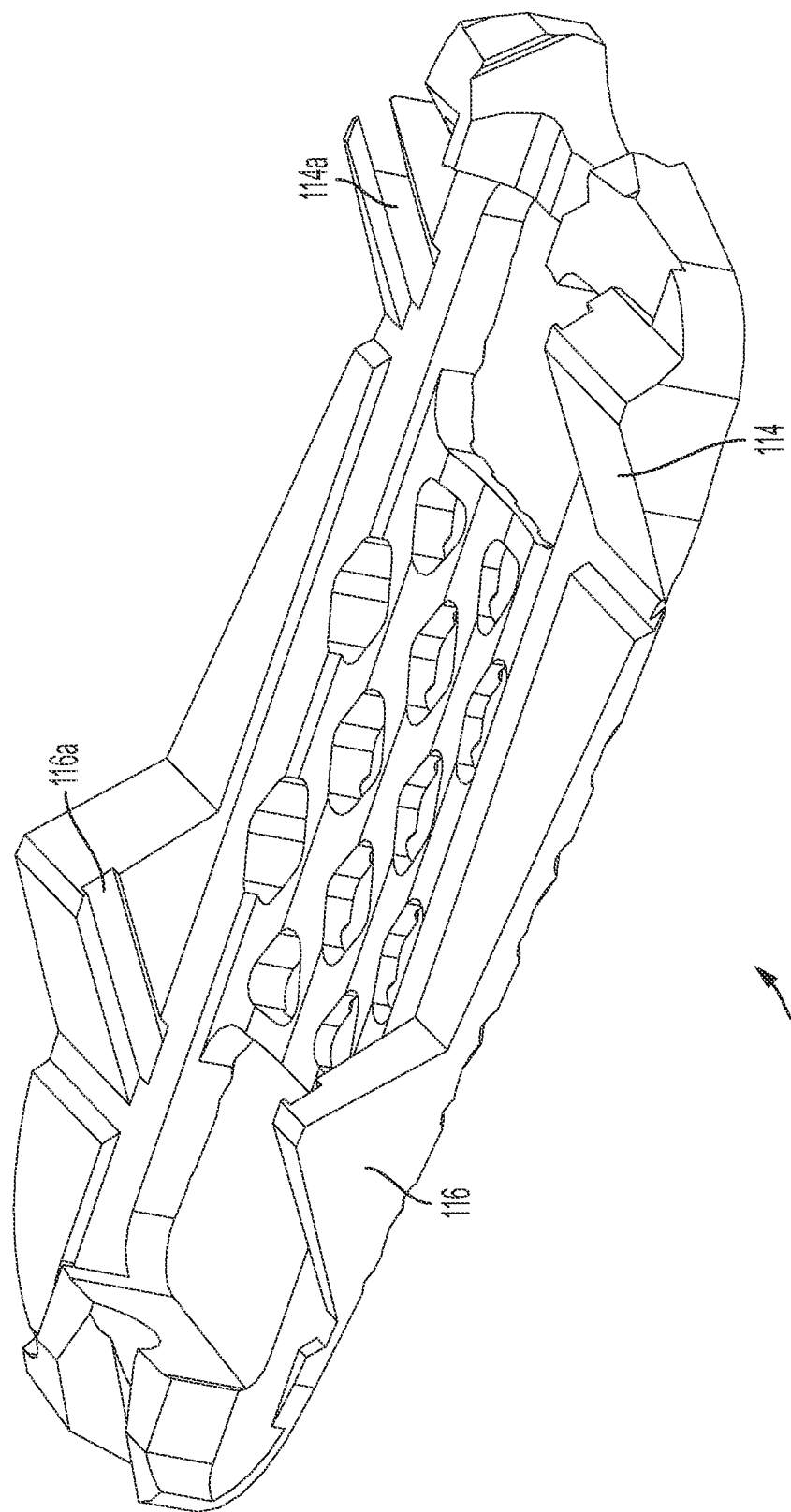
FIG. 46A is perspective view of an endplate for use with the embodiment of FIG. 43 in accordance with the principles of the present disclosure.

Referring generally to FIGS. 43-47 various perspective views an expandable spinal implant 200 are shown. Spinal implant 200 may feature the same, or substantially the same features and components, or a selection of some features or aspects, as described with respect to spinal implant 100. Accordingly, duplicative description thereof will be omitted. As illustrated, spinal implant 200 includes a moving mechanism 2500 that may be miss aligned. For example, second reference axis $A_2$ may extend diagonally in the longitudinal direction of moving mechanism 2500 and may be offset with respect to first reference axis $A_1$ of spinal implant 100 (see FIG. 2). In the disclosed embodiment, moving mechanism 2500 features the same parts as moving mechanism 250 and may operate under the same principles as explained previously. In the disclosed embodiment, moving mechanism 2500 may be miss aligned by about 10° when compared with moving mechanism 250 of spinal implant 100. In other embodiments, moving mechanism 2500 may be miss aligned within any suitable range, e.g., from about 5° to 25°. FIG. 44 is a perspective view of the embodiment of FIG. 43 with a top endplate 1100 removed for ease of understanding. As illustrated, moving mechanism 2500 may be misaligned and the top and bottom endplates 1100, 1200 have a different geometry to accommodate the miss aligned moving mechanism 2500. Top and bottom endplates 1100, 1200 may feature the same or substantially the same characteristics as previously disclosed. FIG. 45 is an alternate perspective view of the embodiment of FIG. 44 with a top endplate 1100 removed for ease of understanding. FIG. 46A is a top down view of an exemplary top endplate 1100 for use with the embodiment of FIG. 43 and FIG. 46B is a top down view of an exemplary bottom endplate 120 for use with the embodiment of FIG. 43.

Figure 47:
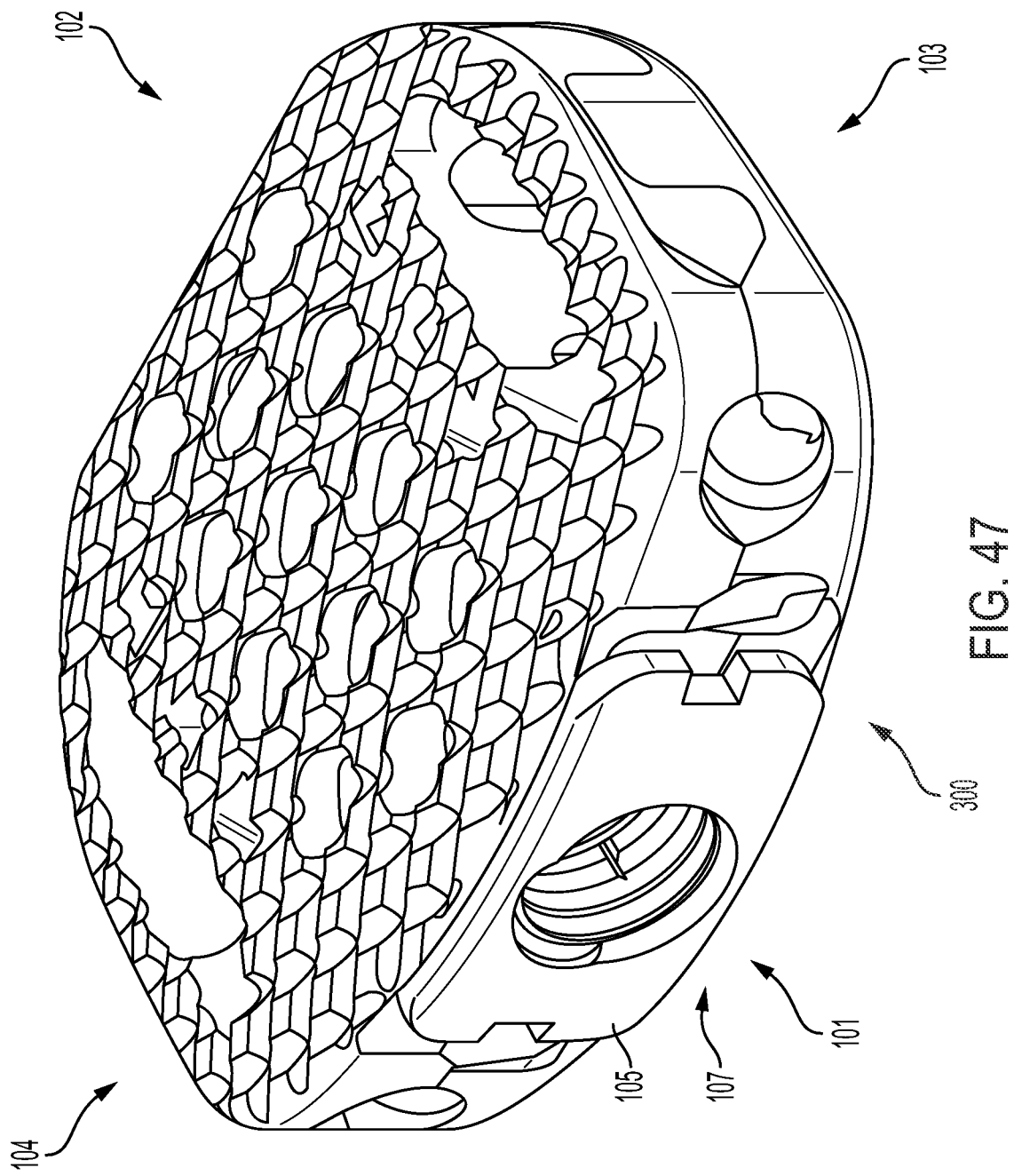
FIG. 47 is a perspective view of a different expandable spinal implant in accordance with the principles of the present disclosure.

Referring generally to FIGS. 47-49 various views of an expandable spinal implant 300 are disclosed. Spinal implant 300 may be configured for anterior and/or oblique surgical techniques. Spinal implant 300 may adjust the alignment of a patient's spine in the sagittal plane (see FIG. 63). Spinal implant 300 may feature the same, or substantially the same features and components, or a selection of some features or aspects, as described above with respect to spinal implant 100. Accordingly, duplicative description thereof will be omitted. Similar to spinal implant 100, spinal implant 300 may feature a moving mechanism 250 configured to move forward and backwards along a third reference axis $A_3$. Third spinal implant 300 differs from spinal implant 100, in that top endplate 310 and bottom endplate 320 each have a footprint configured for anterior and/or oblique surgical techniques. Additionally, the interior surfaces of endplates 310, 320 may have a substantially similar arrangement of acting surfaces, ramps, channels, grooves, and etc. as explained above with respect to spinal implant 100.

Figure 49A:
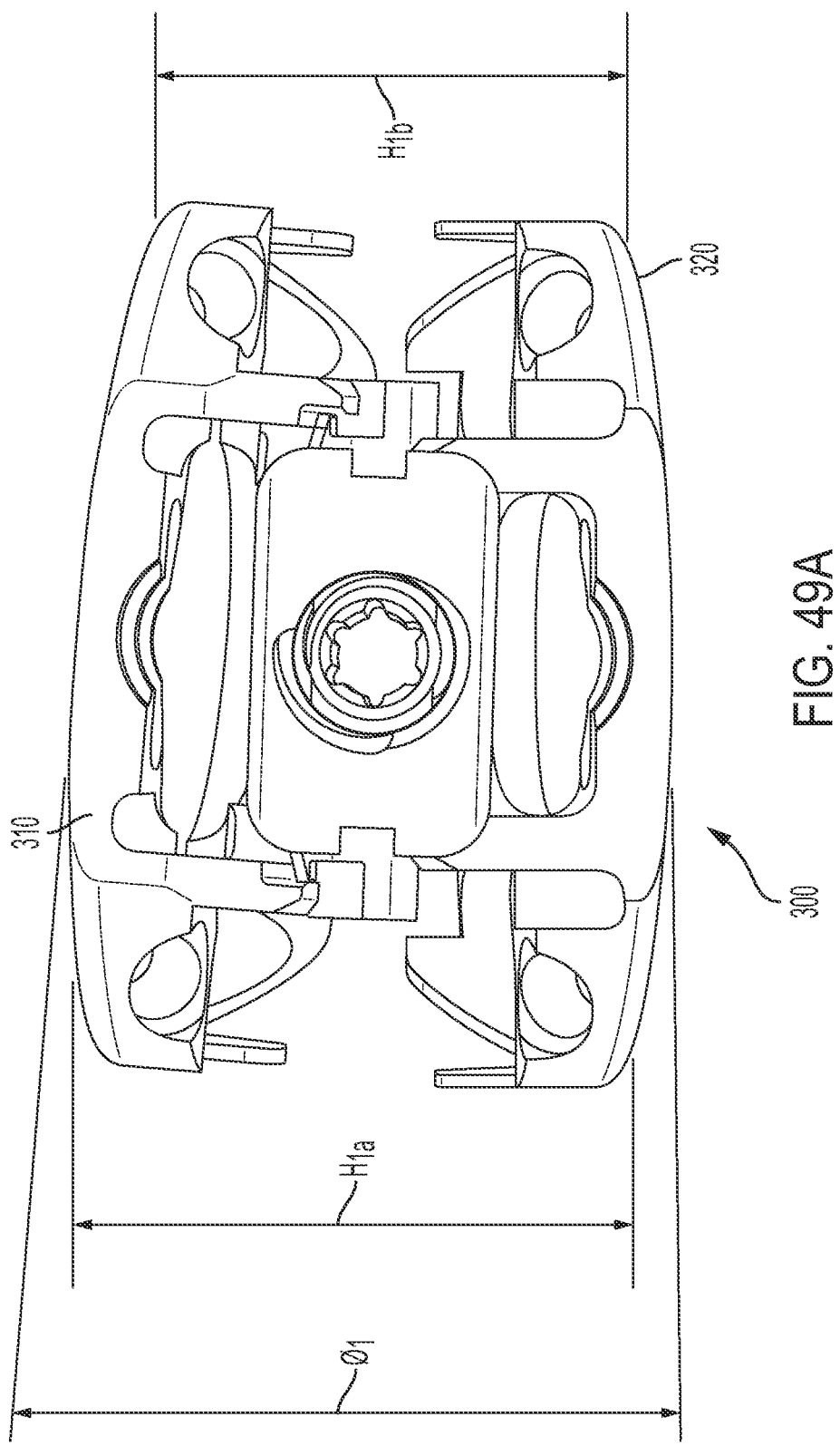
FIGS. 49A-49B are a front side views of the embodiment of FIG. 47 in accordance with the principles of the present disclosure.
Figure 49B:
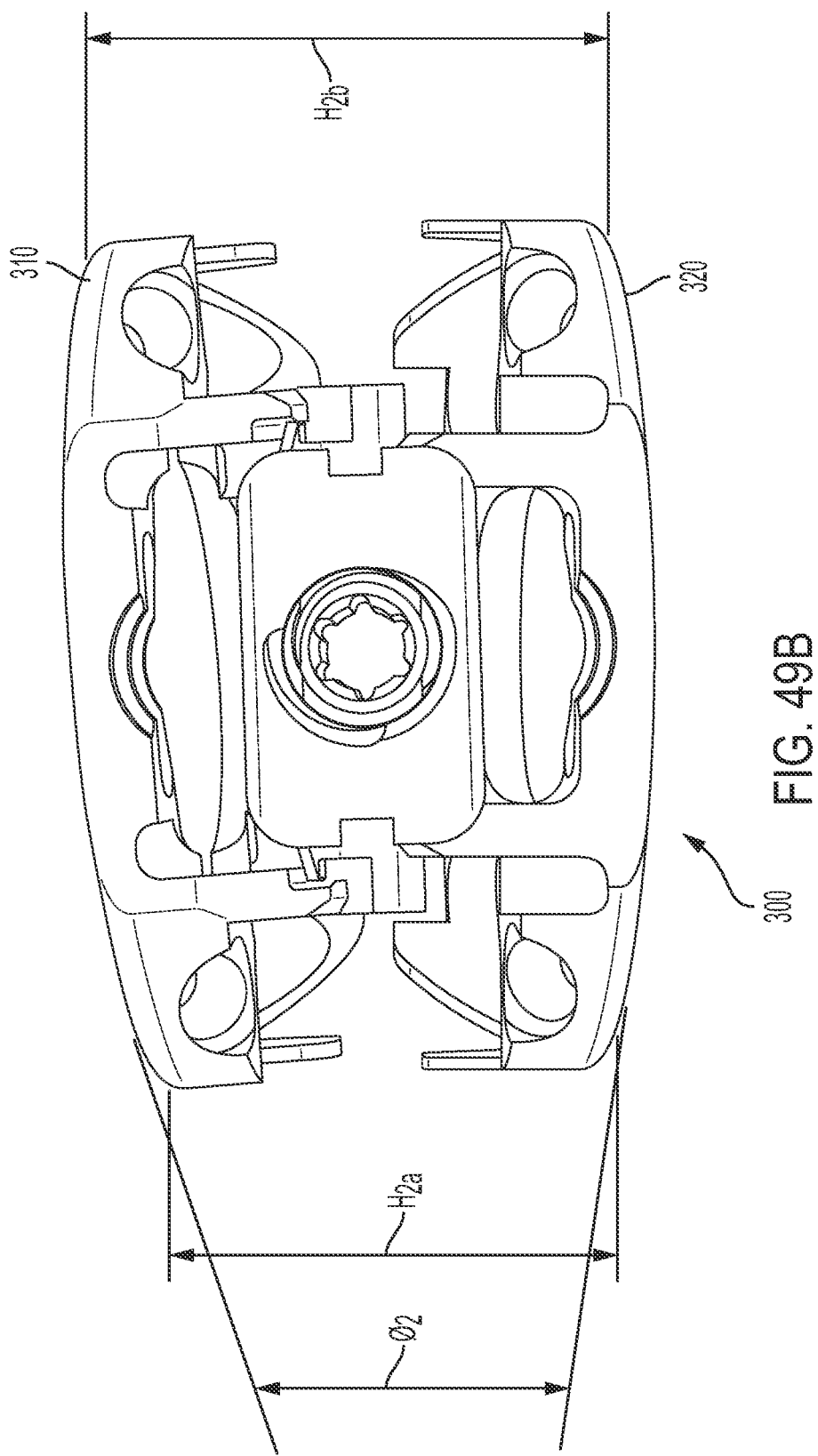

FIG. 49A illustrates spinal implant 300 in a first position and FIG. 49B illustrates spinal implant 300 in a second position. In the first position, a first height $H_{1A}$ between endplates 310, 320 of first lateral end 103 may be relatively greater than a first height $H_{1B}$ between endplates 310, 320 of second lateral end 104. In the second position, a second height $H_{2A}$ between endplates 310, 320 of first lateral end 103 may be relatively smaller than a second height $H_{2B}$ between endplates 310, 320 of second lateral end 104. Similarly, a first angle of inclination $\theta_1$ between endplates 310, 320 may be relatively less than a second angle of inclination $\theta_2$ between endplates 310, 320. Spinal implant 300 may be adjusted into the first position and second position in the same, or substantially the same, way as explained above with respect to spinal implant 100. For example, first surgical tool 400 may be insert into a first position to operably adjust the height between endplates 310, 320 and first surgical tool 400 may be insert into a second position to operably adjust an inclination between endplates 310, 320.

Figure 50:
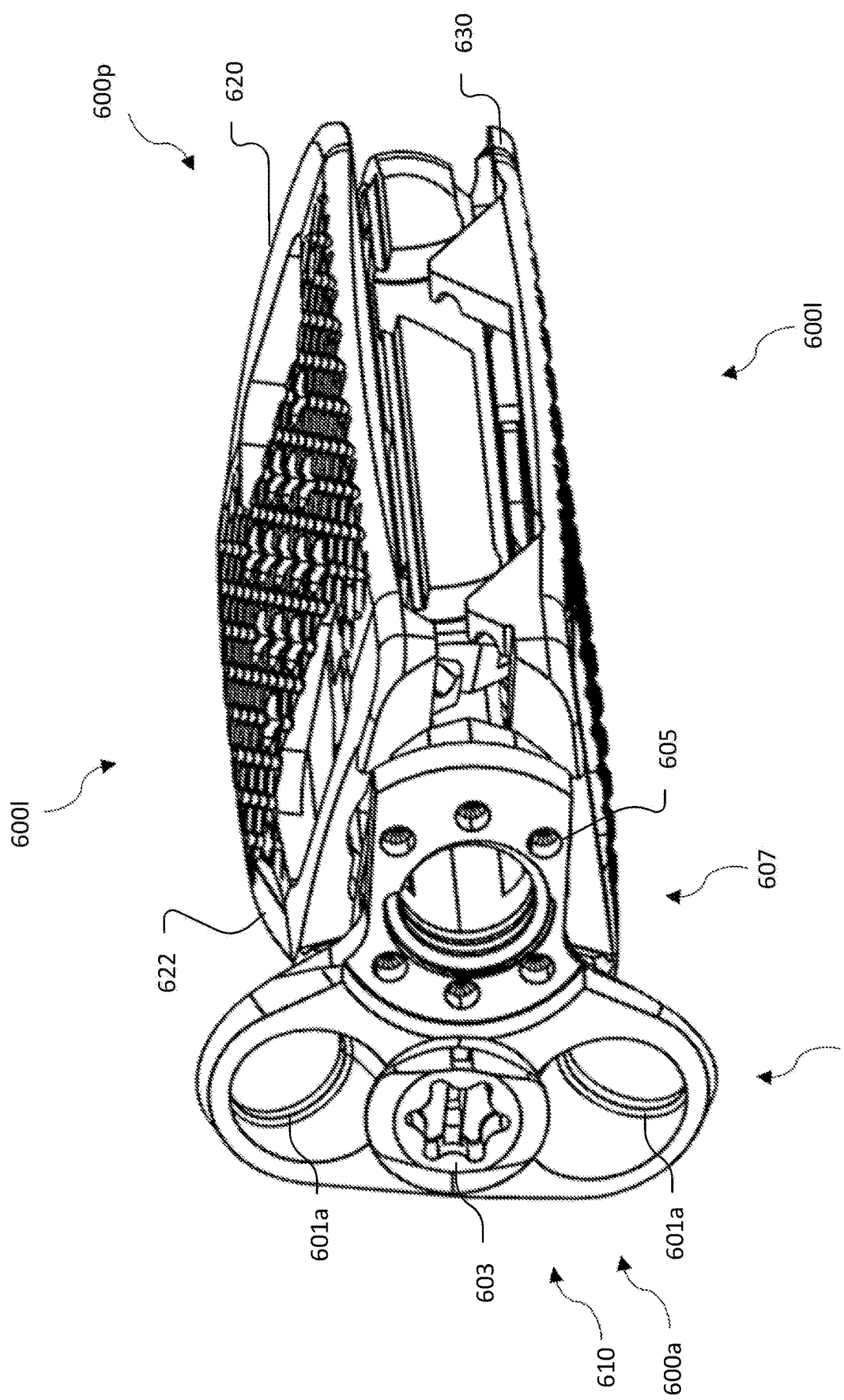
FIG. 50 is a perspective view of a spinal implant including a proximal end plate in accordance with the principles of the present disclosure.
Figure 51:
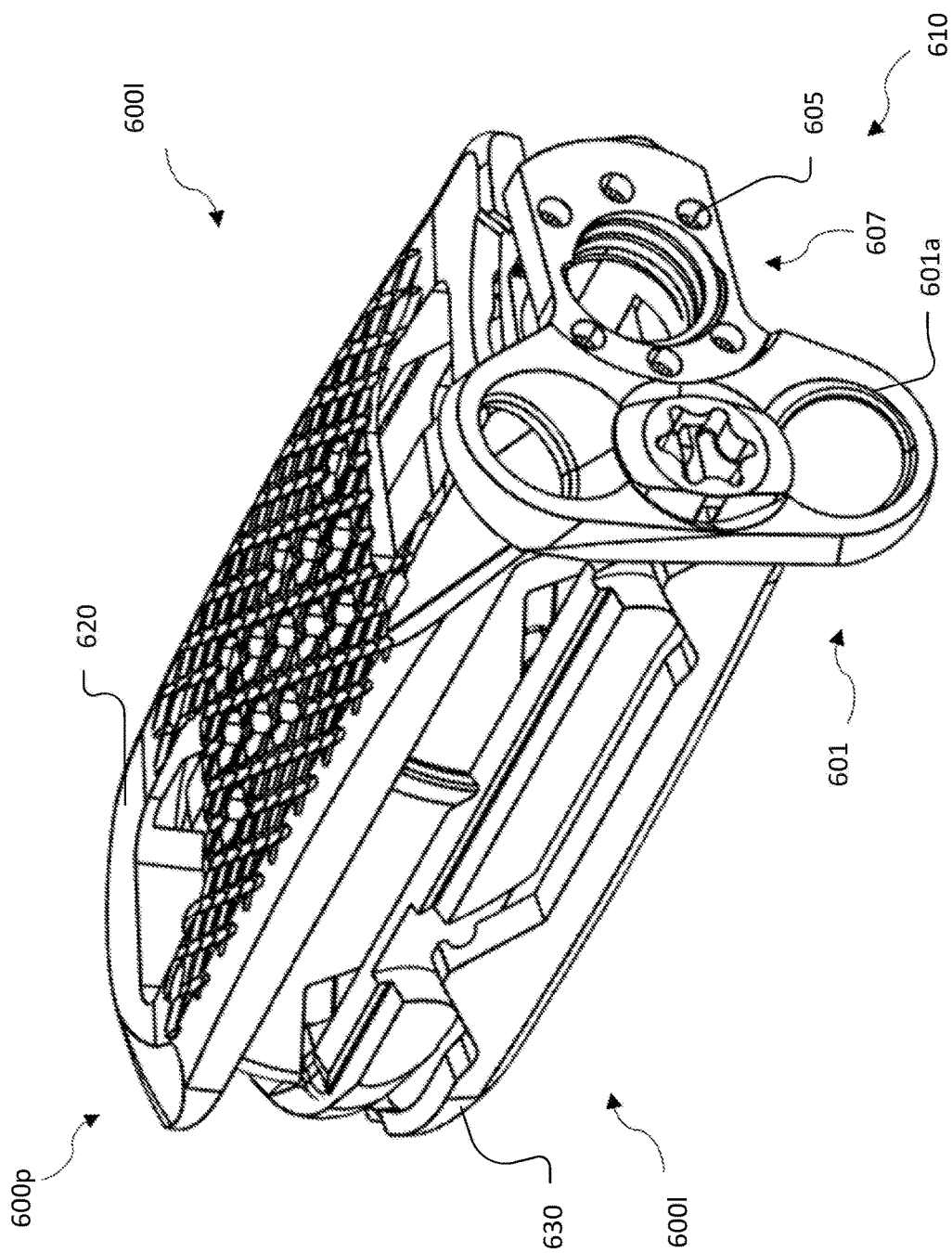
FIG. 51 is an alternate perspective view of the spinal implant of FIG. 50 including a proximal end plate in accordance with the principles of the present disclosure.
Figure 52:
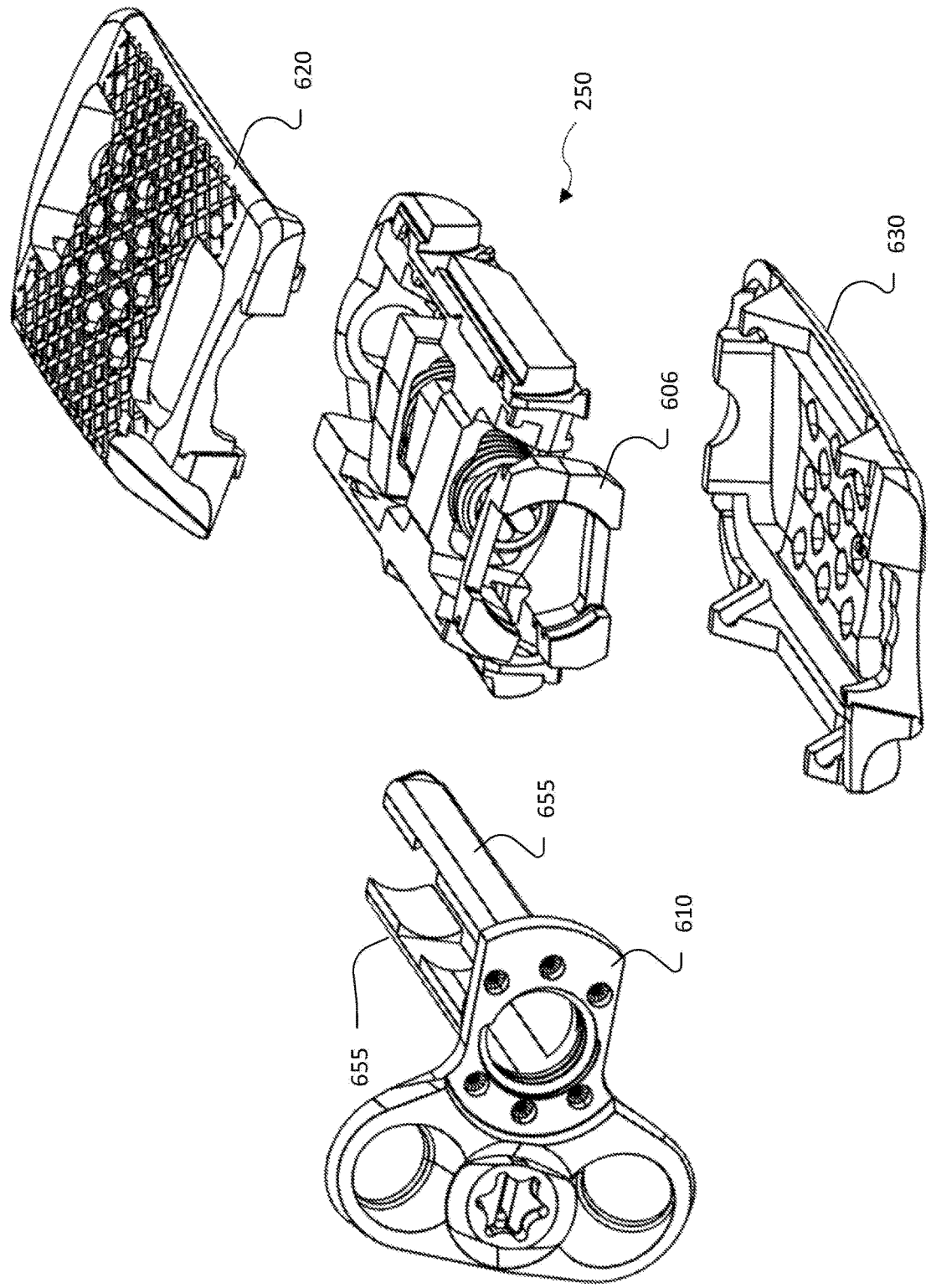
FIG. 52 is an exploded parts view of the spinal implant of FIG. 50 including a proximal end plate in accordance with the principles of the present disclosure.

FIGS. 50 and 51 are perspective views of a spinal implant 600 including a proximal end plate 610 in accordance with the principles of the present disclosure. In some embodiments, proximal end plate 610 may be referred to as a front endplate, anterior endplate, rear endplate, third endplate, or may be referred to as a medial, lateral, or posterior endplate depending upon orientation or approach employed and the specific configuration and shape of the implant and the location, side or end to which it is affixed or located with respect to a patient's body. FIG. 52 is an exploded parts view of spinal implant 600 in accordance with the principles of the present disclosure. Expandable spinal implant 600 may include the same, substantially the same, and/or similar features as the various above disclosed embodiments. For example, moving mechanism 250 may operate in the same, substantially the same, and/or similar manner as explained above. However, implant 600 may include a proximal end plate 610, a top endplate 620 (superior endplate), and a bottom endplate 630 (inferior endplate) having different characteristics as will be explained in further detail below. Additionally, in various embodiments, the proximal end plate 610 may replace the screw guide endplate 105 shown in FIG. 13 above, for example.

Implant 600 may include an anterior side 600a (may also be referred to as a proximal side), a posterior side 600p (may also be referred to as a distal side) and two opposing lateral sides 6001, for example Proximal end plate 610 may include a plurality of circular bone screw apertures 601, for example. In the example embodiment, two circular bone screw apertures 601 are illustrated that are vertically aligned and disposed proximate one of the two lateral sides 6001, for example a first lateral side 6001. However, in other embodiments, the number of bone screw apertures 601 may be more or less and their orientation may be different from shown. For example, in some embodiments there may be a single bone screw aperture 601 and in other embodiments there may be an additional 3$^{rd}$ and 4$^{th}$ bone screw aperture in the medial location or on the opposite lateral side 6001 (not illustrated). For example, in some embodiments there may be a total of four bone screw apertures with a pair of vertically aligned bone screw apertures adjacent each lateral side 6001, respectively (not illustrated). In various embodiments, the upper bone screw aperture 601 may project over (across) the top endplate 620 and the lower bone screw aperture 601 may project beneath (across) the bottom endplate 620, for example.

In various embodiments, each bone screw aperture 601 may include at least one circular ring portion 601a that facilitates seating of a bone screw 711 (see FIG. 63) and/or facilitates the alignment of a drill in a coaxial relationship, e.g., surgical tool 500 as disclosed above. For example, the ring portion 601a may define a bearing surface for seating an inclined surface 712 of an outdented rail 713 of a head portion of a bone screw 711, for example. In various embodiments, the ring portion 601a may have a size and shape generally corresponding to a size and shape of the inclined surface 712 and define an interior diameter that is less than a cross sectional diameter of the outdented rail 713. Additionally, in various embodiments, the ring portion 601a of bone screw apertures 601 may allow about +/−10° and in some embodiments about +/−5° of freedom to the corresponding bone screw 711 due to the inclined surface 712, for example.

In various embodiments, proximal end plate 610 may include at least one attachment point 605 for connecting implant 600 with a surgical tool, for example surgical tool 400 as disclosed above. In the disclosed embodiment, a plurality of attachment points 605 are distributed around screw guide aperture 607. In the disclosed embodiment, six attachment points 605 are radially distributed around central screw guide aperture 607 although other embodiments may have more or less, e.g. 2, 3, 4, 5, 7 or 8. The variability in multiple attachment points 605 may assist a surgeon in positioning implant 600 according to various surgical techniques such as lateral, oblique, and anterior techniques to facilitate positioning of implant 600 around various anatomical features such as the pelvic ring, for example.

Figure 53A:
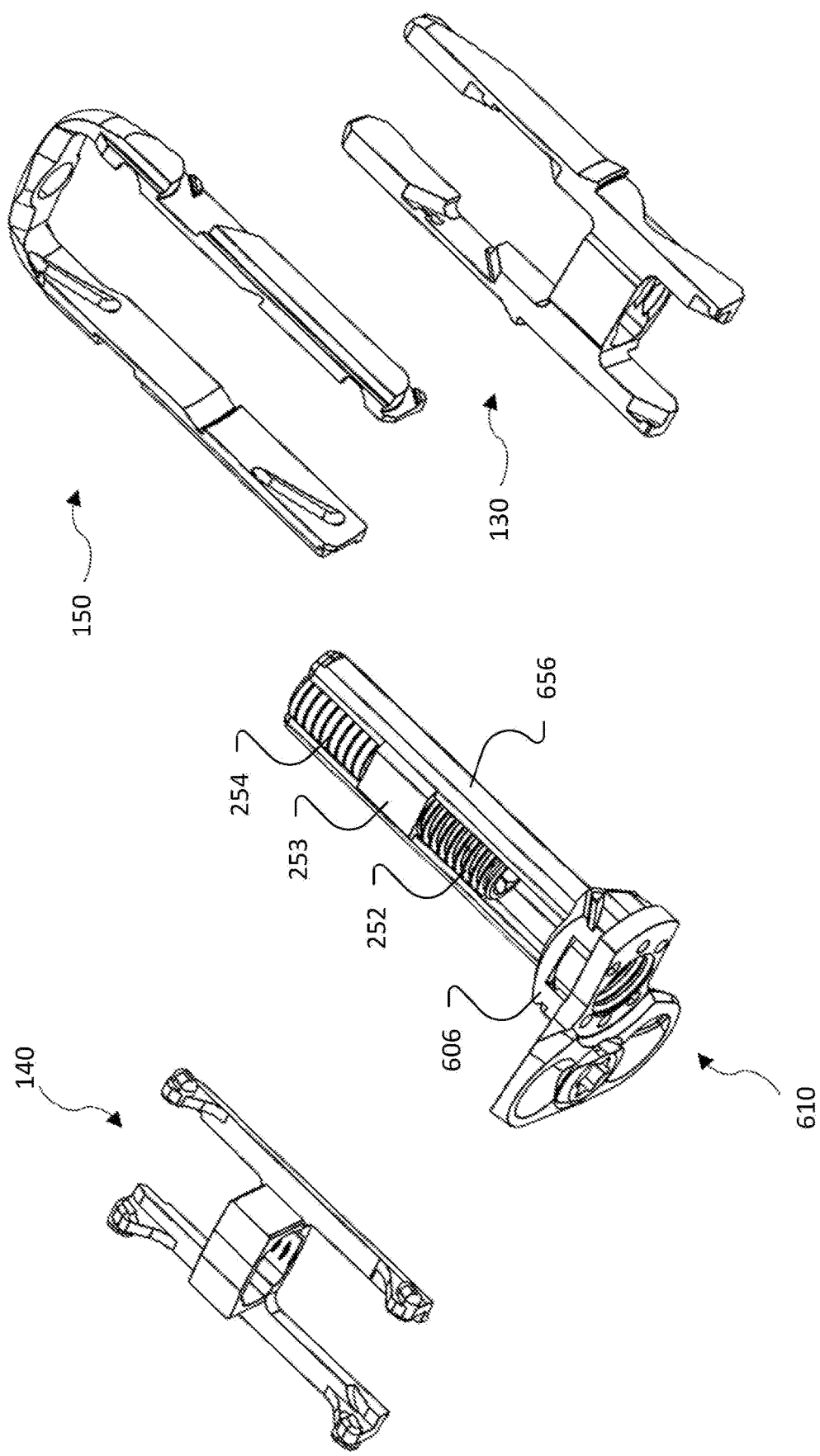
FIG. 53A is an exploded parts view of an example proximal end plate, top sliding frame, bottom sliding frame, and angled wedge in accordance with the principles of the present disclosure.

FIG. 53A is an exploded parts view of the proximal end plate 610, bottom sliding frame 130, angled wedge 140, and top sliding frame 150. FIG. 53B is an exploded parts view of the proximal end plate 610, top endplate 620 and bottom endplate 630. Proximal end plate 610 may include a contoured block 606 having various engagement surfaces and features such as inclined surfaces 606i and channels 606c at a distal side thereof, for example. The inclined surfaces 606i and channels 606c may engage corresponding engagement surfaces of the top endplate 620 and bottom endplate 630, for example. In various embodiments, channels 606c may interface with inclined medial proximal ramps 626 and 636 such that rail portions 626r and 636r are seated within a corresponding channel 606c and are slidable therein, for example. In this way, the proximal end plate may be operably and slidably coupled to the top endplate 620 and bottom endplate 630. Additionally, in various embodiments, contoured block 606 may be separable on at least one end such that in the expanded position a gap 606g is formed on at least one end. For example, contoured block 606 may function like a hinge in some embodiments. In the closed or collapsed position, the gap 606g may be closed on the at least one end, for example.

Figure 54A:
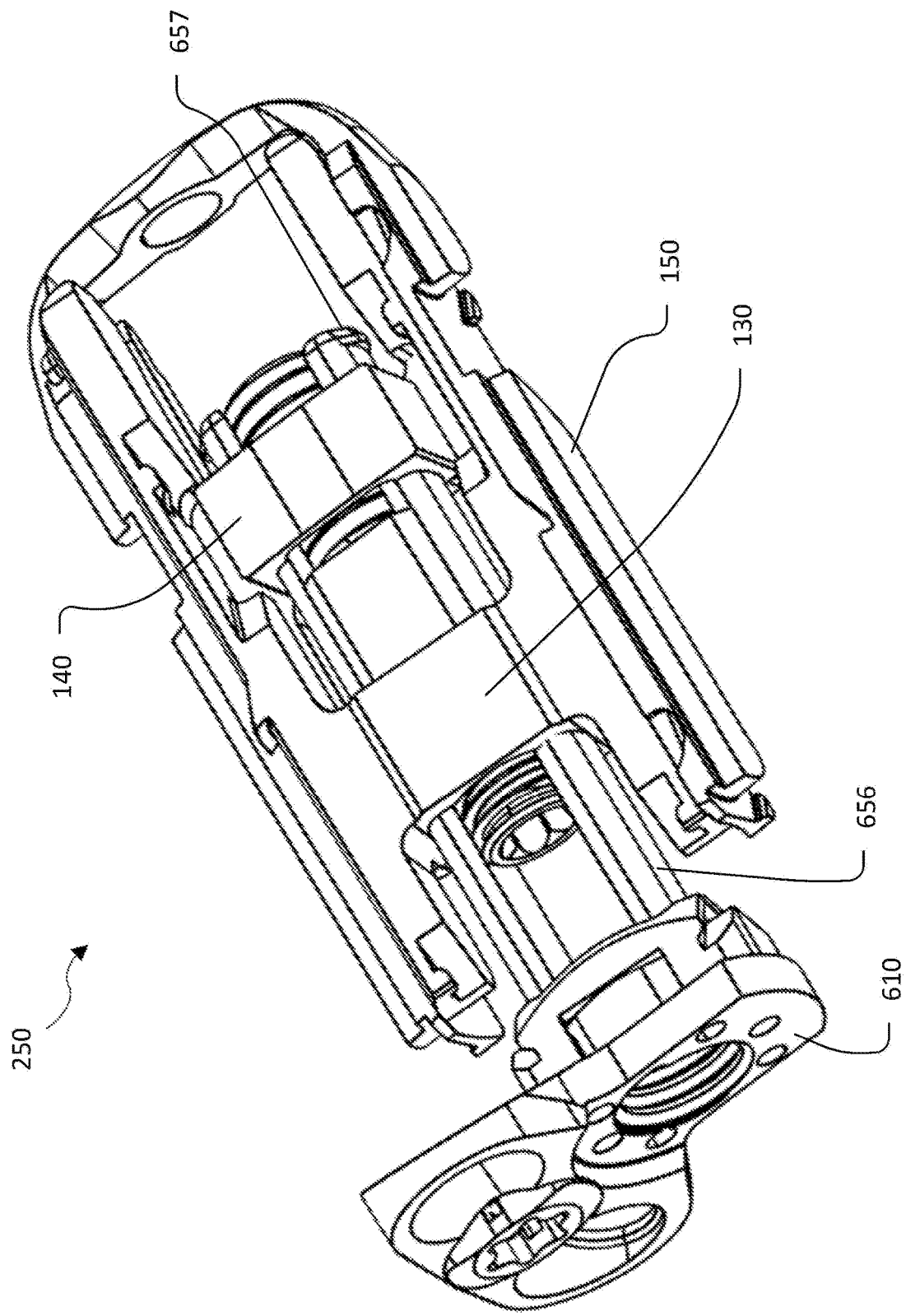
FIG. 54A is a perspective view of the spinal implant of FIG. 50 with some parts removed for ease of understanding in accordance with the principles of the present disclosure.
Figure 54B:
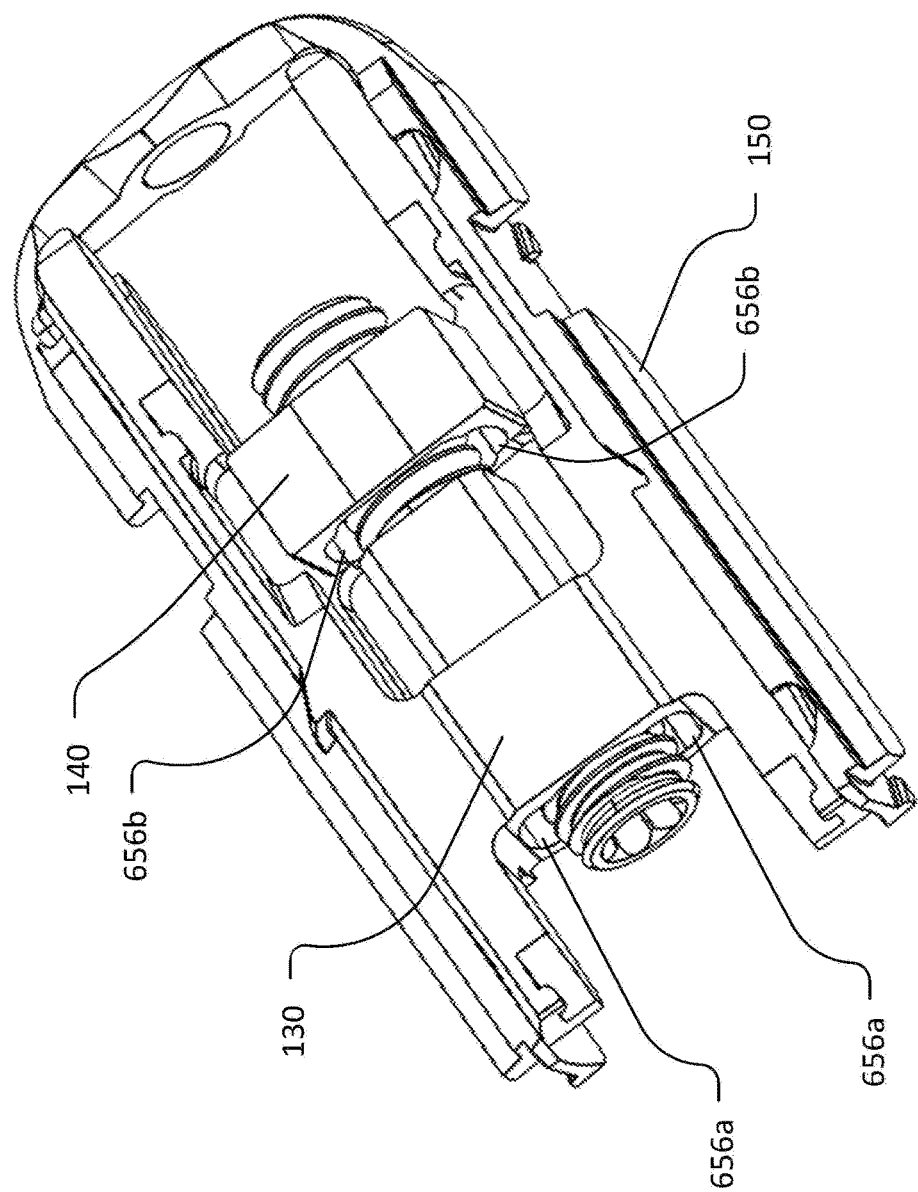
FIG. 54B is a perspective view of the spinal implant of FIG. 50 with some parts removed for ease of understanding in accordance with the principles of the present disclosure.
Figure 55:
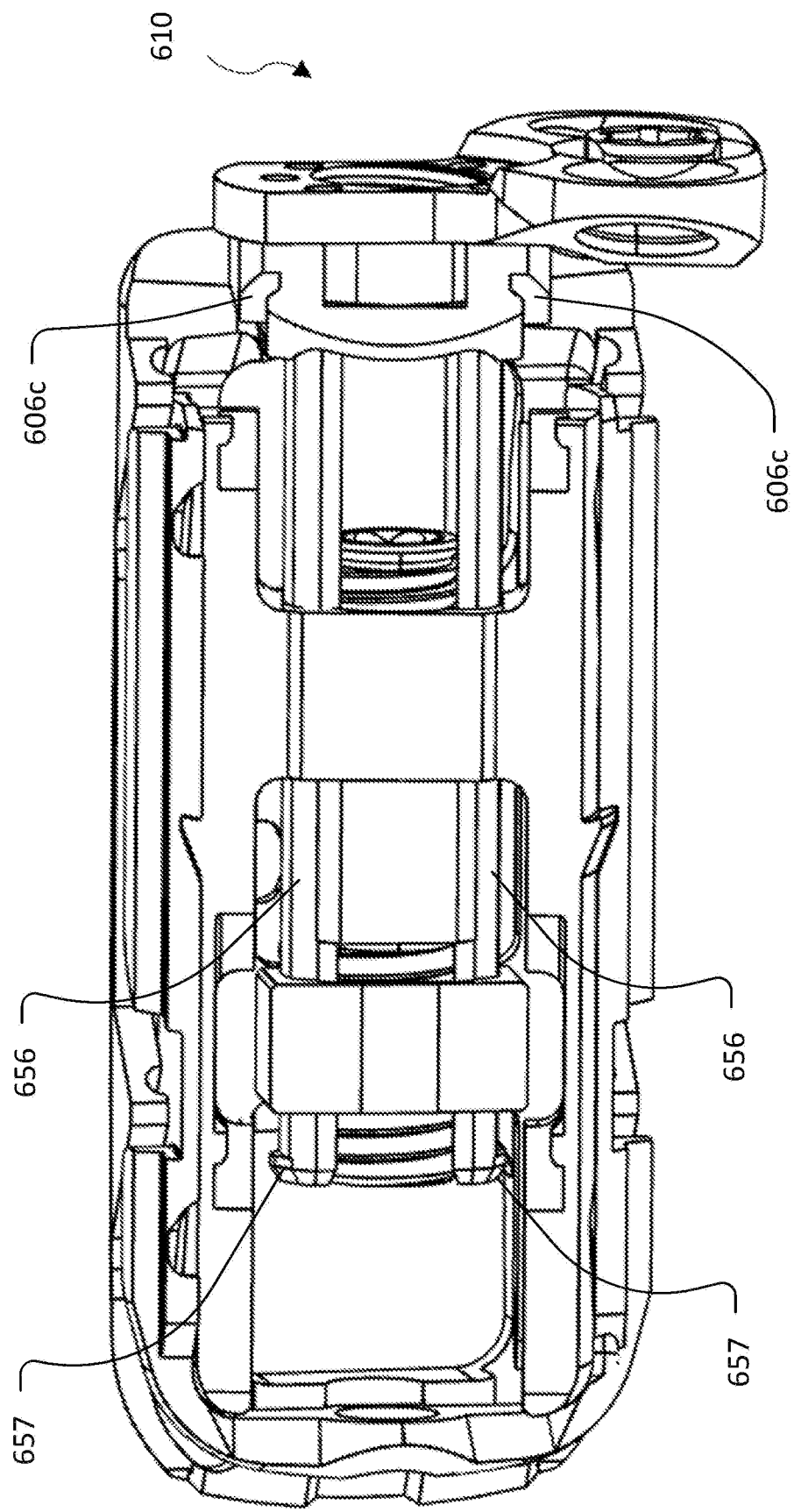
FIG. 55 is a perspective view of the spinal implant of FIG. 50 with some parts removed for ease of understanding in accordance with the principles of the present disclosure.

FIG. 54A is a perspective view of the spinal implant 800 with the top and bottom endplates 620, 630 removed for ease of understanding of how proximal end plate 610 is operably engaged with and/or coupled with the moving mechanism 250 via the bottom sliding frame 130 and angled wedge 140 (see FIGS. 11-12D), for example. FIG. 54B is a perspective view of the components of FIG. 54A with the proximal end plate 610 removed for ease of understanding and FIG. 55 is a top down view of spinal implant 600 with top endplate 620 removed for ease of understanding of the interior components. In the example illustrations, proximal end plate 610 includes a pair of rail portions 656 that define a screw guide body which may be the same and/or similar in functionality and structural design to the screw guide body 256 of previously disclosed embodiments (see FIG. 13). Rail portions 656 may extend from the inside of proximal end plate 610 longitudinally towards the distal end of implant 600 through corresponding apertures 656a of bottom sliding frame 130 and corresponding apertures 656b of angled wedge 140, for example Rail portions 656 may include a stopping feature 657 that project laterally away from the side surface of rail portion 656 that prevents rail portions 656 from uncoupling from angled wedge 140, for example. In this way, rail portions 656 may be operably coupled to moving mechanism 250 by extending through apertures 656a and 656b, for example.

Figure 56:
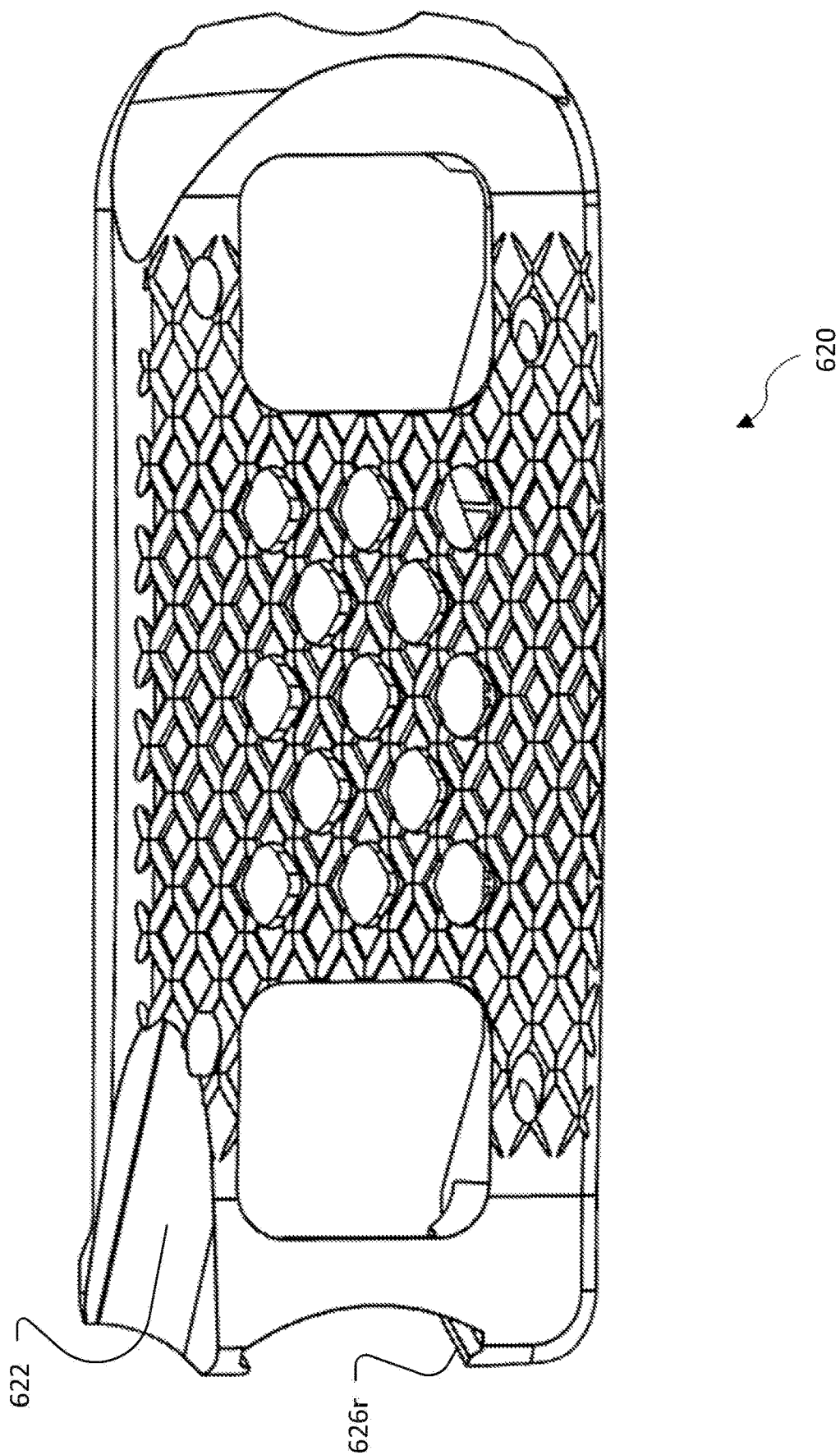
FIG. 56 is a top down view of a top endplate in accordance with the principles of the present disclosure.
Figure 57:
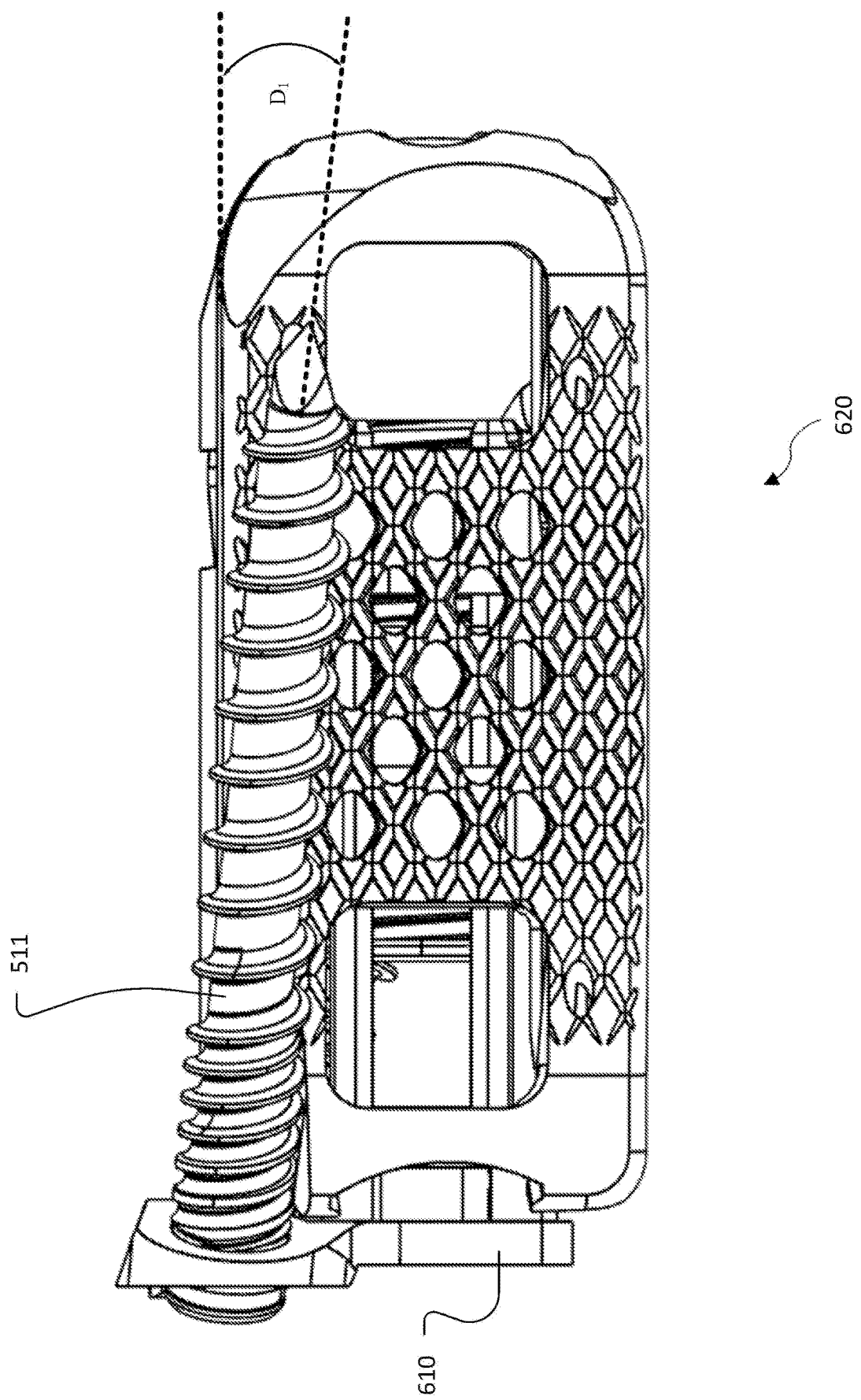
FIG. 57 is a top down view of a top endplate including a bone screw in accordance with the principles of the present disclosure.
Figure 58:
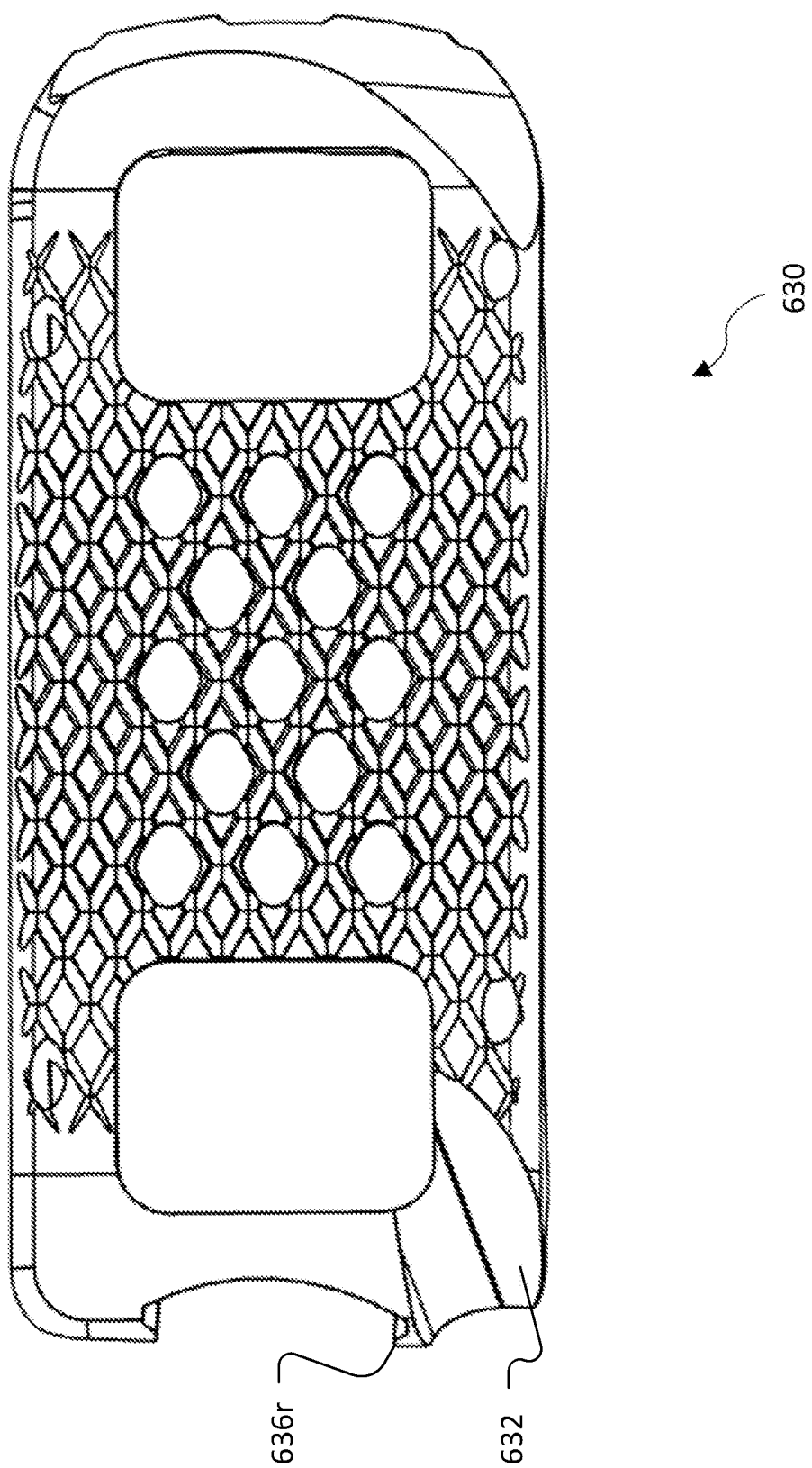
FIG. 58 is a top down view of a bottom endplate in accordance with the principles of the present disclosure.
Figure 59:
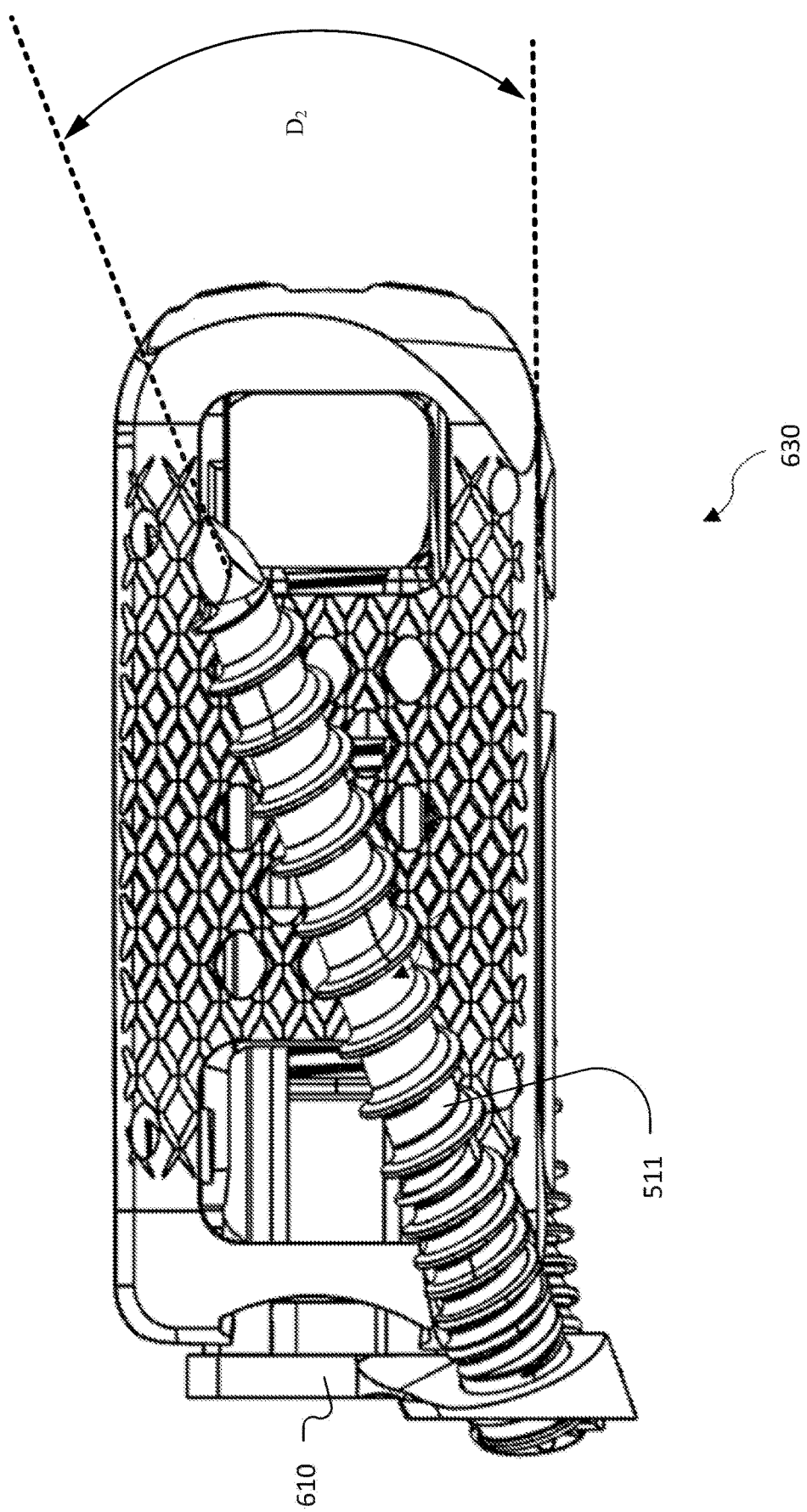
FIG. 59 is a top down view of a bottom endplate including a bone screw in accordance with the principles of the present disclosure.

FIG. 56 is a top down view of a top endplate 620 and FIG. 57 is a top down view of top endplate 620 including a bone screw 711 in accordance with the principles of the present disclosure. In the example illustrations, top endplate 620 includes a first bone screw relief 622 on an outside surface thereof. FIG. 58 is a top down view of a bottom endplate 630 and FIG. 59 is a top down view of bottom endplate 630 including a bone screw 711 in accordance with the principles of the present disclosure. In the example illustrations, bottom endplate 630 includes a second bone screw relief 632 on an outside surface thereof. Bone screw reliefs 622 and 632 may comprise an arcuate channel and/or conical channel defining a portion of the outside surface of the corresponding endplate, for example. The arcuate channel and/or conical channel may extend in a direction corresponding to a trajectory defined by bone screw apertures 601, for example. In FIG. 57, it is shown that an upper aperture 601 may orient a first bone screw 711 diagonally across and above top endplate 620 such that the first bone screw 711 does not come into contact with the first bone screw relief 622. Additionally, in various embodiments, the upper aperture 601 may orient the first bone screw 711 such that it may be angled at a first degree $D_1$ with respect to the adjacent lateral side of implant 600 as shown in FIG. 57, for example. Similarly, in FIG. 59 it is shown that a lower aperture 601 may orient a second bone screw 711 diagonally across and below bottom endplate 620 such that the second bone screw 711 does not come into contact with the second bone screw relief 632. Additionally, in various embodiments the second bone screw 711 may be angled at a second degree $D_2$ with respect to the adjacent lateral side of implant 600 as shown in FIG. 59, for example. Furthermore, in various embodiments, the first and second bone screws 711 may project diagonally across a corresponding outside surface of an endplate by different degrees, i.e., $D_1$ may be less than $D_2$.

In some embodiments, the number of bone screw reliefs 622, 632 may be more or less from shown. For example, there may be multiple bone screw reliefs 622 on the top endplate 620 and multiple bone screw reliefs 632 on the bottom endplate 630 as is consistent with the above disclosure explaining that the number of bone screw apertures 601 may be more or less. Additionally, in various embodiments each bone screw aperture 601 may orient a corresponding bone screw such that it extends over a corresponding bone screw relief 622, 632 without coming into contact with it. For example, in an expanded configuration each of bone screws 711 may extend through a corresponding bone screw apertures 801. In the example embodiment, when implant 600 is in the fully expanded position a trajectory of the bone screws 711 is unaffected by the top endplate 620 and/or bottom endplate 630. For example, the bone screw reliefs 622, 632 allow the implant 600 to fully expand without interfering with bone screws 711. For example still, bone screws 711 may be secured to a boney surface and anchor implant 600 via bone screw apertures 601 of proximal end plate 610.

Figure 60:
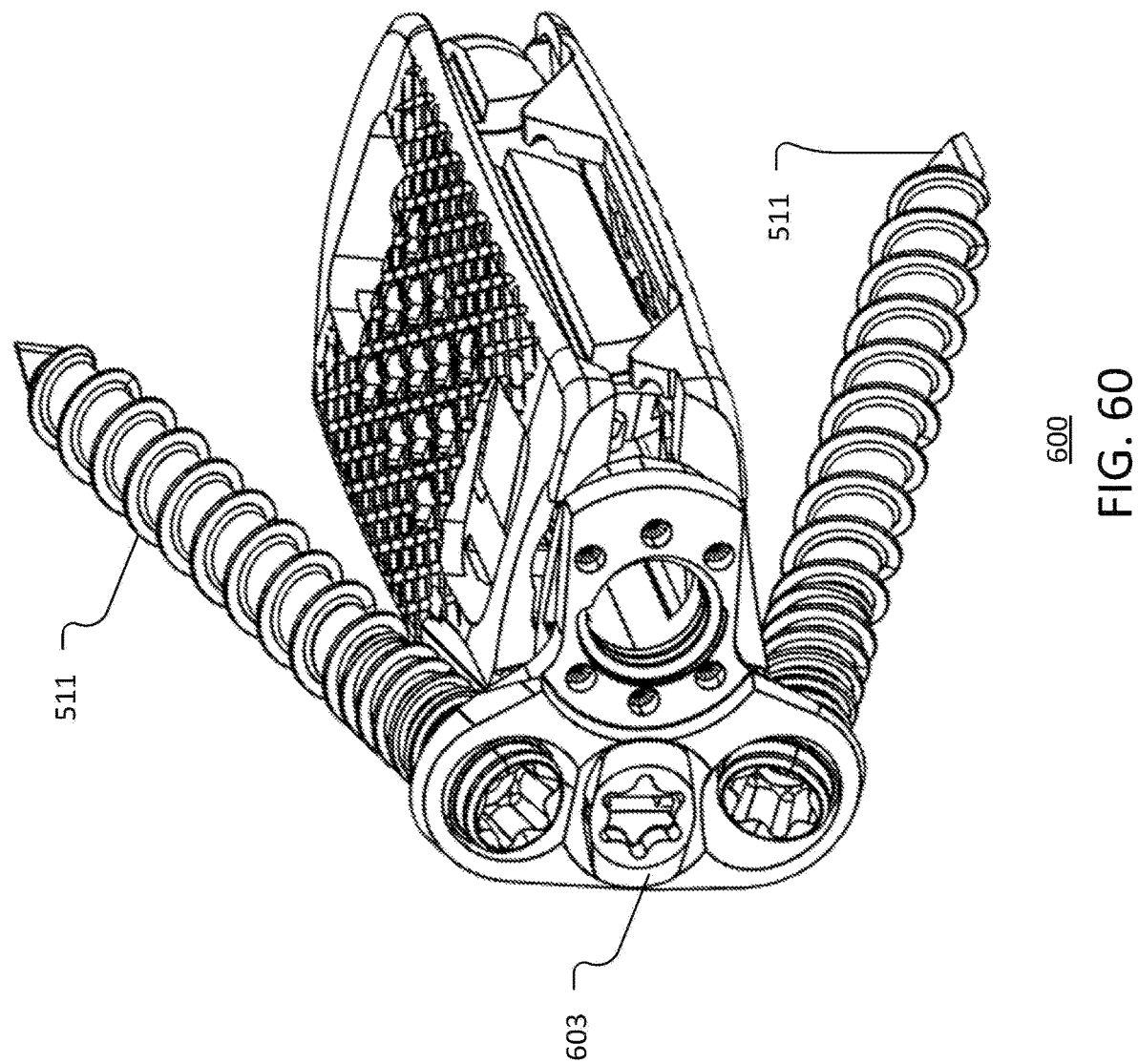
FIG. 60 is a perspective view of the spinal implant of FIG. 50 including a proximal end plate having a bone screw lock in the unlocked position and bone screws in accordance with the principles of the present disclosure.
Figure 61:
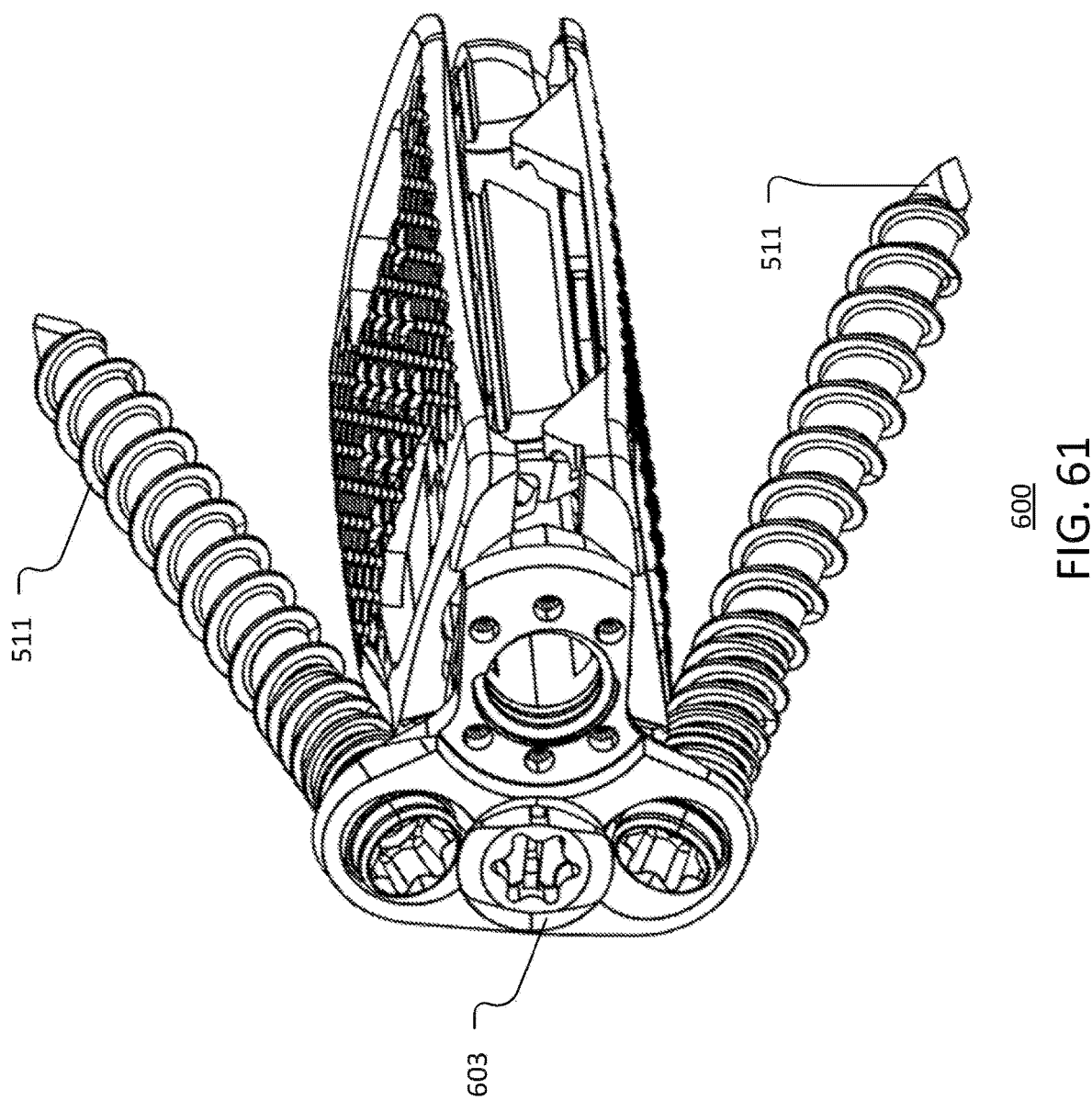
FIG. 61 is a perspective view of the spinal implant of FIG. 50 including a proximal end plate having a bone screw lock in the locked position and bone screws in accordance with the principles of the present disclosure.
Figure 62:
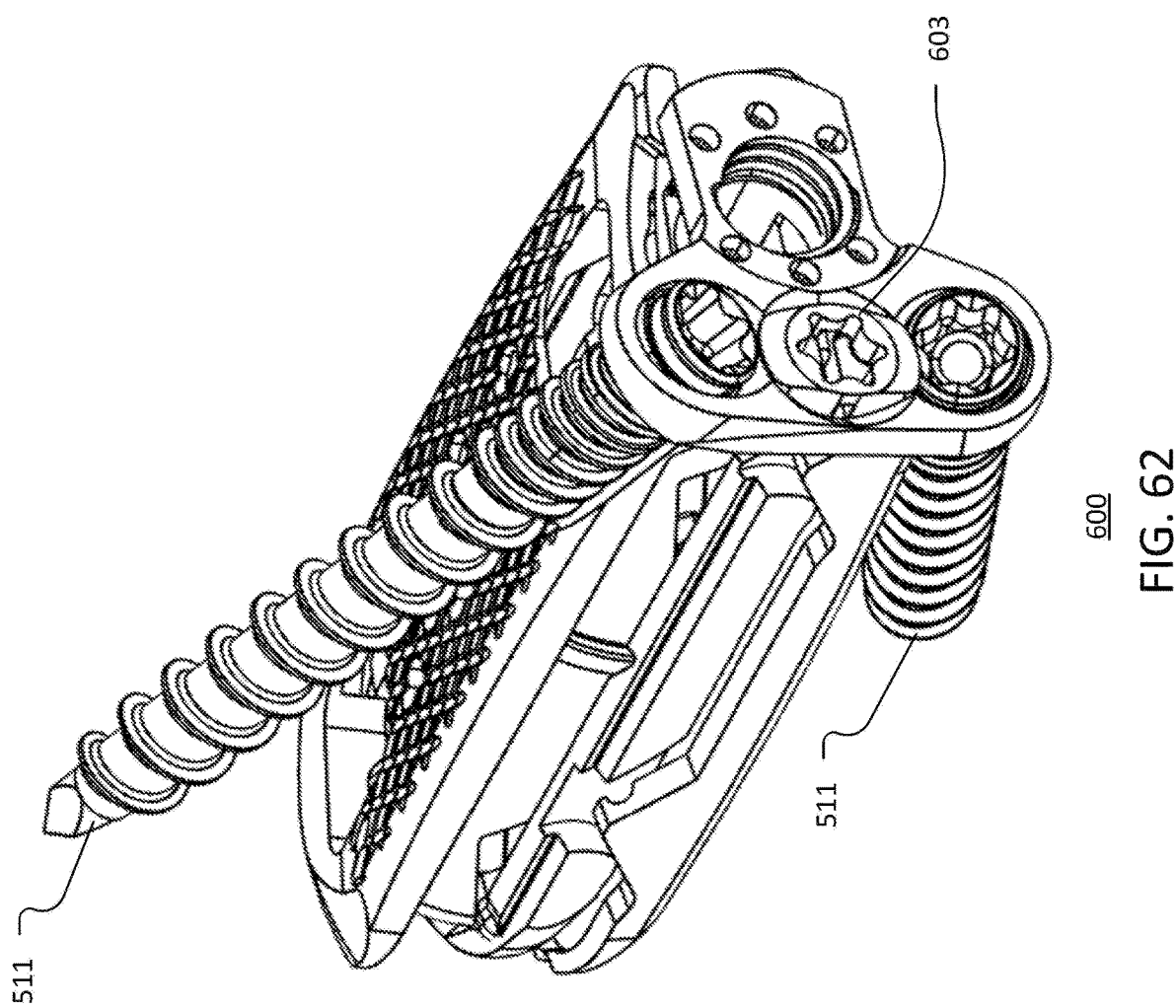
FIG. 62 is a perspective view of the spinal implant of FIG. 50 including a proximal end plate having a bone screw lock in the locked position and bone screws in accordance with the principles of the present disclosure.

FIG. 60 is a perspective view of spinal implant 600 including a proximal end plate 610 having a bone screw lock 603 in the unlocked position and bone screws 711 extending over corresponding bone screw reliefs 622, 632 in accordance with the principles of the present disclosure. FIG. 61 is a first perspective view of spinal implant 600 where the bone screw lock 603 is in the locked position and FIG. 62 is a second perspective view of spinal implant 600 where the bone screw lock 603 is in the locked position. Bone screw lock 603 may be toggled between an unlocked position shown in FIG. 60 to a locked position shown in FIGS. 61 and 62 by rotating the bone screw lock 603 about 90°. In operation, an end user such as a surgeon may place at least one bone screw 711 through a bone screw aperture 601 after the implant 600 is expanded to the desired height and inclination and install the bone screws 711 into an adjacent boney structure such as a superior vertebrae and an inferior vertebrae, for example. Thereafter, the surgeon may move bone screw lock 603 from the unlocked position to the locked position to prevent and/or suppress bone screws 711 from backing out. In some embodiments, even after the bone screw lock 603 is engaged in the locked position the surgeon may drive and install bone screws 711. In other embodiments, the bone screw lock 603 may block access to the head of the bone screw 711 and should therefore be in an unlocked position when driving bone screw 711. Additionally, in the disclosed embodiment a single bone screw lock 603 is illustrated and when moved into the locked position the single bone screw lock 603 prevents and/or suppresses both the upper bone screw 711 and lower bone screw 711 from backing out.

FIG. 62 is an example side view of a bone screw 711. As illustrated in the embodiment of FIG. 62, bone screw 711 may include an inclined surface 712 extending around the circumference of bone screw 711 and terminating into a ring portion 713. In various embodiments, the ring portion 713 may have a size and shape generally corresponding to a size and shape of circular ring portions 601a of bone screw aperture 601, for example. Additionally, in various embodiments the cooperation between the circular ring portions 601a, inclined surface 712, and ring portion 713 may allow about +/−10° of freedom and in some embodiments about 5° of freedom to the corresponding bone screw 711, for example.

FIG. 63 is a reference diagram illustrating various cardinal directions and planes with respect to a patient that the various exemplary embodiments disclosed herein may operate, adjust, and/or move along in accordance with the principles of the present disclosure.

What is claimed is:
1. An expandable spinal implant deployable between a contracted position and an expanded position, comprising:
   a superior endplate, the superior endplate including:
   a first outside surface and a first inside surface opposite the first outside surface, a first proximal end and a first distal end opposite the first proximal end, and a first lateral surface and a second lateral surface opposite the first lateral surface, the first and second lateral surfaces extending between the first proximal end and the first distal end;

an inferior endplate, the inferior endplate including:
a second outside surface and a second inside surface opposite the second outside surface, a second proximal end and a second distal end opposite the second proximal end, and a third lateral surface and a fourth lateral surface opposite the third lateral surface, the third and fourth lateral surfaces extending between the second proximal end and the second distal end;
a proximal end plate including at least one bone screw aperture; and
a moving mechanism operably coupled to the superior endplate and inferior endplate, the moving mechanism including:
a wedge, a first sliding frame and a second sliding frame disposed on opposite sides of the wedge, a screw guide housing a rotatable first set screw and a rotatable second set screw opposite the first set screw, the first set screw being operably coupled to the second sliding frame and the second set screw being operably coupled to the wedge,
wherein the first set screw and second set screw are configured to rotate in a first rotation direction and a second rotation direction about a rotation axis projecting in a longitudinal direction of the moving mechanism,
wherein the moving mechanism is configured to operably adjust a spacing between the superior and inferior endplates upon simultaneous rotation of the first and second set screws along the rotation axis, and
wherein the moving mechanism is configured to operably adjust an angle of inclination between the superior and inferior endplates upon translating either one of the first set screw and second set screw along the rotation axis.

2. The expandable spinal implant of claim 1, wherein the second sliding frame is operably coupled to the first set screw and inferior endplate and movable in the longitudinal direction of the moving mechanism by rotation of the first set screw along the rotation axis.

3. The expandable spinal implant of claim 1, wherein the second sliding frame includes a pair of first protrusions that are operably coupled to corresponding first channels of the first sliding frame, and
wherein upon movement of the second sliding frame in the longitudinal direction the first sliding frame also moves in the longitudinal direction.

4. The expandable spinal implant of claim 1, wherein the superior endplate further includes a first plurality of inclined ramps and the inferior endplate further includes a second plurality of inclined ramps.

5. The expandable spinal implant of claim 4, wherein the first plurality of inclined ramps further include a first plurality of grooves and the second plurality of inclined ramps includes a second plurality of grooves.

6. The expandable spinal implant of claim 5, wherein the first sliding frame further includes first distal contact surfaces and first proximate contact surfaces configured to act against the first plurality of inclined ramps of the superior endplate.

7. The expandable spinal implant of claim 6, wherein the first sliding frame further includes a first plurality of guide walls operably coupled to the first plurality of grooves of the superior endplate.

8. The expandable spinal implant of claim 5, wherein the second sliding frame further includes a second plurality of guide walls operably coupled to the second plurality of grooves of the inferior endplate.

9. The expandable spinal implant of claim 8, wherein the second sliding frame further includes a third plurality of ramps.

10. The expandable spinal implant of claim 9, wherein the wedge further includes a plurality of engagement surfaces configured to operably engage the third plurality of ramps of the second sliding frame.

11. The expandable spinal implant of claim 10, wherein the wedge further includes a plurality of lateral protrusions.

12. The expandable spinal implant of claim 1, wherein the first sliding frame further includes a first plurality of channels and the wedge further includes a second plurality of protrusions operably coupled to the first plurality of channels of the first sliding frame.

13. The expandable spinal implant of claim 1, wherein the proximal end plate includes a plurality of attachment points radially disposed around a central aperture.

14. The expandable spinal implant of claim 1, wherein at least one of the first outside surface and second outside surface includes a bone screw relief and the at least one bone screw aperture is configured to orient a bone screw such that it extends over the bone screw relief without coming into contact with it.

15. The expandable spinal implant of claim 1, wherein:
the proximal end plate includes a contoured block having superior channels and inferior channels,
the superior endplate includes medial proximal rails seated within the superior channels, respectively, and
the inferior endplate includes medial proximal rails seated within the inferior channels, respectively.

16. The expandable spinal implant of claim 1, wherein:
the at least one bone screw aperture comprises a superior bone screw aperture and an inferior bone screw aperture,
the superior endplate comprises a superior bone screw relief,
the inferior endplate comprises an inferior bone screw relief,
the superior bone screw aperture is configured to orient a corresponding superior bone screw such that it extends across the superior bone screw relief without coming into contact with it, and
the inferior bone screw aperture is configured to orient a corresponding inferior bone screw such that it extends across the inferior bone screw relief without coming into contact with it.

17. The expandable spinal implant of claim 16, wherein:
the superior bone screw aperture is configured to orient the corresponding superior bone screw such that it extends diagonally across the superior endplate at a first angle with respect to the first lateral surface,
the inferior bone screw aperture is configured to orient the corresponding inferior bone screw such that it extends diagonally across the inferior endplate at a second angle with respect to the third lateral surface, and
the first angle and second angle are different.

18. The expandable spinal implant of claim 17, wherein:
the proximal end plate includes at least one bone screw lock, the at least one bone screw lock being rotatable between an unlocked position and a locked position, and
when the at least one bone screw lock is in the locked position, the at least one bone screw lock prevents the corresponding superior bone screw and the corresponding inferior bone screw from backing out.

19. A spinal implant system adjustable in situ between vertebral bodies of a patient, the system comprising:
  the expandable spinal implant according to claim 1;
  a first surgical tool configured to adjust the expandable spinal implant; and
  a second surgical tool configured to install at least one bone screw.

20. An expandable spinal implant, comprising:
  a superior endplate and an inferior endplate extending in a longitudinal direction, at least one of the superior endplate and inferior endplate having at least one bone screw relief;
  a proximal end plate including at least one bone screw aperture configured to orient a bone screw such that the bone screw extends across the at least one bone screw relief, the proximal end plate being operably coupled to the superior endplate and the inferior endplate;
  a wedge and a sliding frame operably coupled to the wedge, at least one of the wedge and sliding frame being operably coupled to at least one of the superior endplate and/or inferior endplate; and
  a moving mechanism operably coupled to the wedge and sliding frame, the moving mechanism defining a rotation axis extending in the longitudinal direction,
  wherein the moving mechanism is configured to selectively move at least one of the wedge and sliding frame forward/backward in the longitudinal direction,
  wherein upon moving both the wedge and sliding frame simultaneously forward/backward the superior and inferior endplates expand/contract with respect to one another, and
  wherein the wedge and sliding frame are further configured to selectively rotate, at least partially, about the rotation axis upon movement of the wedge in the longitudinal direction to thereby adjust an inclination of the superior endplate with respect to the inferior endplate in a lateral direction perpendicular to the longitudinal direction.

* * * * *